(12) United States Patent
Chen et al.

(10) Patent No.: US 11,208,457 B2
(45) Date of Patent: Dec. 28, 2021

(54) HIGH THROUGHPUT CLONING OF PAIRED BIPARTITE IMMUNORECEPTOR POLYNUCLEOTIDES AND APPLICATIONS THEREOF

(71) Applicant: RootPath Genomics, Inc., Watertown, MA (US)

(72) Inventors: Xi Chen, Newton, MA (US); Ely Porter, Medford, MA (US)

(73) Assignee: RootPath Genomics, Inc., Watertown, MA (US)

(*) Notice: Subject to any disclaimer, the term of this patent is extended or adjusted under 35 U.S.C. 154(b) by 0 days.

(21) Appl. No.: 17/173,705

(22) Filed: Feb. 11, 2021

(65) Prior Publication Data

US 2021/0171600 A1 Jun. 10, 2021

Related U.S. Application Data

(63) Continuation of application No. PCT/US2019/046170, filed on Aug. 12, 2019.

(60) Provisional application No. 62/823,831, filed on Mar. 26, 2019, provisional application No. 62/818,355, filed on Mar. 14, 2019, provisional application No. 62/732,898, filed on Sep. 18, 2018, provisional application No. 62/725,842, filed on Aug. 31, 2018, provisional application No. 62/718,227, filed on Aug. 13, 2018.

(51) Int. Cl.
*C07K 14/725* (2006.01)
*C07K 14/74* (2006.01)
*G01N 33/50* (2006.01)

(52) U.S. Cl.
CPC .... *C07K 14/7051* (2013.01); *C07K 14/70539* (2013.01); *G01N 33/5005* (2013.01)

(58) Field of Classification Search
None
See application file for complete search history.

(56) References Cited

U.S. PATENT DOCUMENTS

| | | | |
|---|---|---|---|
| 5,858,358 A | 1/1999 | June et al. | |
| 5,883,223 A | 3/1999 | Gray | |
| 6,120,766 A | 9/2000 | Hale et al. | |
| 6,352,694 B1 | 3/2002 | June et al. | |
| 6,534,055 B1 | 3/2003 | June et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 7,749,697 B2 | 7/2010 | Oleksiewicz et al. | |
| 9,738,699 B2 | 8/2017 | Johnson et al. | |
| 9,926,555 B2 | 3/2018 | Johnson et al. | |
| 10,221,437 B2 | 3/2019 | Weitz et al. | |
| 2003/0049712 A1 | 3/2003 | Haugwitz | |
| 2003/0050453 A1 | 3/2003 | Sorge | |
| 2006/0121005 A1 | 6/2006 | Berenson et al. | |
| 2007/0065912 A1 | 3/2007 | Carson et al. | |
| 2007/0141048 A1 | 6/2007 | Oleksiewicz et al. | |
| 2010/0285975 A1 | 11/2010 | Mathies et al. | |
| 2010/0310558 A1 | 12/2010 | Oleksiewicz et al. | |
| 2012/0015822 A1 | 1/2012 | Weitz et al. | |
| 2014/0378345 A1 | 12/2014 | Hindson et al. | |
| 2014/0378350 A1 | 12/2014 | Hindson et al. | |
| 2015/0005199 A1 | 1/2015 | Hindson et al. | |
| 2015/0005200 A1 | 1/2015 | Hindson et al. | |
| 2015/0225778 A1 | 8/2015 | Hindson et al. | |
| 2015/0298091 A1 | 10/2015 | Weitz et al. | |
| 2016/0122817 A1 | 5/2016 | Jarosz et al. | |
| 2017/0335391 A1 | 11/2017 | Emerson et al. | |
| 2018/0080078 A1 | 3/2018 | Robins et al. | |
| 2018/0282808 A1 | 10/2018 | Milla et al. | |
| 2019/0008899 A1 | 1/2019 | Moriarity et al. | |
| 2019/0025299 A1 | 1/2019 | Vigneault et al. | |

FOREIGN PATENT DOCUMENTS

| | | |
|---|---|---|
| CN | 106103711 A | 11/2016 |
| CN | 107002076 A | 8/2017 |
| CN | 107849560 A | 3/2018 |

(Continued)

OTHER PUBLICATIONS

Song, I. et al., Nat. Structural Mol. Biol.;vol. 24, 2017: pp. 395-409.*
International Search Report and Written Opinion for corresponding PCT Application No. PCT/US2020/060998 dated Mar. 11, 2021.
"Abate, et al., "Corrections and Editorial Expression of Concern", PNAS vol. 104, No. 14 (2010)".
"Abatemarco, et al., "RNA-aptamers-in-droplets (RAPID) high-throughput screening for secretory phenotypes" Nature Communications, 8:332 (2017)".
"Sandberg, et al., "Rapid flow-sorting to simultaneously resolve multiplex massively parallel sequencing products" Scientific Reports (2011)".
"Anna, et al., "Formation of dispersions using "flow focusing" in microchannels" Applied Physics Letters, vol. 82, No. 3, (2003)".
"Ayub et al., Advanced Materials Research 1125(2015):84."

(Continued)

*Primary Examiner* — Michael D Burkhart
(74) *Attorney, Agent, or Firm* — Wilson Sonsini Goodrich & Rosati

(57) ABSTRACT

Provided herein are compositions and methods for high throughput cloning of fused bipartite immunoreceptor polynucleotides encoding cognate pairs of bipartite immunoreceptors. Also provided herein are various applications of the fused bipartite immunoreceptor polynucleotides, expression vectors containing the fused bipartite immunoreceptor polynucleotides, or cells containing the fused bipartite immunoreceptor polynucleotides or expression vectors.

26 Claims, 30 Drawing Sheets

Specification includes a Sequence Listing.

(56) References Cited

FOREIGN PATENT DOCUMENTS

| | | |
|---|---|---|
| EP | 1516929 A2 | 3/2005 |
| EP | 1670912 B1 | 3/2008 |
| EP | 1921144 A2 | 5/2008 |
| EP | 3095879 A1 | 11/2016 |
| WO | WO-2013126712 A1 | 8/2013 |
| WO | WO-2017053902 A1 | 3/2017 |
| WO | WO-2017177217 A2 | 10/2017 |
| WO | WO-2018132739 A2 | 7/2018 |
| WO | WO-2019126466 A1 | 6/2019 |
| WO | WO-2019196088 A1 | 10/2019 |
| WO | WO-2020036875 A1 | 2/2020 |
| WO | WO-2020206238 A2 | 10/2020 |

OTHER PUBLICATIONS

"Battista, et al., "Bioengineering Microgels and Hydrogel Microparticles for Sensing Biomolecular Targets" Gels, 3, 20 (2017)".

"Bethune, et al., "Domain-swapped T cell receptors improve the safety of TCR gene therapy", eLIFE (2016) pp. 1-24".

"Betz K et al., Nat. Chem. Biol. Jul. 2012;8(7):612-4".

"Brenner (2000) Genome Biol.1:1".

"Brenner (2004) Genome Biol. 5:240".

"Brosseau, et al., "Microfluidic Dynamic Interfacial Tensiometry (uDIT)", Royal Societ of Chemistry, 10, 3066-3076 (2014)".

"Browne, et al. "Selection methods for high-procuding mammalian cells lines", TRENDS in Biotechnology vol. 25, No. 9 (2009)".

"Bunse, et al., "RNAi-mediated TCR Knockdown Prevents Autoimmunity in Mice Caused by Mixed TCR Dimers Following TCR Gene Transfer" Molecular Therapy (2014) vol. 22, No. 11, pp. 1983-1991".

"Cao, et al., "Comprehensive single cell transcriptional profiling of a multicellular organism by combinatorial indexing", (2017) University of Washinton pp. 1-35".

"Chomczynski, et al., "Alkaline polyethylene glycol-based method for direct PCT from bacteria, eukaryotic tissue samples, and whole blood" BioTechniques 40: 454-458 (2016)".

"Cochran, et al., "A diverse set of oligomeric class II MHC-peptide complexes for probing T-cell receptor interactions" Chemistry & Biology (2000) vol. 7, No. 9".

"Cusanovich, et al., "Multiplex Single Cell Profiling of Chromatin Accessibility by Combinatorial Cellular Indexing" Science 348(6237) pp. 910-914 (2015)".

"DeJournette, et al., "Creating Biocompatible Oil-Water Interfaces without Synthesis: Direct Interactions bettween Primary Amines and Carboxylated Perfluorocarbon Surfactants" Anal Chem (2013) 85, 10556-10564".

"Eason et al. (2004) Proc. Natl. Acad. Sci. USA 101:11046;".

"Eyer (2017) Single-cell deep phenotyping of IgG-secreting cells for high-resolution immune monitoring; Nature Biotechnology vol. 35, pp. 977-982".

"Eyer, et al., "Supplementary Notes" Nature Biotechnology (2017), pp. 1-35".

"Geng, et al., "Single-Cell Forensic Short Tandem Repeat Typing within Microfluidic Droplets", Anal. Chem (2014)".

"Geng, et al., "Minimizing inhibition of PCT-STR typing using digital agarose droplet microfluidics" Forensic Scinece International: Genetics 14 (2015) 203-209".

"Giaever et al. (2004) Proc. Natl. Acad. Sci. USA 101:793;".

"Hongkai Zhang et al., Chemistry & biology 20(5):734-741, May 2013".

"International Search Report and Written Opinion for corresponding PCT Application No. PCT/US2018/066748 dated Mar. 18, 2019".

"International Search Report and Written Opinion for corresponding PCT Application No. PCT/US/2019/046170 dated Dec. 3, 2019".

"International Search Report and Written Opinion for corresponding PCT Application No. PCT/US/2020/026558 dated Oct. 1, 2020".

"Ismagilov, et al., "Reactions in Droplets in Microfluidic channels" Angew. Chem. Ed. 45, p. 7336-7356 (2006)".

"Jelena Skuljec et al., Front Immunol. 2017; 8:1125".

"Skhiri, et al., "Dynamics of molecular trnasport by surfactants in emulsions", Soft Matter (2012)".

"Kim, et al., "Single-cell RT-PCT in microfluidic droplets with integrated chemical lysis" Anal. Chem (2017)".

"Klein, et al., "Droplet Barcoding for Single-Cell Transcriptomics Applied to Embryonic Stem Cells", Cell 161, 1187-1201 (2015)".

"Kojima et al., Chem Mater 10(1998):3429,".

"Kuball, et al., "Facilitating matched pairing and expression of TCR chains introduced into human T cells" Blood, (2007) vol. 109, No. 6".

"Kumar et al. (2001) Nature Rev. 2:302;".

"Lagus, et al., "A review of the theory, methods and recent applications of high-throughput single-cell droplet microfluidics", J. Phys. D: Appl. Phys. 46 (2013)".

"Liau, et al., "Mixing Crowded Biological Solutions in Milliseconds" Ana. Chern., 77, 7618-7625 (2005)".

"Liu, et al., "Shape-controlled Production of Biodegradable Calcium Alginate Gel Microparticles Using a Novel Microfluidic Device" Langmuir (2006) 22, 9453-9457".

"Lorenz, Fkm et al.) Unbiased Identification of T-Cell Receptors Targeting Immunodominant Peptide-MHC Complexes for T-Cell Receptor Immunotherapy. Human Gene Therapy. 26, Sep. 2017; vol. 28, No. 12;".

"Mahal et al., (1997) Science 276:1125-1128)".

"Mazutis, et al., "Single-cell analysis and sorting using droplet-based microfluidics" Nature Protocols (2013) vol. 8, No. 5".

"Mazutis, et al., "Microfluidic Production of Alginate Hydrogel Particles for Antibody Encapsulation and Release" Macromolecular Bioscience, p. 1-6 (2015)".

"Nguyen, et al., "Bioactive factor delivery strategies from engineered polymer hydrogels for therapeutic medicine" Pro Polym Sci 39(7), pp. 1236-1265, (2014)".

"Novak, et al., "Single-Cell Multiplex Gtene Detection and Sequencing with Microfluidically Generated Agarose Emulsions" Angew. Chem. Int. Ed., 50, pp. 390-395 (2011)".

"Song, et al., "A Microfluidic System for Controlling Reaction Networks in Time", Angew. Chem. Int. 42, No. 7 pp. 767-772 (2003)".

"Ottino, et al., "Designing Optimal Micromixers" Science vol. 305 pp. 485-486 (2004)".

"Pawer and Edgar, Biomaterials 33(2012), 3279".

"Provasi, et al., "Editing T cell specificity towwards leukemia by zinc finger nucleases and lentiviral gene transfer" Nature Medicine (2012) vol. 18, No. 5".

"Tice, et al., "Formation of Droplets and Mixing in Multiphase Microfluidics at Low values of the Reynolds and the Capillary Numbers", Langmuir 19, pp. 9127-9133 (2003)".

"Uckert, et al., "TCR transgenes and transgene cassettes for TCR gene therapy: status in 2008" Cancer Immunol Immunother (2009) 58: 809-822".

"U.S. Appl. No. 62/609,756, filed Dec. 17, 2017".

"U.S. Appl. No. 62/674,214, filed May 26, 2018".

"Walseng, et al., "A TCR-based Chimeric Antigen Receptor" Scientific Reports (2017) 7:10713".

"Ward, et al., "Microfluidic flow focusing: Drop size and scalling in pressure versus flow-rate-driven pumping" Electrophoresis, 26, pp. 3716-3724 (2005)".

"Wetmur, et al., "Molecular haplotyping by linking emulsion PCT: analysis of paraoxonase 1 haplotypes and phenotypes", Nucleic Acids Research (2005) vol. 33, No. 8 pp. 2615-2619".

"Winzeler et al. (1999) Science 285:901;".

"Yang, et al., "Fluid mixing in droplet-based microfluidics with T junction and convergent-divergent sinusoidal microchannels" Electrophoresis, 39, pp. 512-520 (2018)".

"Zhang, et al., "Lab on a Chip", Manuscript, Royal Society of Chemistry, (2016)".

"Zilionis, et al., "Single-cell barcoding and sequencing using droplet microfluidics" Nature Protocols vol. 12, No. 1, pp. 44-73 (2017)".

"Zucca, Agarose and Its Derivatives as Supports for Enzyme Immobilization, Molecules 2016, 21, 1577".

\* cited by examiner (Continue to FIG. 5C)

SEQUENCE LISTING

```
<160> NUMBER OF SEQ ID NOS: 21

<210> SEQ ID NO 1
<211> LENGTH: 5
<212> TYPE: PRT
<213> ORGANISM: Unknown
<220> FEATURE:
<223> OTHER INFORMATION: Description of Unknown:
      Enterokinase cleavage site

<400> SEQUENCE: 1

Asp Asp Asp Asp Lys
1               5

<210> SEQ ID NO 2
<211> LENGTH: 4
<212> TYPE: PRT
<213> ORGANISM: Unknown
<220> FEATURE:
<223> OTHER INFORMATION: Description of Unknown:
      Factor Xa cleavage site

<400> SEQUENCE: 2

Ile Glu Gly Arg
1

<210> SEQ ID NO 3
<211> LENGTH: 6
<212> TYPE: PRT
<213> ORGANISM: Unknown
<220> FEATURE:
<223> OTHER INFORMATION: Description of Unknown:
      Thrombin cleavage site

<400> SEQUENCE: 3

Leu Val Pro Arg Gly Ser
1               5
```

<210> SEQ ID NO 4
<211> LENGTH: 8
<212> TYPE: PRT
<213> ORGANISM: Unknown
<220> FEATURE:
<223> OTHER INFORMATION: Description of Unknown:
      Renin cleavage site

<400> SEQUENCE: 4

His Pro Phe His Leu Val Ile His
1               5

<210> SEQ ID NO 5
<211> LENGTH: 4
<212> TYPE: PRT
<213> ORGANISM: Unknown
<220> FEATURE:
<223> OTHER INFORMATION: Description of Unknown:
      Caspase protease cleavage site

<400> SEQUENCE: 5

Asp Glu Val Asp
1

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgggaaagca ga                                                         12

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttgagaatca aaatcggtga ata                                             23

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgtgcacctc cttccc                                                     16

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
aagcagtggt atcaacgcag agtacatggg                                    30

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcagtggtat caacgcagag tac                                           23

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gaccctgccg tgtaccag                                                 18

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tgtgtttgag ccatcagaag cagag                                         25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 13
agcagagcug guacacggca gggtc                                         25

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 14
accagctcug cutctgatgg ctcaaacaca                                    30

<210> SEQ ID NO 15
<211> LENGTH: 57
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 15
gcgacgaatt ttagtttgct taagcaagcc ggagatgtgg aggaaaatcc tggaccg        57

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
acaagtttgt acaaaaaagc aggcttacc                                       29

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctctgcttct gatggctcaa acaca                                           25

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaccctgccg tgtaccagc                                                  19

<210> SEQ ID NO 19
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(72)

<400> SEQUENCE: 19 aga gcc aaa aga agt ggt tct ggc tac cgt tcg tat agc ata cat tat      48
Arg Ala Lys Arg Ser Gly Ser Gly Tyr Arg Ser Tyr Ser Ile His Tyr
1               5                   10                  15 acg aac ggt agc gcg acg aat ttt                                      72
Thr Asn Gly Ser Ala Thr Asn Phe
            20

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 20

Arg Ala Lys Arg Ser Gly Ser Gly Tyr Arg Ser Tyr Ser Ile His Tyr
1               5                   10                  15

Thr Asn Gly Ser Ala Thr Asn Phe
            20

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tttttttttt tttttttttt tttttttttt                                              30
```

HIGH THROUGHPUT CLONING OF PAIRED BIPARTITE IMMUNORECEPTOR POLYNUCLEOTIDES AND APPLICATIONS THEREOF

CROSS-REFERENCE

This application is a Continuation Application of PCT/US19/46170, filed Aug. 12, 2019, which claims priority to U.S. Provisional Patent Application No. 62/718,227, filed Aug. 13, 2018, U.S. Provisional Patent Application No. 62/725,842, filed Aug. 31, 2018, U.S. Provisional Patent Application No. 62/732,898, filed Sep. 18, 2018, U.S. Provisional Patent Application No. 62/818,355, filed Mar. 14, 2019, and U.S. Provisional Patent Application No. 62/823,831, filed Mar. 26, 2019, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Feb. 10, 2021, is named 53563_704_301_SL.txt and is 5.934 bytes in size.

BACKGROUND OF THE INVENTION

The T-cell receptor (TCR) is responsible for the recognition of the antigen-major histocompatibility complex, leading to the initiation of an inflammatory response. Many T cell subsets exist, including cytotoxic T cells and helper T cells. Cytotoxic T cells (also known as CD8+ T cells) kill abnormal cells, for example virus-infected or tumor cells. Helper T cells (also known as CD4+ T cells) aid in the activation and maturation of other immune cells. Both cytotoxic and helper T cells carry out their function subsequent to the recognition of specific target antigens which triggers their respective responses. The antigen specificity of a T cell can be defined by the TCR expressed on the surface of the T cell. T cell receptors are heterodimer proteins composed of two polypeptide chains, most commonly an alpha and beta chain, but a minority of T cells can express a gamma and delta chain. The specific amino acid sequence of the TCR and the resultant three-dimensional structure defines the TCR antigen specificity and affinity. The amino acid and coding DNA sequences of the TCR chains for any individual T cell are almost always unique or at very low abundance in an organism's entire TCR repertoire, since there are a vast number of possible TCR sequences. This large sequence diversity is achieved during T cell development through a number of cellular mechanisms and may be a critical aspect of the immune system's ability to respond to a huge variety of potential antigens.

Analyzing the TCR repertoire may help to gain a better understanding of the immune system features and of the aetiology and progression of diseases, in particular those with unknown antigenic triggers. The extreme diversity of the TCR repertoire and the bipartite nature of TCRs represent a major analytical challenge. High-throughput sequencing can allow greater sequencing depth and significantly more accurate quantification of TCR clonotype abundance, albeit at a greater expense than spectratyping. However, high-throughput sequencing is still subject to PCR bias and sequencing error, with the consequences that clonotype abundances can be drastically distorted and that non-existent clonotypes can be recorded, thus falsely increasing the observed diversity. Moreover, selection and/or synthesis of cognate pairs of the TCR chains from the sequencing data for downstream applications such as cloning, functional study and therapeutic use can be time consuming. And the library of selected and synthesized cognate pairs of the TCR chains is small or has low diversity.

SUMMARY OF THE INVENTION

Provided herein are compositions and methods for high throughput cloning of natively paired TCRs which can be used for various applications. The compositions and methods provided herein can surpass sequencing and synthesis and provide fused nucleic acid molecules encoding cognate pairs of TCRs for direct expression in host cells. The compositions and methods can also be applied for other bipartite immunoreceptors, such as B-cell receptors (BCRs).

According to an aspect, provided herein is a composition comprising a plurality of fused T-cell receptor (TCR) polynucleotides, wherein each fused TCR polynucleotide of the plurality comprises: a first nucleic acid sequence and a second nucleic acid sequence, wherein (1) the first nucleic acid sequence encodes a first variable domain of a first TCR peptide chain, wherein the first variable domain comprises a CDR2 and a CDR3, and (2) the second nucleic acid sequence encodes a second variable domain of a second TCR peptide chain, wherein the second variable domain comprises a CDR2 and a CDR3; wherein the first and the second nucleic acid sequence of each fused TCR polynucleotide encode a cognate pair of the first and the second TCR peptide chain from an immune cell; wherein the plurality of fused TCR polynucleotides encode at least 50 different cognate pairs; and wherein the plurality of fused TCR polynucleotides comprise V regions from at least 5, 10, or 20 different V genes. In some embodiments, the first TCR peptide chain is a T-cell receptor (TCR) alpha peptide chain, and the second TCR peptide chain is a TCR beta peptide chain. In some embodiments, the first TCR peptide chain is a TCR gamma peptide chain, and the second TCR peptide chain is a TCR delta peptide chain. In some embodiments, the first variable domain further comprises a CDR1, and/or the second variable domain further comprises a CDR1. In some embodiments, the first variable domain of the first TCR peptide chain is a first full-length variable domain comprising FR1, CDR1, FR2, CDR2, FR3, and CDR3, and/or the second variable domain of the second TCR peptide chain is a second full-length variable domain comprising FR1, CDR1, FR2, CDR2, FR3, and CDR3. In some embodiments, the first nucleic acid sequence further encodes a first constant domain or a portion thereof of the first TCR peptide chain and/or the second nucleic acid sequence further encodes a second constant domain or a portion thereof of the second TCR peptide chain. In some embodiments, the first constant domain is a first extracellular domain, and/or the second constant domain is a second extracellular domain. In some embodiments, the first constant domain comprises a first extracellular domain, a first hinge region, a first transmembrane region and a first cytoplasmic tail of the first TCR chain, and/or the second constant domain comprises a second extracellular domain, a second hinge region, a second transmembrane region and a second cytoplasmic tail of the second TCR peptide chain. In some embodiments, each fused TCR polynucleotide of the plurality is at least 800, at least 900, at least 1000, or at least 1500 base pairs in length. In some embodiments, each fused TCR polynucleotide of the plurality is at least 1000, at least 1500, or at least 2000 base pairs in length. In some embodiments, the first nucleic acid sequence and the second nucleic acid sequence are obtained or released from an immune cell.

In some embodiments, the immune cell is isolated from a sample. In some embodiments, the sample is obtained from a subject. In some embodiments, the immune cell is a lymphocyte. In some embodiments, the lymphocyte is a T cell. In some embodiments, the T cell is an inflammatory T cell, a cytotoxic T cell, a regulatory T cell, a helper T cell, a natural killer T cell, or a combination thereof. In some embodiments, the T cell is a CD4+ T cell or a CD8+ T cell. In some embodiments, the immune cell is expanded in vitro. In some embodiments, the sample is a blood cell sample, a bone marrow sample, a cord blood sample, an ascites sample, a pleural effusion sample, a cerebrospinal sample, a seminal fluid sample, a sputum sample, a urine sample, a stool sample, or a combination thereof. In some embodiments, the sample is a tissue sample obtained from brain, liver, lung, kidney, prostate, ovary, spleen, lymph node, tonsil, thyroid, pancreas, heart, skeletal muscle, intestine, larynx, esophagus, thymus, stomach, tumor, site of infection, or a combination thereof. In some embodiments, the subject is a mammal. In some embodiments, the mammal is a human, a dog, a cat, a mouse, or a rat. In some embodiments, the subject is a healthy subject or a diseased subject. In some embodiments, the immune cell is isolated from the sample by a marker. In some embodiments, the marker is a cell surface marker. In some embodiments, the cell surface marker is CD39, CD69, CD103, CD25, PD-1, TIM-3, OX-40, 4-1BB, CD137, CD3, CD28, CD4, CD8, CD45RA, and CD45RO, GITR, FoxP3, or a combination thereof. In some embodiments, the marker is a cytokine. In some embodiments, the cytokine is IFN-γ, TNF-alpha, IL-17A, IL-2, IL-3, IL-4, GM-CSF, IL-10, IL-13, granzyme B, perforin, or a combination thereof.

In some embodiments, each fused TCR polynucleotide of the plurality further comprises a promoter. In some embodiments, the promoter is constitutive or inducible. In some embodiments, the promoter is a tetracycline-responsive promoter. In some embodiments, the promoter is a viral promoter. In some embodiments, the promoter is a β-actin promoter, a SV40 early promoter, a SV40 late promoter, an immunoglobulin promoter, a cytomegalovirus promoter, a retrovirus promoter, a Friend spleen focus-forming virus promoter, a Herpes virus TK promoter, a Rous sarcoma virus promoter; a mouse mammary tumor virus promoter, a metallothionein promoter, an adenovirus late promoter, a vaccinia 7.5K promoter, or an enolase promoter. In some embodiments, the first nucleic acid and the second nucleic acid are fused in-frame such that expression of the first variable domain and the second variable domain is under control of one promoter. In some embodiments, each fused TCR polynucleotide of the plurality further comprises a sequence encoding a protease cleavage site. In some embodiments, the protease cleavage site is a cellular protease cleavage site or a viral protease cleavage site. In some embodiments, the protease cleavage site is an enterokinase cleavage site, a factor Xa cleavage site, a thrombin cleavage site, a renin cleavage site, a collagenase cleavage site, a trypsin cleavage site, a caspase protease cleavage site, a furin cleavage site, a PC5/6 protease cleavage site; a PACE protease cleavage site, a LPC/PC7 protease cleavage site, a Factor Xa protease cleavage site, a genenase I cleavage site, a MMP protease cleavage site, or a KEX2 protease cleavage site. In some embodiments, the protease cleavage site is a viral 2A protease cleavage site, a viral 3C protease cleavage site, an infectious pancreatic necrosis virus (IPNV) VP4 protease cleavage site, a tobacco etch virus (TEV) protease cleavage site, or a nuclear inclusion protein a (N1a) of turnip mosaic potyvirus cleavage site. In some embodiments, each fused TCR polynucleotide of the plurality comprises a sequence encoding a self-cleaving peptide. In some embodiments, the self-cleaving peptide is an intein peptide, a hedgehog peptide, or a 2A peptide. In some embodiments, the at least 20 different V genes comprise at least 10 different TRAV genes and/or at least 10 different TRBV genes. In some embodiments, the TRAV genes and TRBV genes are human or mouse TRAV genes and TRBV genes.

In some embodiments, the at least 10 different TRAV genes are selected from the group consisting of human TRAV1-1, TRAV1-2, TRAV2, TRAV3, TRAV4, TRAV5, TRAV6, TRAV7, TRAV8-1, TRAV8-2, TRAV8-3, TRAV8-4, TRAV8-6, TRAV9-1, TRAV9-2, TRAV10, TRAV12-1, TRAV12-2, TRAV12-3, TRAV13-1, TRAV13-2, TRAV14, TRAV16, TRAV17, TRAV18, TRAV19, TRAV20, TRAV21, TRAV22, TRAV23, TRAV24, TRAV25, TRAV26-1, TRAV26-2, TRAV27, TRAV29, TRAV30, TRAV34, TRAV35, TRAV36, TRAV38-1, TRAV38-2, TRAV39, TRAV40, TRAV41. In some embodiments, the at least 10 different TRBV genes are selected from the group consisting of human TRBV2, TRBV3-1, TRBV4-1, TRBV4-2, TRBV4-3, TRBV5-1, TRBV5-4, TRBV5-5, TRBV5-6, TRBV5-8, TRBV6-1, TRBV6-2, TRBV6-3, TRBV6-4, TRBV6-5, TRBV6-6, TRBV6-8, TRBV6-9, TRBV7-2, TRBV7-3, TRBV7-4, TRBV7-6, TRBV7-7, TRBV7-8, TRBV7-9, TRBV9, TRBV10-1, TRBV10-2, TRBV10-3, TRBV11-1, TRBV11-2, TRBV11-3, TRBV12-3, TRBV12-4, TRBV12-5, TRBV13, TRBV14, TRBV15, TRBV16, TRBV18, TRBV19, TRBV20-1, TRBV24-1, TRBV25-1, TRBV27, TRBV28, TRBV29-1, and TRBV30.

In some embodiments, the at least 20 different V genes comprise at least 20 different V gene subgroups. In some embodiments, the at least 20 different V gene subgroups comprise at least 10 different TRAV gene subgroups and/or at least 10 different TRBV gene subgroups. In some embodiments, the at least 10 different TRAV gene subgroups are selected from the group consisting of human TRAV1, TRAV2, TRAV3, TRAV4, TRAV5, TRAV6, TRAV7, TRAV8, TRAV9, TRAV10, TRAV12, TRAV13, TRAV14, TRAV16, TRAV17, TRAV18, TRAV19, TRAV20, TRAV21, TRAV22, TRAV23, TRAV24, TRAV25, TRAV26, TRAV27, TRAV29, TRAV30, TRAV34, TRAV35, TRAV36, TRAV38, TRAV39, TRAV40, and TRAV41 subgroup. In some embodiments, the at least 10 different TRBV gene subgroups are selected from the group consisting of human TRBV2, TRBV3, TRBV4, TRBV5, TRBV6, TRBV7, TRBV9, TRBV10, TRBV11, TRBV12, TRBV13, TRBV14, TRBV15, TRBV16, TRBV18, TRBV19, TRBV20, TRBV24, TRBV25, TRBV27, TRBV28, TRBV29, and TRBV30 subgroup.

In some embodiments, the at least 10 different TRAV genes are selected from the group consisting of mouse TRAV1, TRAV2, TRAV3-1, TRAV3-3, TRAV3-4, TRAV3D-3, TRAV3N-3, TRAV4-2, TRAV4-3, TRAV4-4, TRAV4D-2, TRAV4D-3, TRAV4D-4, TRAV4N-3, TRAV4N-4, TRAV5-1, TRAV5-2, TRAV5-4, TRAV5D-2, TRAV5D-4, TRAV5N-2, TRAV5N-4, TRAV6-1, TRAV6-2, TRAV6-3, TRAV6-4, TRAV6-5, TRAV6-6, TRAV6-7, TRAV6D-3, TRAV6D-4, TRAV6D-5, TRAV6D-6, TRAV6D-7, TRAV6N-5, TRAV6N-6, TRAV6N-7, TRAV7-1, TRAV7-2, TRAV7-3, TRAV7-4, TRAV7-5, TRAV7-6, TRAV7D-2, TRAV7D-3, TRAV7D-4, TRAV7D-5, TRAV7D-6, TRAV7N-4, TRAV7N-5, TRAV7N-6, TRAV8-1, TRAV8-2, TRAV8D-1, TRAV8D-2, TRAV8N-2, TRAV9-1, TRAV9-2, TRAV9-3, TRAV9-4, TRAV9D-1, TRAV9D-2, TRAV9D-3, TRAV9D-4, TRAV9N-2, TRAV9N-3, TRAV9N-4, TRAV10, TRAV10D, TRAV10N, TRAV11, TRAV11D, TRAV11N, TRAV12-1, TRAV12-2, TRAV12-3, TRAV12D-1, TRAV12D-2, TRAV12D-3, TRAV12N-1, TRAV12N-2, TRAV12N-3, TRAV13-1, TRAV13-2, TRAV13-3, TRAV13-4, TRAV13-5, TRAV13D-1, TRAV13D-2, TRAV13D-3, TRAV13D-4, TRAV13N-1, TRAV13N-2, TRAV13N-3, TRAV13N-4, TRAV14-1, TRAV14-2, TRAV14-3, TRAV14D-1, TRAV14D-2, TRAV14D-3, TRAV14N-1, TRAV14N-2, TRAV14N-3, TRAV15-1, TRAV15-2, TRAV15D-1, TRAV15D-2, TRAV15N-1, TRAV15N-2, TRAV16, TRAV16D, TRAV16N, TRAV17, TRAV18, TRAV19, TRAV20, and TRAV21.

In some embodiments, the at least 10 different TRBV genes are selected from the group consisting of mouse TRBV1, TRBV2, TRBV3, TRBV4, TRBV5, TRBV8, TRBV9, TRBV10, TRBV12-1, TRBV12-2, TRBV13-1, TRBV13-2, TRBV13-3, TRBV14, TRBV15, TRBV16, TRBV17, TRBV19, TRBV20, TRBV21, TRBV23, TRBV24, TRBV26, TRBV29, TRBV30, and TRBV31. In some embodiments, the at least 10 different TRAV gene subgroups are selected from the group consisting of TRAV1, TRAV2, TRAV3, TRAV4, TRAV5, TRAV6, TRAV7, TRAV8, TRAV9, TRAV10, TRAV11, TRAV12, TRAV13, TRAV14, TRAV15, TRAV16, TRAV17, TRAV18, TRAV19, TRAV20, and TRAV21 subgroup. In some embodiments, the at least 10 different TRBV gene subgroups are selected from the group consisting of mouse TRBV1, TRBV2, TRBV3, TRBV4, TRBV5, TRBV8, TRBV9, TRBV10, TRBV12, TRBV13, TRBV14, TRBV15, TRBV16, TRBV17, TRBV19, TRBV20, TRBV21, TRBV23, TRBV24, TRBV26, TRBV29, TRBV30, and TRBV31 subgroup.

In some embodiments, each fused TCR polynucleotide of the plurality is circularized. In some embodiments, the plurality of fused TCR polynucleotides comprise at least 100, at least 200, at least 500, at least 1,000, at least 10,000, at least 100,000, at least 1,000,000, or at least 10,000,000 different sequences.

According to another aspect, provided herein is a plurality of vectors, each comprising a different fused TCR polynucleotide from an immune cell. In some embodiments, the plurality of vectors comprises at least 100, at least 200, at least 500, at least 1,000, at least 10,000, at least 100,000, at least 1,000,000, or at least 10,000,000 vectors. In some embodiments, the plurality of vectors is self-amplifying RNA replicons, plasmids, phages, transposons, cosmids, viruses, or virions. In some embodiments, the plurality of vectors are derivatives of the TC-83 alphavirus replicon that have been selected or engineered to reduce host cell type I interferon production, prolong the duration of expression, increase the levels of protein production, and/or express additional agent(s) of therapeutic benefit in addition to the bipartite immunoreceptor. In some embodiments, the plurality of vectors is viral vectors. In some embodiments, the viral vectors are derived from a retrovirus, a lentivirus, an adenovirus, an adeno-associated virus, a herpes virus, a pox virus, an alpha virus, a vaccina virus, a hepatitis B virus, a human papillomavirus or a pseudotype thereof. In some embodiments, the plurality of vectors is non-viral vectors. In some embodiments, the non-viral vectors are nanoparticles, cationic lipids, cationic polymers, metallic nanopolymers, nanorods, liposomes, micelles, microbubbles, cell-penetrating peptides, or lipospheres.

Also provided herein is a plurality of TCRs, each encoded by a different fused TCR polynucleotide from the composition described herein, or a different fused TCR polynucleotide from the plurality of vectors of described herein, wherein the plurality of TCRs comprises at least 100, at least 200, at least 500, at least 1,000, at least 10,000, at least 100,000, at least 1,000,000, or at least 10,000,000 TCRs.

Also provided herein is a plurality of host cells, each comprising a different fused TCR polynucleotide from the composition described herein, a different vector of the plurality of vectors described herein, or a different TCR of the plurality of TCRs described herein. In some embodiments, the plurality of host cells is T cells or B cells. In some embodiments, the T cells are an inflammatory T cell, a cytotoxic T cell, a regulatory T cell, a helper T cell, a natural killer T cell, or a combination thereof. In some embodiments, the T cells are CD4+ T cells or CD8+ T cells. In some embodiments, the plurality of host cells is autologous cells. In some embodiments, the plurality of host cells is allogeneic cells. In some embodiments, the plurality of host cells is obtained from a donor. In some embodiments, the donor is a human. In some embodiments, the donor is a healthy donor or a diseased donor. In some embodiments, the plurality of host cells is obtained from a sample. In some embodiments, the sample is a blood sample, a bone marrow sample, a cord blood sample, a ascites sample, a pleural effusion sample, a cerebrospinal sample, a seminal fluid sample, a sputum sample, a urine sample, a stool sample, or a combination thereof.

In some embodiments, the sample is a tissue sample obtained from brain, liver, lung, kidney, prostate, ovary, spleen, lymph node, tonsil, thyroid, pancreas, heart, skeletal muscle, intestine, larynx, esophagus, thymus, stomach, tumor, site of infection, or a combination thereof. In some embodiments, the plurality of host cells is cell line cells. In some embodiments, the cell line cells are CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; or Molt 4 cells. In some embodiments, the plurality of host cells are genetically modified cells.

In some embodiments, an endogenous gene encoding a TCR alpha peptide chain, a TCR beta peptide chain, a TCR gamma peptide chain, a TCR delta peptide chain, a BCR heavy peptide chain, or a BCR light peptide chain is downregulated or inactivated. In some embodiments, an additional endogenous gene is downregulated or inactivated, wherein the additional endogenous gene is selected from the group consisting of PD1, CTLA-4, LAG3, Tim3, BTLA, BY55, TIGIT, B7H5, LAIR1, SIGLEC10, 2B4, and any combination thereof. In some embodiments, each of the plurality of host cells is engineered to express an additional agent to enhance a function of the host cell. In some embodiments, the function is a cytotoxic function, a pro-inflammatory function, or an anti-inflammatory function. In some embodiments, the additional agent is a cytokine. In some embodiments, the cytokine is a pro-inflammatory cytokine. In some embodiments, the cytokine is an anti-inflammatory cytokine. In some embodiments, the cytokine is tumor necrosis factor alpha (TNFα); interleukin (IL)-1α; IL-10; IL-2; IL-5; IL-6; IL-8; IL-15; IL-18; interferon (IFN-γ); platelet-activating factor (PAF); Monocyte chemotactic proteins 1 and 2 (MCP-1, MCP-2); macrophage migration inhibitory factor (MIF); CXCL8; CXCL9; CXCL10; high mobility group box protein 1 (HMGB-1), IL-1ra, IL-4, IL-10, IL-11, IL-13, transforming growth factor beta (TGF-β), IL-16, or any combination thereof.

According to another aspect, provided herein is a composition comprising a plurality of vectors, each vector of the plurality comprises a fused T-cell receptor (TCR) polynucleotide having a first nucleic acid sequence and a second nucleic acid sequence, wherein (1) the first nucleic acid sequence encodes a first variable domain of a first TCR peptide chain, wherein the first variable domain comprises a CDR1, a CDR2 and a CDR3, and (2) the second nucleic acid sequence encodes a second variable domain of a second TCR peptide chain, wherein the second variable domain comprises a CDR1, a CDR2, and a CDR3; wherein the first and the second nucleic acid sequence of each fused TCR polynucleotide encode a cognate pair of the first and the second TCR peptide chain from an immune cell; and wherein the plurality of fused TCR polynucleotides comprises V regions from at least 20 different V genes. In some embodiments, the plurality of vectors comprises at least 50, at least 100, at least 200, at least 500, at least 1,000, at least 10,000, at least 100,000, or at least 1,000,000 different cognate pairs. In some embodiments, the plurality of vectors comprises at least about 5, 10, 50, 100, 250, 500, 750, 1000, 1500, 2000, 2500, 5000, 7500, or 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000, or more different cognate pairs. In some embodiments, the plurality of vectors comprises at least 50, at least 100, at least 200, at least 500, at least 1,000, at least 10,000, at least 100,000, at least 1,000,000, or at least 10,000,000 different sequences. In some embodiments, the at least 20 different V genes comprise at least 10 different TRAV gene subgroups and/or at least 10 different TRBV gene subgroups.

According to another aspect, provided herein is a composition comprising a plurality of hydrogel particles or beads, each hydrogel particle or bead of the plurality comprising: a first nucleic acid molecule and a first amplification product thereof encoding a first variable domain of a first immunoreceptor peptide chain, wherein the first variable domain comprises a CDR3, a second nucleic acid molecule and a second amplification product thereof encoding a second variable domain of a second immunoreceptor peptide chain, wherein the second variable domain comprises a CDR3, wherein the first amplification product and the second amplification product are embedded or entrapped within a matrix having a polymerized or gelled plurality of polymers and/or monomers, wherein diffusion of the first amplification product and the second amplification product are restricted.

According to another aspect, provided herein is a composition comprising a plurality of hydrogel particles or beads, each hydrogel particle or bead of the plurality comprising: a first nucleic acid molecule and a first primer extension product thereof encoding a first variable domain of a first immunoreceptor peptide chain, wherein the first variable domain comprises a CDR3, and a second nucleic acid molecule and a second primer extension product thereof encoding a second variable domain of a second immunoreceptor peptide chain, wherein the second variable domain comprises a CDR3, wherein the first primer extension product and the second primer extension product are embedded or entrapped within a matrix having a polymerized or gelled plurality of polymers and/or monomers, wherein diffusion of the first primer extension product and the second primer extension product are restricted.

In some embodiments, the first and the second primer extension product comprise an adaptor having a pre-designed sequence. In some embodiments, the adaptor is not hybridizable or complementary to the first or the second nucleic acid. In some embodiments, the adaptor comprises a sequence or a reverse complement sequence of a template-switch oligonucleotide. In some embodiments, the first and the second primer extension product is a reverse transcription (RT) product. In some embodiments, the first and the second primer extension product is a second strand synthesis (SSS) product. In some embodiments, the RT product is linked to a diffusion-restricting agent. In some embodiments, the SSS product is linked to a diffusion-restricting agent.

In some embodiments, the SSS product is indirectly linked to the diffusion restricting agent. In some embodiments, the first and the second primer extension product are a first and a second amplification product. In some embodiments, the first amplification product and/or the second amplification product is linked to a diffusion restricting agent. In some embodiments, the first amplification product and/or the second amplification product is linked to a diffusion restricting agent through a capture agent. In some embodiments, the capture agent comprises an oligonucleotide having a complementary sequence to an adaptor sequence of the first amplification product and/or the second amplification product.

In some embodiments, the diffusion restricting agent is a polymer. In some embodiments, the polymer is a polyacrylamide, a polyethylene glycol, or a polysaccharide. In some embodiments, the diffusion restricting agent is a particle. In some embodiments, the particle has a diameter that is larger than a pore size of the matrix. In some embodiments, the diffusion restricting agent is the matrix. In some embodiments, the first nucleic acid molecule and the second nucleic acid molecule are released from a cell. In some embodiments, the cell is a single cell. In some embodiments, the cell is a lymphocyte. In some embodiments, the cell is a T cell or a B cell. In some embodiments, the T cell is a CD3+ T cell, a CD28+ T cell, a CD4+ T cell, a CD8+ T cell, a CD45RA+ T cell, a CD45RO+ T cell, or any combination thereof. In some embodiments, the B cell is a plasmablast cell, a plasma cell, a lymphoplasmacytoid cell, a memory B cell, a follicular B cell, a marginal zone B cell, a B-1 cell, a B-2 cell, or a regulatory B cell. In some embodiments, the first immunoreceptor peptide chain is a TCR alpha peptide chain and the second immunoreceptor peptide chain is a TCR beta peptide chain. In some embodiments, the first immunoreceptor peptide chain is a TCR gamma peptide chain and the second immunoreceptor peptide chain is a TCR delta peptide chain. In some embodiments, the first immunoreceptor peptide chain is an immunoglobulin heavy peptide chain and the second immunoreceptor peptide chain is an immunoglobulin light peptide chain. In some embodiments, the first immunoreceptor peptide chain and the second immunoreceptor peptide chain is a cognate pair of a bipartite immunoreceptor. In some embodiments, the first amplification product and the second amplification product are linked to form a continuous polynucleotide strand. In some embodiments, the first amplification product and/or the second amplification product comprises at least 100, at least 500, at least 1000, at least 10000, or more copies of the first nucleic acid molecule and/or the second nucleic acid molecule. In some embodiments, the first or the second nucleic acid is diffusion restricted. In some embodiments, the first nucleic acid molecule and/or the second nucleic acid molecule is a deoxyribonucleic acid or a ribonucleic acid. In some embodiments, the first nucleic acid molecule and/or the second nucleic acid molecule is a single-stranded nucleic acid or a double-stranded nucleic acid. In some embodiments, the first nucleic acid molecule further encodes a first constant domain and/or the second nucleic acid molecule further encodes a second constant domain. In some embodiments, the first constant domain is a first extracellular constant domain, and/or the second constant domain is a second extracellular constant domain. In some embodiments, the first constant domain comprises a first extracellular constant domain, a first hinge region, a first transmembrane domain, and a first cytoplasmic tail, and/or the second constant domain comprises a second extracellular constant domain, a second hinge region, a second transmembrane domain, and a second cytoplasmic tail.

In some embodiments, the plurality of hydrogel particles or beads comprises at least 50, at least 100, at least 200, at least 500, at least 1,000, at least 10,000, at least 100,000, at least 1,000,000, or at least 10,000,000 hydrogel particles or beads. In some embodiments, the plurality of hydrogel particles or beads comprises at least 50, at least 100, at least 200, at least 500, at least 1,000, at least 10,000, at least 100,000, at least 1,000,000, or at least 10,000,000 different cognate pairs of a bipartite immunoreceptor. In some embodiments, the polymers are polysaccharides, polyacrylamides, or a combination thereof. In some embodiments, the polysaccharides are agarose, hyaluronic acids, carboxymethycellose, chitosan, starch, dextran, or alginate. In some embodiments, the monomers are acrylamide or methacrylamide monomers. In some embodiments, the polymerized or gelled plurality of polymers and/or monomers comprises a mixture of agarose and polyacrylamides. In some embodiments, the polymerized or gelled plurality of polymers and/or monomers is cross-linked. In some embodiments, the first variable domain and/or the second variable domain further comprises a CDR1, a CDR2, or a combination thereof. In some embodiments, each hydrogel particle or bead is an agarose gel particle.

According to another aspect, provided herein is a composition comprising a plurality of at least five hydrogel particles, wherein each of the at least five hydrogel particles comprises polynucleotides comprising (a) a first polynucleotide comprising a sequence encoding a first immunoreceptor peptide chain and (b) a second polynucleotide comprising a sequence encoding a second immunoreceptor peptide chain, wherein each of the first and second immunoreceptor peptide chains comprise unique cognate immunoreceptor paired chains, wherein the first polynucleotide and the second polynucleotide of an individual hydrogel particle of the at least five hydrogel particles are from a single cell, and (ii) linked to each other; and wherein diffusion of the first polynucleotide and the second polynucleotide from the hydrogel particle is restricted. In some embodiments, the first polynucleotide or the second polynucleotide is a DNA. In some embodiments, the DNA is an amplification product. In some embodiments, the first polynucleotide and the second polynucleotide are covalently linked. In some embodiments, the first polynucleotide and the second polynucleotide are linked by a phosphodiester bond. In some embodiments, the first polynucleotide or the second polynucleotide is linked to a diffusion-restricting agent.

According to another aspect, provided herein is a composition comprising a plurality of at least five hydrogel particles, wherein each of the at least five hydrogel particles comprises (a) a first RNA comprising a sequence encoding a first immunoreceptor peptide chain and (b) a second RNA comprising a sequence encoding a second immunoreceptor peptide chain, wherein each of the first and second immunoreceptor peptide chains comprise unique cognate immunoreceptor paired chains, wherein each first RNA and second RNA of an individual hydrogel particle of the at least five hydrogel particles is from a single cell, and wherein (1) each first RNA is hybridized to a first cDNA comprising a reverse complement sequence of the first RNA and (2) each second RNA is hybridized to a second cDNA comprising a reverse complement sequence of the second RNA; and wherein diffusion of the first cDNA and the second cDNA from the hydrogel particle is restricted. In some embodiments, the first cDNA or the second cDNA further comprises a sequence that is not hybridizable or complementary to the first RNA or the second RNA. In some embodiments, the first cDNA or the second cDNA further comprises reverse complement sequence of a template-switch oligonucleotide. In some embodiments, the first cDNA or the second cDNA is linked to a diffusion-restricting agent.

According to another aspect, provided herein is a composition comprising a plurality of at least five hydrogel particles, wherein each of the at least five hydrogel particles comprises (a) a first polynucleotide comprising a sequence encoding a first immunoreceptor peptide chain and (b) a second polynucleotide comprising a sequence encoding a second immunoreceptor peptide chain, wherein each of the first and second immunoreceptor peptide chains comprise unique cognate immunoreceptor paired chains, wherein each first polynucleotide and second polynucleotide of an individual hydrogel particle of the at least five hydrogel particles is from a single cell, and wherein (1) each first polynucleotide is hybridized to a first primer and (2) each second polynucleotide is hybridized to a second primer; and wherein diffusion of the first primer and the second primer from the hydrogel particle is restricted.

In some embodiments, the first primer or the second primer is a reverse transcription primer. In some embodiments, the first primer or the second primer is an amplification primer. In some embodiments, the first polynucleotide or the second polynucleotide is RNA. In some embodiments, the first polynucleotide or the second polynucleotide is DNA. In some embodiments, the first primer or the second primer is linked to a diffusion-restricting agent.

According to another aspect, provided herein is a composition comprising a plurality of at least five hydrogel particles, wherein each of the at least five hydrogel particles comprises (a) a first DNA comprising a sequence encoding a first immunoreceptor peptide chain and (b) a second DNA comprising a sequence encoding a second immunoreceptor peptide chain, wherein each of the first and second immunoreceptor peptide chains comprise unique cognate immunoreceptor paired chains, wherein each first DNA and second DNA of an individual hydrogel particle of the at least five hydrogel particles is from a single cell, and wherein (1) each first DNA is hybridized to a first polynucleotide comprising a reverse complement sequence of the sequence encoding the first immunoreceptor chain and (2) each second DNA is hybridized to a second polynucleotide comprising a reverse complement sequence of the sequence encoding the second immunoreceptor chain; and wherein diffusion of the first polynucleotide and the second polynucleotide from the hydrogel particle is restricted.

In some embodiments, the first DNA or the second DNA is cDNA. In some embodiments, the first DNA or the second DNA is genomic DNA. In some embodiments, the first polynucleotide or the second polynucleotide is RNA. In some embodiments, the RNA is a messenger RNA. In some embodiments, diffusion of the first DNA or the second DNA from the hydrogel particle is restricted. In some embodiments, the first polynucleotide or the second polynucleotide is an amplification product. In some embodiments, the amplification product comprises an adaptor that is not hybridizable or complementary to the first or the second DNA. In some embodiments, the adaptor further hybridizes to a capture agent. In some embodiments, the capture agent is linked to a diffusion-restricting agent. In some embodiments, the diffusion-restricting agent is a polymer or a particle. In some embodiments, the first and the second immunoreceptor peptide chains are TCR alpha and TCR beta peptide chains, TCR gamma and TCR delta peptide chains, or BCR heavy and light peptide chains. In some embodiments, the single cell is an immune cell. In some embodiments, the immune cell is a T cell or a B cell.

According to another aspect, provided herein is a method for preparing a fused bipartite immunoreceptor polynucleotide library, comprising: (a) generating a plurality of vessels, each comprising (1) a cell, wherein the cell comprises a first nucleic acid encoding a first peptide chain of a bipartite immunoreceptor and a second nucleic acid encoding a second peptide chain of the bipartite immunoreceptor, and (2) a plurality of polymerizable or gellable polymers and/or monomers; and (b) polymerizing or gelling the plurality of polymerizable or gellable polymers and/or monomers to form a plurality of hardened particles, each hardened particle of the plurality having a matrix composed of the polymerized or gelled plurality of polymers and/or monomers, wherein each hardened particle of the plurality comprises a first primer extension product of the first nucleic acid and a second primer extension product of the second nucleic acid; wherein the first primer extension product and the second primer extension product are embedded or entrapped within the matrix, and wherein diffusion of the first primer extension product and the second primer extension product are restricted.

In some embodiments, the first and the second primer extension product is a reverse transcription (RT) product, a second strand synthesis (SSS) product, or an amplification product. In some embodiments, the first and/or the second primer extension product comprise an adaptor sequence. In some embodiments, the adaptor sequence is not hybridizable or complementary to the first or the second nucleic acid molecule. In some embodiments, the first and the second primer extension product encode a variable domain. In some embodiments, the variable domain comprises CDR1, CDR2, and CDR3. In some embodiments, the first and/or the second primer extension product further encodes a constant domain.

In some embodiments, the method further comprises lysing the cell to release the first nucleic acid and the second nucleic acid. In some embodiments, the method further comprises reverse transcribing the first nucleic acid and the second nucleic acid. In some embodiments, the reverse transcribing is performed by using a RT primer. In some embodiments, the RT primer is linked to a diffusion-restricting agent, wherein the diffusion-restricting agent restricts diffusion of the RT primer within the matrix. In some embodiments, the method further comprises performing a template-switch reaction or a SSS reaction. In some embodiments, the method further comprises amplifying the first nucleic acid and the second nucleic acid to generate a first and a second amplification product. In some embodiments, for each of the first or the second nucleic acid, the amplifying is performed by using a first amplification primer and a second amplification primer. In some embodiments, the first amplification primer is linked to a diffusion-restricting agent, wherein the diffusion-restricting agent restricts diffusion of the first amplification primer within the matrix.

In some embodiments, the method further comprises washing the plurality of hardened particles. In some embodiments, the method further comprises washing the plurality of hardened particles to allow a reagent to diffuse out from the plurality of hardened particles. In some embodiments, the reagent comprises a RT primer, an amplification primer, a template-switch primer, a SSS primer, or any combination thereof. In some embodiments, the method further comprises repeatedly washing the plurality of hardened particles. In some embodiments, the method further comprises emulsifying the plurality of hardened particles in oil after a washing step, thereby forming an additional plurality of vessels, each vessel of the additional plurality of vessels comprising a single hardened particle of the plurality of hardened particles. In some embodiments, the first and the second primer extension product are linked to a diffusion-restricting agent. In some embodiments, the diffusion-restricting agent is a polymer. In some embodiments, the polymer is a polyacrylamide, a polyethylene glycol, or a polysaccharide. In some embodiments, the diffusion restricting agent is a particle. In some embodiments, the particle has a diameter that is larger than a pore size of the matrix. In some embodiments, the diffusion restricting agent is the matrix. In some embodiments, the first and the second primer extension product is linked to the diffusion-restricting agent through a capture agent. In some embodiments, the capture agent comprises an immobilization moiety. In some embodiments, the immobilization moiety links the capture agent to the diffusion-restricting agent.

In some embodiments, the immobilization moiety comprises a reactive group. In some embodiments, the capture agent further comprises a targeting moiety. In some embodiments, the targeting moiety is a capture oligonucleotide. In some embodiments, the first amplification primer comprises an oligonucleotide sequence that hybridizes to the capture oligonucleotide. In some embodiments, the first and the second amplification product comprise the oligonucleotide sequence that hybridizes to the capture oligonucleotide, thereby linking the first and the second amplification product to the capture agent and thereby linking to the diffusion-restricting agent. In some embodiments, the reactive group is a succinimidyl ester, an amide, an acrylamide, an acyl azide, an acyl halide, an acyl nitrile, an aldehyde, a ketone, an alkyl halide, an alkyl sulfonate, an anhydride, an aryl halide, an aziridine, a boronate, a carbodiimide, a diazoalkane, an epoxide, a haloacetamide, a haloplatinate, a halotriazine, an imido ester, an isocyanate, an isothiocyanate, a maleimide, a phosphoramidite, a silyl halide, a sulfonate ester, a sulfonyl halide, an amine, an aniline, a thiol, an alcohol, a phenol, a hyrazine, a hydroxylamine, a carboxylic acid, a glycol, or a heterocycle. In some embodiments, the method further comprises linking the first amplification product and the second amplification product to form a fused bipartite immunoreceptor polynucleotide within each vessel of the additional plurality of vessels, thereby generating the fused bipartite immunoreceptor polynucleotide library having a plurality of fused bipartite immunoreceptor polynucleotides. In some embodiments, the first amplification product and the second amplification product are linked by ligation or PCR. In some embodiments, the first amplification product and the second amplification product are linked by a phosphodiester bond to form a continuous polynucleotide. In some embodiments, the first amplification product and the second amplification product are linked in-frame.

In some embodiments, the method further comprises releasing the plurality of fused bipartite immunoreceptor polynucleotides from the additional plurality of vessels.

In some embodiments, the method further comprises circularizing each fused bipartite immunoreceptor polynucleotide of the plurality. In some embodiments, the method further comprises inserting each fused bipartite immunoreceptor polynucleotide of the plurality into a vector. In some embodiments, the vector is a self-amplifying RNA replicon, a plasmid, a phage, a transposon, a cosmid, a virus, or a virion. In some embodiments, the vector is a viral vector. In some embodiments, the viral vector is derived from a retrovirus, a lentivirus, an adenovirus, an adeno-associated virus, a herpes virus, a pox virus, an alpha virus, a vaccina virus, a hepatitis B virus, a human papillomavirus or a pseudotype thereof. In some embodiments, the vector is a non-viral vector. In some embodiments, the non-viral vector is a nanoparticle, a cationic lipid, a cationic polymer, a metallic nanopolymer, a nanorod, a liposome, a micelle, a microbubble, a cell-penetrating peptide, or a liposphere. In some embodiments, the bipartite immunoreceptor is a T-cell receptor (TCR) or a B-cell receptor (BCR). In some embodiments, the TCR comprises a TCR alpha peptide chain and a TCR beta peptide chain, or a TCR gamma peptide chain and a TCR delta peptide chain; the BCR comprises a heavy peptide chain and a light peptide chain. In some embodiments, the cell is an immune cell. In some embodiments, the immune cell is a lymphocyte. In some embodiments, the lymphocyte is a T cell or a B cell. In some embodiments, the T cell is an inflammatory T cell, a cytotoxic T cell, a regulatory T cell, a helper T cell, a natural killer T cell, or a combination thereof. In some embodiments, the T cell is a CD4+ T cell or a CD8+ T cell. In some embodiments, the B cell is a plasmablast cell, a plasma cell, a lymphoplasmacytoid cell, a memory B cell, a follicular B cell, a marginal zone B cell, a B-1 cell, a B-2 cell, or a regulatory B cell. In some embodiments, the immune cell is isolated from a tumor tissue or a blood sample. In some embodiments, the method further comprises delivering the fused bipartite immunoreceptor polynucleotide into a host cell. In some embodiments, the fused bipartite immunoreceptor polynucleotide library comprise at least 50, at least 100, at least 200, at least 500, at least 1,000, at least 10,000, at least 100,000, at least 1,000,000, or at least 10,000,000 different fused bipartite immunoreceptor sequences. In some embodiments, the first peptide chain and the second peptide chain are a cognate pair of the bipartite immunoreceptor. In some embodiments, the vessel is a droplet. In some embodiments, the droplet is a water-in-oil droplet. In some embodiments, the hardened particle is a hydrogel particle. In some embodiments, the polymers are polysaccharides, polyacrylamides, or a combination thereof. In some embodiments, the polysaccharides are agarose, hyaluronic acids, carboxymethycellose, chitosan, or alginate. In some embodiments, the monomers are acrylamide or methacrylamide monomers. In some embodiments, the polymerized or gelled plurality of polymers and/or monomers comprises a mixture of agarose and polyacrylamides. In some embodiments, the polymerized or gelled plurality of polymers and/or monomers is cross-linked. In some embodiments, polymerizing or gelling the plurality of polymerizable or gellable polymers and/or monomers comprises using an initiator. In some embodiments, the initiator is a UV light or a chemical. In some embodiments, polymerizing or gelling the plurality of polymerizable or gellable polymers and/or monomers comprises reducing temperature of the vessel.

According to another aspect, provided herein is a method performed in a liquid comprising: (a) extending a first oligonucleotide hybridized to a nucleic acid molecule, thereby forming a first extension product; (b) amplifying the first extension product or a reverse complement strand thereof with a primer set comprising a first primer and a second primer, thereby forming a first amplification product; (c) generating a polymer matrix in the liquid to form a hydrogel particle, thereby restricting diffusion of the first amplification product; and (d) washing the hydrogel particle, thereby depleting the second primer from the hydrogel particle. In some embodiments, the first primer or the first amplification product is linked to a diffusion-restricting agent.

According to another aspect, provided herein is a method performed in a liquid comprising: (a) extending a first oligonucleotide hybridized to a nucleic acid molecule, thereby forming a first extension product; (b) generating a polymer matrix in the liquid to form a hydrogel particle, thereby restricting diffusion of the first extension product or a reverse complement strand thereof; (c) washing the hydrogel particle; and (d) amplifying the first extension product or the reverse complement strand thereof with a primer set comprising a first primer and a second primer, thereby forming a first amplification product.

In some embodiments, the first oligonucleotide or the first extension product is linked to a diffusion-restricting agent. In some embodiments, the method further comprises extending a second oligonucleotide hybridized to an additional nuclei acid molecule. In some embodiments, the nucleic acid molecule and the additional nucleic acid molecule encode a first peptide chain and a second peptide chain of an immunoreceptor, wherein the first peptide chain and the second peptide chain are a cognate pair of the immunoreceptor. In some embodiments, the diffusion-restricting agent is a polymer or a particle. In some embodiments, the polymer is a polyacrylamide, a polyethylene glycol, or a polysaccharide. In some embodiments, the particle has a diameter that is larger than a pore size of the polymer matrix. In some embodiments, the diffusion-restricting agent is the polymer matrix. In some embodiments, the nucleic acid molecule is DNA or RNA. In some embodiments, the nucleic acid molecule is a genomic DNA. In some embodiments, the nucleic acid molecule is a messenger RNA. In some embodiments, the first oligonucleotide is a reverse transcription (RT) primer. In some embodiments, the method further comprises extending the RT primer with a template-switch oligonucleotide, thereby generating the first extension product having a reverse complement sequence of the template-switch oligonucleotide. In some embodiments, the method further comprises using a second strand synthesis (SSS) primer having an adaptor sequence to synthesize the reverse complement strand of the first extension product. In some embodiments, the adaptor sequence is not hybridizable or complementary to the nucleic acid molecule or the first extension product. In some embodiments, the first extension product comprises the adaptor sequence. In some embodiments, the nucleic acid molecule encodes a peptide chain of an immunoreceptor. In some embodiments, the method further comprises, after or during washing the hydrogel particle, contacting a reagent with the hydrogel particle such that the reagent diffuses into the hydrogel particle. In some embodiments, the reagent is an oligonucleotide or an enzyme. In some embodiments, the enzyme is a polymerase. In some embodiments, the method further comprises emulsifying the hydrogel particle in oil after washing.

According to another aspect, provided herein is a method performed in a liquid comprising: (a) forming a plurality of droplets, wherein at least two droplets of the plurality comprise a single cell; (b) extending a first oligonucleotide hybridized to a first nucleic acid molecule from the single cell, thereby forming a first extension product; and extending a second oligonucleotide hybridized to a second nucleic acid molecule from the single cell, thereby forming a second extension product; (c) amplifying the first extension product or a reverse complement strand thereof with a first primer set comprising a first primer and a second primer, thereby forming a first set of amplification products; and amplifying the second extension product or a reverse complement strand thereof with a second primer set comprising a third primer and a fourth primer, thereby forming a second set of amplification products; and (d) linking an amplification product of the first set of amplification products to an amplification product of the second set of amplification products, wherein linking comprises linking in the liquid in the absence of the second and the fourth primer.

According to another aspect, provided herein is a method performed in a liquid comprising: (a) forming a plurality of droplets, wherein at least two droplets of the plurality comprise a single cell; (b) extending a first oligonucleotide hybridized to a first nucleic acid molecule from the single cell, thereby forming a first extension product; and extending a second oligonucleotide hybridized to a second nucleic acid molecule from the single cell, thereby forming a second extension product; (c) amplifying the first extension product or a reverse complement strand thereof with a first primer set comprising a first primer and a second primer, thereby forming a first set of amplification products; and amplifying the second extension product or a reverse complement strand thereof with a second primer set comprising a third primer and a fourth primer, thereby forming a second set of amplification products; (d) removing the second and the fourth primer; and linking an amplification product of the first set of amplification products to an amplification product of the second set of amplification products.

In some embodiments, each droplet comprises a plurality of polymerizable or gellable polymers and/or monomers. In some embodiments, the method further comprises generating a polymer matrix in the liquid to form a hydrogel particle, thereby restricting diffusion of the first set of amplification products and the second set of amplification products. In some embodiments, the method further comprises washing the hydrogel particle, thereby depleting the second primer and the fourth primer from the hydrogel particle. In some embodiments, linking comprises generating a sticky end on the amplification product of the first and the second set. In some embodiments, generating the sticky end on the amplification product comprises using a USER enzyme. In some embodiments, linking comprises hybridizing the amplification product of the first and the second set. In some embodiments, linking comprises ligating the amplification product of the first and the second set. In some embodiments, the first primer and the third primer are the same primer. In some embodiments, the first primer, the third primer, the first set of amplification products, or the second set of amplification products is linked to a diffusion-restricting agent.

According to another aspect, provided herein is a method performed in a liquid comprising: (a) forming a plurality of droplets, wherein at least two droplets of the plurality comprise a single cell; (b) extending a first oligonucleotide hybridized to a first nucleic acid molecule from the single cell, thereby forming a first extension product; and extending a second oligonucleotide hybridized to a second nucleic acid molecule from the single cell, thereby forming a second extension product; (c) generating a polymer matrix in the liquid to form a hydrogel particle, thereby restricting the diffusion of the first extension product and the second extension product are restricted; (d) amplifying the first extension product or a reverse complement strand thereof with a first primer set comprising a first primer and a second primer, thereby forming a first set of amplification products; and amplifying the second extension product or a reverse complement strand thereof with a second primer set comprising a third primer and a fourth primer, thereby forming a second set of amplification products; and (e) linking an amplification product of the first set of amplification products to an amplification product of the second set of amplification products.

In some embodiments, the method further comprises washing the hydrogel particle after (c). In some embodiments, the method further comprises contacting a reagent with the hydrogel particle such that the reagent diffuses into the hydrogel particle. In some embodiments, the reagent comprises an enzyme or an oligonucleotide. In some embodiments, the oligonucleotide comprises the first primer set and/or the second primer set. In some embodiments, the enzyme is a polymerase, a ligase, a USER enzyme, or a combination thereof. In some embodiments, the method further comprises emulsifying the hydrogel particle in oil after washing. In some embodiments, the first oligonucleotide or the second oligonucleotide is linked to a diffusion-restricting agent. In some embodiments, the first oligonucleotide or the second oligonucleotide is a RT primer. In some embodiments, the method further comprises using a second strand synthesis (SSS) primer to synthesize the reverse complement strand of the first and/or the second extension product. In some embodiments, the SSS primer comprises an adaptor sequence. In some embodiments, the adaptor sequence is not hybridizable or complementary with the first and/or the second extension product. In some embodiments, the method further comprises extending the RT primer with a template-switch oligonucleotide. In some embodiments, the single cell is an immune cell. In some embodiments, the immune cell is a T cell or a B cell. In some embodiments, the first nucleic acid molecule and the second nucleic acid molecule are DNA or RNA. In some embodiments, the DNA is a genomic DNA. In some embodiments, the RNA is a messenger RNA.

In some embodiments, the first nucleic acid molecule encodes a first peptide chain of an immunoreceptor and the second nucleic acid molecule encodes a second peptide chain of the immunoreceptor. In some embodiments, the first peptide chain and the second peptide chain are a cognate pair of the immunoreceptor. In some embodiments, the first peptide chain or the second peptide chain comprises a variable domain. In some embodiments, the variable domain comprises a CDR1, CDR2, CDR3, or a combination thereof. In some embodiments, the first peptide chain or the second peptide chain comprises a constant domain. In some embodiments, the first peptide chain or the second peptide chain comprises a transmembrane region and/or a cytoplasmic tail. In some embodiments, the immunoreceptor is a B-cell receptor. In some embodiments, the immunoreceptor is a T-cell receptor. In some embodiments, the diffusion-restricting agent is a polymer or a particle. In some embodiments, the polymer is a polyacrylamide, a polysaccharide, or a polyethylene glycol. In some embodiments, the particle has a diameter that is larger than a pore size of the hydrogel particle. In some embodiments, the diffusion-restricting agent is the polymer matrix. In some embodiments, linking comprises generating a sticky end on the amplification product of the first and the second set. In some embodiments, generating the sticky end on the amplification product comprises using a USER enzyme. In some embodiments, linking comprises hybridizing the amplification product of the first and the second set. In some embodiments, linking comprises ligating the amplification product of the first and the second set.

According to another aspect, provided herein is a method comprising: (a) obtaining a population of host cells, each host cell in the population expressing a TCR having a natively paired TCR alpha and beta peptide chains or a BCR having a natively paired BCR heavy and light peptide chain; enriching (i) a subpopulation of host cells from the population, or (ii) expressed TCRs or BCRs of a subpopulation of host cells from the population, wherein the subpopulation of host cells or the expressed TCRs or BCRs of the subpopulation of host cell bind to a target antigen or a target MHC-antigen complex; and (b) administering the subpopulation of host cells or the expressed TCRs or BCRs of the subpopulation enriched from step (b) to a subject expressing the target antigen or the target MHC-antigen complex.

In some embodiments, obtaining comprises using any of the methods described herein. In some embodiments, (b) comprises contacting the population of host cells or the expressed TCRs or BCRs with the target antigen or the target MHC-antigen complex. In some embodiments, the MHC is an MHC tetramer. In some embodiments, (c) comprises administering by injection. In some embodiments, the injection comprises injecting intravenously, subcutaneously, intradermally, or intramuscularly. In some embodiments, the target antigen is a neoantigen or a tumor-associated antigen.

According to another aspect, provided herein is a method comprising: (1) providing a plurality of at least 1,000 cells, each cell of the at least 1,000 cells comprising a TCR alpha chain and a TCR beta chain; (2) providing a plurality of at least 1,000 compartments, each compartment of the at least 1,000 compartments comprising a solid support, wherein the solid support comprises: (a) a first polynucleotide, comprising a first common sequence, a second common sequence, and a protein-coding sequence encoding a TCR alpha chain between the first and the second common sequence, (b) a second polynucleotide, comprising a third common sequence, a fourth common sequence, and a protein-coding sequence encoding a TCR beta chain between the third and the fourth common sequence, wherein, the TCR alpha chain and the TCR beta chain in each compartment is a cognate pair present in at least one of the plurality of cells, thereby providing a first plurality of protein-coding sequences each encoding a TCR alpha chain and a second plurality of protein-coding sequences each encoding a TCR beta chain; and (3) physically linking the first polynucleotide and the second polynucleotide in each compartment. In some embodiments, the first plurality of protein-coding sequences comprises at least 10 TRAV subgroups and the second plurality of protein-coding sequences comprises at least 10 TRBV subgroups. In some embodiments, each compartment of the at least 1,000 compartments comprise a cell from the plurality of at least 1,000 cells. In some embodiments, the compartment is a well, a microwell, or a droplet. In some embodiments, the solid support is a bead, a hydrogel particle, or a surface of the well or microwell. In some embodiments, the first common sequence, the second common sequence, the third common sequence, or the fourth common sequence is the same in the plurality of at least 1,000 compartments.

According to another aspect, provided herein is a composition comprising a plurality of at least 1,000 compartments, each compartment of the at least 1,000 compartments comprising a solid support, wherein the solid support comprises: (a) a first polynucleotide, comprising a first common sequence, a second common sequence, and a protein-coding sequence encoding a TCR alpha chain between the first and the second common sequence, and (b) a second polynucleotide, comprising a third common sequence, a fourth common sequence, and a protein-coding sequence encoding a TCR beta chain between the third and the fourth common sequence, wherein, (i) the TCR alpha chain and the TCR beta chain in each compartment is a cognate pair, (ii) a plurality of first common sequences in the plurality of compartments has the same sequence and is hybridizable or complementary to a first primer, (iii) a plurality of second common sequences in the plurality of compartments has the same sequence and is hybridizable or complementary to a second primer, (iv) a plurality of third common sequences in the plurality of compartments has the same sequence and is hybridizable or complementary to a third primer, and (v) a plurality of fourth common sequences in the plurality of compartments has the same sequence and is hybridizable or complementary to a fourth primer.

In some embodiments, each compartment further comprises the first primer, the second primer, the third primer, and the fourth primer. In some embodiments, the concentration of the first primer is at least 1 nM, the concentration of the second primer is at least 1 nM, the concentration of the third primer is at least 1 nM, and concentration of the fourth primer is at least 1 nM. In some embodiments, the second common sequence is hybridizable or complementary to the fourth common sequence or a reverse complement sequence thereof in each compartment.

According to another aspect, provided herein is a composition comprising a plurality of at least 1,000 compartments, each compartment of the at least 1,000 compartments comprising: (a) a first fully or partially single-stranded polynucleotide, comprising a first common sequence at the 5' end, a second common sequence at the 3' end, and a protein-coding sequence encoding a TCR alpha chain between the first and the second common sequence, and (b) a second fully or partially single-stranded polynucleotide, comprising a third common sequence at the 5' end, a fourth common sequence at the 3' end, and a protein-coding sequence encoding a TCR beta chain between the third and the fourth common sequence, wherein, (i) the TCR alpha chain and the TCR beta chain is a cognate pair, and (ii) the second common sequence is hybridized to the fourth common sequence. In some embodiments, the first common sequence, the second common sequence, the third common sequence, or the fourth common sequence is the same in the plurality of at least 1,000 compartments. In some embodiments, each compartment further comprises a solid support. In some embodiments, the solid support is a bead or a hydrogel particle.

According to another aspect, provided herein is a method of identifying a target-reactive T-cell receptor (TCR), comprising: (a) providing a plurality of T cells expressing a plurality of TCRs, wherein each T cell of the plurality of T cells expresses a cognate pair of a TCR of the plurality of TCRs; (b) partitioning the plurality of T cells into a plurality of compartments, wherein each compartment comprises an individual T cell of the plurality of T cells; (c) within each compartment, linking a first polynucleotide encoding a first TCR chain and a second polynucleotide encoding a second TCR chain of the cognate pair of the TCR of the individual T cell, thereby generating a plurality of fused polynucleotides, wherein (i) the first polynucleotide and the second polynucleotide are transcribed or amplified products of endogenous nucleic acids of the individual T cell or (ii) the first polynucleotide and the second polynucleotide are not chemically synthesized using phosphoramidite; (d) generating a plurality of vectors comprising the plurality of fused polynucleotides, each vector of the plurality of vectors comprising a fused polynucleotide of the plurality of fused polynucleotides; (e) delivering the plurality of vectors into a plurality of cells, wherein each cell of the plurality of cells comprises at least one vector of the plurality of vectors; (f) expressing the plurality of fused polynucleotides from the plurality of vectors in the plurality of cells, wherein a subset of the plurality of cells expresses a plurality of target-reactive TCRs; (g) contacting the plurality of cells with one or more target antigens, wherein the subset of the plurality of cells expressing the plurality of target-reactive TCRs binds to the one or more target antigens; and (h) identifying a target-reactive TCR of the plurality of target-reactive TCRs of the subset of the plurality of cells.

According to another aspect, provided herein is a method of identifying a target-reactive T-cell receptor (TCR), comprising: (a) providing a plurality of T cells expressing a plurality of TCRs, wherein each T cell of the plurality of T cells expresses a cognate pair of a TCR of the plurality of TCRs; (b) partitioning the plurality of T cells into a plurality of compartments, wherein each compartment comprises an individual T cell of the plurality of T cells; (c) within each compartment, linking a first polynucleotide encoding a first TCR chain and a second polynucleotide encoding a second TCR chain of the cognate pair of the TCR of the individual T cell, thereby generating a plurality of fused polynucleotides, wherein the first polynucleotide and the second polynucleotide are transcribed or amplified products of endogenous nucleic acids of the individual T cell or (ii) the first polynucleotide and the second polynucleotide are not chemically synthesized using phosphoramidite; (d) delivering the plurality of fused polynucleotides into a plurality of cells, wherein each cell of the plurality of cells comprises at least one fused polynucleotide of the plurality of fused polynucleotides; (e) expressing the plurality of fused polynucleotides from the plurality of vectors in the plurality of cells, wherein a subset of the plurality of cells expresses a plurality of target-reactive TCRs; (f) contacting the plurality of cells with one or more target antigens, wherein the subset of the plurality of cells expressing the plurality of target-reactive TCRs binds to the one or more target antigens; and (g) identifying a target-reactive TCR of the plurality of target-reactive TCRs of the subset of the plurality of cells.

In some cases, the method further comprises, prior to delivering, generating a plurality of vectors comprising the plurality of fused polynucleotides, each vector of the plurality of vectors comprising a fused polynucleotide of the plurality of fused polynucleotides. In some cases, the plurality of cells is a plurality of recipient cells. In some cases, the endogenous nucleic acids are deoxyribonucleic acids (DNAs) or ribonucleic acids (RNAs). In some cases, the DNAs are genomic DNAs. In some cases, the RNAs are messenger RNAs. In some cases, contacting further comprises contacting the population of cells with one or more cells presenting the one or more target antigens. In some cases, the one or more cells are one or more tumor cells, tumorspheres, tumor lysate-pulsed antigen-presenting cells (APCs) or APCs engineered to present the one or more target antigens. In some cases, the one or more APCs engineered to present the one or more target antigens are delivered (e.g., transfected or electroporated) with a target antigen coding DNA or RNA. In some cases, contacting further comprises contacting the population of cells with a tumor tissue. In some cases, the one or more target antigens are in complex with a major histocompatibility complex (MHC). In some cases, the MHC is a MHC tetramer. In some cases, the first TCR chain is a TCR alpha chain and the second TCR chain is a TCR beta chain. In some cases, the first TCR chain is a TCR gamma chain and the second TCR chain is a TCR delta chain. In some cases, the plurality of cells is cell line cells. In some cases, the cell line cells are CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; or Molt 4 cells. In some cases, the plurality of cells is isolated from a sample from a subject. In some cases, the plurality of T cells is isolated from a sample from a subject. In some cases, the sample is a tumor tissue, a blood sample, a peripheral blood mononuclear cell (PBMC) sample, or a combination thereof. In some cases, the tumor tissue is at most about 2000 mm$^3$. In some cases, the blood sample comprises peripheral blood mononuclear cells (PBMCs). In some cases, the plurality of T cells is tumor-infiltrating T cells or peripheral T cells. In some cases, the plurality of T cells comprises CD8+ T cells, CD4+ T cells, exhausted T cells, regulatory T cells, or any combinations thereof. In some cases, the method further comprises isolating at least one cell of the subset of the plurality of cells. In some cases, the at least one cell of the subset of the plurality of cells is isolated by FACS. In some cases, the at least one cells of the subset of the plurality of cells is isolated based on a marker. In some cases, the marker is a cell surface marker or a cytokine. In some cases, the cell surface marker is CD39, CD69, CD103, CD25, PD-1, TIM-3, OX-40, 4-1BB, CD137, CD3, CD28, CD4, CD8, CD45RA, CD45RO, GITR, FoxP3, or a combination thereof. In some cases, the cytokine is IFN-γ, TNF-alpha, IL-17A, IL-2, IL-3, IL-4, GM-CSF, IL-10, IL-13, granzyme B, perforin, or a combination thereof. In some cases, the method further comprises administering (i) at least one cell of the subset of the plurality of cells into the subject or (ii) an autologous or allogeneic cell comprising an identified target-reactive TCR into the subject. In some cases, the autologous or the allogeneic cell comprises a polynucleotide encoding the identified target-reactive TCR. In some cases, the polynucleotide encoding the identified target-reactive TCR is the fused polynucleotide or an amplified product thereof, or comprises a sequence encoding the first TCR chain and the second TCR chain of the fused polynucleotide.

According to another aspect, provided herein is a method of identifying a plurality of target-reactive T-cell receptors (TCRs), comprising: (a) providing a plurality of cells expressing a plurality of TCRs, each cell of the plurality of cells expressing a TCR of the plurality of TCRs, wherein the plurality of TCRs comprises at least 50 different cognate pairs and comprises V regions from a plurality of V genes, and wherein the plurality of TCRs are exogenous to the plurality of cells; (b) contacting the plurality of cells with one or more target antigens, wherein a subset of the plurality of cells expressing the plurality of target-reactive TCRs bind to the one or more target antigens; and (c) identifying at least two cells of the subset of the plurality of cells, which at least two cells express at least two target-reactive TCRs of the plurality of target-reactive TCRs, thereby identifying the at least two target-reactive TCRs of the plurality of target-reactive TCRs.

In some cases, the plurality of V genes comprises at least 10 different V genes. In some cases, the plurality of cells is a plurality of genetically engineered cells. In some cases, the plurality of cells is not isolated from a patient. In some cases, the plurality of cells is isolated from a sample from a subject. In some cases, the sample is a tissue sample, a blood sample, a PBMC sample, or a combination thereof. In some cases, the plurality of cells does not comprise exhausted T cells. In some cases, the plurality of TCRs comprises at least 100 different cognate pairs. In some cases, the method further comprises isolating the at least two cells of the subset of the plurality of cells. In some cases, (b) comprises contacting the plurality of cells with one or more cells presenting the one or more target antigens. In some cases, the one or more cells are one or more tumor cells, tumorspheres, tumor lysate-pulsed antigen-presenting cells (APCs) or APCs engineered to present the one or more target antigens. In some cases, the one or more APCs engineered to present the one or more target antigens comprise a target antigen coding DNA or RNA. In some cases, (b) comprises contacting the plurality of cells with a tumor tissue. In some cases, (b) comprises contacting the plurality of cells with the one or more target antigens in complex with a major histocompatibility complex (MHC). In some cases, the MHC is a MHC tetramer. In some cases, sequence or identity of the one or more target antigens is unknown. In some cases, the method further comprises administering at least one of the at least two cells of the subset of the plurality of cells into a subject. In some cases, each cell of the plurality of cells comprises a reporter gene, which reporter gene is regulated to send a signal when a TCR of the cell binds to a target antigen of the one or more target antigens. In some cases, the plurality of cells is cell line cells. In some cases, the plurality of TCRs comprises at least 100 different VJ combinations.

According to another aspect, provided herein is a method of treating a cancer in a subject, comprising: (a) providing a plurality of T cells expressing a plurality of TCRs, wherein each T cell of the plurality of T cells expresses a cognate pair of a TCR of the plurality of TCRs; (b) partitioning the plurality of T cells into a plurality of compartments, wherein each compartment comprises an individual T cell of the plurality of T cells; (c) within each compartment, linking a first polynucleotide encoding a first TCR chain and a second polynucleotide encoding a second TCR chain of the cognate pair of the TCR of the individual T cell, thereby generating a plurality of fused polynucleotides, wherein (i) the first polynucleotide and the second polynucleotide are transcribed or amplified products of endogenous nucleic acids of the individual T cell or (ii) the first polynucleotide and the second polynucleotide are not chemically synthesized using phosphoramidite; (d) delivering the plurality of fused polynucleotides into a plurality of cells, wherein each cell of the plurality of cells comprises at least one fused polynucleotide of the plurality of fused polynucleotides; (e) expressing the plurality of fused polynucleotides in the plurality of cells, wherein a subset of the plurality of cells expresses a plurality of target-reactive TCRs from a subset of the plurality of fused polynucleotides; (f) identifying the plurality of target-reactive TCRs from the subset of the plurality of fused polynucleotides; (g) delivering one or more fused polynucleotides or a derivative thereof of the subset of the plurality of fused polynucleotides into a plurality of recipient cells, wherein each cell of the plurality of recipient cells comprises at least one of the one or more fused polynucleotides or a derivative thereof of the subset of the plurality of fused polynucleotides; and (h) administering (i) at least one recipient cell of the plurality of recipient cells into the subject or (ii) at least two recipient cells of the plurality of recipient cells into the subject, wherein the at least two recipient cells express different TCRs.

In some cases, the plurality of T cells is tumor-infiltrating T cells or peripheral T cells. In some cases, the plurality of T cells comprises CD8+ T cells, CD4+ T cells, exhausted T cells, regulatory T cells, or any combinations thereof. In some cases, the plurality of T cells are activated and/or expanded in vitro. In some cases, the plurality of fused polynucleotides is delivered in a plurality of vectors, wherein each vector of the plurality of vectors comprises a fused polynucleotide of the plurality of fused polynucleotides. In some cases, the method further comprises, prior to delivering in (d), generating the plurality of vectors. In some cases, identifying in (f) comprises contacting the plurality of cells with one or more target antigens, wherein the subset of the plurality of cells expressing the plurality of target-reactive TCRs bind to the one or more target antigens. In some cases, the one or more target antigens are presented by one or more tumor cells or antigen-presenting cells (APCs). In some cases, the one or more APCs (i) are pulsed by the one or more target antigens or (ii) comprise a target antigen coding DNA or RNA. In some cases, each antigen of the one or more antigens is in complex with a major histocompatibility complex (MHC). In some cases, the MHC is a MHC tetramer. In some cases, the method further comprises, prior to delivering in (g), isolating one or more cells of the subset of the plurality of cells. In some cases, the method further comprises isolating the plurality of T cells expressing the plurality of TCRs from the subject. In some cases, administering is performed at most about 60 days, 50 days, 40 days, 30 days, 20 days or less after isolating the plurality of T cells. In some cases, the plurality of recipient cells is allogeneic cells, autologous cells, or cell line cells. In some cases, the plurality of cells is genetically engineered cells or cell line cells. In some cases, the method further comprises, prior to (h), expanding the plurality of recipient cells. In some cases, the derivative comprises a sequence of the one or more fused polynucleotides. In some cases, the derivative is an amplified product or a synthesized product of the one or more fused polynucleotides.

According to another aspect, provided herein is a method of treating a tumor in a subject, comprising: (a) isolating a plurality of T cells from the subject expressing a plurality of T-cell receptors (TCRs), wherein each T cell of the plurality of T cells expresses a cognate pair of TCR of the plurality of TCRs, wherein the plurality of TCRs comprises a plurality of tumor-reactive TCRs; (b) identifying the plurality of tumor-reactive TCRs from the plurality of TCRs; (c) delivering polynucleotides encoding the plurality of tumor-reactive TCRs or a subset thereof into a plurality of recipient cells, wherein each recipient cell of the plurality of recipient cells comprises at least one polynucleotide of the polynucleotides encoding the plurality of tumor-reactive TCRs or a subset thereof; (d) expressing the plurality of tumor-reactive TCRs or a subset thereof in the plurality of recipient cells; and (e) administering (i) at least one recipient cell of the plurality of recipient cells into the subject or (ii) at least two recipient cells of the plurality of recipient cells into the subject, wherein the at least two recipient cells express different TCRs, wherein administering is performed at most about 60 days, 50 days, 40 days, 30 days, 20 days or less after isolating the plurality of T cells in (a).

According to another aspect, provided herein is a method of treating a tumor in a subject, comprising: (a) isolating a plurality of T cells from the subject expressing a plurality of T-cell receptors (TCRs), wherein each T cell of the plurality of T cells expresses a cognate pair of TCR of the plurality of TCRs, wherein the plurality of TCRs comprises a plurality of tumor-reactive TCRs; (b) identifying the plurality of tumor-reactive TCRs from the plurality of TCRs; (c) delivering polynucleotides encoding the plurality of tumor-reactive TCRs or a subset thereof into a plurality of recipient cells, wherein each recipient cell of the plurality of recipient cells comprises at least one polynucleotide of the polynucleotides encoding the plurality of tumor-reactive TCRs or a subset thereof; (d) expressing the plurality of tumor-reactive TCRs or a subset thereof in the plurality of recipient cells; and (e) administering (i) at least one recipient cell of the plurality of recipient cells into the subject or (ii) at least two recipient cells of the plurality of recipient cells into the subject, wherein the at least two recipient cells express different TCRs, wherein the tumor of the subject has not progressed for more than about 60 days, 50 days, 40 days, 30 days, 20 days or less from isolating the plurality of T cells from the subject to administering the at least one or the at least two recipient cells of the plurality of recipient cell into the subject.

According to another aspect, provided herein is a method of treating a tumor in a subject, comprising: (a) isolating a plurality of T cells from the subject expressing a plurality of T-cell receptors (TCRs), wherein each T cell of the plurality of T cells expresses a cognate pair of TCR of the plurality of TCRs, wherein the plurality of TCRs comprises a plurality of tumor-reactive TCRs; (b) identifying the plurality of tumor-reactive TCRs from the plurality of TCRs; (c) delivering polynucleotides encoding the plurality of tumor-reactive TCRs or a subset thereof into a plurality of recipient cells, wherein each recipient cell of the plurality of recipient cells comprises at least one polynucleotide of the polynucleotides encoding the plurality of tumor-reactive TCRs or a subset thereof; (d) expressing the plurality of tumor-reactive TCRs or a subset thereof in the plurality of recipient cells; and (e) administering (i) at least one recipient cell of the plurality of recipient cells into the subject or (ii) at least two recipient cells of the plurality of recipient cells into the subject, wherein the at least two recipient cells express different TCRs, wherein (i) a size of the tumor has increased by less than about 50%, 30%, 40%, 20%, 15%, 10%, 5% or 2%, or (ii) number of tumor cells in the subject has not increased by about 2 fold, 3 fold, 4 fold, 5 fold or more, from isolating the plurality T cells to administering the at least one or the at least two recipient cells of the plurality of recipient cells.

According to another aspect, provided herein is a method of treating a tumor in a subject, comprising: (a) isolating a plurality of T cells from the subject expressing a plurality of T-cell receptors (TCRs), wherein each T cell of the plurality of T cells expresses a cognate pair of TCR of the plurality of TCRs, wherein the plurality of TCRs comprises a plurality of tumor-reactive TCRs; (b) identifying the plurality of tumor-reactive TCRs from the plurality of TCRs; (c) delivering polynucleotides encoding the plurality of tumor-reactive TCRs or a subset thereof into a plurality of recipient cells, wherein each recipient cell of the plurality of recipient cells comprises at least one polynucleotide of the polynucleotides encoding the plurality of tumor-reactive TCRs or a subset thereof; (d) expressing the plurality of tumor-reactive TCRs or a subset thereof in the plurality of recipient cells; and (e) administering (i) at least one recipient cell of the plurality of recipient cells into the subject or (ii) at least two recipient cells of the plurality of recipient cells into the subject, wherein the at least two recipient cells express different TCRs, wherein the tumor has not progressed to a new stage from isolating the plurality of T cells to administering the at least one or the at least two recipient cells of the plurality of recipient cells.

According to another aspect, provided herein is a method of treating a tumor in a subject, comprising: (a) isolating a plurality of T cells from the subject expressing a plurality of T-cell receptors (TCRs), wherein each T cell of the plurality of T cells expresses a cognate pair of TCR of the plurality of TCRs from endogenous nucleic acids, wherein the plurality of TCRs comprises a plurality of tumor-reactive TCRs; (b) identifying the plurality of tumor-reactive TCRs from the plurality of TCRs; (c) delivering polynucleotides encoding the plurality of tumor-reactive TCRs or a subset thereof into a plurality of recipient cells, wherein each recipient cell of the plurality of recipient cells comprises at least one polynucleotide of the polynucleotides encoding the plurality of tumor-reactive TCRs or a subset thereof, wherein (i) the polynucleotides are transcribed or amplified products of the endogenous nucleic acids or (ii) the polynucleotides are not chemically synthesized using phosphoramidite; (d) expressing the plurality of tumor-reactive TCRs or a subset thereof in the plurality of recipient cells; and (e) administering (i) at least one recipient cell of the plurality of recipient cells into the subject or (ii) at least two recipient cells of the plurality of recipient cells into the subject, wherein the at least two recipient cells express different TCRs.

In some cases, the method does not comprise chemical synthesis of the polynucleotides encoding the plurality of tumor-reactive TCRs or a subset thereof using phosphoramidite. In some cases, the plurality of T cells is tumor-infiltrating T cells or peripheral T cells. In some cases, the plurality of T cells comprises CD8+ T cells, CD4+ T cells, exhausted T cells, regulatory T cells, or any combinations thereof. In some cases, the plurality of recipient cells is allogeneic T cells, autologous T cells, or cell line cells. In some cases, the method further comprises, prior to (b), expressing the plurality of TCRs in a plurality of reporter cells. In some cases, expressing comprises delivering nucleic acid sequences encoding the plurality of TCRs by a virus vector. In some cases, the virus vector is a lentivirus vector. In some cases, each reporter cell of the plurality of reporter cells comprises a reporter gene. In some cases, in (b), identifying comprises contacting the plurality of TCRs with one or more target antigens, or a cell or a tissue presenting one or more target antigens. In some cases, the one or more target antigens are presented by one or more tumor cells or antigen presenting cells (APCs). In some cases, the one or more APCs comprise a target antigen coding DNA or RNA. In some cases, the one or more target antigens are in complex with a MHC. In some cases, the MHC is a MHC tetramer. In some cases, the plurality of tumor-reactive TCRs of the plurality of TCRs comprises at least 2, 5, 10, 15, or 20 different cognate pairs of TCRs. In some cases, each TCR of the plurality of tumor-reactive TCRs is specific to a different epitope or a different protein. In some cases, each TCR of the plurality of tumor-reactive TCRs comprises a different (i) TCR alpha CDR3 sequence, (ii) TCR beta CDR3 variable domain sequence, (iii) TCR alpha variable domain sequence, (iv) TCR beta variable domain sequence, or (v) TCR alpha and TCR beta variable domain sequence in combination. In some cases, the plurality of tumor-reactive TCRs binds to a tumor cell from the subject but does not bind to a healthy cell from the subject or bind to the healthy cell from the subject with at least 10-fold less affinity than to the tumor cell. In some cases, the plurality of recipient cells administered in (e) comprises at least 10, at least 20, at least 50, at least 100, at least 500, at least 1,000, at least 5,000, at least 10,000, at least 100,000, or at least 1,000,000 times more cells than the plurality of T cells isolated in (a).

According to another aspect, provided herein is a method of treating a tumor in a subject, comprising: (a) isolating a population of T cells from the subject that expresses a population of T-cell receptors (TCRs), wherein the population of T cells comprises at most about 10,000 cells; (b) identifying a plurality of tumor-reactive TCRs from the population of TCRs; and (c) administering a plurality of cells expressing the plurality of tumor-reactive TCRs or a subset thereof into the subject, wherein the plurality of tumor-reactive TCRs or a subset thereof comprises at least 2 different cognate pairs.

According to another aspect, provided herein is a method of treating a tumor in a subject, comprising: (a) identifying a plurality of tumor-reactive T-cell receptors (TCRs) from a population of TCRs, wherein the population of TCRs comprise at least 50 different cognate pairs of TCRs; and (b) administering a plurality of cells expressing the plurality of tumor-reactive TCRs or a subset thereof into the subject, wherein the plurality of tumor-reactive TCRs or a subset thereof comprises at least 5, at least 10, at least 15, or at least 20 different cognate pairs of the at least 50 different cognate pairs, wherein the plurality of tumor-reactive TCRs are exogenous to the plurality of cells. In some cases, the plurality of tumor-reactive TCRs or a subset thereof comprises at least 5 TCRs, and wherein each TCR of the at least 5 TCRs (1) is specific to a different epitope or a different protein or (2) comprises a different (i) TCR alpha CDR3 sequence, (ii) TCR beta CDR3 variable domain sequence, (iii) TCR alpha variable domain sequence, (iv) TCR beta variable domain sequence, or (v) TCR alpha and TCR beta variable domain sequence in combination.

In some cases, the method further comprises, prior to (a), isolating a population of T cells expressing the population of TCRs from the subject. In some cases, the at least 50 different cognate pairs comprise V regions from at least 5, 10, 15, or 20 different V genes. In some cases, identifying comprises isolating the plurality of tumor-reactive TCRs by a marker. In some cases, the plurality of cells expressing the plurality of tumor-reactive TCRs or a subset thereof is a plurality of allogeneic cells, autologous cells or cell line cells. In some cases, the plurality of allogeneic cells expresses a protein that binds to an inhibitory Natural Killer (NK) cell receptor. In some cases, the protein is a B2M-HLA-E or B2M-HLA-G fusion protein.

According to another aspect, provided herein is a method for identifying a target-reactive T-cell receptor (TCR), comprising: (a) contacting a plurality of T cells from a first sample with a second sample comprising tumor cells from a subject or a third sample, wherein the third sample is derived from the second sample, and wherein the third sample comprises: (i) a target antigen from the tumor cells of the second sample or a nucleic acid encoding the target antigen, and an MHC, (ii) a cell presenting the target antigen in an MHC, or (iii) a cell comprising an MHC and a protein product encoded by the nucleic acid, and wherein a subset of the plurality of T cells binds to the target antigen in complex with the MHC; (b) isolating the subset of the plurality of T cells or a portion thereof of the first sample; (c) partitioning the subset of the plurality of T cells or a portion thereof into a plurality of compartments, wherein each compartment comprises an individual T cell of the subset of the plurality of T cells or a portion thereof; and (d) within each compartment, identifying a first polynucleotide encoding a first TCR chain and a second polynucleotide encoding a second TCR chain of a cognate pair of TCR of the individual T cell, thereby generating one or more paired polynucleotides.

In some cases, identifying comprises physically linking the first polynucleotide encoding the first TCR chain and the second polynucleotide encoding the second TCR chain of a cognate pair of TCR of the individual T cell. In some cases, the one or more paired polynucleotides are one or more fused polynucleotides. In some cases, identifying comprises sequencing the first polynucleotide encoding the first TCR chain and the second polynucleotide encoding the second TCR chain of a cognate pair of TCR of the individual T cell.

In some cases, the first polynucleotide and the second polynucleotide are not chemically synthesized using phosphoramidite. In some cases, the first polynucleotide and the second polynucleotide are transcribed or amplified products of endogenous nucleic acids of the individual T cell. In some cases, the first sample or the second sample is isolated from a subject. In some cases, the first sample and the second sample are isolated from a same subject. In some cases, the first sample and the second sample are isolated from a different subject. In some cases, the first sample or the second sample is a tissue sample, a blood sample, a PBMC sample, or a combination thereof. In some cases, the tissue sample is a tumor tissue or a healthy tissue. In some cases, the first sample or the second sample is isolated from a subject by core biopsy, fine-needle biopsy, or apheresis. In some cases, isolating comprises isolating the subset of the plurality of T cells or a portion thereof by a marker. In some cases, the marker is a cell surface marker or a cytokine. In some cases, the cell surface marker is CD39, CD69, CD103, CD25, PD-1, TIM-3, OX-40, 4-1BB, CD137, CD3, CD28, CD4, CD8, CD45RA, CD45RO, GITR, FoxP3, or a combination thereof. In some cases, the cell presenting the target antigen is a tumor cell, an antigen-presenting cell (APC), an artificial APC, or any combinations thereof. In some cases, the APC or the aAPC is pulsed with the target antigen. In some cases, the cell comprising a protein product encoded by the nucleic acid is an APC or an aAPC delivered (e.g., transfected or electroporated) with the nucleic acid or a derivative thereof. In some cases, the APC or the aAPC is further delivered an additional nucleic acid encoding an MHC. In some cases, the nucleic acid or a derivative thereof is a DNA or a RNA. In some cases, the cell presenting the target antigen or the cell comprising a protein product encoded by the nucleic acid is isolated from a subject or is a cell line cell. In some cases, the cell presenting the target antigen or the cell comprising a protein product encoded by the nucleic acid is isolated from the same subject from which the first sample and the second sample are isolated. In some cases, the method further comprises generating one or more vectors comprising the one or more fused polynucleotides, each vector of the one or more vectors comprising a fused polynucleotide of the one or more fused polynucleotides. In some cases, the method further comprises delivering the one or more vectors into a plurality of cells, wherein each cell of the plurality of cells comprises at least one vector of the one or more vectors. In some cases, the method further comprises expressing the one or more fused polynucleotides in the plurality of cells, wherein a subset of the plurality of cells expresses a plurality of target-reactive TCRs. In some cases, the method further comprises contacting the plurality of cells with one or more target antigens, wherein the subset of the plurality of cells expressing the plurality of target-reactive TCRs binds to the one or more target antigens. In some cases, the method further comprises identifying one or more target-reactive TCR of the plurality of target-reactive TCRs. In some cases, the method further comprises delivering a polynuclotide encoding the one or more target-reactive TCR into a plurality of recipient cells. In some cases, the method further comprises administering one or more cells of the plurality of recipient cells into the subject.

According to another aspect, provided herein is a pharmaceutical composition comprising a recipient cell comprising a sequence encoding a target-reactive or tumor-reactive TCR identified by a method described herein.

According to another aspect, provided herein is a method comprising administering the pharmaceutical composition described herein into a subject in need thereof. In some cases, the recipient cell is administered at a dose from about $1 \times 10^9$ cells to about $1 \times 10^{11}$ cells.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure", "FIG.", and "FIGURE" herein) of which:

DETAILED DESCRIPTION OF THE INVENTION

Figure 1:
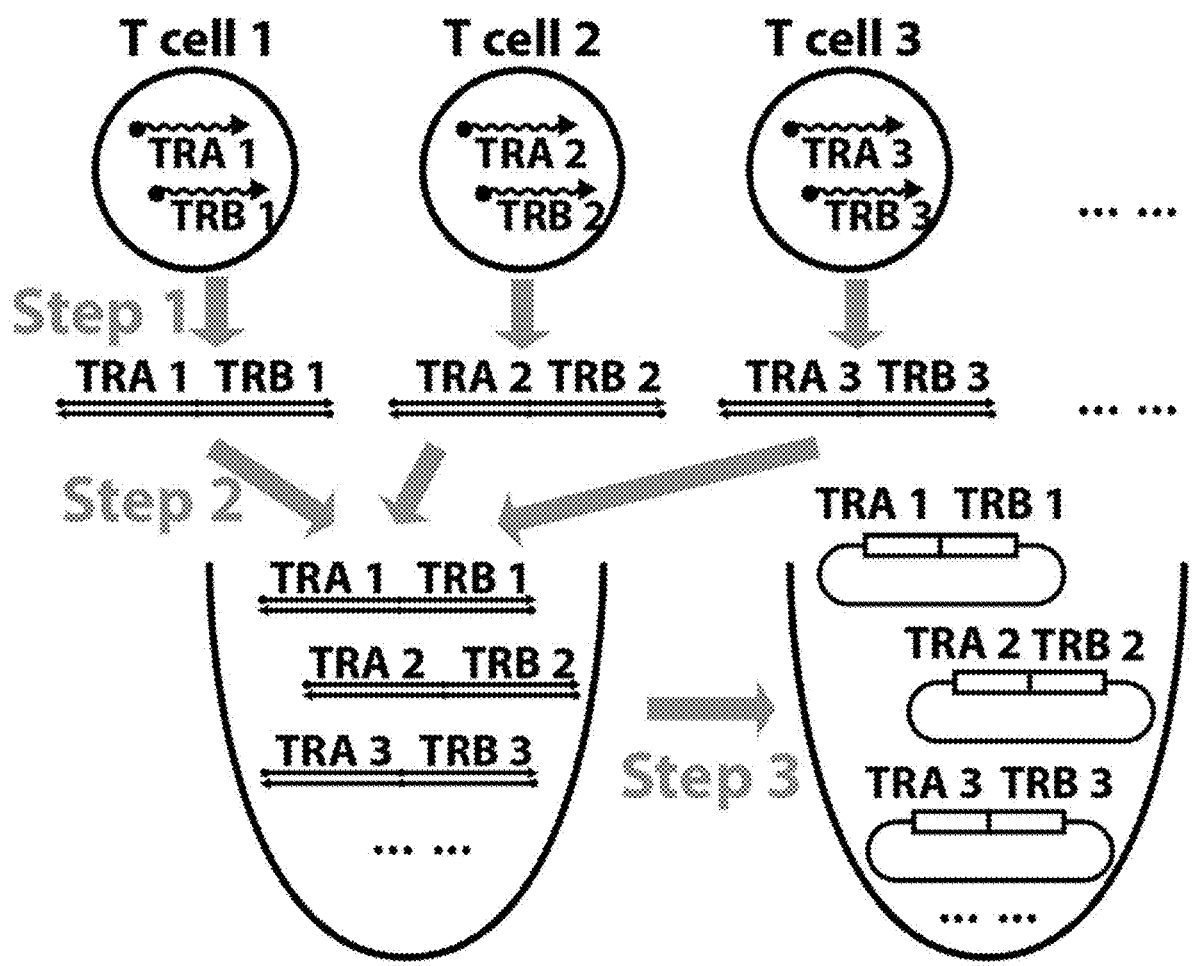
FIG. 1 depicts an example scheme of the general concept of producing fused bipartite immunoreceptor polynucleotides and immunoreceptor-expressing vectors. Multiple source immunoreceptor-expressing cells (e.g., three T cells are shown) can be processed simultaneously. For each cell, the sequences for the two genes of the bipartite immunoreceptor (e.g., T cell receptor alpha locus gene TRA and T cell receptor beta locus gene TRB of T cell 1, named TRA 1 and TRB 1, respectively) are fused to create a fused DNA molecule which encodes both chains, which can be referred to as a fused bipartite immunoreceptor gene (Step 1). The fused bipartite immunoreceptor polynucleotides can be mixed into one vessel, such as a test tube (Step 2). The fused DNA molecules can be made into immunoreceptor-expressing vectors (Step 3).

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

In this disclosure, the use of the singular includes the plural unless specifically stated otherwise. Also, the use of "or" means "and/or" unless stated otherwise. Similarly, "comprise," "comprises," "comprising" "include," "includes," and "including" are not intended to be limiting.

Definitions

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "immunoreceptor" refers to a receptor protein or a receptor protein complex that an immune cell produces to recognize its target. The target may be an antigen or a portion thereof (e.g., an epitope). The antigen can be a protein or a peptide. The target may be an MHC-bound peptide. Examples of immunoreceptors include B cell receptors (BCRs), antibodies (used interchangeably with "immunoglobulins"), and T cell receptors (TCRs).

The term "immunoreceptor chain" refers to a polypeptide that functions as a subunit of an immunoreceptor. Examples of immunoreceptor chains include the heavy chain of an immunoglobulin (Ig), the light chain of an immunoglobulin, the alpha chain of a TCR, the beta chain of a TCR, the gamma chain of a TCR, the delta chain of a TCR.

The term "bipartite immunoreceptor" refers to an immunoreceptor that is formed by polypeptides encoded by two genes. In cells, the two genes may be located on different loci of a chromosome, or different chromosomes. The two genes can be rearranged genes, such as V(D)J-rearranged genes. V(D)J-rearranged genes can be generated through a mechanism called V(D)J recombination, which occurs in the primary lymphoid organs and in a nearly random fashion rearranges variable (V), joining (J), and in some cases, diversity (D) gene segments. Examples of bipartite immunoreceptor include, but are not limited to, BCR (encoded by rearranged heavy chain gene and rearranged light chain gene), antibody (encoded by rearranged heavy chain gene and rearranged light chain gene), and TCR (encoded by rearranged TRA gene and rearranged TRB gene, or encoded by rearranged TRG gene and rearranged TRD gene).

The term "gene" refers to a nucleic acid sequence that can be potentially transcribed and/or translated (this definition includes the regulatory elements in 5' and 3', and the introns, if present). Orphons and pseudogenes are also instances of the "gene" concept. Generally, V, D, and J genes refer to the gene segments in the germline, and these germline gene sequences can be found in IMGT database. After V(D)J recombination, the V, D, and J gene segments in the rearranged genes are referred to as V region, D region, and J region, respectively. The V region, D region, and J region in the rearranged gene originate from V gene, D gene, or J gene in the germline, respectively.

The term "source immunoreceptor-expressing cells" refers to immunoreceptor-expressing cells whose immunoreceptors can be cloned into immunoreceptor-expressing vectors. If the immunoreceptor is a bipartite immunoreceptor, these cells can be used as input cells in the methods described herein to produce fused bipartite immunoreceptor polynucleotides, which in turn, can be converted to immunoreceptor-expressing vectors. For example, the source immunoreceptor-expressing cells can be source BCR-expressing cells, source antibody-expressing cells, or source TCR-expressing cells.

The term "fused bipartite immunoreceptor polynucleotide" refers to a continuous polynucleotide molecule comprising coding sequences for both genes (including rearranged genes) of a bipartite immunoreceptor, in which the coding sequences can be full or partial sequences encoding the immunoreceptor chain. For example, a fused bipartite immunoreceptor polynucleotide can be a fused BCR polynucleotide, a fused antibody polynucleotide, or a fused TCR polynucleotide.

The term "immunoreceptor-expressing vector" refers to a polynucleotide vector (such as a plasmid or a viral vector) that (1) comprises a fused bipartite immunoreceptor polynucleotide and (2) can be used to express the immunoreceptor in a host cell (e.g., a recipient cell described herein). For example, an immunoreceptor-expressing vector can be a BCR-expressing vector, an antibody-expressing vector, or a TCR-expressing vector.

The term "recipient cell" refers to a cell to which an immunoreceptor-expressing vector can be functionally introduced. The phrase "functionally introduced" means that the immunoreceptor encoded in the immunoreceptor-expressing vector can be expressed in the recipient cell. Examples of recipient cells include, but are not limited to, CD45+ cells, T cells, B cells, macrophages, natural killer (NK) cells, stem cells, bacterial cells, yeast cells, and cell lines.

The term "immunoreceptor-programmed recipient cell" refers to a recipient cell engineered to carry an immunoreceptor-expressing vector to express the immunoreceptor. When appropriate, the word "immunoreceptor" in the phrase "immunoreceptor-programmed recipient cell" can be replaced by "BCR", "antibody", or "TCR". When appropriate, the phrase "recipient cell" in the phrase "immunoreceptor-programmed recipient cell" can be replaced by the type of cell used as the recipient cell, for example, "CD45+ cell", "T cell', "B cell", "macrophage", "NK cell", "stem cell", "HeLa cell", "CHO cell", "bacterial cell" and "yeast cell". For example, immunoreceptor-programmed recipient cell can be a TCR-programmed T cell, a BCR-programmed B cell, or an antibody-programmed CHO cell.

The term "engineered" and its grammatical equivalents as used herein can refer to one or more alterations of a nucleic acid (e.g., the nucleic acid within an organism's genome) or a polypeptide. The one or more alterations can include modifications, additions, and/or deletions of genes. An engineered cell can refer to a cell with an added, deleted and/or altered gene.

The term "polyclonal immunoreceptor-programmed recipient cells" refers to a population of immunoreceptor-programmed recipient cells having more than one different immunoreceptor expressed. Each of the more than one different immunoreceptor expressed may react against a different epitope, a different antigen, or epitope presented by a different MHC. The total number of different immunoreceptors expressed in a population of polyclonal immunoreceptor-programmed recipient cells may exceed 100, 1,000, 10,000, 100,000, or 1,000,000. In some cases, the total number of different immunoreceptors expressed in a population of polyclonal immunoreceptor-programmed recipient cells may be at least 50, at least 100, at least 150, at least 200, at least 250, at least 300, at least 500, at least 1,000, at least 2,000, at least 5,000, at least 10,000, at least 50,000, at least 100,000, at least 500,000, at least 1,000,000, at least 5,000,000, or more.

Domain-level description of sequence: in the present disclosure, the polynucleotide sequence may be described at domain level. Each domain name can correspond to a specific polynucleotide sequence. For example, domain 'A' may have a sequence of 5'-TATTCCC-3', domain 'B' may have a sequence of 5'-AGGGAC-3', and domain 'C' may have a sequence of 5'-GGGAAGA-3'. In this case the polynucleotide having a sequence that is the concatenation of domains A, B, and C, can be written as [A|B|C}. The symbol '[' denotes the 5' end, the symbol '}' denotes the 3' end, and the symbol '|' separates domain names. An ssDNA or a section of ssDNA having sequence 'X' can be referred to as [X}. An asterisk sign shows sequence complementarity. For example domain [X*} is the reverse complement of domain [X}. The notation ds[X} can be used to describe a double-stranded DNA formed by [X} and [X*}. In some cases, especially in situation where it is not necessary to distinguish dsDNA and ssDNA, a dsDNA whose one strand has the sequence [X} may also be loosely referred to as [X}. A single-stranded RNA molecule or segment with the sequence identical to [X} (except replacing T with U) may also be referred to as [X}. Depending on the context, the domain name may refer to an exact sequence or describe a general function of a DNA or domain. For example, [RBS} may be used to describe a ribosome binding site, although the exact sequence for [RBS} may vary. Parentheses can be used to group a concatenation of domains, and the reverse-complement operation (denoted by '*') can be applied to the concatenation by adding the '*' following the closing parenthesis. For example [(X|Y)*} is the same as [Y*|X*}.

The terms "polynucleotide," "nucleic acid" and "oligonucleotide" are used interchangeably. They can refer to a polymeric form of nucleotides of any length, either deoxyribonucleotides or ribonucleotides, or analogs thereof. A polynucleotide may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. Polynucleotides may have any three-dimensional structure, and may perform various functions. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), circular RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

Polynucleotides may include one or more nucleotide variants, including nonstandard nucleotide(s), non-natural nucleotide(s), nucleotide analog(s) and/or modified nucleotides. Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. In some cases, nucleotides may include modifications in their phosphate moieties, including modifications to a triphosphate moiety. Non-limiting examples of such modifications include phosphate chains of greater length (e.g., a phosphate chain having, 4, 5, 6, 7, 8, 9, 10 or more phosphate moieties) and modifications with thiol moieties (e.g., alpha-thiotriphosphate and beta-thiotriphosphates). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as amino ally 1-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs are compatible with natural and mutant polymerases for de novo and/or amplification synthesis.

The term "peptide" is a polymer of amino acids and which are joined together through amide bonds and is alternatively referred to as a "polypeptide". In the context of this specification it should be appreciated that the amino acids may be the L-optical isomer or the D-optical isomer. Peptides are two or more amino acid monomers long, and often can be more than 20 amino acid monomers long. A polypeptide can be linearly unstructured or folded in three-dimensional structure. A structured polypeptide can be a protein. In some cases, a peptide is a neoantigen peptide. In some cases, a peptide is a tumor-associated antigen peptide.

The term "neoantigen" refers to a class of tumor antigens that arises from a tumor-specific mutation(s) which alters the amino acid sequence of genome encoded proteins.

The term "sequence" and its grammatical equivalents as used herein can refer to a polypeptide sequence or a polynucleotide sequence. A polynucleotide sequence can be DNA or RNA; can be linear, circular or branched; and can be either single-stranded or double-stranded. A sequence can be mutated. A sequence can be of any length, for example, between 2 and 1,000,000 or more amino acids or nucleotides in length (or any integer value there between or there above), e.g., between about 100 and about 10,000 nucleotides or between about 200 and about 500 amino acids or nucleotides. The sequence of a nucleic acid can encompass the actual sequence and a reverse complement sequence of the sequence.

The term "vessel" used herein refers to a compartment (e.g. a microfluidic channel, a well, a tube, or a droplet) in which a biochemical reaction (e.g., target protein and antibody binding, nucleic acid hybridization and primer extension) may occur. The terms "vessel" and "compartment" can be used interchangeably. The vessel or compartment may be solid-walled (when the boundary of the vessel or compartment is a solid such as glass, plastic, or polydimethylsiloxane (PDMS)) or liquid-walled (when the boundary of the vessel or compartment is a liquid such as oil). Solid-walled vessels may contain a solid scaffold, which is a continuous solid that connects all the vessels. The volume of the compartment may be as large as 1 mL or as small as 1 picoLiter. In some embodiments, the median size of the compartments of a plurality of compartments is from 1 to 10 picoLiter, from 10 to 100 picoLiter, from 100 picoLiter to 1 nanoLiter, from 1 to 10 nanoLiter, from 10 to 100 nanoLiter, from 100 nanoLiter to 1 microLiter, from 1 to 10 microLiter, from 10 to 100 microLiter, or from 100 to 1000 microLiter. The volume of the aqueous content in the compartment can be smaller than or about equal to the volume of the compartment. In some embodiments, the median volume of the aqueous content in the compartments is 1 microLiter or less. The vessel can comprise a plurality of polymerizable or gellable polymers and/or monomers. The plurality of polymerizable or gellable polymers and/or monomers may form a hydrogel or hardened matrix upon polymerization or gelation, thereby forming a hardened particle. The hardened particle can be a bead. The hardened particle can be a porous particle. The hardened particle can be a hydrogel particle. The hydrogel particle may be made of gelled polymers such as cross-linked polyacrylamide, cross-linked PEG, agarose, or alginate. The hardened particle may be melted upon treatment or stimulus. For example, agarose particles can be melted by high temperature. Polyacrylamide particles having a disulfide bond in the crosslinker may be melted by treating with a reducing agent such as beta mercaptoethanol or DTT.

The term "droplet" refers to a volume of liquid. An "emulsion" refers to a dispersion of minute droplets of a first liquid in a second liquid in which the first liquid is not soluble or miscible in the second liquid. Examples of emulsions include water-in-oil emulsion, water-in-oil-in-water emulsion, or water in a lipid layer (liposome) emulsion. As used herein: "water-in-oil emulsion" refers to a water-in-oil mixture in which the oil forms a continuous phase and the water is in discontinuous droplets. In some embodiments, droplets can be of uniform size or heterogeneous size. In some embodiments, the median diameter of the droplets in a plurality of droplets can range from about 0.001 μm to about 1 mm. In some embodiments, the median volume of the droplets in a plurality of droplets can range from 0.01 nanoLiter to 1 microLiter.

The term "particle" refers to an insoluble material of any configuration, including spherical, thread-like, brush-like and many irregular shapes. Particles can be porous with regular or random channels inside. Examples include silica, cellulose, sepharose beads, polystyrene (solid, porous and derivitized) beads, controlled-pore glass, gel beads, sols, biological cells, subcellular particles, microorganisms (protozoans, bacteria, yeast, viruses, etc.) micelles, liposomes, cyclodextrins, two phase systems (e.g. agarose beads in wax) etc. and other structures which can entrap or encapsulate a material.

The term "partition," as used herein, may be a verb or a noun. When used as a verb (e.g., "to partition," or "partitioning"), the term generally refers to the fractionation (e.g., subdivision) of a species or sample between vessels that can be used to sequester one fraction (or subdivision) from another. Such vessels are referred to using the noun "partition." Partitioning may be performed, for example, using microfluidics, dispensing, vortexing, and the like. A partition may be, for example, a well, a microwell, a hole, a droplet (e.g., a droplet in an emulsion), a continuous phase of an emulsion, a test tube, a spot, a capsule, a bead, a surface of a bead in dilute solution, or any other suitable container for sequestering one fraction of a sample from another. A partition may also comprise another partition. A water-in-oil emulsion can be created by using microfluidics or by physical agitation of a mixture of aqueous phase and an oil phase, optionally in the presence of a surfactant.

The term "polymerizable or gellable polymers and/or monomers" refers to any polymers or monomers that are capable of forming a matrix through a polymerization or a non-polymerization mechanism. Polymerizable or gellable polymers suitable for use in the present disclosure are those which are soluble or dispersible in an aqueous liquid. Polymerizable or gellable polymers include those which are capable of crosslinking with a suitable crosslinking agent via crosslinkable groups. The "polymerizable" can encompass the meaning of "crosslinkable". Polymerization can be a process of polymer formation from monomers, and can also be a process of crosslinked polymer formation from linear polymers. The polymerizable polymer can be a macromer. The term "macromer," as used herein, refers to any polymer or oligomer that has a functional group that can take part in further polymerization.

The terms "matrix," "framework," and "polymer framework" can be used interchangeably and refer to the polymer network formed within a vessel.

The terms "solid support," "support," "solid phase support," "substrate" and other grammatical equivalents refer to any material that can be modified to contain individual sites appropriate for the attachment or association of molecules. They can be a material or group of materials having a rigid or semi-rigid surface or surfaces. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. The solid support or substrate can be a multi-well plate. In some embodiments, at least one surface of the solid support can be substantially flat, although in some embodiments it may be useful to physically separate regions for different molecules or reactions with, for example, wells, raised regions, pins, etched trenches, or the like.

In some embodiments, the solid support(s) can take the form of beads, resins, particles, gels, microspheres, or other geometric configurations.

The terms "enriching," "isolating," "separating," "sorting," "purifying," "selecting" or equivalents thereof can be used interchangeably and refer to obtaining a subsample with a given property from a sample. For example, they can refer to obtaining a cell population or cell sample that contains at least about 30%, 40%, 50%, 55%, 60%, 65%, 70%, 75%, 80%, 85%, 90%, 95%, or 100% of the desired cell lineage or a desired cell having a certain cell phenotype, e.g., expressing a certain cell marker or not expressing a certain cell marker gene characteristic of that cell phenotype.

Overview

Immunoreceptors, for example, B-cell receptors (BCRs) and T cell receptors (TCRs), can be formed by multiple subunits, or chains. A BCR (as well as the soluble form of BCR, namely antibody) molecule can be formed by two identical copies of the heavy chain (H chain) and two identical copies of the light chain (L chain). A TCR molecule can be formed by an alpha chain ($\alpha$ chain or TCR$\alpha$ chain, encoded by TRA gene/sequence) and a beta chain ($\beta$ chain or TCR$\beta$ chain, encoded by TRB gene/sequence), or a gamma chain ($\gamma$ chain or TCR$\gamma$ chain, encoded by TRG gene/sequence) and a delta chain ($\delta$ chain or TCR$\delta$ chain, encoded by TRD gene/sequence). These immunoreceptor chains can have variable domains (e.g., encoded by the rearranged VDJ or VJ regions). Parts of the variable domains can be hypervariable. The hypervariable regions can include complementarity determining regions (CDRs), for example, CDR1, CDR2 and CDR3. In some cases, within one B cell, only one functional H chain sequence and one functional L chain sequence may be expressed. In some cases, within one T cell, only one functional $\alpha$ chain sequence and one functional $\beta$ chain sequence may be expressed. In some cases, within one T cell, only one functional $\gamma$ chain sequence and one functional $\delta$ chain sequence may be expressed.

Cloning of these immunoreceptors can be useful for further functional study and applications. However, the bipartite nature of these immunoreceptors may make them difficult to manipulate using conventional technologies. For example, if a hundred T cells are lysed, one may be able to sequence and/or clone a hundred TCR$\alpha$ chains and a hundred TCR$\beta$ chains, but it may be difficult to know which TCR$\alpha$ chain is paired with which TCR$\beta$ chain in the source TCR-expressing cells. From these one hundred T cells, it may be more valuable if one hundred physically fused DNA molecules each comprising a first sequence that encodes a TCR$\alpha$ chain and a second sequence that encodes a TCR$\beta$ chain can be obtained (FIG. 1, Step 1). The TCR$\alpha$ chain and TCR$\beta$ chain can then be co-expressed in one source TCR-expressing cell. Such fused molecules can be sequenced to obtain paired TRA and TRB sequences. In addition, these fused molecules can be further engineered and inserted into a vector backbone (e.g., a plasmid backbone) to create expression vectors (FIG. 1, Step 3) so that the paired TRA and TRB sequences can be expressed in new host cells which are called recipient cells as described herein to produce immunoreceptor-programmed recipient cells. In this case, the first sequence may comprise all three CDR sequences of the TCR$\alpha$ chain, and the second sequence may comprise all three CDR sequences of the TCR$\beta$ chain. Similar operation can be performed on a population of B cells. These immunoreceptor-expressing vectors can be used in multiple applications such as TCR-T therapy, antibody therapy, antibody engineering, and identification of TCRs or antibodies that recognize a particular antigen or a set of antigens.

Generation of fused immunoreceptor chains can be performed in a single-cell reactor. The single-cell reactor may be a droplet or a hydrogel particle. The compositions and methods using single-cell reactors as described herein can enable high throughout cloning of a population of fused bipartite immunoreceptor polynucleotides and generate a library of fused bipartite immunoreceptor polynucleotides, immunoreceptor-expressing vectors, or immunoreceptor-programmed recipient cells containing at least about 1,000, 10,000, 100,000, 1,000,000, or 10,000,000 unique cognate pairs of bipartite immunoreceptors.

T-Cell Receptor (TCR)

The immunoreceptor described herein can be a T cell receptor (TCR). Compositions and methods provided herein can be used to produce a fused TCR polynucleotide comprising a first nucleic acid sequence encoding a TCRα chain and a second nucleic acid sequence encoding TCRβ chain, or a first nucleic acid sequence encoding a TCRγ chain and a second nucleic acid sequence encoding TCRδ chain. The fused TCR polynucleotide may further comprise a promoter and/or may be inserted into a vector in order to be expressed in a recipient cell.

The TCR can be used to confer the ability of T cells to recognize antigens associated with various cancers or infectious organisms. The TCR is made up of both an alpha (α) chain and a beta (β) chain or a gamma (γ) and a delta (δ) chain. The proteins which make up these chains are encoded by DNA, which employs a unique mechanism for generating the tremendous diversity of the TCR. This multi-subunit immune recognition receptor associates with the CD3 complex and binds peptides presented by the MHC class I and II proteins on the surface of antigen-presenting cells (APCs). Binding of a TCR to the antigenic peptide on the APC can be a central event in T-cell activation, which occurs at an immunological synapse at the point of contact between the T cell and the APC.

The TCR may recognize the T cell epitope in the context of an MHC class I molecule. MHC class I proteins can be expressed in all nucleated cells of higher vertebrates. The MHC class I molecule is a heterodimer composed of a 46-kDa heavy chain which is non-covalently associated with the 12-kDa light chain 3-2 microglobulin. In humans, there are several MHC alleles, such as, for example, HLA-A2, HLA-A1, HLA-A3, HLA-A24, HLA-A28, HLA-A31, HLA-A33, HLA-A34, HLA-B7, HLA-B45 and HLA-Cw8. In some embodiments, the MHC class I allele is an HLA-A2 allele, which in some populations is expressed by approximately 50% of the population. In some embodiments, the HLA-A2 allele can be an HLA-A*0201, *0202, *0203, *0206, or *0207 gene product. In some cases, there can be differences in the frequency of subtypes between different populations. For example, in some embodiments, more than 95% of the HLA-A2 positive Caucasian population is HLA-A*0201, whereas in the Chinese population the frequency has been reported to be approximately 23% HLA-A*0201, 45% HLA-A*0207, 8% HLA-A*0206 and 23% HLA-A*0203.

In some embodiments, the TCR may recognize the T cell epitope in the context of an MHC class II molecule. MHC class II proteins can be expressed in a subset of APCs. In humans, there are several MHC class II alleles, such as, for example, DR1, DR3, DR4, DR7, DR52, DQ1, DQ2, DQ4, DQ8 and DPI. In some embodiments, the MHC class II allele is an HLA-DRB1*0101, an HLA-DRB*0301, an HLA-DRB*0701, an HLA-DRB*0401 or an HLA-DQB1*0201 gene product.

Similar to immunoglobulins expressed by B cells—membrane bound immunoglobulins are often referred to as B-cell receptors (BCRs)—the TCR chains consist of a variable domain (or variable region) and a constant domain (or constant region). A full-length constant domain/region can comprise an extracellular portion (referred to as "extracellular constant domain" herein), a hinge region, a transmembrane region, and a cytoplasmic tail. In various embodiments, a constant domain can be a full-length constant domain or a portion thereof, for example, the extracellular constant domain. The variable domain of TCRα and δ chains is encoded by a number of variable (V) and joining (J) genes, while TCRβ and γ chains are additionally encoded by diversity (D) genes. During VDJ recombination, one random allele of each gene segment is recombined with the others to form a functional variable domain. Recombination of the variable domain with a constant gene segment can result in a functional TCR chain transcript. Additionally, random nucleotides may be added and/or deleted at the junction sites between the gene segments. This process can lead to strong combinatorial (depending on which gene regions will recombine) and junctional diversity (depending on which and how many nucleotides will be added/deleted), resulting in a large and highly variable TCR repertoire, which can ensure the identification of a plethora of antigens. Additional diversity can be achieved by the pairing (also referred to as "assembly") of α and β or γ and δ chains to form a functional TCR. By recombination, random insertion, deletion and substitution, the small set of genes that encode the T cell receptor has the potential to create between $10^{15}$ and $10^{20}$ TCR clonotypes. As used herein, a "clonotype" refers to a population of immune cells that carry an identical immunoreceptor. For example, a clonotype refers to a population of T cells that carry an identical TCR, or a population of B-cells that carry an identical BCR (or antibody). "Diversity" in the context of immunoreceptor diversity refers to the number of immunoreceptor (e.g., TCR, BCR and antibody) clonotypes in a population. As used herein, a "cognate pair combination" refers to the native combination of the two chains (e.g., TCRα and TCRβ, TCRγ and TCRδ, or heavy chain and light chain) of a bipartite immunoreceptor within an immune cell. The same cognate pair combination of the two chains can result in the same TCR. For example, the T cells having the same clonotype have the same cognate pair combinations of TCRα and TCRβ chains. The higher diversity in clonotype may indicate higher diversity in cognate pair combination.

Each TCR chain contains three hypervariable loops in its structure, termed complementarity determining regions (CDR1-3). CDR1 and 2 are encoded by V genes and may be required for interaction of the TCR with the MHC complex. CDR3, however, is encoded by the junctional region between the V and J or D and J genes and therefore can be highly variable. CDR3 may be the region of the TCR in direct contact with the peptide antigen. CDR3 can be used as the region of interest to determine T cell clonotypes. The sum of all TCRs by the T cells of one individual is termed the TCR repertoire or TCR profile. The TCR repertoire can change with the onset and progression of diseases. Therefore, determining the immune repertoire status under different disease conditions, such as cancer, autoimmune, inflammatory and infectious diseases may be useful for disease diagnosis and prognosis.

TCR may be a full-length TCR as well as antigen-binding portion or antigen-binding fragment (also called MHC-peptide binding fragment) thereof. In some embodiments, the TCR is an intact or full-length TCR. In some embodiments, the TCR is an antigen-binding portion that is less than a full-length TCR but that binds to a specific antigenic peptide bound to an MHC molecule, i.e., an MHC-peptide complex. An antigen-binding portion or fragment of a TCR can contain only a portion of the structural domains of a full-length or intact TCR, but yet is able to bind the epitope (e.g., MHC-peptide complex) to which the full TCR binds. In some cases, an antigen-binding portion or fragment of a TCR contains the variable domains of a TCR, such as variable α chain and variable β chain of a TCR, sufficient to form a binding site for binding to a specific MHC-peptide complex, such as generally where each chain contains three complementarity determining regions. Polypeptides or proteins having a binding domain which is an antigen-binding domain or is homologous to an antigen-binding domain are included.

B-Cell Receptor (BCR) and Antibody

The immunoreceptor described herein can be a B-cell receptor (BCR). In some embodiments, the immunoreceptor described herein is an antibody (or an immunoglobulin). Compositions and methods provided herein can be used to produce a fused BCR or antibody polynucleotide comprising a first nucleic acid sequence encoding a heavy chain and a second nucleic acid sequence encoding a light chain. The fused bipartite BCR or antibody polynucleotide may further comprise a promoter and/or may be inserted into a vector in order to be expressed in a recipient cell.

The BCR consists of a plasma membrane-bound antibody that is associated with a pair of signaling proteins. Antigen binding to the BCR can stimulate B cells to differentiate into antibody-secreting cells. The BCR may play an important role in the clonal selection of B cells and their differentiation into antibody-secreting plasma cells. Mature B cells may have both immunoglobulin M (IgM) and IgD isotypes of BCRs, which can both be associated with the signaling subunits Igα and Igβ, but differ in their membrane-bound heavy chain isoforms.

A whole immunoglobulin or antibody typically can consist of four polypeptides: two identical copies of a heavy (H) chain polypeptide and two identical copies of a light (L) chain polypeptide. In mammals, antibodies are divided into five isotypes: IgG, IgM, IgA, IgD and IgE. The isotypes differ in their biological properties, functional locations and ability to deal with different antigens. The type of heavy chain present defines the class of an antibody. There are five types of mammalian Ig heavy chain denoted by Greek letters: α, δ, ε, γ and μ. These chains are found in IgA, IgD, IgE, IgG and IgM antibodies, respectively. Heavy chains differ in size and composition; α and γ contain approximately 450 amino acids, while μ and ε have approximately 550 amino acids. Each of the heavy chains can contain one N-terminal variable ($V_H$) region and three C-terminal constant ($C_H1$, $C_H2$, and $C_H3$) regions, and each light chain can contain one N-terminal variable ($V_L$) region and one C-terminal constant ($C_L$) region. Immunoglobulin light chains can be assigned to one of two distinct types, either kappa (κ) or lambda (λ), based upon the amino acid sequences of their constant domains. In a typical immunoglobulin, each light chain can be linked to a heavy chain by disulfide bonds, and the two heavy chains can be linked to each other by disulfide bonds. In some embodiments, a provided heavy chain, light chain and/or antibody agent has a structure that includes one or more disulfide bonds. In some embodiments, the one or more disulfide bonds are or include a disulfide bond at the expected position for an IgG4 immunoglobulin. The light chain variable domain can be aligned with the variable domain of the heavy chain, and the light chain constant domain can be aligned with the first constant domain of the heavy chain. The remaining constant domains of the heavy chains can be aligned with each other.

The variable domains of each pair of light and heavy chains can form the antigen binding site of an antibody.

Antibodies can comprise an antigen-binding fragment (Fab) and a fragment crystallizable region(Fc). The Fc region can interact with cell surface receptors which can allow antibodies to activate the immune system. In IgG, IgA and IgD antibody isotypes, the Fc region is composed of two identical protein fragments, derived from the second and third constant domains of the antibody's two heavy chains; IgM and IgE Fc regions contain three heavy chain constant domains ($C_H$ domains 2-4) in each polypeptide chain. The Fc regions of IgGs bear a highly conserved N-glycosylation site. Glycosylation of the Fc fragment can be essential for Fc receptor-mediated activity. The N-glycans attached to this site can predominantly be core-fucosylated diantennary structures of the complex type. Examples of antibody fragments include, but are not limited to, (1) a Fab fragment, which is a monovalent fragment consisting of the $V_L$, $V_H$, $C_L$, and $C_H1$ domains, (2) a F(ab')$_2$ fragment, which is a bivalent fragment comprising two Fab fragments linked by a disulfide bridge at the hinge region, (3) a Fv fragment consisting of the $V_L$ and $V_H$ domains of a single arm of an antibody, (4) a Fab' fragment, which results from breaking the disulfide bridge of an F(ab')$_2$ fragment using mild reducing conditions, (5) a disulfide-stabilized Fv fragment (dsFv), and (6) a single domain antibody (sdAb), which is an antibody single variable domain ($V_H$ or $V_L$) polypeptide that specifically binds antigen.

While the constant domains of the light and heavy chains may not be directly involved in binding of the antibody to an antigen, the constant domains can influence the orientation of the variable domains. The constant domains can also exhibit various effector functions, such as participation in antibody-dependent complement-mediated lysis or antibody-dependent cellular toxicity via interactions with effector molecules and cells.

An antibody can also include chimeric antibodies, humanized antibodies, and recombinant antibodies, human antibodies generated from a transgenic non-human animal, as well as antibodies selected from libraries using enrichment technologies.

An antibody can be a protein that is found in blood or other bodily fluids of vertebrates, which is used by the immune system to identify and neutralize foreign objects, such as bacteria and viruses. An antibody can include monoclonal antibodies, polyclonal antibodies, multispecific antibodies (for example, bispecific antibodies and polyreactive antibodies), and antibody fragments. Thus, an antibody can include, but not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). Antibody fragments are produced by recombinant DNA techniques, or by enzymatic or chemical cleavage of intact antibodies. An antibody other than a "bispecific" or "bifunctional" antibody is understood to have each of its binding sites identical. A monoclonal antibody can be obtained from a population of substantially homogeneous antibodies, i.e., the individual antibodies comprising the population are identical except for possible naturally occurring mutations that may be present in minor amounts. A polyclonal antibody can be a preparation that includes different antibodies directed against different determinants (epitopes).

Variable domains of many immunoreceptors (e.g., TCR alpha chain, TCR beta chain, antibody heavy chain, antibody light chain) can have the same general structure, with each domain comprising four framework (FW or FR) regions, connected by three complementarity determining regions (CDRs). The term "framework region," as used herein, can refer to the relatively conserved amino acid sequences within the variable domain which are located between the hypervariable or complementarity determining regions (CDRs). In a typical immunoglobulin or TCR chain, there can be four framework regions in each variable domain, which are designated FR1, FR2, FR3, and FR4. The framework regions form 3 sheets that provide the structural framework of a variable domain. In a typical immunoglobulin or TCR chain, there can be three complementary determining regions (CDRs) in each variable domain, which are designated CDR1, CDR2, and CDR3. The CDRs form the "hypervariable region" of an antibody, which can be responsible for antigen binding.

Single-Cell Reactors

Figure 2:
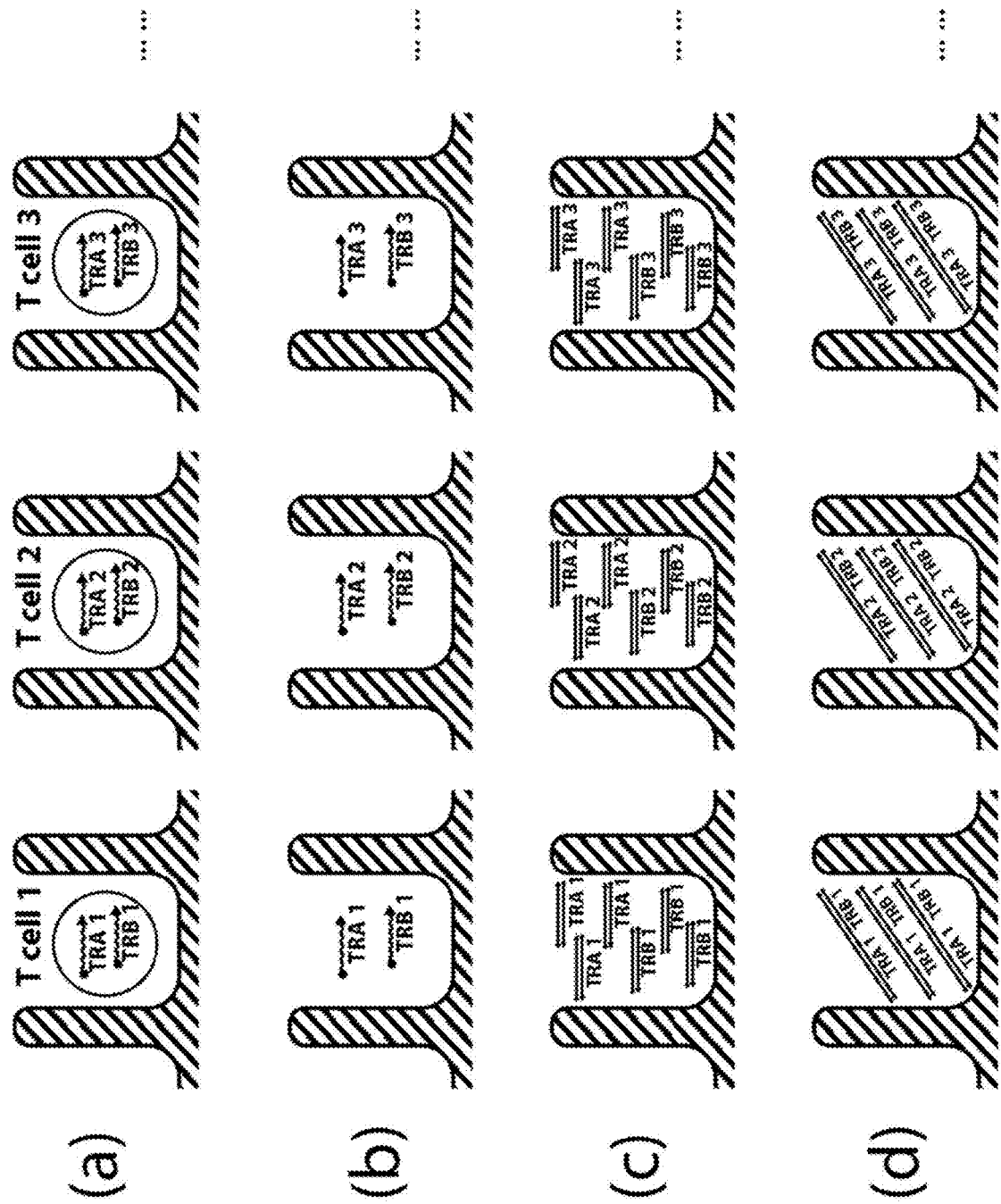
FIG. 2 depicts an example scheme of the concept of single-cell reactor to produce fused bipartite immunoreceptor polynucleotides, using three T cells (T cell 1, T cell 2, and T cell 3 as shown in the figure) as an example. (a) Each cell can be placed in a single-cell reactor. (b) Cells can be lysed in their respective single-cell reactors to release mRNA molecules encoding the two chains (e.g., TRA and TRB from T cell 1, named TRA 1 and TRB 1, respectively). (c) Each mRNA molecule can then be converted to DNA molecule and amplified. (d) Fused DNA molecules (e.g., fused bipartite immunoreceptor polynucleotides) can be created by ligating the amplification product of each chain. Because of the barriers between single-cell reactors, mispairing of TRA and TRB from different cells (e.g., TRA 1 fused with TRB 2) can be minimized.

Provided herein are compositions and methods to produce a library of fused bipartite immunoreceptor polynucleotides. The fused bipartite immunoreceptor polynucleotide can comprise the coding sequences of two V(D)J-rearranged genes encoding a bipartite immunoreceptor from a single cell. Single-cell reactors can be used to produce fused bipartite immunoreceptor polynucleotides from a single cell. An example scheme of the method described herein is depicted in FIG. 2. By using single cell reactors (conceptually shown by the shaded structure in FIG. 2), contact between nucleic acid molecules encoding different immunoreceptor chains from different cells (i.e., inter-cell sequence contact), which may cause mispairing, can be minimized. For example, as depicted in FIG. 2, nucleic acid molecules (TRA 1) encoding TCRα chain 1 may not contact nucleic acid molecules (TRB 2) encoding TCRβ chain 2.

As illustrated by this example scheme, a single-cell reactor can be a container in which molecules of interest from a single biological particle (e.g., a single cell) can react with a reagent or with each other. A single-cell reactor may comprise two components: (1) a solid support to which molecules of interest from a single cell can be associated, and (2) an aqueous content for the biochemical reactions to happen. Molecules of interest in single-cell reactors may undergo reactions during which molecules of interest from different cells do not contact each other or mix. The molecules of interest may be nucleic acids, proteins or other molecules present in a cell. The nucleic acids may be DNA, RNA, mRNA, miRNA, tRNA, etc. The nucleic acids may encode an immunoreceptor or an immunoreceptor chain.

In some cases, the solid support can be batch processed. For example, the solid support can be beads, in which case the many beads can be immersed in a continuous volume of aqueous solution so that all molecules on all beads can access the reactants in the aqueous solution. For example, the solid support can be the surface of solid microwells patterned on a larger solid surface. In this case the entire solid surface can be immersed in a continuous volume of aqueous solution so that all molecules on all microwells can access the reactants in the aqueous solution.

Single-Cell Reactors: Shape and Form

A single-cell reactor may have a barrier where the barrier restricts content of different single-cell reactors from contacting each other.

When a single-cell reactor has a barrier the single-cell reactor can be a vessel. In this case the single-cell reactor can be solid-walled or liquid-walled. The barrier may be an oil barrier, a solid barrier, or other barriers. For example, the barrier of a single-cell reactor can be a tube, a well, a microwell, or a water-in-oil droplet. In some cases, a single-cell reactor is a water-in-oil droplet in an emulsion. Using water-in-oil droplets as single-cell reactors can offer ultra-high throughput since millions or more of such droplets can be created in a few minutes to hours. Generation of water-in-oil droplets can be achieved by vortexing or using microfluidic chips such as a flow-focusing microfluidics chip.

In some embodiments, the emulsion is formed passively using a microfluidics device. These methods can involve squeezing, dripping, jetting, tip-streaming, tip-multi-breaking, or similar. Passive microfluidic droplet generation can be modulated to control the particle number, size, and diameter by altering the competing forces of two different fluids. These forces can be capillary, viscosity, and/or inertial forces upon the mixing of two solutions.

In some embodiments, the emulsion is formed by active control of a microfluidics chip. In active control, droplet generation can be manipulated via external force application, such as electric, magnetic, or centripetal forces. A popular method for controlling active manipulation of droplets in a microfluidic chip is to modify intrinsic forces by tuning fluid velocities of two mixing solutions, such as oil and water.

Standard molecular biology reactions such as reverse transcription and polymerase chain reaction (PCR) can be performed in water-in-oil emulsions. Surfactant may be added to the aqueous or oil phase to stabilize the emulsions.

In some cases, a single-cell reactor does not have a barrier. For example, a hydrogel particle (e.g., such as an agarose particle with a diameter of ~100 micron) may comprise a polymer matrix to which molecules of interest from a single cell are stably attached. The aqueous content of the hydrogel may comprise a reactant that may react with the molecules of interests. In some embodiments, because the molecules of interests are stably attached to the polymer matrix of the hydrogel particles, molecules of interests from different cells do not contact each other or mix.

As another example, a non-porous particle (e.g., a polystyrene particle with a diameter of ~10 micron) may comprise a surface to which molecules of interest from a single cell are stably attached. The solid particles may be immersed in a solution comprising reactants that react with the molecules of interest on the surface of the particles. In this case, the particle along with the solution surrounding it constitutes a single-cell reactor. In some cases, such non-porous particle may be further comprised in a vessel. For example, the single-cell reactor can be a bead surrounded by a liquid in a droplet of an emulsion, or a bead surround by a liquid in a well.

Single-Cell Reactors: Solid Support—General

Various types of solid support and various attachment chemistries can be used to provide solid support to which molecules of interest from a single cell can be stably associated. It is not intended that the present disclosure be limited to any particular type of solid support material or configuration.

Solid supports can be flat or planar, or can have substantially different conformations. For example, the solid support can exist as particles, beads, strands, precipitates, gels, sol-gels, sheets, tubing, spheres, containers, capillaries, pads, slices, films, plates, dipsticks, slides, etc. Magnetic beads or particles, such as magnetic latex beads and iron oxide particles, are examples of solid substrates.

Example materials that can form solid supports include glasses or other ceramics, plastics, polymers, metals, metalloids, alloys, composites, organics, etc. For instance, the solid supports can comprise a material selected from a group consisting of: silicon, silica, quartz, glass, controlled pore glass, carbon, alumina, titania, tantalum oxide, germanium, silicon nitride, zeolites, and gallium arsenide. Many metals such as gold, platinum, aluminum, copper, titanium, and their alloys are also options for use as solid supports. In addition, many ceramics and polymers can also be used as solid supports. Polymers which can be used as solid supports include, but are not limited to, the following: polystyrene; poly(tetra)-fluoroethylene (PTFE); polyvinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PMI); poly atkenesulfone (PAS); polypropylene; polyethylene; polyhydroxyethylmethacrylate (HEMA); polydimethyl-siloxane; poly acrylamide; polyimide; and block-copolymers. Substrates for the array include silicon, silica, glass, and polymers. The solid support can be composed of a single material (e.g., glass), mixtures of materials (e.g., copolymers) or multiple layers of different material (e.g., metal coated with a monolayer of small molecules, glass coated with a BSA, etc.).

The configuration of a solid support can be any appropriate form, e.g., can comprise beads, spheres, particles, granules, a gel, a sol-gel, a self-assembled monolayer (SAM) or a surface (which can be flat, or can have shaped features). The solid support can include semisolid supports. Surfaces of the solid support can be planar, substantially planar, or non-planar. Solid supports can be porous or non-porous, and can have swelling or non-swelling characteristics. A solid support can be configured in the form of a well, depression or other container, vessel, feature or location. A plurality of solid supports can be configured in an array at various locations, addressable for robotic delivery of reagents, or by detection means including scanning by laser or other illumination and CCD, confocal or deflective light gathering.

In some embodiments, the solid support is in the form of a bead (synonymous with particle). A bead can be made of any substrate material, including biological, non-biological, organic, inorganic, polymer, metal, or a combination of any of these. The surface or interior of the bead can be chemically modified and subject to any type of treatment or coatings, e.g., coatings that contain reactive groups that permit binding interactions with the tool molecules.

In some embodiments, the solid support can be a cell. The cell can be a source immunoreceptor-expressing cell (e.g., a source T cell having a TRA gene/mRNA and a TRB gene/mRNA) may be a solid support. The cell can be fixed using formaldehyde, paraformaldehyde, glutaraldehyde, or similar fixatives, or a combination thereof. After fixation, the cell can be permeabilized using detergents such as Triton-X100. The fixed and permeabilized cell can be considered a porous particle, a particle and a solid support. Because the cell is fixed, its TRA- and TRB-containing DNA (part of genomic DNA) and mRNA may be diffusion-restricted in the cell or stably attached to the cell. Because the cell is permeabilized and porous, reagents such as reverse transcriptase, DNA polymerase, primer, template switching oligo (TSO) can be diffused into the cell to contact the DNA or RNA (e.g., TRA and TRB mRNA) to perform reactions such as reverse transcription, primer extension, and template switching.

In some embodiments, the beads can be produced in a way that facilitates their rapid isolation and/or purification. For example, magnetic beads can be manipulated by applying a magnetic field to rapidly isolate the beads from a liquid phase within a plate well.

Single-Cell Reactors: Solid Support—Hydrogel

A solid support may comprise hydrogel. A solid support may be a hydrogel particle. Hydrogel can be made into hydrogel particles using existing methods. For example, the sol state or the precursors of the hydrogel can be made into water-in-oil emulsions. The aqueous droplets can be turned into gel state (e.g., by polymerization of the precursors, or by lowering the temperature for thermo-reversible hydrogels such as agarose) to yield 'hydrogel-in-oil' emulsions. Polymerization of the precursors can be triggered by light or by adding initiator or accelerator (e.g., TEMED) in the oil phase. This emulsion can be demulsified to yield hydrogel particles suspended in aqueous solution.

In some embodiments, the hydrogel is a reversible hydrogel which can be reversible between gel phase and solution (sol) phase. In some embodiments, the transition between the gel and sol phase of the reversible hydrogel is controlled by temperature (i.e., thermally controlled or thermo-reversible). For example, a thermally controlled reversible (or thermo-reversible) hydrogel can be an agarose hydrogel. A useful property of reversible hydrogel can be that, in the sol phase, the capture agent, molecules attached to the capture agent, and other molecules of interest can diffuse freely, making certain reactions more efficient.

There are other methods to provide thermo-sensitive or thermo-reversible hydrogels, e.g., by using thermo-responsive polymers. Temperature-sensitive polymers can be synthesized by post-polymerization grafting of a hydrophobic block to a hydrophilic block or by co-polymerization to create amphiphilic diblock (AB), triblock (ABA or BAB type) or multiblock copolymers. A is a hydrophilic block like PEG (also known as poly(ethylene oxide) (PEO)) while B is a hydrophobic block such as a polyester, poly(propylene oxide) (PPO) (also called poly(propylene glycol) (PPG)), or poly(N-isopropylacrylamide) (PNIPAm). The amphiphilic block copolymers self-assemble in water to form micelles with shells of hydrophilic blocks and cores of hydrophobic blocks at low temperatures, and association of the micelles at elevated temperatures triggers gelation. The temperature at which a thermo-responsive polymer solution changes to a gel is called the gelation temperature. Poloxamer (ABA type PEO-PPO-PEO polymer), known commercially as Pluronic® (BSAF) or Synperonic® PE (ICI), can be used to form thermo-sensitive hydrogels. An aqueous solution of Pluronic® self-assembled to form micelles at ambient temperature, and gelation occurred as a result of association of the micelles at body temperature. Multiblock copolymers of Pluronic® can be prepared by coupling PEO and PPO segments or Pluronics® using phosgene or hexamethylene diisocyanate (HDI) as coupling agents, respectively. Aliphatic esters, like poly(ε-caprolactone) (PCL) and poly (lactic acid) (PLA), can be coupled to the ends of Pluronic® via ring opening polymerization (ROP) of corresponding ε-caprolactone (CL) and lactic acid (LA) monomers using stannous octoate $(Sn(oct)_2)$ as a catalyst to prepare hydrolytically degradable Pluronic® hydrogels. A multiblock copolymer of Pluronic® based on acid labile acetal linkages can be created by reaction of Pluronic® and di-(ethylene glycol) divinylether (DEGDVE) in the presence of a p-toluenesulfonic anhydride (p-TSA) catalyst.

Thermo-reversible hydrogels based on PEG with aliphatic esters such as PLA, PCL, poly(glycolic acid) (PGA), and poly[(R)-3-hydroxybutyrate] (PHB) can be used. For example, ABA type PEG-poly(D,L-lactide-co-glycolide)-PEG (PEG-PLGA-PEG) triblock copolymers formed hydrolytically degradable hydrogels. The copolymers can be synthesized by two steps. First, the diblock copolymers of monomethoxy PEG-PLGA (MPEG-PLGA) can be synthesized via ROP of D,L-lactide (DLLA) and glycolide (GA) on MPEG in the presence of $Sn(oct)_2$ as a catalyst, and subsequently, the triblock PEG-PLGA-PEG copolymers can be prepared by coupling the diblock MPEG-PLGA copolymers to each other using an HDI coupling agent. The copolymer solutions can exist at low temperatures, but become gels at 37° C. (sol-to-gel transition). BAB type triblock copolymers with PLGA blocks flanked by a central PEG block (PLGA-PEG-PLGA) can be synthesized via ROP of DLLA and GA on PEG without the need of a coupling agent. PLGA-PEG-PLGA exhibits a similar sol-to-gel transition trend to PEG-PCLA-PEG. Gelation and degradation of these hydrogels can be tailored by varying the molecular weight of the hydrophobic and hydrophilic blocks, the composition of the hydrophobic blocks, polymer concentration and additives. Gelation behavior of PLGA-PEG-PLGA can be modulated by incorporation of various end groups (i.e., hydroxyl, acetyl, propionyl, and butanoyl groups).

PNIPAm is soluble in aqueous solution at room temperature but precipitates above 32° C. (phase transition temperature) due to its coil-to-globule transition. Incorporation of PNIPAm with other polymers can result in copolymers that exhibit sol-to-gel phase transition in aqueous solution in response to increased temperature. Radical polymerization can be used to incorporate NIPAm with other methacrylate or acrylate monomers/polymers to create PNIPAm-based polymers. For example, a PNIPAm-poly(2-metha-cryloyloxyethyl phosphorylcholine)-PNIPAm (PNIPAm-MPC-PNIPAm) copolymer can be synthesized via atom transfer radical polymerization (ATRP). ATRP of NIPAm can take place in two steps: (1) the preparation of macro-initiator and (2) the addition of NIPAm to the macro-initiator to result in block copolymers. The polymer solution can form a gel as temperature is raised above 32° C. due to hydrophobic interactions between the polymer chains during the formation of a network.

Thermo-responsive polyphosphazenes can also display sol-to-gel phase transition in aqueous solutions with increasing temperature. These polymers can be prepared through multi-step syntheses. First, dichlorophosphazene polymers can be synthesized via melt polymerization reaction of hexachlorocyclotriphosphazenes using aluminum chloride ($AlCl_3$) as a catalyst. Then, a hydrophilic PEG block and a hydrophobic block can be conjugated to the dichlorophosphazene polymer backbone to obtain hydrogel macromers. The hydrophobic blocks can be di-, tri-, and oligo-peptides or single modified amino acids (e.g., L-isoleucine ethyl ester (IleOEt), D,L-leucine ethyl ester (LeuOEt), L-valine ethyl ester (ValOEt)).

An ABA-type triblock copolymer consisting of MPEG and poly(propylene fumarate) (PPF) can result in a thermosensitive gel that can be further stabilized through crosslinking of unsaturated double bonds on PPF.

Mixing of enantiomeric PEG-P(L-lactide)-PEG (PEG-PLLA-PEG) and PEG-P(D-lactide)-PEG (PEG-PDLA-PEG) triblock copolymers can induce sol-to-gel transition. Hydrogels can be formed when temperature is increased to 37° C. and they can become solutions above 70° C. Similarly, hydrogels can be formed by stereocomplexation of enantiomeric PEG-(PLLA)8 and PEG-(PDLA)8 star block, and PEG-(PLLA)2 and PEG-(PDLA)2 triblock copolymers.

In addition to self-assembly of synthetic polymers, natural materials chemically modified with synthetic molecules can also self-assemble in aqueous media to form hydrogels. For example, chitosan, a polysaccharide derived from the partial deacetylation of naturally abundant chitin, can be used for hydrogel formation. Chitosan can form physical hydrogels when conjugated with several polymers. For instance, PEG-aldehyde can be coupled to chitosan via Schiff's base reaction followed by reduction with sodium cyanoborohydride ($NaBH_3CN$) to yield PEG-g-chitosan. The resulting graft polymer is a solution at low temperatures and can transform to a gel at around 37° C. temperature. The gelation can be attributed to hydrophobic interactions between the polymer chains, which lead to association of chitosan segments and a decrease in PEG mobility. Similarly, Pluronic®-g-chitosan also exhibits thermo-reversible sol-to-gel transition upon heating.

Polyacrylamide can be the polymer framework for the hydrogel. The polyacrylamide gel can be polymerized from monomers (e.g., acrylamide) and crosslinkers (e.g., bis-acrylamide) in the droplets which offers some advantage such as low viscosity and ease of immobilizing the capture agent with high immobilization efficiency.

Self-assembly of polymers can provide a simple method to prepare physically crosslinked hydrogels. Self-assembly occurs with some polymers as a result of intra- and inter-molecular forces, such as hydrogen bonding and hydrophobic interactions. Aqueous solutions of these polymers undergo sol-to-gel transition upon self-assembling in response to external stimuli such as pH and temperature. Self-assembly of thermo-responsive polymers is a way to fabricate hydrogels by a simple change in temperature.

In addition, several polysaccharide-based polymers can be considered, such as alginate and agarose. Alginate can be readily derivatized which offers many options to immobilize the capture agent (see, e.g., Pawer and Edgar, Biomaterials 33(2012), 3279). Even when the polymer is not derivatized, one may still be able to achieve stable physical association between the capture agent and the polymer framework. For example, large particles (e.g., micron-sized streptavidin-coated beads) can be entrapped in underivatized polymer framework, and the capture agent can form stable physical association with the surface or interior of the large particle.

With some polymers, the gelling can be reversed. That is, the hydrogel particles can be converted from a gel state to a fluid state. In other words, the gel can be melted. This may be useful in some situations such as recovering the target molecule or DNA from the hydrogel particles. For example, the bis-acrylamide in polyacrylamide gel can be replaced with crosslinkers such as DATD (diallyl-tartardiamide), DHEBA (dihydroxyethylene-bis-acrylamide), and BAC (bis-acrylylcystamine). These crosslinkers can be cleaved by several reducing agents or oxidizing agents. Alginate gels can be easily melted by EDTA, and agarose gel can be melted by high temperature.

Single-Cell Reactors: Solid Support—Hydrogel: Triggered Gelling and Hardened Particles In some cases, an aqueous solution comprising polymerizable or gellable polymer and/or monomer can be converted to a hydrogel by forming a matrix through a polymerization or a non-polymerization mechanism. This process is called gelling. When such aqueous solution is the content of a compartment, the hydrogel formed by the gelling process can be a hydrogel particle. A hydrogel particle formed from the content in the aqueous phase of a compartment (e.g., a microwell or a water-in-oil droplet) is referred to as a hardened particle.

An example of a matrix formed by polymerization mechanism includes, but is not limited to, polyacrylamide. Polyacrylamide can be a matrix formed from monomers of acrylamide and bis-acrylamide. The polymerization reaction can be a vinyl addition catalyzed by free radicals. The reaction can be initiated by TEMED, which induces free radical formation from ammonium persulphate (APS). The free radicals transfer electrons to the acrylamide/bisacrylamide monomers, radicalizing them and causing them to react with each other to form the polyacrylamide chain. In the absence of bis-acrylamide, the acrylamide may polymerize into long strands, not a porous gel. Bis-acrylamide can cross-link the acrylamide chains and give rise to the formation of the porous gel matrix. The amount of crosslinking, and therefore the pore size and consequent separation properties of the gel can be controlled by varying the ratio of acrylamide to bis-acrylamide. An example of a matrix formed by a non-polymerization mechanism includes, but is not limited to, an agarose gel. Agarose can be a polysaccharide. The monomeric unit of agarose can be a disaccharide of D-galactose and 3,6-anhydro-L-galactopyranose. In aqueous solutions below a certain temperature (a gelation temperature), for example 35° C., these polymer strands can be held together in a porous gel structure by non-covalent interactions like hydrogen bonds and electrostatic interactions. Heating the solution to increase the temperature above the gelation temperature can break these non-covalent interactions and separate the strands. Then as the solution cools, these non-covalent interactions can be re-established and the gel can form. Therefore, agarose gels can form by gelation through hydrogen bonding and electrostatic interactions. The gelling and melting temperatures may vary depending on the type of agarose. Standard agaroses derived from Gelidium can have a gelling temperature of 34-38° C. (93-100° F.) and a melting temperature of 90-95° C. (194-203° F.), while those derived from *Gracilaria*, due to its higher methoxy substituents, can have a gelling temperature of 40-52° C. (104-126° F.) and melting temperature of 85-90° C. (185-194° F.). The melting and gelling temperatures may be dependent on the concentration of the gel, particularly at low gel concentration of less than 1%. The gelling and melting temperatures are therefore usually given at a specified agarose concentration. Natural agarose can contain uncharged methyl groups and the extent of methylation can be directly proportional to the gelling temperature. Synthetic methylation however can have the reverse effect, whereby increased methylation can lower the gelling temperature. A variety of chemically modified agaroses with different melting and gelling temperatures are available through chemical modifications.

When making polyacrylamide hydrogel particles in droplets, the polymerization initiator may be ammonium persulfate (APS) or a water-soluble photoinitiator. In the situations where APS is used as the initiator, accelerator tetramethylethylenediamine (TEMED) may be added to the carrier oil. For example, 2.5 mL of carrier oil and 10 μL of TEMED may be combined to form TEMED-containing carrier oil. If APS and TEMED-containing carrier oil are used, then the resulting emulsion can be incubated at 65° C. for overnight to induce the polymerization of the polyacrylamide hydrogel. Other water-soluble photoinitiators can be used. In some cases, the photoinitiator can be excited with 365 nm UV (which can be considered safe for nucleic acids). Several options other than LAP exist, such as (a) sodium 4-[2-(4-morpholino)benzoyl-2-dimethylamino]-butylbenzenesulfonate (MBS) which can be synthesized, such as by the methods described in Kojima et al., Chem Mater 10(1998):3429, and (b) molecular complex formed by 2,2-dimethoxy-2-phenyl acetophenone and methylated-β-cyclodextrin (DMPA:MDCD complex) which can be prepared, such as by the methods described in Ayub et al., Advanced Materials Research 1125(2015):84.

In the situations where alginate is used as the polymer framework, the gelling can be triggered by delivering calcium ions directly to the droplets in the microfluidic device, or by releasing of photocaged calcium. In the situations where agarose is used as the polymer framework, the gelling can be triggered by lowering the temperature.

After the biological particles are distributed to multiple partitions and the target nucleic acid has been released, the monomers and cross-linkers within the partition can be polymerized to form a cross-linked polymer network which supports the hydrogel. Several methods can be used to trigger such polymerization. An example method can be using ammonium persulfate (APS) and N,N,N',N'-tetramethylethane-1,2-diamine (TEMED). The APS can be included in the aqueous phase (e.g., in the droplets) and the TEMED can be added to the partitioning oil. After droplet generation, the emulsion can be heated (e.g., at 65° C.) for a prolonged period of time (e.g., overnight), which triggers the polymerization. However, in some applications such process may create difficulties in other aspects such as maintaining the quality of the target nucleic acid. Therefore, in some cases it may be desirable to trigger the polymerization faster and with a milder treatment. Long wavelength UV (e.g., >360 nm) photo-initiation can be an option. Long wavelength UV is usually regarded as safe for most biological molecules (including protein and nucleic acid). Convenient LED-based light source may be available for at least 360 nm, 361 nm, 362 nm, 363 nm, 364 nm, 365 nm, or more illumination.

A number of molecules or molecular complexes can be water-soluble photo-initiator that is compatible with long wavelength UV, for example, lithium- and magnesium phenyl-2,4,6-trimethylbenzoylphosphinates (TMPPL and TMPPM). They are effective water-soluble photo-initiators for the free-radical polymerization of appropriate monomers such as acrylamide and methacrylamide in aqueous solution. TMPPL (also called LAP) can be used to trigger the formation of biocompatible hydrogel. Similarly, sodium 4-[2-(4-morpholino)benzoyl-2-dimethylamino]-butylbenzenesulfonate (MBS), via sulfonation of 2-benzyl-2-(dimethylamino)-1-(4-morpholinophenyl)-1-butanone (BDMB), can be used as water-soluble long wavelength UV photo-initiator. Water-insoluble photo-initiators may also be formulated in water-soluble form such as by complexing with methylated-β-cyclodextrin (MOCD). For example, 2,2-dimethoxy-2-phenyl acetophenone (DMPA) complexed with MOCD as water-soluble photo-initiator can be used.

Single-Cell Reactors: Attachment Chemistry to Solid Support—General

Molecules of interest can be attached to the solid support in a non-specific fashion such as via electrostatic interactions or physical entrapment. For example, solid phase reversible immobilization (SPRI) beads made of polystyrene surrounded by a layer of magnetite, which is further coated with carboxyl molecules, can stably bind polynucleotides in the presence of the "crowding agent" polyethylene glycol (PEG) and salt (e.g., 20% PEG, 2.5M). Similarly, silica beads can stably bind polynucleotides in the presence of guanidium. Variously positively charged beads have been described to bind polynucleotides. As an example of entrapment, when the solid support is a hydrogel and a molecule of interest with hydrodynamic radius larger than the pore size of the hydrogel, the molecule of interest may be attached to the hydrogel-based solid support by physical entrapment.

For more specific attachment, a capture agent may be used. A capture agent can be a chemical composition that mediates the stable attachment of molecules of interest (e.g., polynucleotides of interest) to the solid support. The capture agent may mediate the stable attachment via multiple functions such as binding to a target molecule, serving as a primer to extend on a target nucleic acid molecule, reacting with a target molecule.

Single-Cell Reactors: Attachment Chemistry to Solid Support—General: Capture Agent The compositions or methods provided herein may comprise a capture agent. The capture agent can function as an anchor to immobilize or entrap a molecule of interest (synonymous to target molecule) within a single-cell reactor.

On one hand, the capture agent can bind to a target molecule. On the other hand, the capture agent can associate with the solid support to restrict its own diffusion which in turn results in limited diffusion of the target molecule. In some embodiments, the capture agent is linked to a diffusion-restricting agent within the framework of a hydrogel. A target molecule can be a nucleic acid template or copies thereof, for example, a nucleic acid encoding an immunoreceptor chain or copies thereof.

A capture agent can comprise two moieties: a targeting moiety and an immobilization moiety. The immobilization moiety can be responsible for attaching the capture agent to the solid support including a non-porous solid support and a porous solid support such as a hydrogel. In the case of hydrogel, the immobilization moiety can be attached to the polymer framework (e.g. matrix) supporting a hydrogel or a diffusion-restricting agent. The targeting moiety can be responsible for making stable interaction with the nucleic acid template or copies thereof. The capture agent can be one molecule wherein the targeting moiety and the immobilization moiety are two portions of the same molecule and are covalently bound. The capture agent can be more than one molecule, wherein the targeting moiety and the immobilization moiety can be covalently linked through a linker or non-covalently linked. For example, the immobilization moiety can be a first polynucleotide linked to the polymer framework, and the targeting moiety can comprise a second polynucleotide which can hybridize with the first polynucleotide. It is to be understood that there is no limitation on the type of interaction between the targeting moiety and the immobilization moiety of the capture agent.

In some embodiments, the capture agent comprises a targeting moiety. In some embodiments, the targeting moiety is a polynucleotide, a polypeptide, or a chemical group. In some embodiments, the polynucleotide is a primer or an oligonucleotide aptamer. In some embodiments, the primer is a reverse transcription primer. In some embodiments, the reverse transcription primer comprises a poly-deoxy-thymidine nucleotides sequence. In some embodiments, the polypeptide is an antibody or a fragment thereof, or a peptide aptamer. In some embodiments, the chemical group is a reactive group. In some embodiments, the reactive group forms a covalent bond with a nucleobase of the nucleic acid template. In some embodiments, the reactive group is an NHS ester, a maleimide group, or Label-IT linker and reactive group. In some embodiments, the nucleobase is guanine.

For example, when polynucleotides are molecules of interest, the targeting moiety can be an oligonucleotide which hybridizes with a target polynucleotide. The targeting moiety can be a reverse transcription primer which hybridizes with all mRNA species in a cell. The targeting moiety can be a primer having a specific or designed sequence which hybridizes with a particular DNA or RNA of interest.

Depending on the application and the target molecule, the targeting moiety may be a primer (which can be extended by a polymerase or a reverse transcriptase), an affinity agent that stably binds the target molecule non-covalently, or a bonding agent that forms covalent bond with the target molecule. In some cases, the targeting moiety can be an oligonucleotide that binds its target polynucleotide molecules (e.g., polynucleotide encoding an immunoreceptor chain or copies thereof) by base-pairing.

In some embodiments, the targeting moiety is ACO that can hybridize with an adaptor sequence (e.g., ARS) on a primer thereby linking the primer to the solid support. In some cases, the targeting moiety is an oligonucleotide serving as a primer, e.g., a RT primer or a PCR primer. An extension product from the primer may also be linked to the solid support through the capture agent.

The capture agent can comprise an immobilization moiety. The immobilization moiety can link the capture agent to the solid support. The capture agent can comprise a linker or be attached to a solid support through a linker. The linker can be pre-formed (e.g., PEG linker) or formed by a first reactive group on the capture agent and a second reactive group immobilized on the solid support.

The immobilization moiety may be an NHS ester, a biotin, a maleimide group, a thiol group, an azide group, an avidin or streptavidin, a single-stranded polynucleotide, a biotin group, a methacryl group, or the reaction product thereof. The immobilization moiety may comprise a reactive group.

Examples of the reactive group include a succinimidyl ester, an amide, an acrylamide, an acyl azide, an acyl halide, an acyl nitrile, an aldehyde, a ketone, an alkyl halide, an alkyl sulfonate, an anhydride, an aryl halide, an aziridine, a boronate, a carbodiimide, a diazoalkane, an epoxide, a haloacetamide, a haloplatinate, a halotriazine, an imido ester, an isocyanate, an isothiocyanate, a maleimide, a phosphoramidite, a silyl halide, a sulfonate ester, a sulfonyl halide, an amine, an aniline, a thiol, an alcohol, a phenol, a hyrazine, a hydroxylamine, a carboxylic acid, a glycol, and a heterocycle.

In some embodiments, the reactive group on the immobilization moiety is an electrophilic moiety, which can react to a nucleophilic moiety on the solid support, or vice versa. Either the nucleophilic moiety or the electrophilic moiety can be attached to the immobilization moiety or the solid support. Such electrophilic moieties include, but are not limited to, e.g., carbonyl group, a sulfonyl group, an aldehyde group, a ketone group, a hindered ester group, a thioester group, a stable imine group, an epoxide group, an aziridine group, etc.

Reactive group chemistries that can be used in the present disclosure are not limited to those itemized above. By way of example, in other embodiments, the reaction between the first and second reactive groups can proceed via a dipolarophile reaction. For example, the first reactive group can be an azide and the second reactive group can be an alkyne. Alternatively, the first reactive group can be an alkyne and the second reactive group can be an azide. Cycloaddition reaction involving azide or alkyne-containing polynucleotides can be carried out at room temperature under aqueous conditions by the addition of Cu(II) (e.g., in the form of a catalytic amount of $CuSO_4$) in the presence of a reducing agent for reducing Cu(II) to Cu(I), in situ, in catalytic amount. Reducing agents include ascorbate, metallic copper, quinine, hydroquinone, vitamin K, glutathione, cysteine, $Fe^{2+}$, $Co^{2+}$, and an applied electric potential. Still other reactive chemistries that can be used in the present disclosure, including but not limited to the Staudinger ligation and the olefin metathesis chemistries (see, e.g., Mahal et al., (1997) Science 276:1125-1128).

In some embodiments, the attachment between the capture agent (or molecule of interest) and the solid support is a non-covalent attachment. For example, the capture agent (or molecule of interest) having suitable acidic groups can form strong associations with solid supports carrying hydroxyl or other negatively charged groups. In other variations of this system, other types of moieties having a strong affinity for each other can be incorporated into the reactive groups on the capture agent (or molecule of interest) and the solid support. For example, a capture agent (or molecule of interest) can be coupled with biotin through a suitable reactive group, while the solid support can be coated with avidin, resulting in an extremely strong non-covalent binding between the capture agent (or molecule of interest) and the solid support.

Single-Cell Reactors: Attachment Chemistry to Solid Support—Hydrogel

When the solid support comprises a hydrogel, the immobilization moiety of a capture agent can be attached to the polymer framework (e.g., matrix) supporting a hydrogel or a diffusion-restricting agent.

The immobilization moiety can be reacted with a reactive group on the polymer framework (e.g. hydrogel framework) or the diffusion-restricting agent using chemistries described herein for general solid support. In certain cases, the interaction between the capture agent and the polymer framework can be reversible so that capture agent can be released from the framework if needed. For example, when the immobilization moiety comprises a streptavidin and the polymer framework comprises a biotin, the interaction between the streptavidin and biotin can be reversed by adding an excess amount of free biotins in the presence of denaturant (such as formamide) and with heating. For another example, when the interaction between the immobilization moiety and the polymer framework is through nucleic acid hybridization, the interaction can be reversed by increasing the temperature to melt the nucleic acid duplex.

In some embodiments, the immobilization moiety can associate the matrix or polymer framework through covalent bond or non-covalent interaction. The immobilization moiety can comprise (a) a chemical that is incorporated into the polymer framework, (b) a chemical or protein that stably interact with the polymer framework directly, or (c) a chemical or protein that that stably interacts with the polymer framework indirectly. An example of (a) can be methacryl group, which can be co-polymerized into polyacrylamide gel. An example of (b) can be NHS ester, which can react with primary amine group to form a stable covalent interaction. This example may be applicable if the polymer framework contains primary amine groups. Another example of (b) can be maleimide, which can react with thiol group to form a stable covalent interaction. This example may be applicable if the polymer framework contains thiol groups. Another example of (b) is thiol group, which can react with C—C double bond-containing groups (such as maleimide and acrylate) to form a stable covalent interaction. This example may be applicable if the polymer framework contains C—C double bond-containing groups. Another example of (b) can be azide group, which can react with alkyne group to for a stable covalent interaction. This example may be applicable if the polymer framework contains alkyne group. Another example of (b) can be avidin or streptavidin, which can interact with biotin to for a stable noncovalent interaction. This example may be applicable if the polymer framework contains biotin groups. Another example of (b) can be a single-stranded DNA polynucleotide, which can interact with single-stranded polynucleotide of the reverse complementary sequence, to form a stable noncovalent interaction. This example may be applicable if the polymer framework contains single-stranded polynucleotide. An example of (c) can be biotin. This example may be applicable if the polymer contains biotin, and the hydrogel further contain streptavidin tetramer. In this case, one monomer of the streptavidin can stably interact with the biotin as the immobilization moiety and another monomer of the same streptavidin can stably interact with the biotin on the polymer. In this manner the immobilization moiety can stably interact with the polymer indirectly.

To entrap a nucleic acid molecule within a hydrogel the nucleic acid molecule can be immobilized within the matrix of the hydrogel to prevent the nucleic acid molecule from diffusing out of the hydrogel. The immobilization can be achieved through a capture agent that binds to the nucleic acid molecule either directly or indirectly and also interacts with the matrix of the hydrogel. In some embodiments, the capture agent is linked to the nucleic acid template. In some embodiments, the capture agent is linked to a copy of the nucleic acid template. The capture agent can bind to the matrix through covalent bond or non-covalent interaction.

When the solid support comprises a hydrogel, hydrogel can be functionalized to attach capture probes (or targeting moiety) to the hydrogel framework. Creating hydrogel modified with an immobilized or diffusion-restricted capture agent (e.g., ACO) can be an example of creating functionalized hydrogel. In some embodiments, the capture agent is linked to the polymer framework. In some embodiments, the capture agent is linked to a diffusion-restricting agent (see below). Creating a functionalized hydrogel may be useful to restrict a nucleic acid of interest within the hydrogel so that the nucleic acid of interest, as well as other molecules bound by the nucleic acid of interest (1) does not diffuse within or out of the hydrogel, or (2) can diffuse within or out of the hydrogel in a controlled fashion. In some embodiments, the hydrogel is in the form of hydrogel particle.

When the solid support is hydrogel made of polymerizable monomer or gellable polymer, the immobilization moiety can be a chemical that is co-polymerized with the polymers and/or monomers, a chemical or protein that stably interact with the polymers and/or monomers or a diffusion-restricting agent directly, or a chemical or protein that stably interacts with the polymers and/or monomers or a diffusion-restricting agent indirectly.

The hydrogel particles may be functionalized by directly modifying the building blocks of the hydrogel particles. The building blocks are polymerizable or gellable polymers and/or monomers that are capable of forming a hydrogel or a hardened matrix through a polymerization or a non-polymerization mechanism. For example, when the hydrogel particle is formed by polymerization of building blocks, the capture agent may be attached to the building blocks. Thus, during polymerization, the capture agent can be co-polymerized into the polymer framework. Alternatively, an intermediary molecule (e.g., a linker) may be attached to the building block which can be used to immobilize a tool molecule. The building block of a hydrogel particle may be a monomer. The monomer may be acrylamide, vinyl acetate, vinyl alcohol, methylacrylamide, or acrylic acid. An example of this strategy is co-polymerizing Acrydite™-modified oligonucleotides into polyacrylamide hydrogel. In this example, the oligonucleotide is an example of a capture probe. Another example of this strategy is co-polymerizing 'functionalized acrylate/acrylamide' into polyacrylamide hydrogel. The functionalized acrylate/acrylamide may contain conjugation handles, to which the tool molecule can be attached via conjugation chemistries such as amine-NHS ester reaction, click chemistry, etc. In this example, the conjugation handle may serve as the intermediary molecule. An example of functionalized acrylate/acrylamide can be 3-azidopropyl methacrylate (AzPMA), where the azido group is the conjugation handle to which the capture agent can be attached via click chemistry. Another example of functionalized acrylate/acrylamide is N-(3-aminopropyl)- methacrylamide, where the primary amine group (on the 3-aminopropyl side chain) is the conjugation handle to which the capture agent can be attached via an NHS ester.

The hydrogel particles may be functionalized by modifying the framework instead of the building blocks. After forming a hydrogel particle, the framework of the hydrogel particle can be modified such that the capture agent can be attached. For example, polyhydric character of agarose hydrogel particle can account for its reactivity and therefore hydroxyl functions can be partially or totally derivatized. In this way, several new chemical functions can be grafted along the polymer chain of the agarose gel, such as amine, carboxyl, sulfonate, cyano, and dichlorotriazinyl. For example, glyoxyl agarose can be prepared by etherification of the primary hydroxyl groups of the hydrogel framework with glycidol to introduce diols that can be later oxidized with sodium periodate to generate the glyoxyl group. The modification of the carboxyl group on hydrogels containing acrylic acid can also be readily performed, e.g., using EDC chemistry.

Most of the standard techniques for coupling small molecules, peptides, oligonucleotides, and proteins to hydrogel frameworks can be applicable here. Examples of commonly used derivatization include carboxyl or amine groups, but other functionalities can also be used. Epoxy linkers can be introduced during the polymerization by using a suitable monomer while aldehydes or thiols groups can be introduced after post polymerization procedure in aqueous conditions. Click chemistry can be exploited for the functionalization. Click chemistry reactions and suitable reactive groups for click chemistry reactions include, but are not limited to terminal alkynes, azides, strained alkynes, dienes, dieneophiles, alkoxyamines, carbonyls, phosphines, hydrazides, thiols, and alkenes. For example, in some embodiments, an azide and an alkyne are used in a click chemistry reaction.

The functionalization of polymerizable or gellable polymers or monomers can be used to allow the specific capture of a given target. In certain cases, the desired functionality can be directly added in the prepolymer mixture and allowed to co-polymerize. The feasibility of such approach may depend on the stability of the chosen biomolecules or on the cross-reactivity of certain chemical groups present to the condition of polymerization. However, a small amount of co-monomers with carboxyl or amine functionalities can be used during the polymerization step to allow further functionalization of hydrogels in a post synthesis phase. This approach may be followed for conjugation of molecules that cannot withstand polymerization reaction conditions.

Single-Cell Reactors: Attachment Chemistry to Solid Support—Hydrogel: Diffusion-Restricting Agent In some cases, the capture agent can be immobilized onto a diffusion restricting agent in order to entrap the capture agent within the hydrogel.

A diffusion-restricting agent can be an agent (e.g., a chemical composition) whose diffusion within or out of a hydrogel is restricted. The diffusion-restricting agent may have a hydrodynamic radius that is larger than a pore size of the hydrogel particle. The diffusion-restricting agent may be a particle or a polymer. The particle may be a magnetic bead. The polymer may be polyacrylamide, polyacrylic acid, or PEG.

The diffusion-restricting agent can be a diffusion-restricting polymer. The diffusion-restricting agent can be a long polymer chain directly conjugated on the capture agent so that the conjugated capture agent is large enough to be entangled by the polymer framework. For example, a capture agent can be conjugated with multiple long PEG chains so that the diffusion of the capture agent along with the target molecule is restricted within the framework. In some embodiments, the long polymer chain can be a polyacrylamide chain. In some other cases, the diffusion restricting agent can be a large particle (e.g. micron-sized streptavidin-coated beads). The large particle may be larger than the pore size of the hydrogel so that when the capture agent is associated to the large particle, the capture agent is entrapped within the framework of the hydrogel.

The diffusion-restricting polymer can be a PEG molecule or a polyacrylamide molecule. The diffusion-restriction polymer may or may not participate in forming the framework that supports the mechanical integrity of the hydrogel.

The diffusion-restricting agent can comprise one or more high molecular weight polymers (e.g. polyethylene glycol with molecular weight of 3350, 8000, and 20,000) which may result in a higher hydrodynamic radius than the pore size of the hydrogel or may be otherwise entrapped in the hydrogel, for example by entangling with the polymer framework of the hydrogel. A total molecular weight of the polymer (or chains) can be from 5 kDa to 1000 kDa. In some cases, the total molecular weight of the polymer can be from 5 kDa to 10 kDa, from 10 kDa to 15 kDa, from 15 kDa to 20 kDa, from 20 kDa to 25 kDa, from 25 kDa to 30 kDa, from 30 kDa to 35 kDa, from 35 kDa to 40 kDa, from 40 kDa to 45 kDa, or from 45 kDa to 50 kDa. In some cases, the total molecular weight of the polymer can be from 50 kDa to 100 kDa, from 100 kDa to 150 kDa, from 150 kDa to 200 kDa, from 200 kDa to 250 kDa, from 250 kDa to 300 kDa, from 300 kDa to 350 kDa, from 350 kDa to 400 kDa, from 400 kDa to 450 kDa, or from 450 kDa to 500 kDa. In some cases, the total molecular weight of the polymer can be from 500 kDa to 600 kDa, from 600 kDa to 700 kDa, from 700 kDa to 800 kDa, from 800 kDa to 900 kDa, from 900 kDa to 1000 kDa, from 1000 kDa to 1500 kDa, from 1500 kDa to 2000 kDa, from 2000 kDa to 3000 kDa, or from 3000 kDa to 5000 kDa. The polymer can be a linear polyacrylamide polymer. In some cases, the total molecular weight of the polymer can be at least about 2 kDa, 3 kDa, 4 kDa, 5 kDa, 6 kDa, 7 kDa, 8 kDa, 9 kDa, 10 kDa, 15 kDa, 20 kDa, or more. The liner polyacrylamide polymer may not be used to form the framework of the hydrogel. For example, the linear polyacrylamide polymer can be mixed with agarose in aqueous form above the gelling temperature of the agarose gel, and upon decreasing the temperature to below the gelling temperature, the agarose can go through gelation to form a polymer framework which can trap the linear polyacrylamide polymer within the framework. In some embodiments, the acrylamide monomers can be mixed with agarose in aqueous form during polymerization. The chemistries described herein used to attach capture agent to cross-linked polyacrylamide hydrogel can also be used to attach tool molecules to linear polyacrylamide polymer.

The diffusion-restricting agent may be a large particle. The large particle may have a size that is larger than the pore size of the hydrogel. One can choose a large particle, and adjust the pore size of the hydrogel accordingly. The size (as represented by diameter) of the large particle may be from 0.5 µm to 5 µm. In some cases, the size of the large particle may be from 0.5 µm to 1 µm, from 1 µm to 1.5 µm, from 1.5 µm to 2 µm, from 2 µm to 2.5 µm, from 2.5 µm to 3 µm, from 3 µm to 3.5 µm, from 3.5 µm to 4 µm, from 4 µm to 4.5 µm, or from 4.5 µm to 5 µm. In some other cases, the size of the large particle may be from 5 µm to 10 µm, from 10 µm to 20 µm, from 20 µm to 30 µm, from 30 µm to 40 µm, or from 40 μm to 50 μm. In some cases, the size of the large particle may be at least about 1 μm, 5 μm, 10 μm, 20 μm, or more.

Single-Cell Reactors: Molecules of Interest

In some embodiments, a single-cell reactor comprises molecules of interest. In some embodiments, the molecules of interest are nucleic acids of interest. In some embodiments, the molecules of interests are attached to the solid support. In some embodiments, the nucleic acids of interest are attached to the solid support. In some embodiments, a single-cell reactor may comprise a first nucleic acid and a second nucleic acid. In some embodiments, a single-cell reactor may comprise a solid support to which a first nucleic acid and a second nucleic acid are attached. The attachment may be stable attachment. The attachment may be reversible attachment.

The first and/or the second nucleic acid can be mRNA encoding an immunoreceptor or immunoreceptor chain. The first and/or the second nucleic acid may be the reverse transcription products (i.e., cDNA products) of the mRNAs encoding the immunoreceptor or immunoreceptor chain. The reverse transcription products may be template-switched reverse transcription products. The first and/or the second nucleic acid can further comprise an adaptor sequence. The single-cell reactor may further comprise copies of the first nucleic acid and the second nucleic acid. In some cases, the copies of the first and the second nucleic acid molecules are attached to the solid support.

In various embodiments, a single-cell reactor comprises a fused bipartite immunoreceptor polynucleotide. In some embodiments, the fused bipartite immunoreceptor polynucleotide is bound to the capture agent or the solid support. In some embodiments, the fused bipartite immunoreceptor polynucleotide is a deoxyribonucleic acid (DNA), a ribonucleic acid (RNA), or a combination thereof. The fused bipartite immunoreceptor polynucleotide may be a modified DNA, for example, a methylated DNA. In some embodiments, the single-cell reactor may further comprise a plurality of copies of the fused bipartite immunoreceptor polynucleotide.

In some embodiments, a nucleic acid of interest is a nucleic acid molecule encoding a TCRα chain, a TCRβ chain, a TCRγ chain, a TCRδ chain, a heavy chain, or a light chain. In some embodiments, the nucleic acid of interest is a fused bipartite immunoreceptor polynucleotide or copies thereof.

In some embodiments, a copy of the nucleic acid template is an extended primer (or primer extension product). A copy of a nucleic acid template can include a synthesized product having the same sequence of the nucleic acid template or a reverse complementary sequence of the nucleic acid template. In some embodiments, a copy of the nucleic acid template is an extended forward or reverse primer. In some embodiments, a copy of the nucleic acid template is an extended reverse transcription (RT) primer. In some embodiments, a copy of the nucleic acid template is an extended amplification primer. As used herein, an "extended primer" or "primer extension product" refers to a primer which has undergone primer extension during template-dependent nucleic acid synthesis, including but not limited to nucleic acid amplification, second strand synthesis and reverse transcription. To immobilize or entrap the nucleic acid template or copies thereof, a primer may have an adaptor sequence which is not hybridizable or complementary to the nucleic acid template. The adaptor sequence can be linked to a capture agent, wherein the capture agent is further linked to a diffusion-restricting agent within the framework. In some embodiments, the adaptor sequence hybridizes to a sequence of the capture agent. In some embodiments, the adaptor sequence of the primer can be a nucleic acid sequence continuously from the portion that is hybridizable or complementary to the template. The adaptor sequence itself may not be hybridizable or complementary to the template. In some embodiments, the adaptor sequence of the primer can be linked to the portion that is hybridizable or complementary to the template through a chemical linker. Various chemical linkers can be used such as hexaethyleneglycol.

Single-Cell Reactors: Reactant in Aqueous Phase

The aqueous phase of a single-cell reactor may comprise enzymes which use nucleic acids as a substrate. Examples of these enzymes include DNA polymerase, RNA polymerase, reverse transcriptase, restriction enzymes, endonucleases, exonucleases, enzymes in the USER mix (New England Biolabs), ligases.

The aqueous phase of a single cell reactor may comprise primers. Thus, a single cell reactor may comprise both a primer and a nucleic acid template (e.g., a nucleic acid sequence encoding a chain of an immunoreceptor), wherein the primer may be in the aqueous phase and the nucleic acid template may be attached to the solid support. The primer can be any primer used to perform a template-dependent nucleic acid synthesis, including but not limited to reverse transcription (RT) primer and an amplification primer. In some embodiments, a first primer and/or a second primer are compartmentalized with the nucleic acid template in the vessel. In some embodiments, a forward primer and/or a reverse primer are compartmentalized with the nucleic acid template in the vessel.

The aqueous phase of a single-cell reactor may comprise template-switching oligos (TSOs) which is useful to attach a common sequence (also called an adaptor sequence) to the 3' end of reverse transcription product.

Single-Cell Reactors: Sequential Addition of Reagents

In some embodiments, different reagents may be made to contact the target molecules originating from the same cell in a defined order, rather than simultaneously. Similarly, in some embodiments, some reagents or reaction byproducts may be removed before the next reaction occurs. For example, lysis buffer may be added to lyse the cells (FIG. 2, panel (b)), and reverse transcriptase and thermostable DNA polymerases may be added to reverse transcribe (RT) and PCR-amplify the mRNA (FIG. 2, panel (c)). In this situation, the lysis buffer may inhibit the RT and/or PCR, and may need to be removed before the RT-PCR step. Some aspects of the present disclosure provide methods to achieve these goals.

In the present disclosure, the addition of new reagents and/or removal of old reagents, byproducts and wastes are collectively called "reagent exchange". In the situations where reagent exchange is needed, inter-cell sequence contact (e.g., a sequence from a first cell in contact with another sequence from a second cell) which can result in cross-contamination may need to be minimized during the reagent exchange. Use of solid support may help minimize inter-cell sequence contact. For example, a well or a microwell may be used as a single-cell reactor, and in this situation, the mRNA, cDNA or amplified DNA molecules that encode the immunoreceptor can be attached to the surface of the well or microwell by sequence-specific or non-sequence-specific interactions. For example, an oligonucleotide serving as a capture agent (e.g., "affinity capture oligo (ACO)") can be modified onto the surface by various chemistries provided herein. At the same time, some or all of the RT and PCR primers can be appended with an oligonucleotide whose sequence is complementary to the capture oligo, optionally via a flexible linker (e.g., ethylene glycol spacers such as $PEG_4$ for $PEG_6$). In some examples described herein, the appended oligonucleotide is referred to as "affinity retention sequence (ARS)". The length of ACO or ARS can be from about 5 to about 10, from about 10 to about 15, from about 15 to about 20, from about 20 to about 30, or from about 30 to about 50 nucleotides. The length of ACO or ARS can be at least about 5, 10, 15, 20, 25, 30, or more. The capture ACO:ARS interaction can be replaced by other covalent or non-covalent interactions such as biotin-streptavidin interaction. Alternatively, some or all of the RT or PCR primers may be attached to the surface directly, for example, through chemical bonds formed between reactive groups on the primers and the surface.

For example, the aqueous phase of the water-in-oil droplet may contain monomers or polymers which, upon trigger, can form a hydrogel particle (i.e., a hardened particle). ACOs can be bound to or entrapped in the hydrogel particles such that the diffusion of ACO within or out of the hydrogel particles can be restricted. The ACO can be linked to a diffusion-restricting agent. For example the ACO can be covalently or non-covalently linked to the polymer that serves as the framework of the hydrogel particle. The ACO may also be attached to a particle or a polymer which is entrapped in the hydrogel framework. This way, RT and PCR primers can be appended with ARS (optionally via a flexible linker) to minimize inter-cell sequence contact while other reagents, byproducts and wastes can be diffused into or out of the hydrogel particle. Alternatively, the some or all of the RT or PCR primers may be directly attached to the polymer framework or to the diffusion-restricting agent. When the hydrogel framework is sufficiently dense, large molecules such as mRNA, mRNA:cDNA hybrid and PCR product maybe too large to diffuse out of the hydrogel particle (e.g., 1 kb dsDNA may not diffuse freely in 4% agarose gel), these molecules may be entrapped in the polymer framework without any specific reaction with the polymer framework or diffusion-restriction agent. In a sense, in these situations these large molecules are diffusion-restricted themselves. Methods to entrap nucleic acid templates or copies thereof and biological particles are described in U.S. patent applications 62/609,756 and 62/674,214, each of which is hereby incorporated by reference herein in its entirety.

The diffusion-restricting agent can be an agent that is prevented from free diffusion and/or can function to restrict a target molecule from free diffusion when the target molecule is attached to the agent. A target molecule can be diffusion-restricted within a single-cell reactor when the molecule is, for example, (i) directly or indirectly attached to the surface of a single-cell reactor having a solid support, or (ii) directly or indirectly attached to the polymer framework or a diffusion-restricting agent within a hydrogel, or (iii) entrapped in the hydrogel.

In some cases, reagents, byproducts and wastes may not be diffusion-restricted and can diffuse into and out of hydrogen particles. In some cases, to increase diffusion efficiency, the hydrogel particle may be turned into sol phase.

In some other cases, a reaction in the hydrogel particle may require the temperature to be raised above the melting point of the thermo-reversible gel (e.g., during PCR). The hydrogel particles may be re-emulsified which can be done by simply mixing the hydrogel particles and carrier oil and agitating the mixture (e.g., by vortexing and by flicking) or by using microfluidics chips. The newly formed 'gel-in-oil' droplets may also be used as single-cell reactors. In some embodiments, while the solid support may temporarily lose its mechanical integrity (e.g., the thermo-reversible hydrogel particle such as an agarose particle may melt at high temperature that may be necessary for the primers to bind targets) or the target molecules (e.g., the immunoreceptor-encoding polynucleotide) may temporarily dissociate from the solid support (e.g., if DNA hybridization mediates the attachment of the target molecules to the solid support), once the temperature is lowered, the solid support may form again (e.g., agarose may gel) and the target molecules may re-attach to the solid support. In some embodiments, more than 50%, more than 60%, more than 70%, more than 80%, or more than 90% of the volume in the compartment is occupied by the thermo-reversible particle. In such case, after the melted particle is mixed with other aqueous content in the compartment, the dilution of the gellable polymer can be limited to less than about 2 fold, 1.7 fold, 1.5 fold, 1.3 fold, 1.2 fold or less. Therefore, the diluted gellable polymer may still form gel at appropriate experimental temperature (e.g., room temperature or 4° C.).

In some embodiments, the cycles of (1) carrying out a reaction in emulsion, (2) forming gel (e.g., by cooling), (3) demulsification, (4) diffusion-based reagent exchange, and (5) re-emulsification can be repeated multiple times. In some cases, washing the hydrogel particles may be carried out after demulsification.

As an example of the procedure, one can capture DNAs or RNAs encoding an immunoreceptor from the same cell in a hydrogel particle (which is formed by a water-in-oil droplet containing agarose upon cooling), demulsify the 'gel-in-oil' emulsion, and carry out diffusion-based reagent exchange by washing the hydrogel particles in a buffer. The reagent exchange may be performed at any step during methods described herein, such as after capturing nucleic acids encoding the immunoreceptor, after reverse transcription, after a pre-amplification step, or other steps when performing reagent exchance may be needed. For example, one can capture RNAs encoding an immunoreceptor, perform reverse transcription and/or second strand synthesis (to add adaptor sequences), and then perform reagent exchange to diffuse amplification primers and reagents. For another example, one can capture RNAs encoding an immunoreceptor, perform reverse transcription and/or second strand synthesis (to add adaptor sequences), perform an pre-amplification step, and then perform reagent exchange to diffuse additional amplification primers and reagents. In some cases, the hydrogel particles may be re-emulsified to carry out further reactions. After re-emulsification, each of the re-emulsified hydrogel particles can be encapsulated or surrounded by oil. In some cases, the re-emulsified hydrogel particles may be melted when encapsulated or surrounded by oil. For example, the re-emulsified hydrogel particles may be melted during a reaction carried out at a temperature higher than the gelling temperature of the hydrogel particles.

Solid Supports Modified with Immunoreceptor-Encoding Polynucleotides

The present disclosure provides a plurality of solid supports modified with immunoreceptor-encoding polynucleotides. In some embodiments, a solid support (e.g., a bead or a wall of a microwell) contain target polynucleotides from one cell (a feature called 'single cellularity'). The target polynucleotides may be immunoreceptor-encoding polynucleotides. The immunoreceptor may be a TCR or a BCR.

Providing such plurality of solid supports may involve partitioning immunoreceptor-expressing cells or their nuclei (or source immunoreceptor-expressing biological particles, or referred to as biological particles) into a plurality of compartments.

A plurality of solid supports each modified with a first and a second immunoreceptor-encoding polynucleotides originated from a single biological particle can be provided by (1) partitioning a plurality of biological particles into a plurality of compartments wherein each compartment (a) also contains one or more pre-formed solid support, or (b) can be turned into a hardened particle which may serve as a solid support, (2) in each compartment lyse the biological particle or otherwise release target DNA or mRNA molecules encoding the immunoreceptor chains, (3) in each compartment attach the target DNA or mRNA molecules to the solid support(s).

In some embodiments, the capture agent can be a primer. The primer can be extended using the immunoreceptor-encoding polynucleotides as a template. Therefore the first and second immunoreceptor-encoding polynucleotides attached to a solid support may be primer extension product. The primer may recognize the C region (a region on the polynucleotide encoding the constant domain), J region, or V region of an immunoreceptor-encoding polynucleotide. The primer may be a forward primer (having part of the sense sequence of the immunoreceptor) or reverse primer (having part of the antisense sequence of the immunoreceptor). The capture agent can be attached to the pre-formed solid support or the hardened particle. The cells can be lysed in the compartment by adding lysis buffer to the compartment or by raising temperature. The lysis may cause the release of the immunoreceptor-encoding polynucleotides, which may bind to the capture agent. The compartment can also contain a DNA polymerase or a reverse transcriptase. In this case the primer bound to the immunoreceptor-encoding polynucleotide may be extended using the immunoreceptor-encoding polynucleotide as a template, forming a primer extension product. The compartment may also contain a template-switching oligo (TSO). In some embodiments, the capture agent may comprise a TSO. In the presence of TSO, the reverse transcription product can be extended at its 3' end with a sequence complementary to the TSO. The content of each compartment may comprise two primers described herein, each designed to bind one of the bipartite immunoreceptor chain-encoding polynucleotide. For example, the content of each compartment may comprise two primers, one designed to bind TCR alpha chain-encoding polynucleotide, and the other designed to bind TCR beta chain-encoding polynucleotide.

The primer extension product may have a common sequence on one or both ends. The primer may be designed to bind the C region of the sequence encoding an immunoreceptor. Since the sequence of the C region is constant, only one primer may be needed for one type of immunoreceptor chain (e.g., IgG, IgA, IgM, IgK, IgL, TCR alpha, TCR beta). For example, one primer can be used to capture the TCR alpha chain-encoding polynucleotide from all cells used in one experiment. Therefore, the sequence of the primer can be considered a common sequence. Since C region is downstream of the rearranged V(D)J region on the sense strand, this common sequence is called downstream common sequence. The C region-targeting primer can be used if mRNA is the target polynucleotide. If TSO and a template switching-capable reverse transcriptase are present in the compartment, the 3' end of the RT product can be extended with [TSO*]. Since the TSO sequence may be constant in all compartments, therefore all cells, the TSO sequence is also a common sequence. Since it is upstream of the V(D)J region on the sense strand, it is called an upstream common sequence. Since the TSO sequence can be arbitrarily designed and does not have to bind any part of the target sequence, the TSO sequence is also called an adaptor sequence. In this example, the primer extension product has common sequences both upstream and downstream to the V(D)J region, and these common sequences can be used for further amplification and fusion reactions.

When DNA is used as a template, a panel of primers can be designed for each J region or V region. Since J regions and V regions are not constant, an additional adaptor sequence may be appended at the 5' end of each of the primers in the panel. The adaptor sequence can be a downstream common sequence (e.g., when the primers are designed to bind the J region) or an upstream common sequence (e.g., when the primers are designed to bind the V region).

Methods to partitioning biological particles (e.g., cells, nuclei, exosomes, and the like) include, for example, microfluidics based methods and non-microfluidics based methods (e.g., vortexing). The present disclosure provides methods comprising partitioning source biological particles into compartments so that in some compartments there is only one biological particle in a compartment. In some embodiments, at least about 50%, 60%, 70%, 75%, 80%, 85%, 90%, 95%, 96%, 97%, 98%, 99%, or 100% of the compartments contain zero or only one biological particle. In some embodiments, at least about 50%, 60%, 70%, 75%, 80%, 85%, 90%, 95%, 96%, 97%, 98%, 99%, or 100% of the compartments contain zero or only one primer delivery particle.

The number of partitions or compartments employed can vary depending on the application. For example, the number of partitions or compartments can be about 5, 10, 50, 100, 250, 500, 750, 1000, 1500, 2000, 2500, 5000, 7500, or 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000, or more. The number of partitions or compartments can be at least about 1, 5, 10, 50, 100, 250, 500, 750, 1000, 1500, 2000, 2500, 5000, 7500, or 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000, or more. The number of partitions or compartments can be less than 5, 10, 50, 100, 250, 500, 750, 1000, 1500, 2000, 2500, 5000, 7500, or 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000, or more. The number of partitions or compartments can be about 5-10000000, 5-5000000, 5-1000000, 10-10000, 10-5000, 10-1000, 1000-6000, 1000-5000, 1000-4000, 1000-3000, or 1000-2000.

The number of biological particles that are partitioned into compartments can be about 1, 2, 3, 4, 5, 10, 50, 100, 250, 500, 750, 1000, 1500, 2000, 2500, 5000, 7500, or 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000, or more. The number of biological particles that are partitioned into compartments can be at least about 1, 5, 10, 50, 100, 250, 500, 750, 1000, 1500, 2000, 2500, 5000, 7500, or 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000, or more. The number of biological particles that are partitioned into compartments can be less than 2, 5, 10, 50, 100, 250, 500, 750, 1000, 1500, 2000, 2500, 5000, 7500, or 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000, or more. The number of biological particles that are partitioned into compartments can be about 5-10000000, 5-5000000, 5-1000000, 10-10000, 10-5000, 10-1000, 1000-6000, 1000-5000, 1000-4000, 1000-3000, or 1000-2000.

In some embodiments, the compartments are wells in a standard microwell plate with separation aided by sorting. In some embodiments, the sorter is a fluorescence activated cell sorter (FACS). Additionally, partitioning can be coupled with automated library generation in separated microfluidics chambers, as is the case with the Fluidigm C1. In some embodiments, the partition is a subnanoliter well and particles are sealed by a semipermeable membrane.

After partitioning a single biological particle into an individual compartment, the biological particle can be manipulated to release its constituents. For example, a single cell or nucleus can be lysed to release its DNAs, RNAs, proteins, and/or peptides into the compartment for further analysis. In some embodiments, the DNA or RNA may be immunoreceptor-encoding polynucleotides.

In accordance with certain aspects, the biological particles such as cells may be partitioned along with a lysing agent (e.g., cell lysis reagents) in order to release the contents of the cells within the partition. In such cases, the lysis agents can be contacted with the cell suspension concurrently with, or immediately prior to the introduction of the cells into the partitioning junction/droplet generation zone, e.g., through an additional channel or channels upstream of channel junction. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, Mo.), as well as other commercially available lysis enzymes. Other lysing agents may additionally or alternatively be co-partitioned with the cells to cause the release of the cell's contents into the partitions. For example, in some cases, surfactant based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Similarly, lysis methods that employ other methods may be used, such as electroporation, thermal, acoustic or mechanical cellular disruption may also be used in certain cases, e.g., non-emulsion based partitioning such as encapsulation of cells that may be in addition to or in place of droplet partitioning, where any pore size of the encapsulate is sufficiently small to retain nucleic acid fragments of a desired size, following cellular disruption.

In addition to the lysing agents co-partitioned with the cells described above, other reagents can also be co-partitioned with the cells, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated cells, the cells may be exposed to an appropriate stimulus to release the cells or their contents from a co-partitioned microcapsule. For example, in some cases, a chemical stimulus may be co-partitioned along with an encapsulated cell to allow for the degradation of the microcapsule and release of the cell or its contents into the larger partition.

Additional reagents may also be co-partitioned with the cells, such as endonucleases to fragment the cell's DNA, DNA polymerase enzymes and dNTPs used to amplify the cell's nucleic acid fragments. Additional reagents may also include reverse transcriptase enzymes, including enzymes with terminal transferase activity, primers and oligonucleotides, and switch oligonucleotides (also referred to herein as "switch oligos" or "template switch oligos", or "TSOs") which can be used for template switching. In some cases, template switching can be used to increase the length of a cDNA. In one example of template switching, cDNA can be generated from reverse transcription of a template, e.g., cellular mRNA, where a reverse transcriptase with terminal transferase activity can add additional nucleotides, e.g., polyC, to the cDNA that are not encoded by the template, such, as at an end of the cDNA. Switch oligos can include sequences complementary to the additional nucleotides, e.g. polyG. The additional nucleotides (e.g., polyC) on the cDNA can hybridize to the sequences complementary to the additional nucleotides (e.g., polyG) on the switch oligo, whereby the switch oligo can be used by the reverse transcriptase as template to further extend the cDNA. Switch oligos may comprise deoxyribonucleic acids, ribonucleic acids, modified nucleic acids including locked nucleic acids (LNA), or any combination.

Although the above described agents can be co-partitioned with the cells or other biological particles, it is not necessary to co-partition those agents. Since the methods described herein allow formation of hardened particles and entrapping of target molecules within the hardened particles, various steps can be performed after formation of hardened particles by directly mixing the agents with pooled hardened particle in a test tube. The target molecules originated from a single cell would still maintain their identity without mixing with the target molecules from a different single cell. For example, the lysing agents can be added after pooling the hardened particles. For another example, the agents for reverse transcription can be added after pooling the hardened particles. It is to be understood that the hardened particles with entrapped target moieties allow for various manipulations in bulk.

In various embodiments, the biological particle can be co-partitioned with a solution comprising polymerizable or gellable polymers and/or monomers. In some embodiments, the biological particle is co-partitioned with polymerizable or gellable polymers. In some embodiments, the biological particle is co-partitioned with polymerizable or gellable monomers. In some embodiments, the biological particle is co-partitioned with a mixture of polymerizable or gellable polymers and monomers. The polymers may be of the same chemicals or different chemicals. The monomers may be of the same chemicals or of different chemicals. In some embodiments, the solution further comprises agents necessary for initiating a gelation process. In some embodiments, the solution further comprises agents necessary for initiating a polymerization process of forming a hardened particle (e.g., a hydrogel particle).

After reactions provided herein, the pre-formed solid supports and hardened particles can be retrieved so that they can be immersed in aqueous solutions for further operation.

When the aqueous content of a solid-walled compartment is converted into a hardened particle, the hardened particle can be removed from the compartment by deforming the solid scaffold, dissolving the solid scaffold, using centrifugation force to drive the hardened particles through the opening of the vessel, or a combination thereof.

In some embodiments, the compartments are liquid-walled (e.g., water-in-oil droplets). In this case the hardened particle can be removed from the compartment by coalescing the compartment, e.g., by demulsifying the water-in-oil emulsion. Demulsification can be achieved with demulsifiers, such as perfluorooctanol and chloroform. The demulsification method can depend on the carrier oil used. For fluorocarbon oil, the emulsion can be demulsified by adding 20%-100% (vol/vol) 1H,1H,2H,2H-Perfluorooctanol in HFE-7500 oil (20%-100% PFO). For mineral oil, the emulsion can be demulsified by Phenol/chloroform/isoamyl alcohol (25:24:1; vol/vol/vol; Fisher, cat. no. BP17521). Demulsification can also be achieved by non-chemical methods such as using a hand-held antistatic gun and washing with aqueous solution on top of a cell strainer.

Adaptor Addition

The present disclosure provides methods to obtain a plurality of solid supports each modified with a first and a second immunoreceptor-encoding polynucleotides originated from a single biological particle. In some embodiments, the first and the second polynucleotides have both the upstream common sequence (e.g., TSO sequence) and the downstream common sequence (e.g., sequence of primers binding the C region). In this case, these solid supports can be directly used for pre-amplification or fusion.

In other cases, the first or the second polynucleotides may have zero or only one common sequence either upstream or downstream to the rearranged V(D)J sequence. In this case an additional common sequence can be added. The additional common sequence can be an adaptor sequence. The adaptor sequences can be added by primer extension wherein the primer contains an adaptor sequence at its 5' end. In some embodiment a panel of primers can be used, wherein all primers share the same adaptor sequence. Each primer of the panel may recognize a different V region that may be present in the immunoreceptor repertoire of the source immunoreceptor-expressing cell. Each primer of the panel may recognize a different J region that may be present in the immunoreceptor repertoire of the source immunoreceptor-expressing cell. An example to add upstream adaptor sequences using a panel of primers targeting V regions is provided in the Example section.

To carry out these primer extension reactions while maintaining single cellularity (i.e., ensuring that the immunoreceptor-encoding polynucleotides attached to a solid support originate from one cell), single-cell reactors can be used.

When the mechanical strength and the attachment of the first and second polynucleotide to the solid support can withstand the temperature of the primer-extension reaction, the solid supports can be immersed in the continuous volume of an aqueous solution comprising primers and enzymes. Otherwise, the solid supports can be re-partitioned into compartments wherein each compartment of the majority of the compartments contains no more than one solid support. In this case the compartments may also comprise primers and enzymes for primer-extension reaction.

When the solid supports are particles, the re-partition of solid supports can be done with the same methods that are used to partition biological particles, except the biological particles are replaced by solid supports (e.g., particles). When the solid supports are hydrogel particles, enzymes and primers can be diffused into the hydrogel particles, and the hydrogel particles may be re-emulsified using other methods described herein.

Using the methods described herein, one can provide a plurality of solid supports each modified with a first and a second immunoreceptor-encoding polynucleotide originated from a single biological particle, wherein both the first and the second immunoreceptor-encoding polynucleotide have an upstream common sequence and a downstream common sequence.

Fusion of Paired Bipartite Immunoreceptor Polynucleotides

Provided herein are compositions and methods to produce a fused bipartite immunoreceptor polynucleotide comprising a first nucleic acid sequence and a second nucleic acid sequence. The first nucleic acid sequence can encode a first immunoreceptor chain and the second nucleic acid sequence can encode a second immunoreceptor chain. The first immunoreceptor chain and the second immunoreceptor chain can form a functional immunoreceptor receptor. The nucleic acid sequences encoding the first immunoreceptor chain and the second immunoreceptor chain can be from a single cell. The first immunoreceptor chain and the second immunoreceptor chain can be from a cognate pair combination (or natively paired combination) of an immunoreceptor obtained from a cell (e.g., an immune cell). The first and/or the second nucleic acid sequence can encode a full-length variable domain (e.g., including all three CDRs: CDR1, CDR2, and CDR3) of an immunoreceptor. The first and/or the second nucleic acid sequence can encode a partial variable domain comprising one or more CDRs selected from the group consisting of CDR1, CDR2 and CDR3. The first and/or the second nucleic acid sequence can further encode a constant domain of an immunoreceptor. The constant domain can be a full-length constant domain, or the extracellular constant domain, or any portion of the full-length constant domain. In some cases, the fused bipartite immunoreceptor polynucleotide is at least 600, at least 700, at least 800, at least 900, at least 1000, at least 1200, at least 1500, or more nucleotides (or base pairs) in length. In some cases, the fused bipartite immunoreceptor polynucleotide is at least 1000, at least 1500, at least 2000, at least 2500, or more nucleotides (or base pairs) in length. In some case, the fused bipartite immunoreceptor polynucleotide is from 600 to 1000 or from 1500 to 3000 nucleotides (or base pairs) in length.

Within a single-cell reactor, various methods can be used to fuse the sequences encoding two peptide chains of the bipartite immunoreceptor, such as ligation and PCR-based methods. As used herein, "fuse" refers to link or physically link. The sequences encoding two peptide chains of the bipartite immunoreceptor can be from a single cell (or a single source immunoreceptor-expressing cell as described herein). A choice between copying or amplifying the target nucleic acids from the genomic DNA or from the mRNA by performing RT-PCR can be made based on the nature of the expressed mRNAs. Using the genomic DNA as template may require no reverse transcription step but may have the risk of amplifying non-functional receptors, while using mRNA as the template can benefit from higher copy numbers and can capture functional, expressed receptors. The physical fusion of two nucleic acids encoding two peptide chains of the bipartite immunoreceptor can occur through multiple mechanisms. For example, the physical fusion can be achieved through standard splicing-by-overlap-extension PCR (SOE-PCR) (also known as fusion PCR, crossover PCR, or overlapping extension PCR, abbreviated as OE-PCR), whereby two of the PCR primers have complementary sequences so that the two amplicons function as primers and they fuse to each other. One advantage to this method may be that the overlap sequence can be designed so that the fused construct is immediately in a usable scFv format. For another example, the fusion can be achieved through a mechanism similar to the SOE-PCR in that tags are incorporated into the PCR primers. In this case, the tags can contain loxP sites so that fusion can occur upon Cre-mediated recombination. The physical fusion can also be achieved by ligation including blunt end ligation and sticky end ligation.

Pre-Amplification

Prior to the fusion reaction, the target nucleic acids encoding each of the bipartite immunoreceptor peptide chains can be amplified, referred to as "pre-amplification". The pre-amplification may comprise two procedures, including a preparation procedure and an amplification procedure. During a preparation procedure, one or more reactions may be carried out in order to add an oligonucleotide having a common sequence (e.g., an adaptor sequence) to a target nucleic acid before amplification. For example, the preparation procedure may comprise nucleic acid synthesis of the target nucleic acids using a primer with an adaptor sequence to generate a newly synthesized product with an adaptor. The adaptor may not be hybridizable or complementary to a target nucleic acid. As used herein, "hybridizable" refers to forming stable base pairing between two nucleic acid strands under a given condition. The adaptor can comprise a pre-determined sequence and can be used to bind primers for the amplification procedure. In some cases, after preparation procedure, the newly synthesized product comprises two adaptor sequences, with one adaptor sequence on each end.

The sections above describe general methods to provide a plurality of solid supports each modified with a first and a second immunoreceptor-encoding polynucleotide originated from a single biological particle, wherein both the first and the second immunoreceptor-encoding polynucleotide have an upstream common sequence and a downstream common sequence. Provision of such plurality of supports can be a result of carrying out the preparation procedure.

In some cases, the target nucleic acids are DNA (e.g., genomic DNA), and the preparation procedure can comprise using a first primer with a first adaptor sequence and a second primer with a second adaptor sequence to generate a copy of the DNA. The first adaptor sequence and the second adaptor sequence can be pre-designed or artificial sequence. One of the first primer and the second primer can be used to link the copy of the DNA to a polymer framework of a hydrogel particle. Both adaptor sequences may be used to bind primers for further amplification. The target nucleic acids of the bipartite immunoreceptor can be genomic DNA which may contain introns. Primers may be designed to synthesize (or copy) a region without introns, for example, primers can be designed to synthesize (or copy) only the variable domain for a TCR chain as the introns are usually located between the J region and the C region.

In some cases, the target nucleic acids of the bipartite immunoreceptor are mRNA. And in such cases, an RT step may be carried out prior to amplification by PCR. The RT primer can be diffusion-restricted. In some cases, the RT primer may not be diffusion-restricted. The RT primer can be the targeting moiety of a capture agent. For example, the RT primer can be linked directly or indirectly to a polymer framework if the single-cell reactor is a hydrogel particle. Various methods described herein to immobilize a capture agent on a surface or solid support or framework can be used to link the RT primer to the polymer framework. The RT primer can be linked to a diffusion-restricting agent. As a result of RT step, the RT product (cDNA, or an extended RT primer), can be linked directly or indirectly to the polymer framework (or can be diffusion-restricted). During RT step, template switch using a template switching oligo (TSO) may be carried out. In some cases, a template switch step is carried out during the RT step, and the template-switched RT product is linked to the polymer framework or is diffusion-restricted. The TSO may function as an adaptor sequence which can be used to bind primers during amplification procedure. The RT primer may be a poly-T or a sequence hybridizable or complementary to a sequence of the constant domain. In some other cases, a template switch may not be carried out and a second strand synthesis (SSS) step is carried out after RT step. During the SSS step, a panel of primers having a common adaptor sequence can be used.

In pre-amplification, the amplification product (or amplicon) may encode all CDR sequences of an immunoreceptor peptide chain. There are various ways to amplify the sequence containing all CDR sequences of a nucleic acid (e.g., DNA and mRNA) encoding an immunoreceptor peptide chain. Non-limiting examples are described herein. For example, a template switching reaction can be carried out during RT. If template switching using a TSO is carried out during RT and the cDNA is amplified by a forward primer essentially having the same sequence of the TSO, and a reverse primer recognizing the C region of the immunoreceptor polynucleotide, the entire V region and the V(D)J junction can be amplified, encompassing CDR1, CDR2, and CDR3 sequences of an immunoreceptor chain (e.g., FIG. 4A, arrows (1)-(2)). Alternatively, if template switching is not carried out during RT, a forward primer may be designed to recognize the sequence on or upstream of FR1 (i.e., framework 1, which is upstream of CDR1) segment of the immunoreceptor chain. This forward primer may be used in SSS or PCR (e.g., FIGS. 5A and 5B, arrows (1)-(3)).

The V genes of immunoreceptors can be very diverse. Thus to amplify immunoreceptor chains in a given immune cell type (e.g., T cell or B cell) in a given organism (e.g., human), a panel of 10 to 100 primers (referred to as "V gene primers") may be designed. In some cases, a panel of at least 2, 5, 10, 15, 20, 25, 30, 35, 40, 45, 50, 55, 60, 65, 70, 75, 80, 85, 90, 95, or more primers may be designed to target (e.g., amplify) at least 2, 5, 10, 15, 20, 25, 30, 35, 40, 45, 50, 55, 60, 65, 70, 75, 80, 85, 90, 95, or more different V genes. In some cases, all possible immunoreceptor chains in a given immune cell type in a given organism are amplified.

In human, there can be more than 40 functional V genes for TRA, including TRAV1-1, TRAV1-2, TRAV2, TRAV3, TRAV4, TRAV5, TRAV6, TRAV7, TRAV8-1, TRAV8-2, TRAV8-3, TRAV8-4, TRAV8-6, TRAV9-1, TRAV9-2, TRAV10, TRAV12-1, TRAV12-2, TRAV12-3, TRAV13-1, TRAV13-2, TRAV14, TRAV16, TRAV17, TRAV18, TRAV19, TRAV20, TRAV21, TRAV22, TRAV23, TRAV24, TRAV25, TRAV26-1, TRAV26-2, TRAV27, TRAV29, TRAV30, TRAV34, TRAV35, TRAV36, TRAV38-1, TRAV38-2, TRAV39, TRAV40, and TRAV41. Among these V genes, some of them can be classified into a same subgroup and they are indicated by a same subgroup number immediately following "TRAV" but a different number following "-" sign. For example, TRAV1-1 and TRAV1-2 are from a same subgroup. As used herein, a "group" is a set of genes that share the same "gene type" (e.g., V, D, J or C type) and participate potentially in the synthesis of a polypeptide of the same "chain type". By extension, a group includes the related pseudogenes and orphons. A "subgroup" means a set of genes that belong to the same group, in a given species, and that share at least 75% identity at the nucleotide level (in the germline configuration for V, D, and J).

In human, there can be more than 40 functional V genes for TRB, including TRBV2, TRBV3-1, TRBV4-1, TRBV4-2, TRBV4-3, TRBV5-1, TRBV5-4, TRBV5-5, TRBV5-6, TRBV5-8, TRBV6-1, TRBV6-2, TRBV6-3, TRBV6-4, TRBV6-5, TRBV6-6, TRBV6-8, TRBV6-9, TRBV7-2, TRBV7-3, TRBV7-4, TRBV7-6, TRBV7-7, TRBV7-8, TRBV7-9, TRBV9, TRBV10-1, TRBV10-2, TRBV10-3, TRBV11-1, TRBV11-2, TRBV11-3, TRBV12-3, TRBV12-4, TRBV12-5, TRBV13, TRBV14, TRBV15, TRBV16, TRBV18, TRBV19, TRBV20-1, TRBV24-1, TRBV25-1, TRBV27, TRBV28, TRBV29-1, and TRBV30. V genes for other species, e.g., mouse, can be found on IMGT database.

Figure 5A:
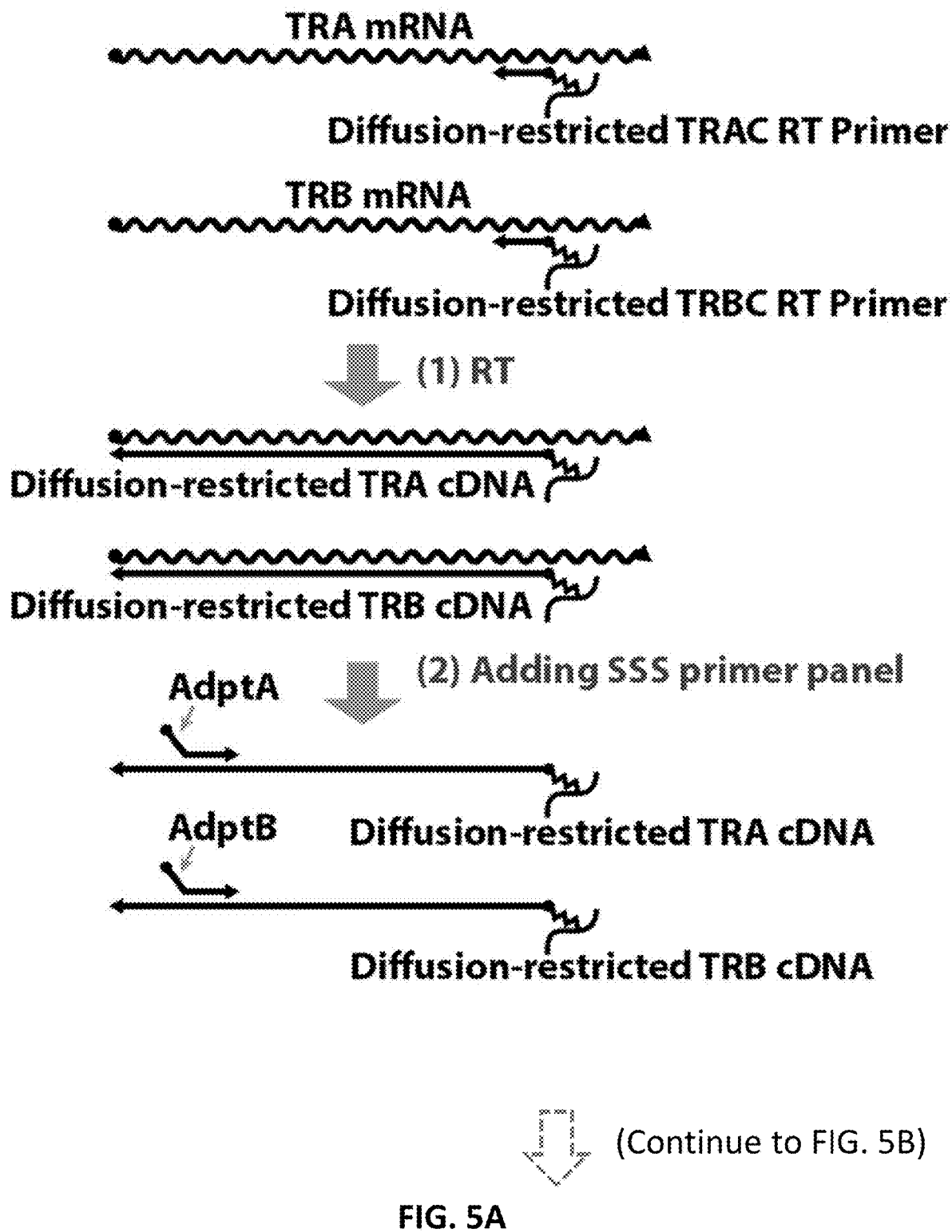
FIG. 5A depicts an example strategy to fuse TRA and TRB in a head-to-tail orientation, in the order of TRA followed by TRB.

In some cases the number of V gene primers used in the pre-amplification is small (e.g., when amplifying BCR or antibody genes, where only about 5, 6, 8, or 10 V gene primers may be needed). In such cases, these primers may be used in multiplexed PCR. In some cases the number of V gene primers used in the pre-amplification is large (e.g., when amplifying TCR genes, where about 50, 80, 100, or more V gene primers may be needed). In such cases, a common adaptor sequence to attach to the 5' end of each V gene primers can be designed, and these primers (referred to as "adaptor-containing V gene primers") can be used to hybridize to the cDNA and carry out a single-cycle primer extension. This step refers to the SSS step, for example, as shown in FIG. 5A. After the SSS step, one common primer pairs—a forward primer targeting the adaptor, and a reverse primer targeting the C region—can be used to amplify possible immunoreceptor chains. For the purpose of fusion and ensuing manipulation, a different adaptor may be used for each chain. For example, a first adaptor sequence may be used for a TRA chain, and a second adaptor sequence may be used for a TRB chain. In some embodiments, a V gene primer may have the sequence of the first 15 to 40 bases of the protein-coding sequence (start with ATG). In this case, the PCR product may comprise the entire coding sequence of the V gene and the VDJ junction. Some examples of such adaptor-containing V gene primers are [AdptA|CDS$_{TRA}$} and [AdptB|CDS$_{TRB}$} as described in FIG. 5A and Example section. A primer of the adaptor-containing V gene primers can be hybridized with a blocker oligonucleotide to protect its 3' end. The blocker oligonucleotide may be two or more separate oligonucleotide strands.

Maintaining sequence specificity when applying 10 to 100 primers in SSS or PCR may be challenging. However, a number of methods can be used to increase the specificity of hybridization for SSS or PCR, including but not limited to using additives such as DMSO and betaine, using chemical modifications such as LNA or ribonucleotide (the latter of which may be used in conjunction with RNase H-dependent PCR), using competitive oligonucleotides such as in Yin-Yang probe or toehold probe.

After carrying out the preparation procedure, a plurality of single-cell reactors each comprising a solid support can be generated, and a one-step fusion reaction such as OE-PCR (see Example 6) may be performed. During the OE-PCR, the outer primer(s) (e.g., pTSO of FIG. 9B) can be used at a higher concentration than the inner primer(s) (e.g., primers 1R and 2R of FIG. 9B). After exponential amplification phase, the outer primer(s) may drive linear amplification resulting in accumulation of single-stranded extension products extended from the outer primer(s). The 3' ends of these single-stranded extension products have overlaps whose sequence is determined by the inner primer(s), and can thus hybridize to each other. The hybridization product can be further extended to produce double-stranded fusion product.

In some embodiments, an amplification procedure can be performed to amplify the immunoreceptor-encoding polynucleotides in single-cell reactors without creating the fusion product. To do this, a plurality of single-cell reactors each comprising a single solid support can be prepared in the preparation procedure, a first pair of primers to amplify the first immunoreceptor-coding polynucleotide (e.g., for TCR alpha chain) via binding to its upstream and downstream common sequences, and a second pair of primers to amplify the second immunoreceptor-coding polynucleotide (e.g., for TCR beta chain) via binding to its upstream and downstream common sequences.

The pre-amplification products may be diffusion-restricted. For example, the primers for this PCR-based pre-amplification can be a capture agent. For example, the primers can be appended with [ARS}. The [ARS} can be linked to the primer sequence via a flexible linker, such as a PEG linker or a Spacer18. Non-limiting examples of these primers include ARS-pTSO in FIGS. 4A and 4B and ht1F, ht2R in FIG. 5B.

After the amplification procedure one can provide a plurality of solid supports each modified with a first plurality of amplification products of a first immunoreceptor-encoding polynucleotide (e.g., encoding a TCR alpha chain) and a second plurality of amplification products of a second immunoreceptor-encoding polynucleotide (e.g., encoding a TCR beta chain), wherein the first and the second immunoreceptor-encoding polynucleotides form a native pair.

Overlap Design

Figure 3:
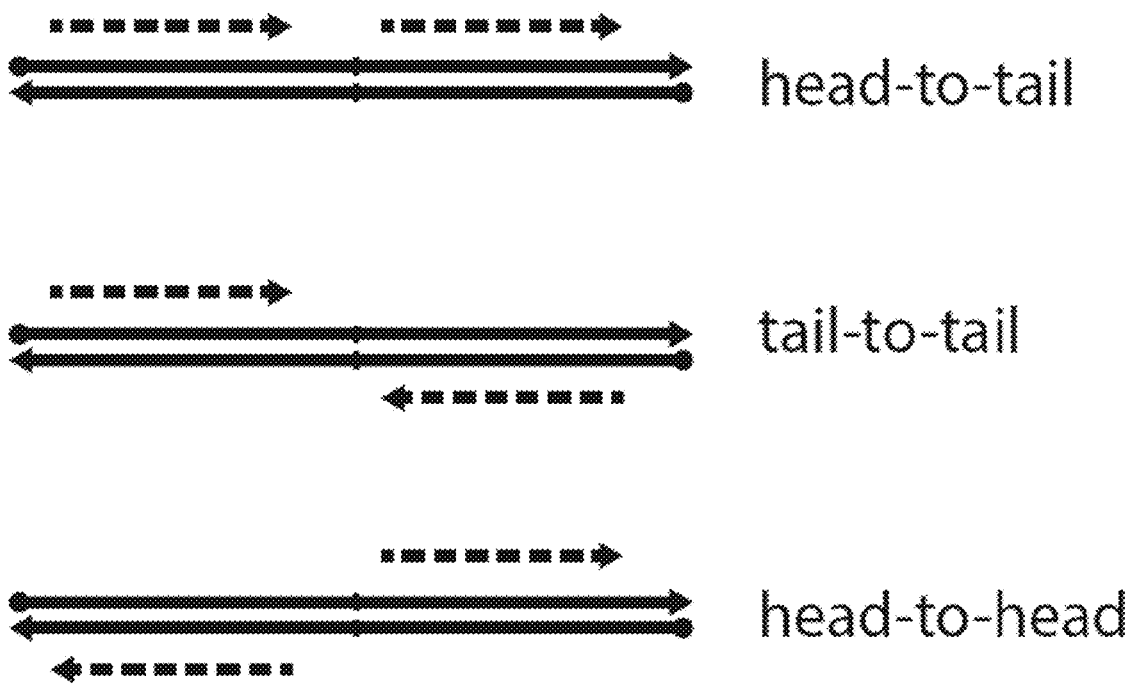
FIG. 3 depicts different possible orientations of the fused bipartite immunoreceptor polynucleotides, using TCR as an example. The dashed arrow depicts the direction of the sense strand of the protein-coding sequence. In this example, the 5' end of the sense strand refers to "head", and the 3' end of the sense strand refers to "tail".

The two nucleic acids encoding two peptide chains of a bipartite immunoreceptor can be fused in several orientations, for example, head-to-head, head-to-tail, and tail-to-tail (FIG. 3). As described herein, "head" refers to "5' end" of a sense nucleic acid strand and "tail" refers to "3' end" of a sense nucleic acid strand. In some cases, the orientation is head-to-tail, the order of the fusion (e.g., TRA followed by TRB, or TRB followed by TRA) can be controlled. To achieve such controllability, sequence-dependent fusion may be carried out. To do this, overlapping sequences may be engineered into the amplification product of the two chains. As described herein, fusing the TRA and TRB polynucleotides of a TCR is used as an example to describe different strategies. The strategies can be applied to BCR chain fusion, antibody chain fusion, and TCRγδ chain fusion.

Tail-to-Tail Design

Figure 4A:
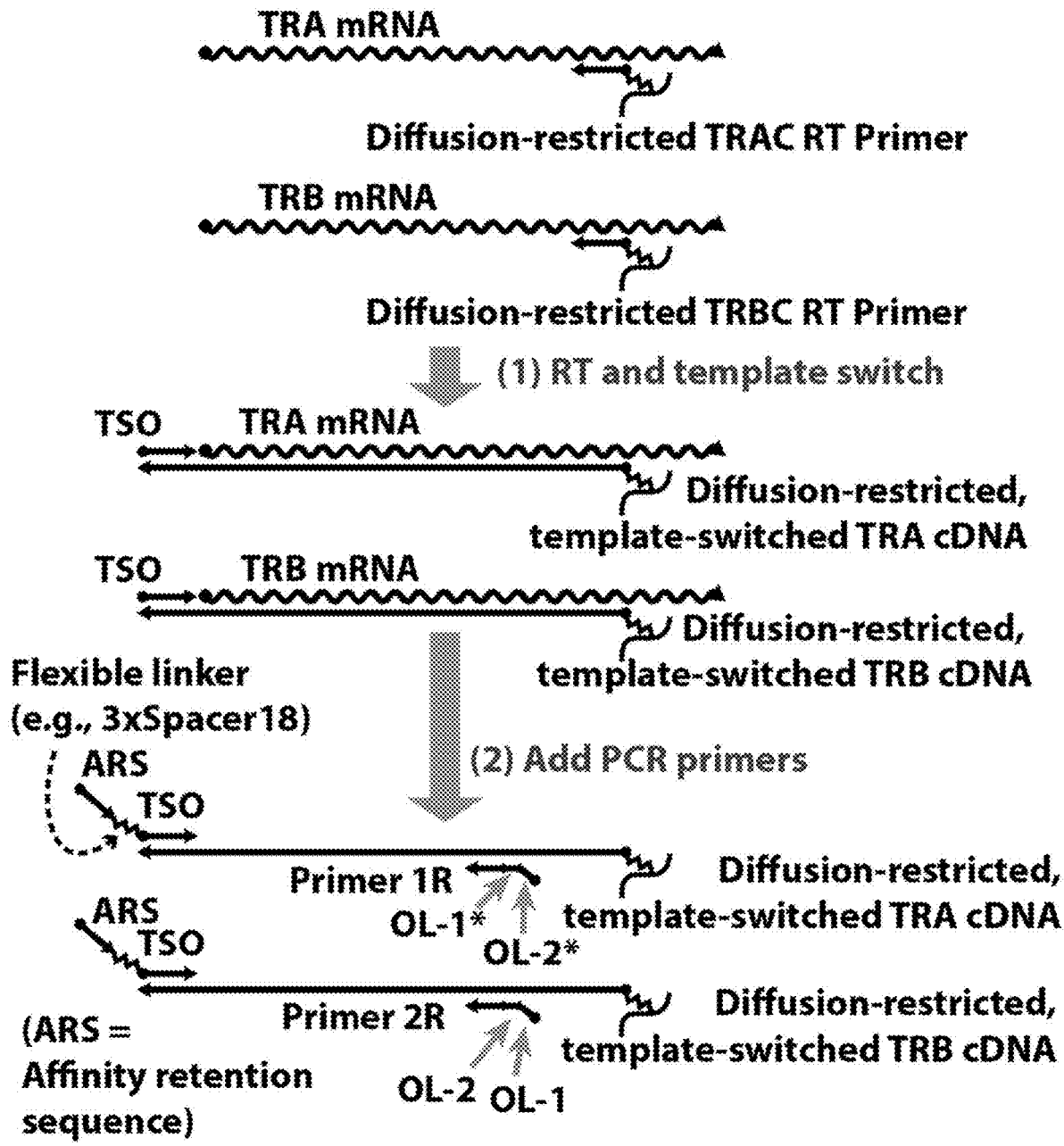
FIG. 4A depicts an example strategy to fuse TRA and TRB in a tail-to-tail orientation.
Figure 4B:
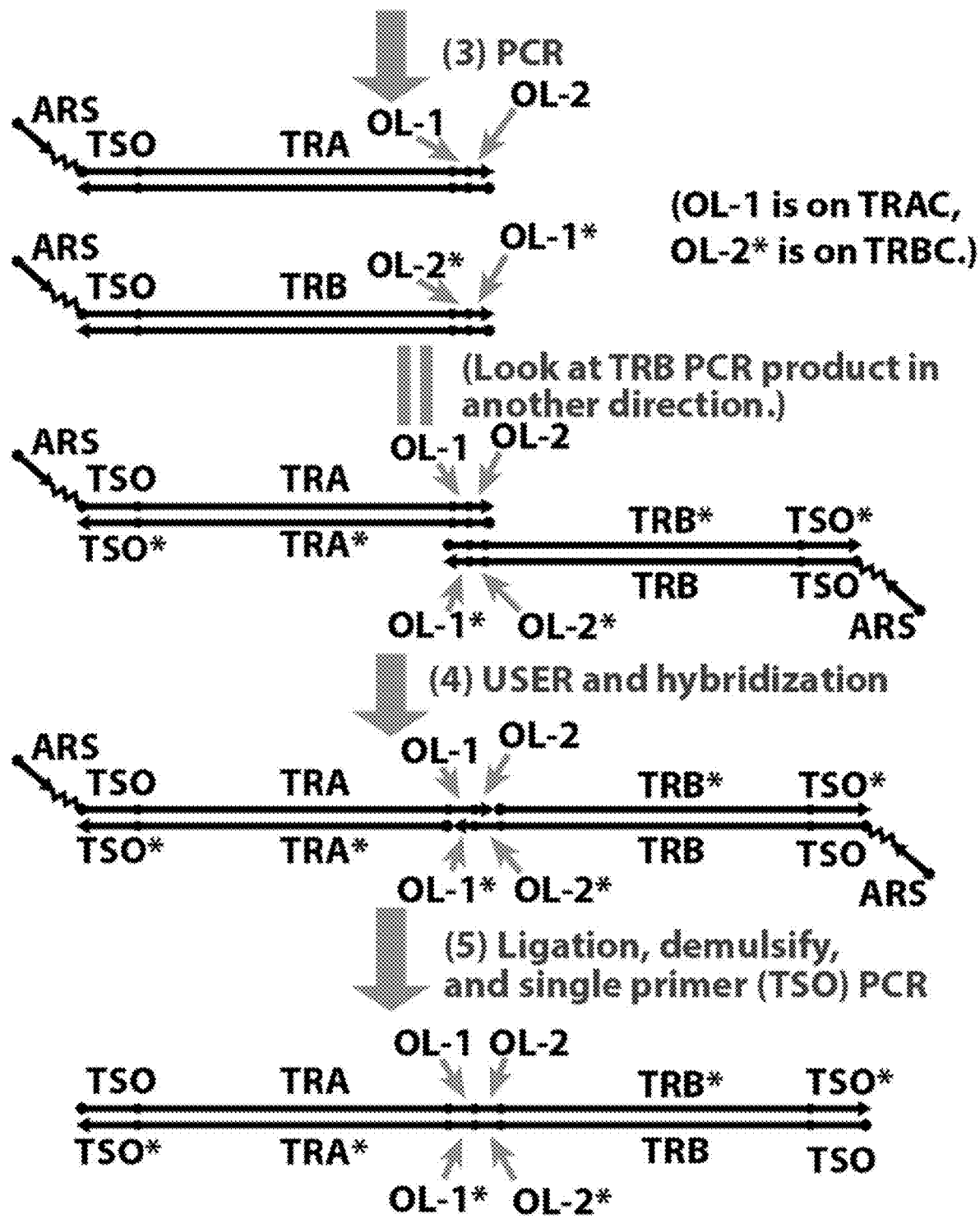
FIG. 4B depicts an example strategy to fuse TRA and TRB in a tail-to-tail orientation.

FIGS. 4A and 4B depict an example of tail-to-tail fusion of the TRA and TRB of a TCR immunoreceptor. For the amplification of TRA segments, a primer that recognizes the C region of TRA (i.e., TRAC) can be used as the reverse primer. The sequence of this primer recognizing TRAC can be denoted as [TRAC-5A*}. A ~10-nt sequence denoted by [OL-2*} can be appended to the 5' end of [TRAC-5A*} to form a primer which is denoted as '1R' with the sequence [OL-2*|TRAC-5A*}. Similarly, for the amplification of TRB segments, a primer that recognizes the C region of TRB (i.e., TRBC) can be used as the reverse primer. The sequence of this primer recognizing TRBC is denoted as [TRBC-5A*}. A ~10-nt sequence denoted by [OL-1} can be appended to the 5' end of [TRBC-5A*} to form a primer which we call '2R' with sequence [OL-1|TRBC-5A*}. In this design, [OL-1*} is the first ~10 bases of [TRAC-5A*}, and [OL-2} is the first ~10 bases of [TRBC-5A*}. Thus the last ~20 bases of the sense strand of the TRA amplification product can have the sequence of [OL-1|OL-2}, and the last ~20 bases of the sense strand of the TRB amplification product can have the sequence of [OL-2*|OL-1*}. The two ends can be fused by ligation after creating long sticky ends using 5'-to-3' exonuclease (e.g, Gibson Assembly), 3'-to-5' exonuclease (e.g., sequence and ligase independent cloning or SLIC), or USER enzyme mix (e.g., USER friendly DNA recombination or USERec). Additional examples of assembly methods include, but are not limited to, circular polymerase extension cloning (CPEC) and seamless ligation cloning extract (SLiCE) assembly. Alternatively, these two ends can be fused by overlapping PCR. Detailed description of a strategy to fuse TRA and TRB in tail-to-tail orientation is further provided in Example 1.

Head-to-Tail Design

Figure 5B:
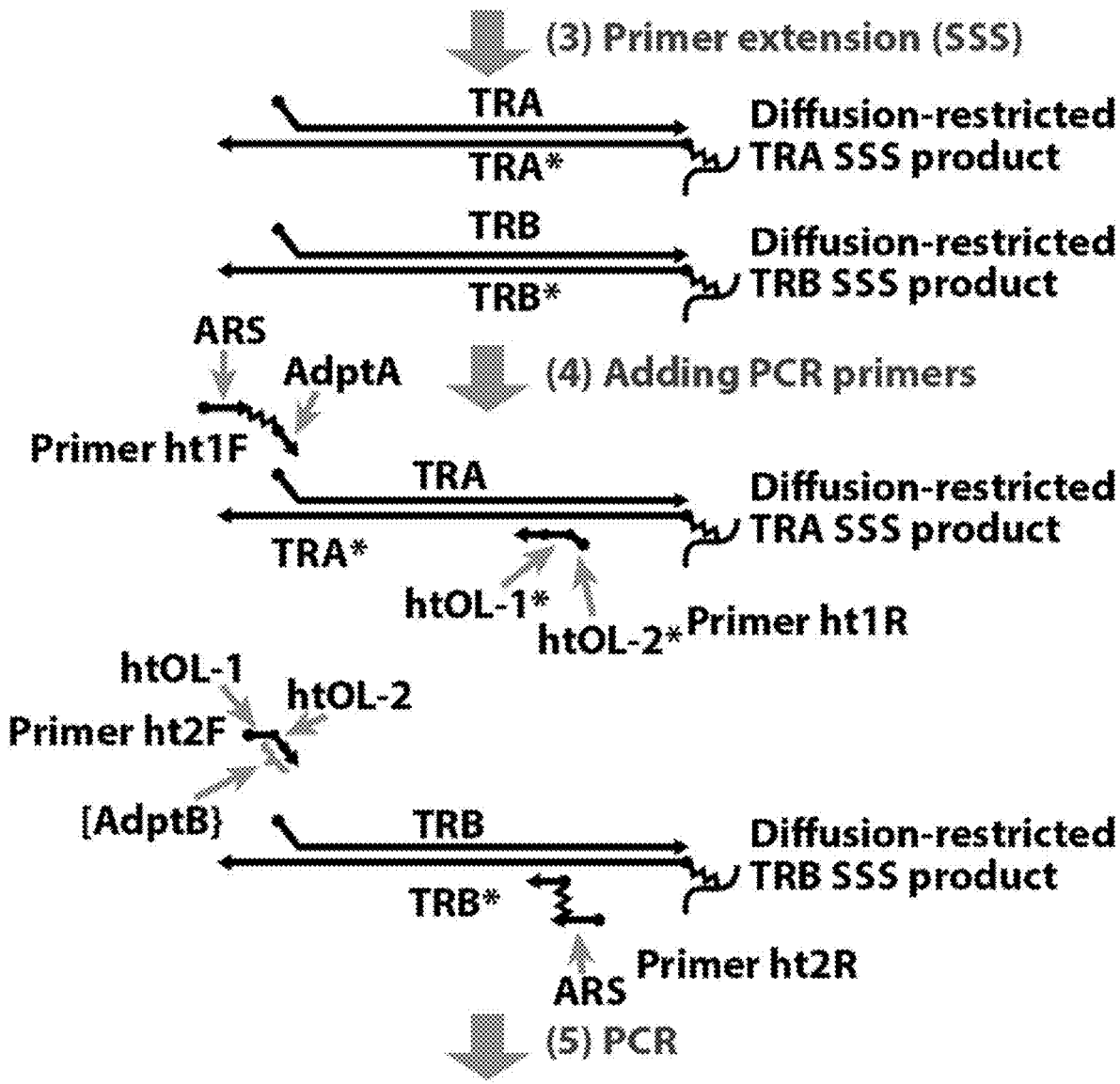
FIG. 5B depicts an example strategy to fuse TRA and TRB in a head-to-tail orientation, in the order of TRA followed by TRB.
Figure 5C:
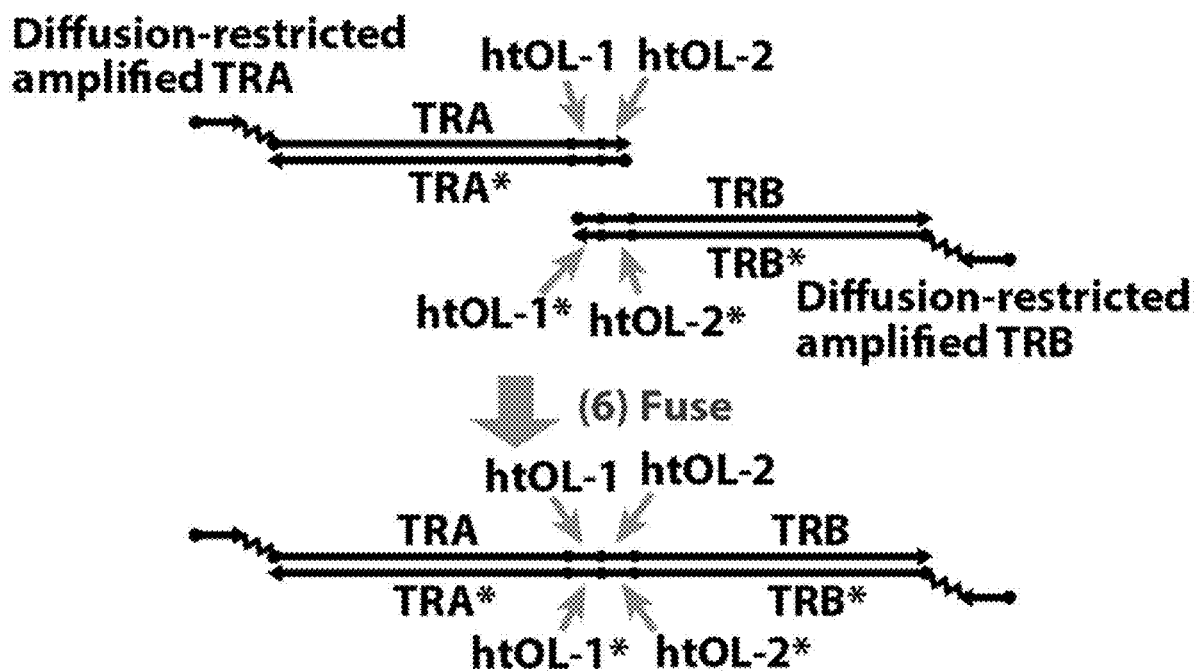
FIG. 5C depicts an example strategy to fuse TRA and TRB in a head-to-tail orientation, in the order of TRA followed by TRB.

FIGS. 5A-5C depict an example of head-to-tail fusion of the TRA and TRB polynucleotides of a TCR immunoreceptor. As described herein, adaptor-containing V gene primers can be used to add adaptor sequences to the V gene sequences during SSS. To perform head-to-tail fusion, two different adaptor sequences, denoted by [AdptA} and [AdptB}, can be used as the adaptor sequences for TRA and TRB, respectively. To create head-to-tail fusion in the order of TRA followed by TRB, the reverse primer to amplify TRA which has the sequence [TRAC-5A*} can be appended with a sequence called [htOL-2*} to form a primer denoted by 'ht1R', with the sequence [htOL-2*|TRAC-5A*}. At the same time, a sequence called [htOL-1} can be added to the primer having the sequence [AdptB} to form a new primer denoted by 'ht2F', with the sequence [htOL-1AdptB}. This primer 'ht2F' can be the forward primer to amplify TRB. In this design, [htOL-1*} can be the first ~10 bases of [TRAC-5A*}, and [htOL-2} can be the first ~10 bases of [AdptB}. The amplification products of TRA and TRB can be fused by a variety of strategies such as ligation and overlapping PCR in single-cell reactors, wherein the amplification products with immunoreceptor-encoding sequences originating from a single cell are attached to a solid support, and there is only one solid support in each single-cell reactor. In these single-cell reactors, the amplification products can be made freely diffusible using methods provided herein (e.g., melting the solid support). For example, the two ends can be fused by ligation after creating long sticky ends using 5'-to-3' exonuclease (e.g, Gibson Assembly), 3'-to-5' exonuclease (e.g., sequence and ligase independent cloning or SLIC), or USER enzyme mix (e.g., USER friendly DNA recombination or USERec). Additional examples of assembly methods include, but are not limited to, circular polymerase extension cloning (CPEC) and seamless ligation cloning extract (SLiCE) assembly. Detailed description of a strategy to fuse TRA and TRB in a head-to-tail orientation, and in the order of TRA followed by TRB, is further provided in Example 2.

Immunoreceptor-Expressing Vector

The fused bipartite immunoreceptor polynucleotides can be inserted into expression vectors in order to be expressed in a host cell, referred to as "recipient cell" in the present disclosure. The fused bipartite immunoreceptor polynucleotide may be delivered into a recipient cell as a linear or circular nucleic acid strand. The fused bipartite immunoreceptor polynucleotide can be delivered into a recipient cell as an expression vector. In some cases, the fused bipartite immunoreceptor polynucleotide or vector can be delivered into a recipient cell by electroporation. In some cases, the fused bipartite immunoreceptor polynucleotide or vector can be delivered by a carrier such as a cationic polymer.

The two chains of a bipartite immunoreceptor can be expressed from a vector such as plasmid, transposon (e.g., Sleeping Beauty, Piggy Bac), and a viral vector (e.g., adenoviral vector, AAV vector, retroviral vector and lentiviral vector). Additional examples of a vector include a shuttle vector, a phagemide, a cosmid and an expression vector. Non-limiting examples of plasmid vectors include pUC, pBR322, pET, pBluescript, and variants thereof. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. In some cases, a vector is a nucleic acid molecule as introduced into a recipient cell, thereby producing a transformed recipient cell. A vector may include nucleic acid sequences that permit it to replicate in a recipient cell, such as an origin of replication. A vector may also include one or more selectable marker genes and other genetic elements. A vector can be an expression vector that includes a fused bipartite immunoreceptor polynucleotide according to the present disclosure operably linked to sequences allowing for the expression of the fused gene. A vector can be a viral or a non-viral vector, such a retroviral vector (including lentiviral vectors), adenoviral vectors including replication competent, replication deficient and gutless forms thereof, adeno-associated virus (AAV) vectors, simian virus 40 (SV-40) vectors, bovine papilloma vectors, Epstein-Barr vectors, herpes vectors, vaccinia vectors, Moloney murine leukemia vectors, Harvey murine sarcoma virus vectors, murine mammary tumor virus vectors, Rous sarcoma virus vectors and nonviral plasmids. Baculovirus vectors can be suitable for expression in insect cells.

In some embodiments, the vector is a self-amplifying RNA replicon, also referred to as self-replicating (m)RNA, self-replication (m)RNA, self-amplifying (m)RNA, or RNA replicon. The self-amplifying RNA replicon is an RNA that can replicate itself. In some embodiments, the self-amplifying RNA replicon can replicate itself inside of a cell. In some embodiments, the self-amplifying RNA replicon encodes an RNA polymerase and a molecule of interest. The RNA polymerase may be a RNA-dependent RNA polymerase (RDRP or RdRp). The self-amplifying RNA replicon may also encode a protease or an RNA capping enzyme. In some embodiments, the self-amplifying RNA replicon vector is of or derived from the Togaviridae family of viruses known as alphaviruses which can include Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, South African Arbovirus No. 86, Semliki Forest virus, Middelburg virus, Chikungunya virus, Onyong-nyong virus, Ross River virus, Barmah Forest Virus, Getah Virus, Sagiyama virus, Bebaru virus, Mayaro virus, Una virus, Aura virus, Whataroa virus, Babanki virus, Kyzylagach virus, Highlands J Virus, Fort Morgan virus, Ndumu virus, Buggy Creek virus, and any other virus classified by the International Committee on Taxonomy of Viruses (ICTV) as an alphavirus. In some embodiments, the self-amplifying RNA replicon is or contains parts from an attenuated form of the alphavirus, such as the VEE TC-83 vaccine strain. In some embodiments, the self-amplifying RNA replicon vector is an attenuated form of the virus that allows for expression of the molecules of interests (including the bipartite immunoreceptors and additional agents as described in sections titled "Additional genome engineering of the recipient cells" and "Additional Agents Expressed by Recipient Cells") without cytopathic or apoptotic effects to the cell. In some embodiments, the self-amplifying RNA replicon vector has been engineered or selected in vitro, in vivo, ex vivo, or in silico for a specific function (e.g. prolonged or increased bipartite immunoreceptor expression) in the host cell, target cell, or organism. For example, a population of host cells harboring different variants of the self-amplifying RNA replicon can be selected based on the expression level of one or more molecules of interested (encoded in the self-amplifying RNA replicon or in the host genome) at different time point. In some embodiments, the selected or engineered self-amplifying RNA replicon has been modified to reduce the type I interferon response, the innate antiviral response, or the adaptive immune response from the host cell or organism which results in the RNA replicon's protein expression persisting longer or expressing at higher levels in the host cell, target cell, or organism. In some embodiments, this optimized self-amplifying RNA replicon sequence is obtained from an individual cell or population of cells with the desired phenotypic trait (e.g., higher or more sustained expression of the molecules of interest, or reduced innate antiviral immune response against the vector compared to the wildtype strains or the vaccine strains). In some embodiments, the cells harboring the desired or selected self-amplifying RNA replicon sequence are obtained from a subject (e.g., a human or an animal) with beneficial response characteristics (e.g., an elite responder or subject in complete remission) after being treated with a therapeutic agent comprising a self-amplifying RNA replicon. In some embodiments, the self-amplifying RNA replicon vector can express additional agents as described in sections titled "Additional genome engineering of the recipient cells" and "Additional Agents Expressed by Recipient Cells". In some embodiments, the additional agents include cytokines such as IL-2, IL-12, IL-15, IL-10, GM-CSF, TNF alpha, granzyme B, or a combination thereof. In some embodiments, the additional agent is capable of modulating the expression of the bipartite immunoreceptor, either by directly affecting the expression of the immunoreceptor or by modulating the host cell phenotype (e.g., inducing apoptosis or expansion). In some embodiments, the self-amplifying RNA replicon can contain one or more sub-genomic sequence(s) to produce one or more sub-genomic polynucleotide(s). In some embodiments, the sub-genomic polynucleotides act as functional mRNA molecules for translation by the cellular translation machinery. A sub-genomic polynucleotide can be produced via the function of a defined sequence element (e.g., a sub-genomic promoter or SGP) on the self-amplifying RNA replicon that directs a polymerase to produce the sub-genomic polynucleotide from a sub-genomic sequence. In some embodiments, the SGP is recognized by an RNA-dependent RNA polymerase (RDRP or RdRp). In some embodiments, multiple SGP sequences are present on a single self-amplifying RNA replicon and can be located upstream of sub-genomic sequence encoding for a bipartite immunoreceptor, a constituent of the bipartite immunoreceptor, or an additional agent. In some embodiments, the nucleotide length or composition of the SGP sequence can be modified to alter the expression characteristics of the sub-genomic polynucleotide. In some embodiments, non-identical SGP sequences are located on the self-amplifying RNA replicon such that the ratios of the corresponding sub-genomic polynucleotides are different from instances where the SGP sequences are identical. In some embodiments, non-identical SGP sequences direct the production of a bipartite immunoreceptor and an additional agent (e.g., a cytokine) such that they are produced at a ratio relative to one another that leads to increased expression of the bipartite immunoreceptor, increased or faster expansion of the target cell without cytotoxic effects to the target cell or host, or dampens the innate or adaptive immune response against the RNA replicon. In some embodiments, the location of the sub-genomic sequences and SGP sequences relative to one another and the genomic sequence itself can be used to alter the ratio of sub-genomic polynucleotides relative to one another. In some embodiments, the SGP and sub-genomic sequence encoding the bipartite immunoreceptor can be located downstream of an SGP and sub-genomic region encoding the additional agent such that the expression of the bipartite immunoreceptor is substantially increased relative to the additional agent. In some embodiments, the RNA replicon or SGP has been selected or engineered to express an optimal amount of the cytokine such that the cytokine promotes the expansion of the T cell or augments the therapeutic effect of the bipartite immunoreceptor but does not cause severe side effects such as cytokine release syndrome, cytokine storm, or neurological toxicity.

In some embodiments, provided herein is a vector comprising a fused bipartite immunoreceptor polynucleotide encoding a TCRα chain and a TCRβ chain. In some embodiments, provided herein is a vector comprising a fused bipartite immunoreceptor polynucleotide encoding a TCRγ chain and a TCRδ chain. In some embodiments, provided herein is a vector comprising a fused bipartite immunoreceptor polynucleotide encoding a BCR or antibody heavy chain and a BCR or antibody light chain. In some embodiments, the vector is a self-amplifying RNA replicon, plasmid, phage, transposon, cosmid, virus, or virion. In some embodiments, the vector is a viral vector. In some embodiments, the vector is derived from a retrovirus, lentivirus, adenovirus, adeno-associated virus, herpes virus, pox virus, alpha virus, vaccina virus, hepatitis B virus, human papillomavirus or a pseudotype thereof. In some embodiments, the vector is a non-viral vector. In some embodiments, the non-viral vector can be formulated into a nanoparticle, a cationic lipid, a cationic polymer, a metallic nanopolymer, a nanorod, a liposome, a micelle, a microbubble, a cell-penetrating peptide, or a liposphere.

The expression of the two chains can be driven by two promoters or by one promoter. In some cases, two promoters are used. In some cases, the two promoters, along with their respective protein-coding sequences for the two chains, can be arranged in a head-to-head, a head-to-tail, or a tail-to-tail orientation. In some cases, one promoter is used. The two protein-coding sequences can be linked in frame such that one promoter can be used to express both chains. And in such cases, the two protein-coding sequences can be arranged in a head-to-tail orientation and can be connected with ribosome binding site (e.g., internal ribosomal binding site or IRES), protease cleavage site, or self-processing cleavage site (such as a sequence encoding a 2A peptide) to facilitate bicistronic expression. In some cases, the two chains can be linked with peptide linkers so that the two chains can be expressed as a single-chain polypeptide. Each expressed chain may contain the full variable domain sequence including the rearranged V(D)J gene. Each expressed chain may contain the full variable domain sequence including CDR1, CDR2, and CDR3. Each expressed chain may contain the full variable domain sequence including FR1, CDR1, FR2, CDR2, FR3, and CDR3. In some cases, each expressed chain may further contain a constant domain sequence.

To create expression vectors, additional sequences may need to be added to the fused immunoreceptor genes. These additional sequences include vector backbone (e.g., elements required for the vector's replication in target cell or in temporary host such as E. coli), promoters, IRES, sequence encoding the self-cleaving peptide, terminators, accessory genes (such as payloads), as well as partial sequences of the immunoreceptor polynucleotides (such as part of the sequences encoding the constant domains).

Protease cleavage sites include, but are not limited to, an enterokinase cleavage site: (Asp)4Lys (SEQ ID NO: 1); a factor Xa cleavage site: Ile-Glu-Gly-Arg (SEQ ID NO: 2); a thrombin cleavage site, e.g., Leu-Val-Pro-Arg-Gly-Ser (SEQ ID NO: 3); a renin cleavage site, e.g., His-Pro-Phe-His-Leu-Val-Ile-His (SEQ ID NO: 4); a collagenase cleavage site, e.g., X-Gly-Pro (where X is any amino acid); a trypsin cleavage site, e.g., Arg-Lys; a viral protease cleavage site, such as a viral 2A or 3C protease cleavage site, including, but not limited to, a protease 2A cleavage site from a picornavirus, a Hepatitis A virus 3C cleavage site, human rhinovirus 2A protease cleavage site, a picornavirus 3 protease cleavage site; and a caspase protease cleavage site, e.g., DEVD (SEQ ID NO: 5) recognized and cleaved by activated caspase-3, where cleavage occurs after the second aspartic acid residue. In some embodiments, the present disclosure provides an expression vector comprising a protease cleavage site, wherein the protease cleavage site comprises a cellular protease cleavage site or a viral protease cleavage site. In some embodiments, the first protein cleavage site comprises a site recognized by furin; VP4 of IPNV; tobacco etch virus (TEV) protease; 3C protease of rhinovirus; PC5/6 protease; PACE protease, LPC/PC7 protease; enterokinase; Factor Xa protease; thrombin; genenase I; MMP protease; Nuclear inclusion protein a(N1a) of turnip mosaic potyvirus; NS2B/NS3 of Dengue type 4 flaviviruses, NS3 protease of yellow fever virus; ORF V of cauliflower mosaic virus; KEX2 protease; CB2; or 2A. In some embodiments, the protein cleavage site is a viral internally cleavable signal peptide cleavage site. In some embodiments, the viral internally cleavable signal peptide cleavage site comprises a site from influenza C virus, hepatitis C virus, hantavirus, flavivirus, or rubella virus.

A suitable IRES element to include in the vector of the present disclosure can comprise an RNA sequence capable of engaging a eukaryotic ribosome. In some embodiments, an IRES element of the present disclosure is at least about 250 base pairs, at least about 350 base pairs, or at least about 500 base pairs. An IRES element of the present disclosure can be derived from the DNA of an organism including, but not limited to, a virus, a mammal, and a *Drosophila*. In some cases, a viral DNA from which an IRES element is derived includes, but is not limited to, picomavirus complementary DNA (cDNA), encephalomyocarditis virus (EMCV) cDNA and poliovirus cDNA. Examples of mammalian DNA from which an IRES element is derived includes, but is not limited to, DNA encoding immunoglobulin heavy chain binding protein (BiP) and DNA encoding basic fibroblast growth factor (bFGF). An example of *Drosophila* DNA from which an IRES element is derived includes, but is not limited to, an Antennapedia gene from *Drosophila melanogaster*. Addition examples of poliovirus IRES elements include, for instance, poliovirus IRES, encephalomyocarditis virus IRES, or hepatitis A virus IRES. Examples of flaviviral IRES elements include hepatitis C virus IRES, GB virus B IRES, or a pestivirus IRES, including but not limited to bovine viral diarrhea virus IRES or classical swine fever virus IRES.

Examples of self-processing cleavage sites include, but are not limited to, an intein sequence; modified intein; hedgehog sequence; other hog-family sequence; a 2A sequence, e.g., a 2A sequence derived from Foot and Mouth Disease Virus (FMDV); and variations thereof for each.

A vector for recombinant immunoglobulin or other protein expression may include any number of promoters, wherein the promoter is constitutive, regulatable or inducible, cell type specific, tissue-specific, or species specific. Further examples include tetracycline-responsive promoters. The vector can be a replicon adapted to the host cell in which the recombinantly fused gene is to be expressed, and it can comprise a replicon functional in a bacterial cell as well, for example, *Escherichia coli*. The promoter can be constitutive or inducible, where induction is associated with the specific cell type or a specific level of maturation, for example. Alternatively, a number of viral promoters can be suitable. Examples of promoters include the (3-actin promoter, SV40 early and late promoters, immunoglobulin promoter, human cytomegalovirus promoter, retrovirus promoter, elongation factor 1A (EF-1A) promoter, phosphoglycerate kinase (PGK) promoter, and the Friend spleen focus-forming virus promoter. The promoters may or may not be associated with enhancers, wherein the enhancers may be naturally associated with the particular promoter or associated with a different promoter.

The recipient cell, which is the host cell for gene expression, can be, without limitation, an animal cell, especially a mammalian cell, or it can be a microbial cell (bacteria, yeast, or fungus) or a plant cell. Examples of host cells include insect cultured cells such as *Spodoptera frugiperda* cells, yeast cells such as *Saccharomyces cerevisiae* or *Pichia pastoris*, fungi such as *Trichoderma reesei, Aspergillus, Aureobasidum* and *Penicillium* species as well as mammalian cells such as CHO (Chinese hamster ovary), BHK (baby hamster kidney), COS, 293, 3T3 (mouse), Vero (African green monkey) cells and various transgenic animal systems, including without limitation, pigs, mice, rats, sheep, goat, cows, can be used as well. Baculovirus, especially AcNPV, vectors can be used for the single ORF immunoreceptor expression and cleavage of the present disclosure, for example with expression of the single ORF under the regulatory control of a polyhedrin promoter or other strong promoters in an insect cell line. Promoters used in mammalian cells can be constitutive (Herpes virus TK promoter; SV40 early promoter; Rous sarcoma virus promoter; cytomegalovirus promoter; mouse mammary tumor virus promoter) or regulated (metallothionein promoter, for example). Vectors can be based on viruses that infect particular mammalian cells, e.g., retroviruses, vaccinia and adenoviruses and their derivatives. Promoters include, without limitation, cytomegalovirus, adenovirus late, and the vaccinia 7.5K promoters. Enolase is an example of a constitutive yeast promoter, and alcohol dehydrogenase is an example of regulated promoter.

The selection of the specific promoters, transcription termination sequences and other optional sequences, such as sequences encoding tissue specific sequences, can be determined by the type of cell in which expression is carried out. The may be bacterial, yeast, fungal, mammalian, insect, chicken or other animal cells.

The immunoreceptors expressed from the immunoreceptor-expressing vectors may be in their natural form or may be in an engineered form. In some cases, the engineered form is a single-chain antibody fragment or a single-chain TCR fragment. For example, a flexible linker can link the variable domain of a heavy chain and the variable domain of a light chain of an antibody, thereby forming a single chain antibody fragment (namely scFv). In some cases, the engineered form is a TCR-CAR. Examples 3, 4, and 5 provide methods to further fuse functional sequences (e.g., constant domain-coding sequences, P2A linker, and promoter) to fused bipartite immunoreceptor polynucleotide in order to create immunoreceptor-expressing vectors. These methods can also be used to introduce functional sequences (e.g., linkersCD28 ™ domains) to fused bipartite immunoreceptor polynucleotide in order to create immunoreceptor-expressing vectors that express these engineered forms of immunoreceptors.

Source Immunoreceptor-Expressing Cells

The source immunoreceptor-expressing cells from which fused bipartite immunoreceptor polynucleotides can be created using the method described herein may be of various cell types, from various organisms, and isolated from various tissues or organs. The source immunoreceptor-expressing cells can be obtained from various samples. The source immunoreceptor-expressing cells can produce immunoreceptors such as BCRs, TCRs, and antibodies. The source immunoreceptor-expressing cells may be immune cells. The immune cell refers to a cell of hematopoietic origin functionally involved in the initiation and/or execution of innate and/or adaptive immune response. The source immunoreceptor-expressing cells may be lymphocytes, e.g., tumor infiltrating lymphocytes (TILs).

The original site that hosts the source immunoreceptor-expressing cells may affect the characteristics of the repertoire of the fused bipartite immunoreceptor polynucleotides, and consequently, the repertoire of the resultant immunoreceptor-expressing vectors and the immunoreceptor-programmed recipient cells. An aspect of the characteristics of such repertoire can be the gene usage diversity.

In some cases, the repertoire may contain more than 2, more than 5, more than 10, more than 50, more than 100, more than 500, more than 1,000, more than 5,000, more than 10,000, more than 50,000, or more than 100,000 V(D)J combinations. In some cases, the repertoire may contain more than 2, more than 5, more than 10, more than 50, more than 100, more than 500, more than 1,000, more than 5,000, more than 10,000, more than 50,000, or more than 100,000 different V(D)J combinations. This is because the polyclonal population of the source immunoreceptor-expressing cells may have highly diverse usage of V, D, and J genes, resulting in highly diverse V(D)J combinations.

A VJ combination of a fused bipartite immunoreceptor polynucleotide or an immunoreceptor-expressing vector may be defined by the V gene and J gene used by both immunoreceptor chains. A V(D)J combination of a fused bipartite immunoreceptor polynucleotide or an immunoreceptor-expressing vector may be defined by the V gene, D gene, and J gene used by both immunoreceptor chains. For example, TRAV8-4/TRAJ45/TRBV29-1/TRBJ1-5 can define a particular VJ recombination of a paired TCR. Given a coding sequence for an immunoreceptor chain, one may deduce the V(D)J combination using computational tools such as V-Quest and MiXCR.

It should be noted that two different fused bipartite immunoreceptor polynucleotides (or two different immunoreceptor-expressing vectors) may share the same V(D)J recombination but have different sequences, this may be because (1) during the V(D)J recombination random insertion and deletions may happen at the V-D, D-J, and V-J junctions, and (2) sequence variations may be artificially created by mutagenesis and gene synthesis, and variable sequences may be introduced during the gene synthesis. For example, two fused TCR genes may have the same VJ recombination but have different CDR3 sequences. The fused bipartite immunoreceptor polynucleotide or expression vector can comprise a cognate pair combination (or a native pair combination in a cell) of a first immunoreceptor chain and a second immunoreceptor chain from a source immunoreceptor-expressing cell. A plurality of fused bipartite immunoreceptor polynucleotides or expression vectors can comprise multiple cognate pair combinations of first immunoreceptor chains and second immunoreceptor chains from a plurality of immunoreceptor-expressing cells. The source immunoreceptor-expressing cells can have different clonotypes, and therefore can result in a polyclonal population of fused bipartite immunoreceptor polynucleotides or expression vectors. Delivering the polyclonal immunoreceptor-expressing vectors into a plurality of recipient cell can produce a polyclonal population of immunoreceptor-programmed recipient cells, expressing at least 100, at least 1,000, at least 10,000, at least 100,000, at least 1,000,000, at least 10,000,000, or at least 100,000,000, or more different immunoreceptors (or different cognate pair combinations of immunoreceptors). Each of the different immunoreceptors can have a unique sequence in the fused bipartite immunoreceptor polynucleotide.

This polyclonal feature can distinguish the library of fused bipartite immunoreceptor polynucleotides, the library of expression vectors and the polyclonal population of immunoreceptor-programmed recipient cells obtained using methods described in this disclosure from previously reported counterparts. For example, one may start with one or a handful of immunoreceptor chain-coding sequences, immunoreceptor domain-coding sequences, or fused bipartite immunoreceptor polynucleotides, and generate a large number of variations of these starting sequences using mutagenesis or error prone PCR to create a large library of fused bipartite immunoreceptor polynucleotides. Thus, these libraries may contain one or a handful of V(D)J gene combinations. In contrast, the library of fused bipartite immunoreceptor polynucleotides, the library of expression vectors and the polyclonal population of immunoreceptor-programmed recipient cells obtained using methods described in this disclosure can contain more than about 1,000, more than about 5,000, more than about 10,000, more than about 50,000, more than about 100,000, more than about 500,000, more than about 1,000,000, more than about 5,000,000, or more than about 10,000,000 sequences and may contain more than about 1,000, more than about 5,000, more than about 10,000, more than about 50,000, more than about 100,000, more than about 500,000, more than about 1,000,000, more than about 5,000,000, or more than about 10,000,000 VJ or VDJ combinations. In some cases, the library of fused bipartite immunoreceptor polynucleotides, the library of expression vectors and the polyclonal population of immunoreceptor-programmed recipient cells obtained using methods described in this disclosure can contain at least 100, at least 200, at least 500, at least 1,000, at least 2,000, at least 5,000, at least 10,000, at least 100,000, at least 1,000,000, or at least 10,000,000 VJ or VDJ combinations. Moreover, the library of fused bipartite immunoreceptor polynucleotides, the library of expression vectors and the polyclonal population of immunoreceptor-programmed recipient cells obtained using methods described in this disclosure may contain at least 10, at least 15, at least 20, or more different TRAV (V gene for TCRα chain) subgroups, and/or at least 10, at least 15, at least 20, or more different TRBV (V gene for TCRβ chain) subgroups.

Sample

The source immunoreceptor-expressing cells can be obtained or isolated from various samples. The source immunoreceptor-expressing cells can be immune cells obtained or isolated from various samples. The samples can be obtained from various sources or subjects described herein. The recipient cells may also be obtained from the samples described herein.

In certain embodiments, source immunoreceptor-expressing cells can be isolated from a blood sample or other biological samples of a subject or host, such as a human or other animal, such as a human or other animal that has been immunized or that is suffering from an infection, cancer, an autoimmune condition, or any other diseases to identify a pathogen-, tumor-, and/or disease specific antibody or TCR of potential clinical significance. For example, the human may be diagnosed with a disease, be exhibiting symptoms of a disease, not be diagnosed with a disease, or not be exhibiting symptoms of a disease. For example, the human may be one that was exposed to and/or who can make useful antibodies or TCRs against an infectious agent (e.g., viruses, bacteria, parasites, prions, etc), antigen, or disease. For example, the animal may be one that was exposed to and/or who can make useful antibodies or TCRs against an infectious agent (e.g., viruses, bacteria, parasites, prions, etc), antigen, or disease. Certain immune cells from immunized hosts can make antibodies or TCRs to one or more target antigens in question and/or one or more unknown antigens. In the present disclosure the lymphocyte pool can be enriched for the desired immune cells by any suitable method, such as screening and sorting the cells using fluorescence-activated cell sorting (FACS), magnetic activated cell sorting (MACS), panning or other screening method to generate a plurality of immune cells from a sample.

The immune cell can be derived from a stem cell. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human stem cells may be CD34+ cells. The isolated immune cell can be a dendritic cell, killer dendritic cell, a mast cell, a natural killer (NK) cell, a NK T cell, a B cell, or a T cell selected from the group consisting of inflammatory T lymphocytes, cytotoxic T lymphocytes, regulatory T lymphocytes or helper T lymphocytes. The T cells can be CD4+T lymphocytes, CD8+T lymphocytes, or CD4+CD8+T lymphocytes.

In some embodiments, the source immunoreceptor-expressing cells can be immune cells isolated from non-immunized human or non-human donors. The sequence diversity of antibody or TCR binding sites may not be encoded directly in the germline but can be assembled in a combinatorial manner from V gene segments. Immunizations may trigger any immune cell making a VH-VL or Vα-Vβ or Vγ-Vδ combination that binds the immunogen to proliferate (clonal expansion) or to secrete the corresponding antibody. However, the use of spleen cells and/or immune cells or other peripheral blood lymphocytes from an unimmunized subject can provide a better representation of the possible antibody or TCR repertoire, and also permit the construction of a subsequent BCR or antibody or TCR library using any animal species.

In some cases, the source immunoreceptor-expressing cells can be obtained from peripheral blood sample. The peripheral blood cells can be enriched for a particular cell type (e.g., mononuclear cells; red blood cells; CD4+ cells; CD8+ cells; immune cells; T cells, NK cells, or the like). The peripheral blood cells can also be selectively depleted of a particular cell type (e.g., mononuclear cells; red blood cells; CD4+ cells; CD8+ cells; immune cells; T cells, NK cells, or the like). A sample can comprise at least about 5, 10, 100, 250, 500, 750, 1000, 2500, 5000, 10000, 25000, 50000, 75000, 10000, 250000, 500000, 750000, 1000000, 2500000, 5000000, 7500000, or 10000000 subsets of or individual immune cells expressing different BCRs (or antibodies) or TCRs.

In some cases, the source immunoreceptor-expressing cells can be obtained from a tissue sample comprising a solid tissue, with non-limiting examples including a tissue from brain, liver, lung, kidney, prostate, ovary, spleen, lymph node (including tonsil), thyroid, thymus, pancreas, heart, skeletal muscle, intestine, larynx, esophagus, and stomach. Additional non-limiting sources include bone marrow, cord blood, tissue from a site of infection, ascites, pleural effusion, spleen tissue, and tumors. In some embodiments, T cell lines may be used. In some embodiments, the cell can be derived or obtained from a healthy donor, from a patient diagnosed with cancer or from a patient diagnosed with an infection. In some embodiments, the cell is part of a mixed population of cells which present different phenotypic characteristics.

The source immunoreceptor-expressing cells can be a tumor-infiltrating lymphocyte (TIL), e.g., tumor-infiltrating T cells. A TIL can be isolated from an organ afflicted with a cancer. One or more cells can be isolated from an organ with a cancer that can be a brain, heart, lungs, eye, stomach, pancreas, kidneys, liver, intestines, uterus, bladder, skin, hair, nails, ears, glands, nose, mouth, lips, spleen, gums, teeth, tongue, salivary glands, tonsils, pharynx, esophagus, large intestine, small intestine, rectum, anus, thyroid gland, thymus gland, bones, cartilage, tendons, ligaments, suprarenal capsule, skeletal muscles, smooth muscles, blood vessels, blood, spinal cord, trachea, ureters, urethra, hypothalamus, pituitary, pylorus, adrenal glands, ovaries, oviducts, uterus, vagina, mammary glands, testes, seminal vesicles, penis, lymph, lymph nodes or lymph vessels. One or more TILs can be from a brain, heart, liver, skin, intestine, lung, kidney, eye, small bowel, or pancreas. TILs can be from a pancreas, kidney, eye, liver, small bowel, lung, or heart. The one or more cells can be pancreatic islet cells, for example, pancreatic β cells. In some cases, a TIL can be from a gastrointestinal cancer. A TIL culture can be prepared a number of ways. For example, a tumor can be trimmed from non-cancerous tissue or necrotic areas. A tumor can then be fragmented to about 2-3 mm in length. In some cases, a tumor can be fragmented from about 0.5 mm to about 5 mm in size, from about 1 mm to about 2 mm, from about 2 mm to about 3 mm, from about 3 mm to about 4 mm, or from about 4 mm to about 5 mm. Tumor fragments can then be cultured in vitro utilizing media and a cellular stimulating agent such as a cytokine. In some cases, IL-2 can be utilized to expand TILs from a tumor fragment. A concentration of IL-2 can be about 6000 IU/mL. A concentration of IL-2 can also be about 2000 IU/mL, 3000 IU/mL, 4000 IU/mL, 5000 IU/mL, 6000 IU/mL, 7000 IU/mL, 8000 IU/mL, 9000 IU/mL, or up to about 10000 IU/mL. Once TILs are expanded they can be subject to in vitro assays to determine tumor reactivity. For example, TILs can be evaluated by FACs for CD3, CD4, CD8, and CD58 expression. TILs can also be subjected to cocultured, cytotoxicity, ELISA, or ELISPOT assays. In some cases, TIL cultures can be cryopreserved or undergo a rapid expansion. A cell, such as a TIL, can be isolated from a donor of a stage of development including, but not limited to, fetal, neonatal, young and adult.

One or more samples can be from one or more sources. One or more of samples may be from two or more sources. One or more of samples may be from one or more subjects. One or more of samples may be from two or more subjects.

One or more of samples may be from the same subject. One or more subjects may be from the same species. One or more subjects may be from different species. The one or more subjects may be healthy. The one or more subjects may be affected by a disease, disorder or condition.

A sample can be taken from a subject with a condition. In some embodiments, the subject from whom a sample is taken can be a patient, for example, a cancer patient or a patient suspected of having cancer. The subject can be a mammal, e.g., a human, and can be male or female. In some embodiments, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

The subject can have a disease in which a target antigen is expressed. For example, the disease can be cancer including, B-cell lymphoma, acute lymphoblastic leukemia (ALL), chronic lymphocytic leukemia, acute myeloid leukemia, adrenocortical carcinoma, adrenal cortex cancer, AIDS-related cancers, anal cancer, appendix cancer, astrocytomas, atypical teratoid/rhabdoid tumor, basal cell carcinoma, bile duct cancer, extrahepatic, bladder cancer, bone cancer (includes ewing sarcoma and osteosarcoma and malignant fibrous histiocytoma), brain tumors, breast cancer, burkitt lymphoma, carcinoid tumor (gastrointestinal), carcinoma of unknown primary, central nervous system, lymphoma, primary, cervical cancer, cholangiocarcinoma, chronic lymphocytic leukemia (cll), chronic myelogenous leukemia (cml), chronic myeloproliferative neoplasms, colorectal cancer, cutaneous t-cell lymphoma, ductal carcinoma in situ (dcis), endometrial cancer, esophageal, ewing sarcoma, extragonadal germ cell tumor, eye cancer, intraocular melanoma, retinoblastoma, fallopian tube cancer, fibrous histiocytoma of bone, malignant, and osteosarcoma, gallbladder cancer, gastric (stomach) cancer, gastrointestinal carcinoid tumor, gastrointestinal stromal tumors (gist), germ cell tumors, extragonadal, ovarian, testicular, gestational trophoblastic disease, gliomas, hairy cell leukemia, head and neck cancer, hepatocellular (liver) cancer, histiocytosis, langerhans cell, hodgkin lymphoma, hypopharyngeal cancer, intraocular melanoma, islet cell tumors, pancreatic neuroendocrine tumors, kaposi sarcoma, kidney, langerhans cell histiocytosis, laryngeal cancer, leukemia, lip and oral cavity cancer, liver cancer (primary), lung cancer, lymphoma, macroglobulinemia, waldenström, male breast cancer, malignant fibrous histiocytoma of bone and osteosarcoma, melanoma, melanoma, intraocular (eye), merkel cell carcinoma, mesothelioma, malignant, metastatic squamous neck cancer with occult primary, mouth cancer, multiple myeloma/plasma cell neoplasms, mycosis fungoides, myelodysplastic syndromes, myelodysplastic/myeloproliferative neoplasms and chronic myeloproliferative neoplasms, myelogenous leukemia, chronic (cml), myeloid leukemia, acute (AML), nasal cavity and paranasal sinus cancer, nasopharyngeal cancer, neuroblastoma, non-hodgkin lymphoma. non-small cell lung cancer, oral cancer, lip and oral cavity cancer and oropharyngeal cancer, osteosarcoma and malignant fibrous histiocytoma of bone, ovarian cancer, pancreatic cancer and pancreatic neuroendocrine tumors (islet cell tumors), paraganglioma, paranasal sinus and nasal cavity cancer, parathyroid cancer, penile cancer, pharyngeal cancer, pheochromocytoma, pituitary tumor, plasma cell neoplasm/multiple myeloma, pregnancy and breast cancer, primary central nervous system (CNS) lymphoma, primary peritoneal cancer, prostate cancer, rectal cancer, renal cell (kidney) cancer, retinoblastoma, salivary gland cancer, sarcoma, ewing sarcoma, kaposi sarcoma, osteosarcoma, rhabdomyosarcoma, uterine sarcoma, sezary syndrome, skin cancer, small cell lung cancer, small intestine cancer, soft tissue sarcoma, squamous cell carcinoma, squamous neck cancer with occult primary, metastatic, stomach (gastric) cancer, t-cell lymphoma, cutaneous, testicular cancer, throat cancer, thymoma and thymic carcinoma, thyroid cancer, transitional cell cancer of the renal pelvis and ureter, ureter and renal pelvis, transitional cell cancer, urethral cancer, uterine cancer, endometrial and uterine sarcoma, vaginal cancer, vulvar cancer, waldenström macroglobulinemia, or wilms tumor.

In some embodiments, a sample is a fluid, such as blood, saliva, lymph, urine, cerebrospinal fluid, seminal fluid, sputum, stool, or tissue homogenates. In some embodiments, the sample is saliva. In some embodiments, the sample is whole blood. In some embodiments, in order to obtain sufficient amount of polynucleotides for testing, a blood volume of at least about 0.001, 0.005, 0.01, 0.05, 0.1, 0.5, 1, 2, 3, 4, 5, 10, 20, 25, 30, 35, 40, 45, or 50 mL is drawn. In some cases, blood can be collected into an apparatus containing a magnesium chelator including but not limited to EDTA, and is stored at 4° C. Optionally, a calcium chelator, including but not limited to EGTA, can be added. In some cases, a cell lysis inhibitor is added to the blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive cross-linkers, sulfhydryl reactive crosslinkers, sulfhydryl addition or disulfide reduction, carbohydrate reactive crosslinkers, carboxyl reactive crosslinkers, photoreactive crosslinkers, or cleavable crosslinkers. In some embodiments, non-nucleic acid materials can be removed from the starting material using enzymatic treatments (such as protease digestion).

A plurality of samples may comprise at least 2, 3, 4, 5, 10, 20, 30, 40, 50, 60, 70, 80, 90 or 100 or more samples. The plurality of samples may comprise at least about 100, 200, 300, 400, 500, 600, 700, 800, 900 or 1000 or more samples. The plurality of samples may comprise at least about 1000, 2000, 3000, 4000, 5000, 6000, 7000, 8000 samples, 9000, or 10,000 samples, or 100,000 samples, or 1,000,000 or more samples. The plurality of samples may comprise at least about 10,000 samples.

A first sample may comprise one or more cells and the second sample may comprise one or more cells. The one or more cells of the first sample may be of the same cell type as the one or more cells of the second sample. The one or more cells of the first sample may be of a different cell type as one or more different cells of the plurality of samples.

The plurality of samples may be obtained concurrently. A plurality of samples can be obtained at the same time. The plurality of samples can be obtained sequentially. A plurality of samples can be obtained over a course of years, e.g., 100 years, 10 years, 5 years, 4 years, 3 years, 2 years or 1 year of obtaining one or more different samples. One or more samples can be obtained within about one year of obtaining one or more different samples. One or more samples can be obtained within 12 months, 11 months, 10 months, 9 months, 8 months, 7 months, 6 months, 4 months, 3 months, 2 months or 1 month of obtaining one or more different samples. One or more samples can be obtained within 30 days, 28 days, 26 days, 24 days, 21 days, 20 days, 18 days, 17 days, 16 days, 15 days, 14 days, 13 days, 12 days, 11 days, 10 days, 9 days, 8 days, 7 days, 6 days, 5 days, 4 days, 3 days, 2 days or 1 day of obtaining one or more different samples. One or more samples can be obtained within about 24 hours, 22 hours, 20 hours, 18 hours, 16 hours, 14 hours, 12 hours, 10 hours, 8 hours, 6 hours, 4 hours, 2 hours or 1 hour of obtaining one or more different samples. One or more samples can be obtained within about 60 seconds, 45 seconds, 30 seconds, 20 seconds, 10 seconds, 5 seconds, 2 seconds or 1 second of obtaining one or more different samples. One or more samples can be obtained within less than one second of obtaining one or more different samples.

Sources of T Cells

T cells can be obtained from a subject (e.g., primary T cells). In some cases, the source TCR-expressing cells are obtained from a subject. T cells may be obtained from any sample described herein. In some cases, the recipient T cells are obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects, T cell lines may be used. T cells can be helper T cells, a cytotoxic T cells, memory T cells, regulatory T cells, natural killer T cells, alpha beta T cells, or gamma delta T cells. In certain aspects of the present disclosure, T cells can be obtained from a unit of blood collected from a subject using a variety of techniques, such as Ficoll™ separation. Cells from the circulating blood of an individual can be obtained by apheresis. The apheresis product may contain lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media for subsequent processing steps. In some cases, the cells can be washed with phosphate buffered saline (PBS). The wash solution may lack calcium or magnesium or other divalent cations. Initial activation steps in the absence of calcium can lead to magnified activation. A washing step may be accomplished by methods such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In an aspect, T cells are isolated from peripheral blood lymphocytes or tissues by lysing the red blood cells and depleting the monocytes, for example, by centrifugation through a PERCOLL™ gradient or by counterflow centrifugal elutriation. When isolating T cells from tissues (e.g., isolating tumor-infiltrating T cells from tumor tissues), the tissues made be minced or fragmented to dissociate cells before lysing the red blood cells or depleting the monocytes. A specific subpopulation of T cells, such as CD3+, CD28+, CD4+, CD8+, CD45RA+, and CD45RO+ T cells, can be further isolated by positive or negative selection techniques. For example, T cells can be isolated by incubation with anti-CD3/anti-CD28 (e.g., 3×28)-conjugated beads, such as DYNABEADS™ M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least or equal to about 1, 2, 3, 4, 5, or 6 hours. In yet another aspect, the time period is 10 to 24 hours. In an aspect, the incubation time period is about 24 hours. Longer incubation times may be used to isolate T cells in any situation where there are few T cells as compared to other cell types, such as in isolating tumor infiltrating lymphocytes (TILs) from tumor tissue or from immunocompromised individuals. Further, use of longer incubation times can increase the efficiency of capture of CD8+ T cells. Thus, by simply shortening or lengthening the time T cells are allowed to bind to the anti-CD3/anti-CD28 beads and/or by increasing or decreasing the ratio of beads to T cells, subpopulations of T cells can be selected for or against at culture initiation or at other time points during the process. Additionally, by increasing or decreasing the ratio of anti-CD3 and/or anti-CD28 antibodies on the beads or other surface, subpopulations of T cells can be selected for or against at culture initiation or at other desired time points. In some cases, multiple rounds of selection can be used. In certain aspects, the selection procedure can be performed and the "unselected" cells (cells that may not bind to the anti-CD3/anti-CD28 beads) can be used in the activation and expansion process. "Unselected" cells can also be subjected to further rounds of selection.

Enrichment of a T cell population by negative selection can be accomplished with a combination of antibodies directed to surface markers unique to the negatively selected cells. One example method is cell sorting and/or selection via negative magnetic immune adherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be useful to enrich for or positively select for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

In one embodiment, a T cell population can be selected that expresses one or more of IFN-γ, TNF-alpha, IL-17A, IL-2, IL-3, IL-4, GM-CSF, IL-10, IL-13, granzyme B, and perforin, or other appropriate molecules, e.g., other cytokines and transcription factors such as T-bet, Eomes, Tcf1 (TCF7 in human). Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, the volume in which beads and cells are mixed together may be decreased (e.g., increase the concentration of cells) to ensure maximum contact of cells and beads. For example, in an aspect, a concentration of 2 billion cells/mL is used. In another aspect, a concentration of 1 billion cells/mL is used. In a further aspect, greater than 100 million cells/mL is used. In a further aspect, a concentration of cells of at least about 10, 15, 20, 25, 30, 35, 40, 45, or 50 million cells/mL is used. In some aspects, a concentration of cells of at least about 75, 80, 85, 90, 95, or 100 million cells/mL is used. In some aspects, a concentration of cells of at least about 125 or 150 million cells/mL can be used. Using high concentrations can result in increased cell yield, cell activation, and cell expansion. Further, use of high cell concentrations can allow more efficient capture of cells that may weakly express target antigens of interest, such as CD28-negative T cells, or from samples where there are many tumor cells present (e.g., leukemic blood, tumor tissue, etc.). Such populations of cells may have therapeutic value. For example, using high concentration of cells allows more efficient selection of CD8+ T cells that may have weaker CD28 expression.

In some cases, lower concentrations of cells may be used. By significantly diluting the mixture of T cells and surface, interactions between the particles and cells can be minimized. This can select for cells that express high amounts of desired antigens to be bound to the particles. For example, CD4+ T cells can express higher levels of CD28 and can be more efficiently captured than CD8+ T cells in dilute concentrations. In some aspects, the concentration of cells used is at least about $5\times10^5$/mL, $5\times10^6$/mL, or more. In other aspects, the concentration used can be from about $1\times10^5$/mL to $1\times10^6$/mL, and any integer value in between. In other aspects, the cells may be incubated on a rotator for varying lengths of time at varying speeds at either 2-10° C. or at room temperature.

T cells for stimulation can also be frozen after a washing step. The freeze and subsequent thaw step may provide a more uniform product by removing granulocytes and to some extent monocytes in the cell population. After the washing step that removes plasma and platelets, the cells may be suspended in a freezing solution. While many freezing solutions and parameters may be useful in this context, one method that can be used involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing Hespan and PlasmaLyte A. The cells can then be frozen to −80° C. and stored in the vapor phase of a liquid nitrogen storage tank. Cell may be frozen by uncontrolled freezing immediately at −20° C. or in liquid nitrogen. In certain aspects, cryopreserved cells are thawed and washed as described herein and allowed to rest for one hour at room temperature prior to activation.

Also contemplated in the context of the present disclosure is the collection of blood samples or apheresis product from a subject at a time period prior to when expanded cells (e.g., engineered cells expressing TCRs for T cell therapy) might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In some cases, a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present disclosure, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Thus, it is contemplated within the context of the present disclosure to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Besides primary T cells obtained from a subject, the T cells used as source cell or recipient cell may be cell-line cells, such as cell-line T cells. Examples of cell-line T cells include, but are not limited to, Jurkat, CCRF-CEM, HPB-ALL, K-T1, TALL-1, MOLT 16/17, and HUT 78/H9.

T cells can be obtained from an in vitro culture. T cells can be activated or expanded in vitro by contacting with a tissue or a cell. See "Activation and Expansion" section. For example, the T cells isolated from a patient's peripheral blood can be co-cultured with cells presenting tumor antigens such as tumor cells, tumor tissue, tumorsphere, tumor lysate-pulsed APC or tumor mRNA-loaded APC. The cells presenting tumor antigens may be APC pulsed with or engineered to express a defined antigen, a set of defined antigens or a set of undefined antigens (such as tumor lysate or total tumor mRNA). For example, in the cases of presenting defined antigens, an APC can express one or more minigens encoding one or more short epitopes (e.g., from 7 to 13 amino acids in length) with known sequences. An APC can also express two or more minigens from a vector containing sequences encoding the two or more epitopes. In the cases of presenting undefined antigens, an APC can be pulsed with tumor lysate or total tumor mRNA. The cells presenting tumor antigens may be irradiated before the co-culture. The co-culture may be in media comprising reagents (e.g., anti-CD28 antibody) that may provide co-stimulation signal or cytokines. Such co-culture may stimulate and/or expand tumor antigen-reactive T cells. These cells may be selected or enriched using cell surface markers described herein (e.g., CD25, CD69, CD137). Using this method, tumor antigen-reactive T cells can be pre-enriched from the peripheral blood of the patient. These pre-enriched T cells can be used as the input to obtain fused (or physically linked) TCR using methods described herein. In some cases, the pre-enriched T cells may be used as the input to be subject to any other methods to identify the cognate pairs of the TCRs, for example, by sequencing using single cell barcodes. The pre-enriched T cells (e.g., CD137+) may contain T cells that acquired marker (e.g., CD137) expression during the co-culture, and may also contain T cells that already express the marker at blood draw. The latter population may nevertheless be tumor reactive. This method can offer an easier alternative to isolating TILs described.

Immunoreceptor-Programmed Recipient Cells

The expression vectors containing fused bipartite immunoreceptor polynucleotides as described herein can be introduced to new host cells (referred to as "recipient cells" in the present disclosure) to create immunoreceptor-programmed recipient cells. For different purposes, different types of immunoreceptor can be introduced to different types of recipient cells. For example, antibody can be introduced to a variety of primary cells (e.g., B cells) or cell lines (e.g., HeLa cells, CHO cells) for expression. For example, TCR can be introduced to T cells to confer the T cells novel specificity. The immunoreceptor-programmed recipient cells may use the newly introduced immunoreceptors to sense (e.g., recognize or bind) target molecules or cells. For example, the target molecule may be an antigen or a fragment thereof. The target molecule may be a peptide. The target molecule may be an epitope.

Source of Recipient Cell

The recipient cells may be obtained from samples as described in the "Sample" section. The T cells as recipient cells may be from sources as described in "Sources of T cells" section. The recipient cells can be T cells, B cells, NK cells, macrophages, neutrophils, granulocytes, eosinophils, red blood cells, platelets, stem cells, iPSCs, or mesenchymal stem cells. In addition, the recipient cell can be a cell line cell. The cell line can be tumorigenic or artificially immortalized cell line. Examples of cell lines include, but are not limited to, CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; and Molt 4 cells. The recipient cell can be an autologous T cell or an allogeneic T cell. The recipient cell can be a genetically modified or engineered cell.

Activation and Expansion

Whether prior to or after transferring the immunoreceptor-expressing vectors to the T cells, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

The T cells can be expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell. As non-limiting examples, T cell populations may be stimulated in vitro such as by contact with an anti-CD3 antibody or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. For example, the agents providing each signal may be in solution or coupled to a surface. The ratio of particles to cells may depend on particle size relative to the target cell. In further embodiments, the cells, such as T cells, are combined with agent-coated beads, the beads and the cells are subsequently separated, and then the cells are cultured. In an alternative embodiment, prior to culture, the agent-coated beads and cells are not separated but are cultured together. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, IL-4, IL-7, GM-CSF, IL-10, IL-2, IL-15, TGFβ, and TNF-α or any other additives for the growth of cells. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. The target cells can be maintained under conditions necessary to support growth, for example, an appropriate temperature (e.g., 37° C.) and atmosphere (e.g., air plus 5% $CO_2$). T cells that have been exposed to varied stimulation times may exhibit different characteristics.

In another embodiment, the cells can be activated or expanded by co-culturing with tissue or cells. The cells used to activate T cells can be APC or artificial APC (aAPC). The APC can be professional APC such as dendritic cell, macrophage, or B cell. The APC can be a monocyte or monocyte-derived dendritic cell. An aAPC can express ligands for T cell receptor and costimulatory molecules and can activate and expand T cells for transfer, while improving their potency and function in some cases. An aAPC can be engineered to express any gene for T cell activation. An aAPC can be engineered to express any gene for T cell expansion. An aAPC can be a bead, a cell, a protein, an antibody, a cytokine, or any combination. An aAPC can deliver signals to a cell population that may undergo genomic transplant. For example, an aAPC can deliver a signal 1, signal, 2, signal 3 or any combination. A signal 1 can be an antigen recognition signal. For example, signal 1 can be ligation of a TCR by a peptide-MHC complex or binding of agonistic antibodies directed towards CD3 that can lead to activation of the CD3 signal-transduction complex. Signal 2 can be a co-stimulatory signal. For example, a co-stimulatory signal can be anti-CD28, inducible co-stimulator (ICOS), CD27, and 4-1BB (CD137), which bind to ICOS-L, CD70, and 4-1BBL, respectively. Signal 3 can be a cytokine signal. A cytokine can be any cytokine. A cytokine can be IL-2, IL-7, IL-12, IL-15, IL-21, or any combination thereof.

In some cases, an aAPC may be used to activate and/or expand a cell population. In some cases, an artificial may not induce allospecificity. An aAPC may not express HLA in some cases. An aAPC may be genetically modified to stably express genes that can be used to activation and/or stimulation. In some cases, a K562 cell may be used for activation. A K562 cell may also be used for expansion. A K562 cell can be a human erythroleukemic cell line. A K562 cell may be engineered to express genes of interest. K562 cells may not endogenously express HLA class I, II, or CD1d molecules but may express ICAM-1 (CD54) and LFA-3 (CD58). K562 may be engineered to deliver a signal 1 to T cells. For example, K562 cells may be engineered to express HLA class I. In some cases, K562 cells may be engineered to express additional molecules such as B7, CD80, CD83, CD86, CD32, CD64, 4-1BBL, anti-CD3, anti-CD3 mAb, anti-CD28, anti-CD28mAb, CD1d, anti-CD2, membrane-bound IL-15, membrane-bound IL-17, membrane-bound IL-21, membrane-bound IL-2, truncated CD19, or any combination. In some cases, an engineered K562 cell can expresses a membranous form of anti-CD3 mAb, clone OKT3, in addition to CD80 and CD83. In some cases, an engineered K562 cell can expresses a membranous form of anti-CD3 mAb, clone OKT3, membranous form of anti-CD28 mAb in addition to CD80 and CD83.

In some cases, restimulation of cells can be performed with antigen and irradiated, histocompatible APCs, such as feeder PBMCs. In some cases, cells can be grown using non-specific mitogens such as PHA and allogenic feeder cells. Feeder PBMCs can be irradiated at 40Gy. Feeder PBMCs can be irradiated from about 10 Gy to about 15 Gy, from about 15 Gy to about 20 Gy, from about 20Gy to about 25 Gy, from about 25 Gy to about 30 Gy, from about 30 Gy to about 35 Gy, from about 35 Gy to about 40 Gy, from about 40 Gy to about 45 Gy, from about 45 Gy to about 50 Gy. In some cases, a control flask of irradiated feeder cells only can be stimulated with anti-CD3 and IL-2.

An aAPC can be a bead. A spherical polystyrene bead can be coated with antibodies against CD3 and CD28 and be used for T cell activation. A bead can be of any size. In some cases, a bead can be or can be about 3 and 6 micrometers. A bead can be or can be about 4.5 micrometers in size. A bead can be utilized at any cell to bead ratio. For example, a 3 to 1 bead to cell ratio at 1 million cells per milliliter can be used. An aAPC can also be a rigid spherical particle, a polystyrene latex microbeads, a magnetic nano- or micro-particles, a nanosized quantum dot, a poly(lactic-co-glycolic acid) (PLGA) microsphere, a nonspherical particle, a carbon nanotube bundle, a ellipsoid PLGA microparticle, a nano-worms, a fluidic lipid bilayer-containing system, a 2D-supported lipid bilayer (2D-SLBs), a liposome, a RAFTsomes/microdomain liposome, an SLB particle, or any combination thereof.

In some cases, an aAPC can expand CD4 T cells. For example, an aAPC can be engineered to mimic an antigen processing and presentation pathway of HLA class II-restricted CD4 T cells. A K562 can be engineered to express HLA-D, DP α, DP β chains, Ii, DM α, DM β, CD80, CD83, or any combination thereof. For example, engineered K562 cells can be pulsed with an HLA-restricted peptide in order to expand HLA-restricted antigen-specific CD4 T cells.

In some cases, the use of aAPCs can be combined with exogenously introduced cytokines for T cell activation, expansion, or any combination. Cells can also be expanded in vivo, for example in the subject's blood after administration of genomically transplanted cells into a subject.

The cells (e.g., recipient cells) can also be expanded in vivo, for example in the subject's blood after administrating the cells into the subject.

Prevention of Mis-Assembly

In some cases, immunoreceptor-expressing vectors may be introduced to recipient cells which express endogenous bipartite immunoreceptors. In such cases, mis-assembly between endogenous and exogenous immunoreceptors may be prevented. For example, if a TCR-expressing vector is introduced to a T cell, both the endogenous (from the genome) TCR chains and the exogenous (from the vector) TCR chains may be expressed. Thus, there is a probability that an endogenous alpha chain may form a dimer with an exogenous beta chain, resulting in unwanted TCR (i.e., mis-assembled TCR). Similar situation may occur in BCR-programmed B cells. Various methods can be used to minimize such mis-assembly by engineering the constant domains of the immunoreceptor chains or knocking out/down endogenous genes encoding immunoreceptors, such as disulfide bond engineering (Kuball 2007), domain swapping (Bethune 2016), knockdown by RNA interference (Bunse 2014), gene knockout (Provasi 2012), murinizing portions of the TCR, expressing TCR as a single chain (Uckert and Schumacher, 2009), and expressing TCR in a TCR-CAR construct (Walseng et al., 2017).

In some cases, a sequence encoding a constant domain of an immunoreceptor chain is engineered by mutagenesis. In some cases, the sequences encoding both constant domains of the two immunoreceptor chains are engineered such that one or more cysteines can be introduced to the contact region of each chain. In some cases, the sequences encoding both constant domains of the two immunoreceptor chains are engineered such that one or more disulfide bonds can be formed between the two chains of the expressed immunoreceptors. For example, one or more cysteines may be introduced into each constant domain of the two chains (e.g., TCRα and TCRβ chains, or BCR heavy chain and light chain) of the immunoreceptor, disulfide bond(s) can be formed between the cysteines.

In some cases, the sequences encoding constant domains of the two chains of an immunoreceptor are engineered such that the sequences encode constant domains found in a species different from the species where the recipient cells are obtained. For example, if the recipient cells are obtained from a human, the sequences encoding constant domains of the two chains of an immunoreceptor may be changed to the sequences encoding constant domains of an immunoreceptor found in mice (i.e., murinization).

In some cases, a first segment of a first sequence encoding a first constant domain of a first chain (e.g., TCRα chain) and a second segment of a second sequence encoding a second constant domain of a second chain (e.g., TCRβ chain) can be swapped. For example, after the swapping the mis-assembled TCR molecules may not properly assemble with CD3 or signal.

In some cases, a first segment of a first sequence encoding a first constant domain of a first chain (e.g., TCRα chain) and a second segment of a second sequence encoding a second constant domain of a second chain (e.g., TCRβ chain) can be changed to an intracellular domain of another protein, for example, CD3-zeta. For example, modified TCRα and TCRβ chains in which the original constant domains downstream of the extracellular cysteine (which mediates the interchain disulphide bridge) can be replaced with complete human CD3-zeta, resulting in an inability of the modified TCR chains to mis-assemble with the endogenous TCR chain and correct pairing of these TCR chains in primary human T cells.

In some cases, a construct encoding a modified TCRα chain linked to a modified TCRβ via a P2A linker can be used.

In some cases, the modified TCRβ chain can be fused to an artificial signaling domain similar to the one used for chimeric antigen receptors (CARs), namely CD28 transmembrane (TM) coding sequence followed by two signaling modules (CD28 and CD3ζ). At the same time, the modified TCRα chain may only contain the extracellular domain of TCRα. In addition, a cysteine replacement can be performed on the constant domain (C-domain) of TCRα chain and TCRβ chain in order to increase the TCR dimer stability. This construct has been referred to as "TCR-CAR". Such TCR-CAR may signal in non-T cells such as NK cells.

The recipient cell may be a genetically modified cell with its endogenous immunoreceptors knocked out or knocked down. The examples described herein use T cell as the recipient cell, but similar strategies can be applied to other cell types.

Gene-editing nucleases may be employed in order to disrupt components of the endogenous TCR. Since the TCR α/β dimer can produce a fully functioning TCR complex, disrupting TCRα and/or TCRβ function may reduce (or even eliminate) endogenous TCR expression. Various methods may be used to disrupt endogenous TCRα or TCRβ genes. For example, four classes of gene editing proteins exist that share a common mode of action in binding a user defined sequence of DNA and mediating a double stranded DNA break (DSB). Zinc finger nucleases (ZFN) are heterodimeric arrays that co-localize at a target DNA site. ZFNs include individual finger subunits that bind DNA and are tethered to the Fokl nuclease domain that cleaves DNA. Transcription activator-like effector nucleases (TALEN) include repeating units that bind DNA by virtue of a hypervariable two amino acid sequence (repeat variable diresidue; RVD) that governs DNA base recognition. Similar to ZFNS, TALENs function as dimeric proteins that are fused to the Fokl endonuclease domain for DSB generation. Meganucleases (MN) are monomeric proteins with innate nuclease activity that are derived from bacterial homing endonucleases and engineered for a unique target site. The clustered regularly interspaced short palindromic repeats (CRISPR) and associated Cas9 nuclease platform involves a small guide RNA (gRNA) transcript that contacts a target DNA sequence via Watson-Crick base pairing and the Cas9 nuclease that cleaves the DNA.

In some cases, introducing the genome-editing nuclease into the T cell includes introducing into the T cell a polynucleotide that encodes the genome-editing nuclease. In some cases, introducing the genome-editing nuclease into the T cell includes introducing into the T cell a Cas9 polypeptide. In some embodiments, the genome-editing nuclease includes a TALEN nuclease, a CRISPR/Cas9 nuclease, or a megaTAL nuclease. In some cases, the CRISPR/Cas9 nuclease is derived from either *Streptococcus pyogenes* or *Staphylococcus aureus*. In some of these embodiments, the CRISPR/Cas9 nuclease includes a nuclease-resistant gRNA such as, for example, at least one 2'-OMe-phosphorothioate modified base, at least one 2'-O-methyl modified base, or at least one 2'-O-methyl 3' thioPACE modified base. In some cases, the TALEN nuclease or the megaTAL nuclease is encoded by an RNA that has an exogenous polyadenylation signal. In some cases, the method described herein may further include culturing the T cell under conditions effective for expanding the population of genome-modified T cells.

Additional Genome Engineering of the Recipient Cells

In some cases, an immunoreceptor-programmed recipient cell comprises an inactivated gene encoding immune checkpoint protein such as PD1 and CTLA-4. This may be made possible by inactivation of genes encoding immune checkpoint protein such as PD1 and CTLA-4. In some cases, the genetic modification relies on the inactivation of one gene, or two genes selected from the group consisting of PD1, CTLA-4, LAG3, Tim3, BTLA, BY55, TIGIT, B7H5, LAIR1, SIGLEC10, 2B4. In some cases, the genetic modification can include knock out of MHC components such as B2M. The genes described herein may also be downregulated, for example, by microRNA.

Additional Agents Expressed by Recipient Cells

The immunoreceptor-programmed recipient cells may be engineered to express an additional agent (e.g., protein or RNA) to enhance the function of these cells. For example, the function may be cytotoxic function, pro-inflammatory function, or anti-inflammatory function. In some cases, the immunoreceptor-programmed recipient cells may be engineered to express an additional agent to enhance anti-tumor efficacy. In some cases, an additional agent is a secreted protein. The secreted protein may be a cytokine, or an antibody or a fragment thereof. In some cases, the secreted protein is a cytokine. In some cases, the secreted protein is a single chain variable fragment (scFv). The secreted protein may inhibit an inhibitory molecule, wherein the inhibitory molecule decreases the ability of an immune cell to mount an immune effector response. The secreted protein can be pro-inflammatory cytokines or anti-inflammatory cytokines. Examples of pro-inflammatory cytokines include, but are not limited to, tumor necrosis factor alpha (TNFα); interleukin (IL)-1α; IL-10; IL-2; IL-5; IL-6; IL-8; IL-15; IL-18; interferon (IFN-γ); platelet-activating factor (PAF); Monocyte chemotactic proteins 1 and 2 (MCP-1, MCP-2); macrophage migration inhibitory factor (MIF); CXCL8; CXCL9; CXCL10; and high mobility group box protein 1 (HMGB-1). Examples of anti-inflammatory cytokines include, but are not limited to, IL-1ra, IL-4, IL-10, IL-11, IL-13, transforming growth factor beta (TGF-β), and IL-16. In some cases, an additional agent is RNA. In some cases, an additional agent may be a DNA encoding the RNA. The RNA may be a guide RNA, a microRNA or a small hairpin RNA (shRNA). The RNA can inhibit the transcription or translation of an inhibitory molecule. Examples of inhibitory molecules include PD1, PD-L1, CTLA4, TIM3, LAG3, VISTA, BTLA, TIGIT, LAIR1, CD160, 2B4 and TGFR beta. In some cases, the RNA can downregulate gene expression of an endogenous gene including TCRα chain, TCRβ chain, beta-2 microglobulin, a HLA molecule, CTLA-4, PD1, and FAS. The endogenous genes encoding these inhibitory molecules may also be knocked out by gene editing methods described herein.

In some embodiments, the immunoreceptor-programmed recipient cell described herein can further express another agent, e.g., an agent which enhances the activity of an immunoreceptor-programmed recipient cell. For example, the agent can be an agent which inhibits an inhibitory molecule. Inhibitory molecules can decrease the ability of an immunoreceptor-programmed recipient cell to mount an immune effector response. Examples of inhibitory molecules include PD1, PD-L1, CTLA4, TIM3, LAG3, VISTA, BTLA, TIGIT, LAIR1, CD160, 2B4 and TGFR beta.

The additional agent may be a switch receptor. For example, the agent which inhibits an inhibitory molecule comprises a first polypeptide, e.g., an inhibitory molecule, associated with a second polypeptide that provides a positive signal to the cell, e.g., an intracellular signaling domain. In some embodiments, the agent comprises a first polypeptide of an inhibitory molecule such as PD1, LAG3, CTLA4, CD160, BTLA, LAIR1, TIM3, 2B4 and TIGIT, or a fragment of any of these (e.g., at least a portion of an extracellular domain of any of these), and a second polypeptide which is an intracellular signaling domain (e.g., a costimulatory domain 4-1BB, CD27 or CD28) and/or a primary signaling domain (e.g., a CD3 zeta signaling domain). In some embodiments, the agent comprises a first polypeptide of PD1 or a fragment thereof (e.g., at least a portion of an extracellular domain of PD1), and a second polypeptide of an intracellular signaling domain such as a CD28 signaling domain or a CD3 zeta signaling domain. The additional agent may be a protein to confer lymphodepletion resistance or reduced graft-versus-host disease potential. For example, the protein can bind to an inhibitory natural killer (NK) cell receptor such that the NK cell can be inhibited from killing the recipient cells. The protein can be HLA-E or HLA-G.

In some embodiments, the additional agents are encoded by or expressed from the immunoreceptor-expressing vector.

Applications

As described herein, a polyclonal population of source immunoreceptor-expressing cells can be converted into a polyclonal population of immunoreceptor-programmed recipient cells, where the engineered immunoreceptor repertoire of the immunoreceptor-programmed recipient cells can comprise the natural immunoreceptor repertoire (e.g., cognate pair combinations of the immunoreceptor chains) of the source immunoreceptor-expressing cells. The bipartite nature of many immunoreceptors made this task difficult with conventional technologies. The methods provided herein can be used to overcome these difficulties. There can be several advantages of using the immunoreceptor-programmed recipient cells over using the source immunoreceptor-expressing cells. For example, the immunoreceptor-programmed recipient cells may be prepared at larger numbers, may have a more ideal functional characteristic, may be in a more ideal epigenetic state, may have a more uniform genetic or phenotypic background, may be engineered to express additional agents to enhance anti-tumor efficacy, or may be engineered to express reporter genes to aid selection. The immunoreceptor-programmed recipient cells may be used in many applications in many areas.

Antibody Discovery

When the source immunoreceptor-expressing cells are B cells, the resultant fused bipartite immunoreceptor polynucleotide library can be a library encoding a variety of antibodies. This library can be screened to find antibodies with desired features. The desired features may include binding to a particular target protein or triggering certain cellular response in a target cell. For antibody discovery, the fused BCR genes may be converted to single-chain Fv constructs (scFv) and scFv-expressing vectors using similar strategies described in Examples, except that the primers and linker sequences may be redesigned to fit the need of scFv construction, which can be done by a skilled artisan. The source immunoreceptor-expressing cells may be plasmablast, plasma cells, lymphoplasmacytoid cell, memory B cell, follicular B cell, marginal zone B cell, B-1 cells, B-2 cells, or regulatory B cells.

Selection for Binding

The antibody-expressing vectors or scFv-expressing vectors may be used with conventional screening technologies such as phage display, yeast display, mammalian cell display, and mRNA display. In addition, the antibody-expressing vector library can be introduced to a B cell line (e.g., Raji cell) to produce a library of engineered antibody-expressing recipient cells. These cells can be used in phenotypic screening described in Eyer et al., 2017 and Mazutis et al., 2013, where the antibody-expressing recipient cells may replace the B cells directly isolated from animals.

Selection for Function

The antibody-expressing vector library can also be introduced to mammalian cells engineered with a reporter circuit for the function of a surface receptor. Direct selection of antibodies that are receptor agonists can be achieved. For example, a library of antibody-expressing vectors in the form of lentiviruses can be used to infect eukaryotic cells that contain a fluorescent reporter system coupled to the receptor for which receptor agonist or antagonist antibodies are sought. In this embodiment of the method, very large numbers of candidate antibodies expressing lentivirus and eukaryotic reporter cells can be packaged together in a format where each is capable of replication, thereby forging a direct link between genotype and phenotype. Following infection and incubation in a diffusion-restricting set up (e.g., in soft agar or in droplets), cells that show an altered fluoresce (possibly due to the action of the secreted antibody encoded by the antibody-expressing vector) can be sorted and the integrated genes encoding the agonist or antagonist antibodies can be recovered. The incubation may be in the presence of a cognate ligand or a known agonist or antagonist antibody of the receptor in order to provide proper background signaling. This system has been validated by illustrating its ability to rapidly generate potent antibody agonists that are complete thrombopoietin phenocopies (Hongkai Zhang et al., Chemistry & biology 20(5):734-741, May 2013). The system can be generalizable to any pathway where its activation can be linked to production of a selectable phenotype.

Therapeutic Use of Polyclonal Antibodies

The methods described herein can be used to prepare recombinant polyclonal antibodies from DNA libraries obtained from B cell and plasma cell repertoires from human donors. The recombinant polyclonal antibodies can be used to treat certain diseases. For example, patients with immune deficiency can be treated with plasma-based drug products derived from plasma samples that are pooled from thousands of human donors. Examples of such products include intravenous immunoglobulin (IVIG) and hyperimmunes, a variation of IVIG prepared from the plasma of donors with high titers of antibodies to a specific pathogen. Hyperimmunes can be used to treat acute infections or prevent infection in immune compromised patients, such as after organ transplantation. Recombinant polyclonal antibodies can be used to replace the current plasma-based products. The recombinant polyclonal antibodies can be engineered to have higher potency than plasma-derived equivalents.

Therapeutic Use of Polyclonal Immunoreceptor-Programmed Recipient Cells

Immunoreceptor-programmed recipient cells can be administered to a patient to treat various diseases. In some embodiments, the immunoreceptor-programmed recipient cells are polyclonal immunoreceptor-programmed recipient cells.

TCR-T Cells for Treatment of Cancer

Many tumors may have large amount of T cells infiltrated into the tumor microenvironment, and many of these tumor-infiltrating T cells (TITs) may have TCR that recognize tumor-expressed antigens. These TITs may be tumor-reacting T cells. The antigens recognized by the TITs may be neoantigens, tumor-specific antigens or tumor-associated antigens. These antigens may be wildtype sequences or mutant sequences. A general strategy to treat cancer may be to enhance the number and/or activity of these TITs. One specific approach embodying this strategy can be ex vivo expansion of TITs. However, this approach may have many limitations. For example, some TITs can exhibit deeply exhausted phenotype partly due to chronic antigen exposure. These T cells may be expanded poorly. In addition, it may take a very long time to expand a small number of T cells isolated from surgically removed tumor to a number large enough to re-infuse into patient body (where hundreds of millions or even billions of cells may be needed). An alternative method enabled by recent advancement of single cell sequencing is to obtain paired TCR sequences from these tumor-infiltrated T cells including the deeply exhausted cells. Next, these TCR sequences can be synthesized to obtain TCR-expressing vectors. And these vectors can be introduced to a large number of fresh host T cells (e.g., isolated from patient's peripheral blood followed by ex vivo expansion, similar to the process in preparing host cells for CAR-T) to produce TCR-T cells. However, due to the limitation of DNA synthesis, only a small number (e.g., less than 100 or less than 50) of unique TCR-expressing vectors can be made at a time. In other words, the TCR-T cells may have a limited exogenous TCR repertoire.

With the technology to rapidly obtain fused bipartite immunoreceptor polynucleotide as described above, one can generate a large number (e.g., more than about 100, more than about 1,000, more than about 10,000, more than about 100,000, or more than about 1,000,000) unique TCR-expressing vectors, encoding a large number of TCRs. These vectors can be introduced to fresh host T cells (as recipient cells) to create polyclonal TCR-T cells with very diverse exogenous TCR repertoire (more than about 100, more than about 1,000, more than about 10,000, more than about 100,000, or more than about 1,000,000 clonotypes). These polyclonal TCR-T cells can then be administered into a patient.

The source TCR-expressing cells used in this application can be TITs isolated from surgically removed tumor. For example, the tumor tissue can be cut up into 3-5 mm$^2$ fragments after trimming away fat and connective tissue and disaggregated in cold RPMI 1640 using gentle mechanical pulverization using a Seward Stomacher device (Fisher, Pittsburgh, Pa.). This process can rapidly produce a single cell suspension without enzymatic digestion. The cell suspension can be filtered through a 75 μm pore-size screen (BD Biosciences, San Jose Calif.) and washed in culture medium. A portion of the cells used for immediate staining and analysis by flow cytometry can be washed in culture medium and the cell suspension can be layered over a discontinuous 70% followed by a 100% Ficoll Isopaque gradient, and centrifuged to separate the tumor cells (70% interface) from the enriched TITs (100% interface). The enriched TITs can be then washed in D-PBS, 1% BSA and then processed. In some cases, the TITs from tumor samples can be expanded in TIT culture medium (TIL-CM) containing RPMI 1640 with Glutamax (Invitrogen), 10% human AB serum (Sigma, St. Louis, Mich.), 50 mM 2-mercaptoethanol (Invitrogen), 1 mM pyruvate, 1× Penicillin/Streptomycin (Invitrogen) using 3,000 IU/ml recombinant IL-2.

In some cases, fresh tumor may not be available, and in such cases, nuclei may be isolated from frozen or fixed tissue. These nuclei may also serve as the input for the paired bipartite immunoreceptor cloning process (in this case paired TCR cloning) to obtain fused bipartite immunoreceptor polynucleotide library. These cells and nuclei can be used without further selection. Alternatively, a specific population of cells or nuclei can be isolated to enrich tumor specific TCRs. For example, expression of cell surface markers CD39, CD69, CD103, CD25, PD-1, TIM-3, OX-40, 4-1BB may be correlated with tumor-reactivity. The cell surface markers can be used to isolate/enrich tumor-reactive TCRs by FACS. In other words, cells with high expression of one or a combination of these markers can be used as the input for the paired TCR cloning.

T cells may be used as the recipient cells to create the polyclonal TCR-T cells. T cells as recipient cells can be obtained from sources as described in "Source of T cells" section and can be obtained from various samples as described in the "Sample" section. In some cases, T cells as recipient cells can be obtained from the peripheral blood of the patient, and expanded ex vivo as described herein.

Alternatively, T cells as recipient cells can be obtained from a donor. The donor can be a healthy donor. The T cells obtained from a donor may be suitably stored, for example, in the freezer, and then infused into allogeneic individuals on demand. The recipient cells or polyclonal TCR-T cells can be cultured or modified using the methods described in sections titled "Source of Recipient Cell", "Activation and Expansion", "Prevention of Mis-assembly", "Additional genome engineering of the recipient cells" and "Additional Agents Expressed by Recipient Cells". When the recipient cell is a T cell, the endogenous TCR of the T cell may be knocked out or knocked down as described herein. When the recipient cell is a T cell, it can be a CD8+ T cell, a CD4+ T cell, or a CD8+CD4+ double-positive T cell. It can be gamma-delta T cells. These TCR-T cells may be further engineered to express cytokines of other regulatory molecules to enhance their antitumor activity as described herein. The recipient cells obtained from a donor (e.g., a subject different from the subject to be treated) can be engineered to express a protein that binds an inhibitory natural killer (NK) cell receptor. The inhibitory NK cell receptor may be a killer-cell immunoglobulin-like receptor (KIR) or a C-type lectin family receptor. The inhibitory NK cell receptor may be NKG/CD94 or KIR2DL4. The protein that binds the inhibitory NK cell receptor may be a transmembrane protein, a cell surface protein, or a secreted protein. The protein that binds the inhibitory NK cell receptor may comprise HLA-E or HLA-G. In some embodiments, the protein that binds the inhibitory NK cell receptor further comprises a B2M domain. In some embodiments, the protein that binds the inhibitory NK cell receptor is B2M-HLA-E fusion or B2M-HLA-G fusion protein.

The methods described herein can enable personalized cancer treatment with oligoclonal or polyclonal TCR-T cells. These TCR-T cells can comprise subject-specific TCRs that may be tumor-relative. An example therapeutic method, termed synthetic TIL or SynTIL, is outlined in FIG. 19. First, resected tumor or tumor biopsy can be obtained from a patient. Tumor-infiltrating T cells can be obtained from the tumor tissue using existing methods (FIG. 19, Step (1)). However, instead of culturing these cells as in conventional TIL methods, the TCRs from these cells can be converted into fused TCR polynucleotides using methods provided herein (FIG. 19, Step (2)). The fused TCR polynucleotides can then be converted to TCR-expressing lentiviral vectors (FIG. 19, Step (3)) which can be used to transduce reporter cells as described herein (FIG. 19, Step (4)). The transduced reporter cells can be incubated with tumor cells or tumor mRNA-loaded APCs after which reporter-positive cells (e.g., tumor-reactive cells) can be identified or isolated (e.g., using FACS) as described herein (FIG. 19, Step (5), see also FIG. 18). Optionally, the TCRs of the identified reportor-positive cells can be sequenced. Next, the fused TCRs from the sorted cells can be re-amplified to create a pool of TCR-expressing vectors where the majority of the TCRs can be expected to be tumor-reactive (FIG. 19, Step (6)). In some cases, allogeneic T cells from a donor can be used to express the identified tumor-reactive cells instead of the autologous T cells. And in such cases, the allogeneic T cells may be engineered as described herein. Different TCR-expressing vectors can be prepared individually or as a pool, and then used to transduce a large number (e.g., hundreds of millions or billions) of autologous T cells from the peripheral blood of the patient using existing TCR-T manufacturing methods (FIG. 19, Step (7)). When the TCR-expressing vectors are prepared individually, a defined subset of them (e.g., 5 to 20 TCRs) can be used to engineer peripheral T cells to create TCR-T cells. These TCR-T cells can be considered oligoclonal. When the TCR-expressing vectors are prepared as a pool, the resultant TCR-T cells can be referred to as polyclonal. For example, the total number of TCR clones in a pool can be more than or equal to about 5, 10, 15, 20, 25, 30, 35, 40, 45, or 50, or more. The total number of TCR clones in a pool can be at least about 20, 30, 40, 50, 60, 80, 100, 200, 300, or 500, or more. The TCR-T cells can be subject to a series of release tests (FIG. 19, Step (8)) and administered (e.g., by infusion) into the patient. Example timing that may be needed for each step is indicated in FIG. 19. In certain situations, the tumor-infiltrating T cells can be replaced with peripheral T cells from the patient to use as source immunoreceptor-expressing cells. These source T cells (e.g., peripheral T cells) can be activated or expanded by co-culturing with tissue or cells. Target-reactive T cells (e.g., tumor-reactive T cells) from the peripheral blood may be enriched (1) based on surface marker expression (e.g., CD25, CD69, CD137, PD-1, and other markers described herein), (2) by in vitro stimulation with APCs pulsed with or engineered to express tumor antigens using a co-culture method described herein, or the combination of the two. The APCs can be professional APCs or non-professional APCs. The APCs may be isolated from a subject, e.g., a patient or a healthy donor. The APCs may be aAPC as described herein (e.g., K562 cells).

The method provided herein can offer faster turnaround time from isolation of T cells to administration of therapeutic cells into a subject than conventional methods. A method of treating a tumor in a subject provided herein can comprise isolating a population of T cells from the subject, wherein the population of T cells express a population of T-cell receptors (TCRs). A subpopulation of the population of TCRs can be enriched, wherein the subpopulation can comprise a plurality of tumor-reactive TCRs. Next, a plurality of recipient cells expressing the plurality of tumor-reactive TCRs or a subset thereof can be administered into the subject. In some cases, the administering is performed at most about 60 days, 50 days, 40 days, 30 days, 20 days or less after isolating the population of T cells. In some cases, the tumor of the subject has not progressed for more than about 60 days, 50 days, 40 days, 30 days, 20 days or less from isolating the population of T cell from the subject to administering the plurality of recipient cell into the subject. In some cases, size of the tumor has increased by less than about 50%, 30%, 40%, 20%, 15%, 10%, 5% or 2%, from isolating the population T cells to administering the plurality of recipient cells. In some cases, a number of tumor cells in the subject has not increased by about 2-fold, 3-fold, 4-fold, or 5-fold from isolating the population T cells to administering the plurality of recipient cells. In some cases, the tumor has not progressed to a new stage from isolating the population of T cells to administering the plurality of recipient cells. For example, the tumor has not progressed from stage I to stage II, from stage II to stage III, or from stage III to stage IV.

A method of treating a tumor in a subject provided herein can comprise isolating a population of T cells from the subject. The population of T cells can express a population of T-cell receptors (TCRs) from endogenous nucleic acids. Next, a subpopulation of the population of TCRs can be enriched, wherein the subpopulation can comprise a plurality of tumor-reactive TCRs. A plurality of recipient cells expressing the plurality of tumor-reactive TCRs or a subset thereof can then be administered into the subject. The polynucleotides encoding the plurality of tumor-reactive TCRs can be copied products (e.g. transcribed or amplified products) of the endogenous nucleic acids. These copied products can be generated by template-dependent nucleic acid synthesis, where a complementary strand is synthesized using an existing strand as a template, such as primer extension, nucleic acid amplification, second strand synthesis, transcription, reverse transcription, etc.

In some cases, the method does not comprise chemical synthesis of the polynucleotides encoding the plurality of tumor-reactive TCRs, for example, by using phosphoamidite. The population of T cells can be tumor-infiltrating T cells. The population of T cells can comprise exhausted T cells or regulatory T cells. The plurality of recipient cells can be allogeneic T cells, autologous T cells, or cell line cells. The method can further comprise expressing the population of TCRs in a population of reporter cells before enriching. In some cases, when expressing, nucleic acid sequences encoding the population of TCRs can be delivered into the population of reporter cells by a virus vector. The virus vector can be any type of vector described herein, for example, a viral vector or a non-viral vector. For example, the viral vector can be a retrovirus, a lentivirus, an adenovirus, an adeno-associated virus, a herpes virus, a pox virus, an alpha virus, a vaccina virus, a hepatitis B virus, a human papillomavirus vector or a pseudotype thereof. Each reporter cell of the population of reporter cells can comprise a reporter gene. When enriching, the population of TCRs can be contacted with tumor cells or tumor RNA-loaded (e.g., mRNA-loaded) antigen presenting cells or one or more antigen/MHC complexes. The identity or the sequence of the antigen may not be known. After enrichment, the subpopulation of the population of TCRs can comprise at least about 2, 5, 10, 15, or 20 different cognate pairs of TCRs. In some cases, the subpopulation may comprise more than or equal to about 20, 30, 40, 50, 60, 100, 200, 300, 400, 500, 1,000, 1,500, 2,000, 2,500, 3,000, 3,500, or 4,000, or more different cognate pairs. Each TCR of the subpopulation of the population of TCRs can be specific to a different epitope or a different protein. Each TCR of the subpopulation of the population of TCRs can comprise a different (i) TCR alpha CDR3 sequence, (ii) TCR beta CDR3 variable domain sequence, (iii) TCR alpha variable domain sequence, (iv) TCR beta variable domain sequence, or (v) TCR alpha and TCR beta variable domain sequence in combination. The plurality of tumor-reactive TCRs can bind to a tumor cell from the subject but does not bind to a healthy cell from the subject or bind to the healthy cell from the subject with at least about 10-fold, 20-fold, 50-fold, 100-fold, 500-fold, or 1000-fold less affinity than to the tumor cell.

The methods provided herein may not require synthesizing of identified cognate pairs by chemical synthesis. A method of treating a cancer in a subject can comprise isolating a first population of T cells from the subject. The first population of T cells can express a population of T-cell receptors (TCRs) from endogenous nucleic acids. Next, nucleic acid sequences encoding the population of TCRs encoded by the endogenous nucleic acids can be expressed in a second population of cells, wherein the nucleic acid sequences are not chemically synthesized, for example, using phosphoramidite. Next, a subpopulation of the population of TCRs can be enriched from the second population of cells, wherein the subpopulation comprises a plurality of tumor-reactive TCRs. A plurality of recipient cells expressing the plurality of tumor-reactive TCRs can then be administered into the subject.

A method of treating a cancer in a subject provided herein can comprise isolating a first population of T cells from the subject, wherein the first population of T cells express a population of T-cell receptors (TCRs) from endogenous nucleic acids. Next, transcribed or amplified products of the endogenous nucleic acids from the first population of T cells can be expressed in a second population of cells, wherein the transcribed or amplified products encode the population of TCRs. The transcribed or amplified products can be nucleic acid strands synthesized by copying a parental strand. Next, a subpopulation of the population of TCRs from the second population of cells can be enriched, wherein the subpopulation comprises a plurality of tumor-reactive TCRs. A plurality of recipient cells expressing the plurality of tumor-reactive TCRs can then be administered into the subject.

A method of treating a cancer in a subject provided herein can comprise isolating a first population of T cells from the subject, wherein the first population of T cells express a population of T-cell receptors (TCRs) from endogenous nucleic acids. Next, the population of TCRs can be expressed in a second population of cells. The second population of cells may not have a phenotypic background/trait of the first population of T cells. For example, the second population of cells may not have the same expression profile of non-TCR genes as the first population of T cells. The second population of cells may not be of the same cell type (e.g., exhausted T cell, activated T cell, memory T cell, or effector T cell) as the first population of T cells. Next, a subpopulation of the population of TCRs can be enriched from the second population of cells, wherein the subpopulation comprises a plurality of tumor-reactive TCRs. Next, a plurality of recipient cells expressing the plurality of tumor-reactive TCRs can be administered into the subject. The first population of T cells can be tumor-infiltrating T cells or peripheral T cells. The first population of T cells can comprise exhausted T cells or regulatory T cells. Administration can be performed at most about 60 days, 50 days, 40 days, 30 days, 20 days or less after isolating the first population of T cells. When enriching, the second population of cells can be contacted with one or more antigen/MHC complexes. The antigen/MHC complex can be an antigen in complex with a MHC tetramer. In some cases, the second population of cells can be contacted with one or more cells, each presenting one or more target antigens (e.g., tumor antigens). For example, the second population of cells can be contacted with tumor cells or tumor RNA-loaded APCs. The plurality of recipient cells can be allogeneic cells, autologous cells, or cell line cells.

The methods provided herein can be used to identify a plurality of tumor-reactive TCRs from a population of TCRs. A method of treating a tumor in a subject provided herein can comprise identifying a plurality of tumor-reactive T-cell receptors (TCRs) from a population of TCRs, wherein the population of TCRs comprise at least about 20, 30, 50, 100, 1,000, 10,000, 100,000, 1,000,000, 10,000,000, or more different cognate pairs. A plurality of cells expressing the plurality of tumor-reactive TCRs or a subset thereof can then be administered into the subject. The plurality of tumor-reactive TCRs or a subset thereof may be exogenous to the plurality of cells. The plurality of tumor-reactive TCRs or a subset thereof can comprise at least 5, at least 10, at least 15, or at least 20 different cognate pairs. In some cases, the plurality of tumor-reactive TCRs or a subset thereof may comprise greater than or equal to about 20, 30, 40, 50, 60, 100, 200, 300, 400, 500, 1,000, 1,500, 2,000, 2,500, 3,000, 3,500, or 4,000, or more different cognate pairs. Each TCR of the plurality of tumor-reactive TCRs may be specific to a different epitope or a different protein or may comprise a different (i) TCR alpha CDR3 sequence, (ii) TCR beta CDR3 variable domain sequence, (iii) TCR alpha variable domain sequence, (iv) TCR beta variable domain sequence, or (v) TCR alpha and TCR beta variable domain sequence in combination. The method can further comprise isolating a population of T cells expressing the population of TCRs from the subject. The different cognate pairs of TCRs may comprise V regions from at least 5, 10, 15, 20, or more different V genes.

The methods provided herein can identify target-reactive TCRs from a sample with a small sample size, such as having at most about 100,000, 10,000, 1,000, 100, or less cells. A method of treating a tumor in a subject provided herein can comprise isolating a population of T cells from the subject that express a population of T-cell receptors (TCRs), wherein the population of T cells comprises at most about 10,000 cells. Next, a plurality of tumor-reactive TCRs can be identified from the population of TCRs. Next, the plurality of tumor-reactive TCRs or a subset thereof can be administered into the subject, wherein the plurality of tumor-reactive TCRs or a subset thereof comprises at least about 2, 5, 10, 15, 20, 30, 40, or 50, or more different cognate pairs. In various embodiments, the plurality of recipient cells can be expanded before administering into a subject.

TCR-Treg Cells for Treatment of Auto-Immune Disease

In addition to create 'killer' cells to treat cancer, one may also create 'healer' cells to treat auto-immune disease. Antigen-specific regulatory T cells can be created by introducing a chimeric antigen receptor (CAR) to Treg cells (Jelena Skuljec et al., Chimeric Antigen Receptor-Redirected Regulatory T Cells Suppress Experimental Allergic Airway Inflammation, a Model of Asthma, Front Immunol. 2017; 8:1125). TCRs specific to a tissue may be introduced to Treg cells using the methods described herein (including the culture and engineering methods), guiding these cells to home to, and protect a specific tissue or organ. The source immunoreceptor-expressing cells can be obtained from tissue-resident T cells or can be selected against a known tissue-specific antigen. Here the tissue-specific antigen can be intracellular or cell surface-bound. These TCR-Treg cells may be further engineered to express additional agents (e.g., cytokines or other regulatory molecules) to enhance their immune-regulatory activity as described herein. Examples of such additional agents include anti-inflammatory cytokines such as IL-1ra, IL-4, IL-10, IL-11, IL-13, transforming growth factor beta (TGF-$\beta$), and IL-16.

Identification of Target-Reactive TCRs

T cells can be screened from multiple organs such as peripheral blood, spleen, lymph node, and tumor (here collectively called 'source TCR-expressing cells', to be consistent with descriptions elsewhere in the present disclosure) in order to identify TCRs that recognize a particular MHC-bound antigen. The polyclonal TCR-programmed recipient cells obtained using methods described herein can replace the source TCR-expressing cells in these applications. In these applications, the recipient cells may be cell-line cells, such as cell-line T cells. Examples of cell-line T cells include, but are not limited to, Jurkat, CCRF-CEM, HPB-ALL, K-T1, TALL-1, MOLT 16/17, and HUT 78/H9. The endogenous TCR of the cell-line T cells may be knocked out or knocked down as described herein.

In some embodiments, the MHC-bound antigen is a peptide MHC complex (pMHC), pMHC tetramer, pMHC oligomer. For example, pMHC can be tetramerized on a streptavidin scaffold, or oligomerized on a variety of chemical scaffolds (Cochran & Stem, 2000). In some embodiments, the pMHC, pMHC tetramer, pMHC oligomer is fluorescently labeled to facilitate FACS sorting of polyclonal TCR-programmed recipient cells that recognize the pMHC.

In some embodiments, the MHC-bound antigen is presented on the surface of a cell. In some cases, the cell is an antigen presenting cell (APC). The APC can be professional APC such as dendritic cell, macrophage, or B cell. The APC may also be other cells (e.g., artificial APC) expressing MHC or HLA. For example, a cell from a cancer cell line can be APC. In some embodiments, the APC can be engineered to express only one Class I MHC allele. In some embodiments, the APC may be engineered to express an arbitrary number of Class I MHC alleles and Class II MHC alleles such as all the Class I or Class II MHC alleles isolated from one subject. The subject may be a human. The human may be a patient. The patient may be a cancer patient.

In some embodiments, the epitope of MHC-bound antigen is well defined. For example, in pMHC tetramer the epitope peptide can be chemically synthesized. In some embodiments, the epitope for the MHC-bound antigen is unknown or not well defined. For example, an antigen protein can be over-expressed in the APC, and multiple epitopes may be presented by the APC. In another example, a small group of proteins (e.g., at least 2 proteins, at least 3 proteins, at least 4 proteins, at least 5 proteins, at least 10 proteins, at least 20 proteins, at least 30 proteins, at least 40 proteins, or at least 50 proteins) can be over-expressed in the APC. In another example, an unknown number of proteins can be over-expressed in the APC, and in such cases, a cDNA pool can be delivered (e.g., transfected, electroporated, or other delivery methods using a vector described herein) into the APC.

In some embodiments, the antigen can be introduced to the APC by transfecting the antigen-coding DNA or mRNA into the APC. In some embodiments, the antigen as proteins may be added to the culture media of the APC. In some embodiments, the antigen as peptides may be added to the culture media of the APC.

The TCR-expressing recipient cells that recognize the MHC-bound antigen may be selected from those that do not. The selection may be based on binding to soluble, fluorescently labeled pMHC, pMHC tetramer or pMHC oligomer. The selection may be based on cell surface marker expression on the TCR-expressing recipient cells after the cells contact MHC-bound antigen. The cell surface marker may be CD25, CD69, CD39, CD103, CD137, as well as other T cell activation markers, or the combination thereof. The selection may be based on calcium influx. The selection may also be based on reporter gene expression. The reporter gene may be a fluorescent protein (such as GFP and mCherry). The reporter gene may be under the control of a transcription factor which is regulated by TCR signaling. Examples of these transcription factors include, but are not limited to, AP-1, NFAT, NF-kappa-B, Runx1, Runx3, etc.

In some embodiments, the selected TCR-programmed recipient cells based on the criteria described above can be propagated and undergo selection again in order to further enrich the TCRs that recognize the MHC-bound antigen. In some embodiments, the fused TCR polynucleotides in the TCR-expressing vectors isolated from the selected TCR-expression recipient cells can be amplified and converted into TCR-expressing vectors. And these TCR-expressing vectors can be used to obtain a new population of TCR-programmed recipient cells. These cells can undergo selection again in order to further enrich the TCRs that recognize the MHC-bound antigen.

Rapid identification of tumor-reactive TCRs without necessarily knowing the identity of the antigen, epitope or the presenting MHC can have broad applications in cancer immunotherapy, and can be achieved by the massively parallel TCR cloning technology described herein combined with a reporter-based selection method.

Figure 18:
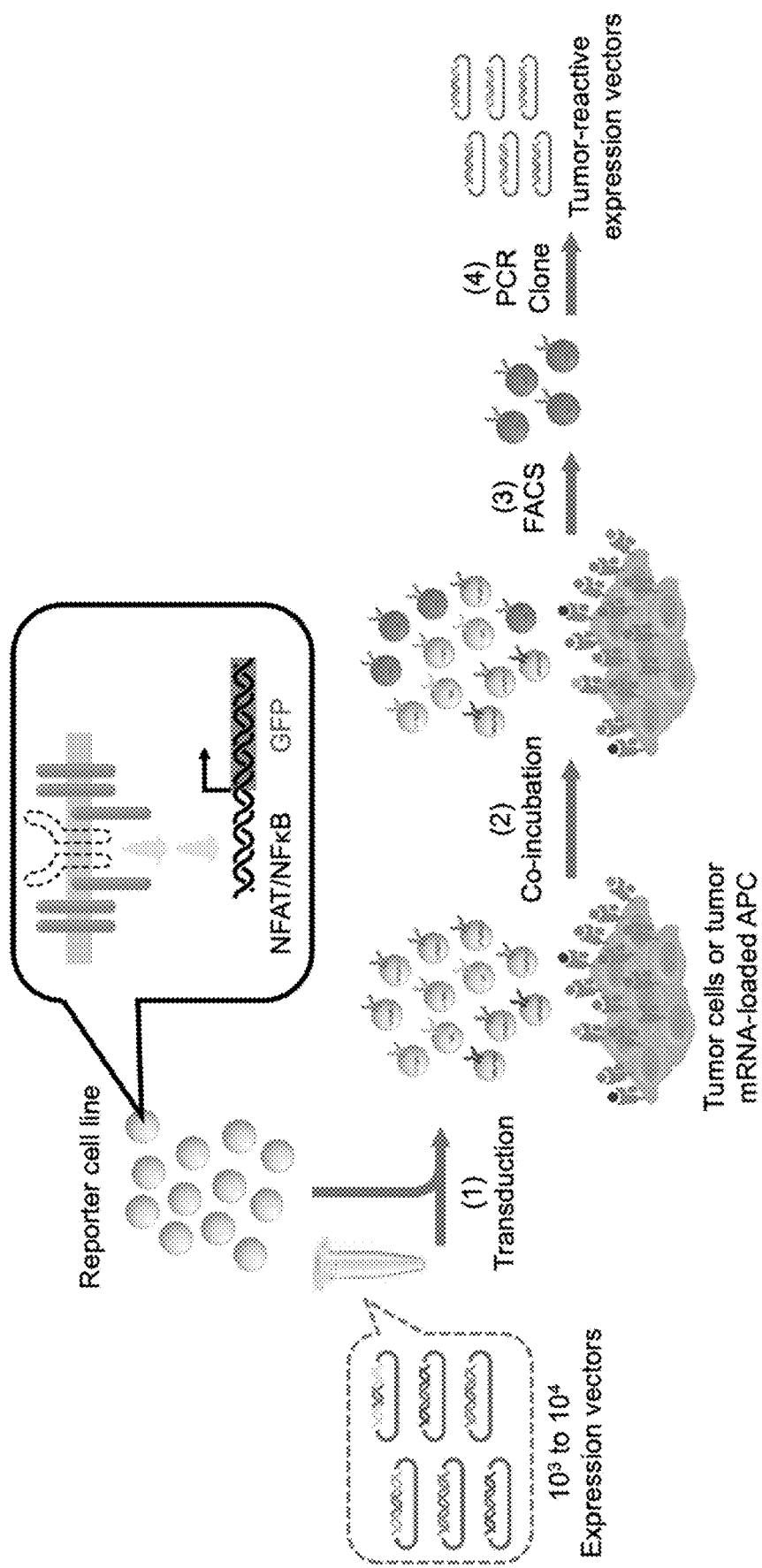
FIG. 18 depicts an example scheme of selecting tumor-reactive (or tumor-specific) TCRs without a priori knowledge about antigen.
Figure 19:
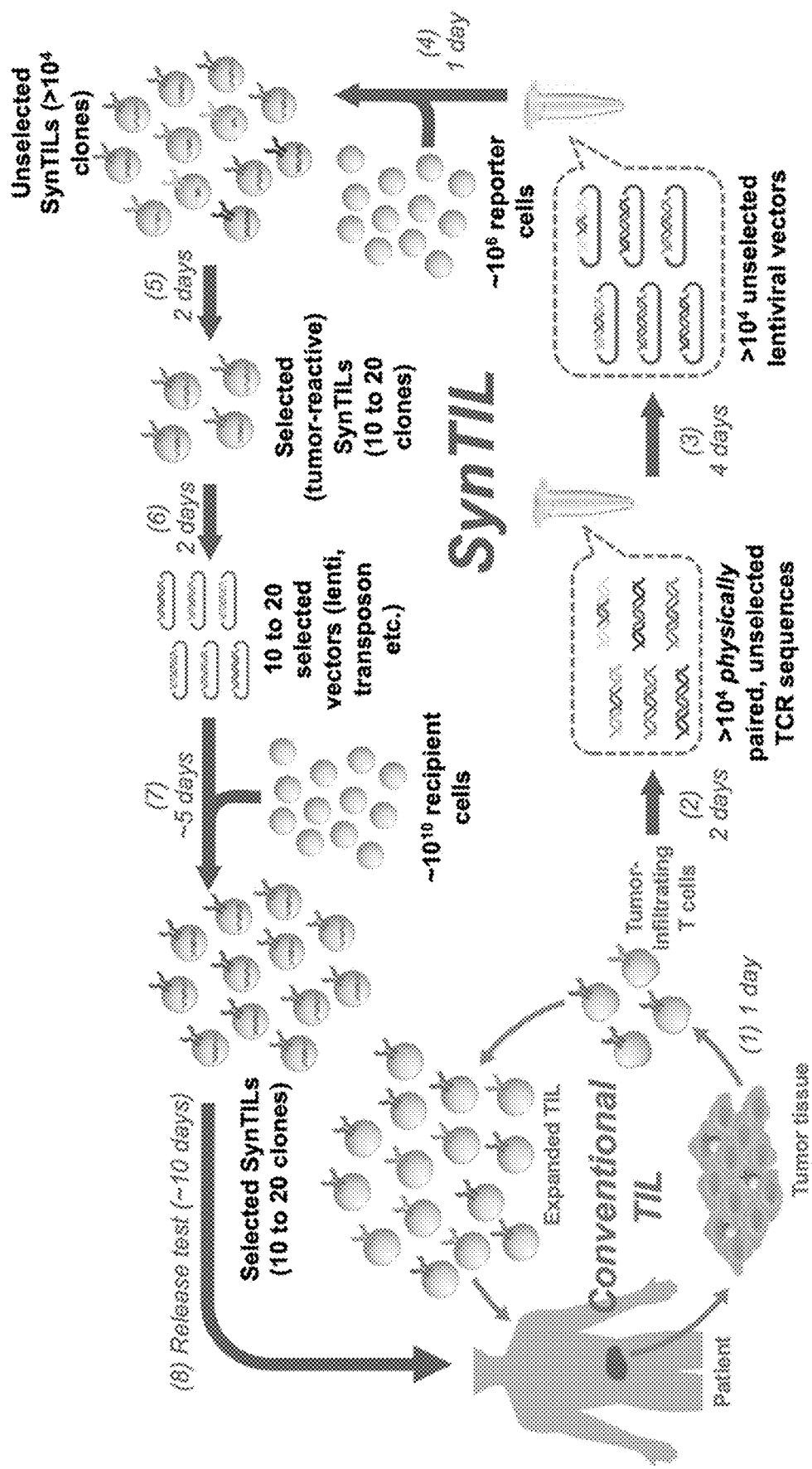
FIG. 19 depicts an example scheme of selecting tumor-reactive (or tumor-specific) TCRs and using recipient cells expressing the TCRs to treat tumor in a subject.

An example scheme of the reporter-based selection method is outlined in FIG. 18. The reporter cell line can be a T cell line (e.g., Jurkat). The reporter cell line may carry a reporter gene (e.g., a florescent protein or a stainable cell surface protein) driven by a promoter controlled by TCR signaling (e.g., NFAT, NF-kappa-B, Nur77). Optionally, the endogenous TCR of the reporter cell line can be knocked out. The reporter cells can be transduced with the polyclonal TCR-expression lentiviral vectors obtained from a population of T cells (e.g., tumor-infiltrating T cells) some of which are tumor reactive (or tumor specific) (FIG. 18, Step (1)). The transduced reporter cells can be incubated (FIG. 18, Step (2)) with tumor cells, tumor tissue, tumor spheres, or APC (either autologous APC or allogeneic APC engineered to express autologous MHC) engineered to express tumor genes (i.e., tumor mRNA-loaded APC which has been studied as cancer vaccine). If the TCR transduced into the reporter cell line is tumor-reactive, the reporter gene in the reporter cell can be expressed and the cell can be identified (e.g., selected/isolated/enriched using FACS or MACS) (FIG. 18, Step (3)). Optionally, the identified TCRs that are tumor-reactive can be sequenced. The already-fused TCRs from the sorted cells can be simply PCR-amplified and cloned into TCR-expressing vectors in batch. Optionally, individual TCRs can be obtained, for example by picking *E. coli* colonies hosting the TCR-expressing vector.

The methods described herein can enable an immuno-monitoring test to quantify tumor-reactive T cells in tumor tissue or peripheral blood of a patient. For example, a tumor biopsy can be obtained from a cancer patient. Peripheral T cells can also be obtained from the same patient. The TCRs from the peripheral T cells can be cloned into TCR-expressing vectors which can in turn be used to engineer reporter cell lines as described herein. Meanwhile, the HLA genes can be amplified from peripheral blood. An APC cell line with no human HLA expression (e.g., a human cell line expressing no or very low level of MHC such as K562 and 721.221, a non-human primate cell line such as COS-7 or a human cell line with endogenous HLA knocked out) can be engineered to express the HLA genes of the patient. The autologous APC (e.g., monocyte-derived dendritic cells, dendritic cells, macrophages, and B cells) from the patient may also be used as APC. The full-length mRNA from the tumor sample (surgical sample or biopsy) can be isolated, amplified and transfected to the autologous or HLA-engineered allogeneic APC described above to create tumor mRNA-loaded APC. The tumor sample can be a biopsy sample such as core biopsy or fine needle biopsy sample. These sample may have a small volume (e.g., <1000 mm$^3$, <500 mm$^3$, <100 mm$^3$, <50 mm$^3$) because even a small volume of tumor sample may contain sufficient mRNA to be amplified. In some cases, the volume of a tumor sample can be equal to or at most about 2000 mm$^3$, 1000 mm$^3$, 800 mm$^3$, 500 mm$^3$, 100 mm$^3$, 50 mm$^3$, or 20 mm$^3$. Thus, this method can be applicable to situations where large surgical tumor sample is difficult to obtain. The TCR-engineered reporter cells and the tumor mRNA-loaded APC can be co-incubated and the reporter-expressing cells, which are tumor-reactive, can be isolated as described above. The TCRs from the isolated cells can be sequenced to provide the sequences and abundance of tumor-reactive TCRs. A report containing such information can be issued. This method can be combined with conventional TCR repertoire analysis to improve the accuracy of the abundance of tumor-reactive TCRs. The methods to obtain and engineer APCs and tumor mRNA-loaded APCs described in this paragraph can also be used in methods described elsewhere in the document.

For example, a method of identifying a plurality of target-reactive T-cell receptors (TCRs) can comprise providing a population of cells expressing a population of TCRs. The population of TCRs may be exogenous to the population of cells. The population of TCRs may comprise different cognate pairs, for example, at least 50 different cognate pairs. The population of TCRs may comprise V regions from at least about 10, 15, 20, 25, 30, 35, 40, or more different V genes. The population of TCRs may comprise at least 100 different VJ combinations. The method can further comprise contacting the population of cells with one or more target antigens, wherein the plurality of target-reactive TCRs bind to the one or more target antigens. The plurality of target-reactive TCRs can then be isolated or enriched. In some cases, the plurality of at least about 5, 10, 15, 20, 30, 50, 100, 200, 300, 400, 500, 600, or more target-reactive TCRs can be isolated or enriched. The population of cells can be engineered cells, non-exhausted cells, or cells not isolated from a patient. The method can further comprise contacting the population of cells with one or more target antigens, wherein the plurality of target-reactive TCRs can bind to the one or more target antigens. The plurality of at least 5 target-reactive TCRs can then be isolated or enriched. The population of TCRs can comprise at least about 100, 200, 500, 1,000, 10,000, 100,000, 1,000,000, or 10,000,000 different cognate pairs. The plurality of target-reactive TCRs comprises V regions from at least 10, at least 15, at least 20, or more different V genes. In some cases, the population of cells is contacted with tumor cells or antigen-presenting cells presenting the one or more target antigens. The target antigens can be tumor antigens or tissue-specific antigens. The one or more target antigens can be in complex with a major histocompatibility complex (MHC). The MHC can be an MHC tetramer. The method can further comprise administering at least one target-reactive TCR of the plurality of target-reactive TCRs into a subject. In some cases, a cell of the population of cells or engineered cells can comprise a reporter gene. The reporter gene can be regulated to send a signal when a TCR of the cell binds to a target antigen of the one or more target antigens. The population of cells or engineered cells can be cell line cells (e.g., Jurkat cells).

For example, a method of identifying a plurality of target-reactive T-cell receptors (TCRs) can comprise providing a plurality of T cells expressing a plurality of TCRs. The plurality of TCRs may comprise at least 50 different cognate pairs comprising V regions from at least 20 different V genes. The method can further comprise physically linking a first polynucleotide encoding a TCR alpha (or gamma) chain and a second polynucleotide encoding a TCR beta (or delta) chain of each TCR of the plurality of TCRs, thereby generating a plurality of fused polynucleotides. The plurality of fused polynucleotides can be expressed in a plurality of cells, wherein a subset of the plurality of cells expresses the plurality of target-reactive TCRs. The plurality of cells can be contacted with one or more target antigens to identify the plurality of target-reactive TCRs. The subset of the plurality of cells expressing the plurality of target-reactive TCRs can bind to the one or more target antigens. The subset of the plurality of cells can be isolated or enriched, thereby isolating or enriching the plurality of target-reactive TCRs.

For example, a method of identifying a plurality of target-reactive T-cell receptors (TCRs) can comprise providing a plurality of T cells expressing a plurality of TCRs. The plurality of TCRs may comprise at least 50 different cognate pairs comprising V regions from at least 20 different V genes. The method can further comprise sequencing one or more cognate pairs of the plurality of TCRs without using any barcoding, e.g., single cell barcoding. For example, sequencing can comprise sequencing TCR chains of the one or more cognate pairs of the plurality of TCRs, wherein the TCR chains do not comprise a same barcode. The one or more cognate pairs encoding the plurality of TCRs or a subset thereof can then be expressed, for example, in soluble form or in a plurality of cells. The plurality of cells used to express the one or more cognate pairs can be cell line cells. The plurality of TCRs or the subset thereof may comprise the plurality of target-reactive TCRs. The plurality of TCRs can then be contacted with one or more target antigens to identify target-reactive TCRs. The plurality of target-reactive TCRs can bind to the one or more target antigens and can then be isolated or enriched. In some cases, when identifying cognate pairs of the TCRs, a first polynucleotide encoding a TCR alpha chain and a second polynucleotide encoding a TCR beta chain of each TCR of the plurality of TCRs can be physically linked, thereby generating a plurality of fused polynucleotides. The method may further comprise sequencing the one or more cognate pairs of the plurality of TCRs. The plurality of T cells can be isolated from a subject. The plurality of T cells can be tumor-infiltrating T cells. The plurality of T cells can comprise exhausted T cells. The plurality of target-reactive TCRs can be isolated or enriched by FACS. The plurality of target-reactive TCRs can be isolated by a cell surface marker or a cytokine marker. For example, the target-reactive TCRs can be isolated or enriched by using antibodies specific to a surface marker such as CD69, CD25 or 41BB for sorting by FACS.

In some cases, a plurality of T cells isolated from a sample can be cultured and stimulated in vitro, for example, with APCs presenting antigens, and a subset of the plurality of T cells can be enriched. These pre-enriched T cells can then be used to identify the target-reactive TCRs. For example, when isolating a plurality of T cells from a blood sample or a PBMC sample, a small fraction of the plurality of T cells may be target-reactive T cells. In such cases, the plurality of T cells can be contacted with one or more target antigens (e.g., in MHC tetramer form or presented on a cell surface) first to activate the T cells. A subset of the plurality of T cells can be enriched or isolated based on a marker (e.g., a surface marker), which can then be used for the subsequent identification methods described herein including fusing the cognate TCR chains. The pre-enriched T cells may also be subject to known methods to identify cognate pairs, for example, using sequencing. The sequencing may use single cell barcoding (e.g., partitioning T cells into individual compartment, barcoding nucleic acids released from a single cell, sequencing the nucleic acids and pair the TCR chains from a single cell based on a same barcode).

Compositions

The present disclosure provides compositions comprising fused immunoreceptor polynucleotides, expression vectors containing the fused immunoreceptor polynucleotides, or host cells comprising the fused immunoreceptor polynucleotides and/or the expression vectors. The present disclosure also provides compositions comprising a plurality of hydrogel particles containing nucleic acids to generate the fused immunoreceptor polynucleotides.

In an aspect, provided herein is a composition comprising a plurality of fused T-cell receptor (TCR) polynucleotides. Each fused TCR polynucleotide of the plurality can comprise a first nucleic acid sequence and a second nucleic acid sequence. The first nucleic acid sequence can encode a first variable domain of a first TCR peptide sequence, wherein the first variable domain comprises a CDR2 and a CDR3, and the second nucleic acid sequence can encode a second variable domain of a second TCR peptide sequence, wherein the second variable domain comprises a CDR2 and a CDR3. The first and the second nucleic acid sequence of each fused TCR polynucleotide can encode a cognate pair of the first and the second TCR peptide sequence from an immune cell. The plurality of fused TCR polynucleotides encode at least about 50, 100, 1,000, 10,000, 100,000, 1,000,000, or 10,000,000 different cognate pairs. The plurality of fused TCR polynucleotides can comprise V regions from at least 5, at least 10, at least 15, at least 20, at least 25, at least 30, at least 35, at least 40, or more different V genes.

The first TCR peptide chain can be a T-cell receptor (TCR) alpha peptide chain, and the second TCR peptide chain can be a TCR beta peptide chain. The first TCR peptide chain can be a TCR gamma peptide chain, and the second TCR peptide chain can be a TCR delta peptide chain. The first variable domain can further comprise a CDR1. The second variable domain can further comprise a CDR1. The first variable domain of the first TCR peptide chain can be a first full-length variable domain comprising FR1, CDR1, FR2, CDR2, FR3, and CDR3. The second variable domain of the second TCR peptide chain can be a second full-length variable domain comprising FR1, CDR1, FR2, CDR2, FR3, and CDR3. The first nucleic acid sequence can further encode a first constant domain or a portion thereof of the first TCR peptide chain. The second nucleic acid sequence can further encode a second constant domain or a portion thereof of the second TCR peptide chain. Each of the fused TCR polynucleotides can be at least 800, at least 900, at least 1000, or at least 1500 base pairs in length. Each of the fused TCR polynucleotides can be at least 1000, at least 1500, or at least 2000 base pairs in length.

The first nucleic acid sequence and the second nucleic acid sequence can be obtained or released from an immune cell. The immune cell can be isolated from a sample. For example, the sample can be a blood sample, a bone marrow sample, a cord blood sample, an ascites sample, a pleural effusion sample, a cerebrospinal sample, a seminal fluid sample, a sputum sample, a urine sample, a stool sample, or a combination thereof. For another example, the sample can be a tissue sample obtained from various sources, including brain, liver, lung, kidney, prostate, ovary, spleen, lymph node, tonsil, thyroid, pancreas, heart, skeletal muscle, intestine, larynx, esophagus, thymus, stomach, tumor, or site of infection. The sample can be obtained from a subject. The subject can be a healthy subject or a diseased subject. In some cases, the subject is a mammal. The mammal can be a human, a dog, a cat, a mouse, or a rat. The immune cell can be various immune cells having or expressing a bipartite immunoreceptor. For example, the immune cell can be a lymphocyte, including but not limited to, a T cell or a B cell. The T cell can be an inflammatory T cell, a cytotoxic T cell, a regulatory T cell, a helper T cell, a natural killer T cell, or a combination thereof. The T cell can be a CD4+ T cell or a CD8+ T cell.

In some cases, the immune cell is expanded in vitro or ex vivo. The immune cell can be isolated from the sample by a marker. The marker may be a cell surface marker. For example, suitable cell surface marker includes, but are not limited to, CD39, CD69, CD103, CD25, PD-1, TIM-3, OX-40, 4-1BB, CD137, CD3, CD28, CD4, CD8, CD45RA, CD45RO, GITR, and FoxP3. The marker can be a cytokine. For example, the cytokine can be IFN-γ, TNF-alpha, IL-17A, IL-2, IL-3, IL-4, GM-CSF, IL-10, IL-13, granzyme B, perforin, or a combination thereof.

The fused TCR polynucleotide can further comprise a promoter. The promoter can be constitutive or inducible. For example, the promoter can be a tetracycline-responsive promoter. The promoter can be a viral promoter. The promoter can be a β-actin promoter, a SV40 early promoter, a SV40 late promoter, an immunoglobulin promoter, a cytomegalovirus promoter, a retrovirus promoter, a Friend spleen focus-forming virus promoter, a Herpes virus TK promoter, a Rous sarcoma virus promoter, a mouse mammary tumor virus promoter, a metallothionein promoter, an adenovirus late promoter, a vaccinia 7.5K promoter, or an enolase promoter.

The first nucleic acid and the second nucleic acid can be fused in-frame such that expression of the first nucleic acid and the second nucleic acid can be under control of one promoter. In some other cases, the first nucleic acid and the second nucleic acid may not be fused in-frame. The expression of the first nucleic acid and the second nucleic acid can be controlled under two promoters. The two promoters may be the same or different.

The fused TCR polynucleotide can further comprise a sequence encoding a protease cleavage site. The protease cleavage site can be a cellular protease cleavage site or a viral protease cleavage site. The protease cleavage site can be an enterokinase cleavage site, a factor Xa cleavage site, a thrombin cleavage site, a renin cleavage site, a collagenase cleavage site, a trypsin cleavage site, a caspase protease cleavage site, a furin cleavage site, a PC5/6 protease cleavage site, a PACE protease cleavage site, a LPC/PC7 protease cleavage site, a Factor Xa protease cleavage site, a genenase I cleavage site, a MMP protease cleavage site, or a KEX2 protease cleavage site. The protease cleavage site can be a viral 2A protease cleavage site, a viral 3C protease cleavage site, an infectious pancreatic necrosis virus (IPNV) VP4 protease cleavage site, a tobacco etch virus (TEV) protease cleavage site, or a nuclear inclusion protein a (N1a) of turnip mosaic potyvirus cleavage site. The fused TCR polynucleotide can comprise a sequence encoding a self-cleaving peptide. The self-cleaving peptide can be an intein peptide, a hedgehog peptide, or a 2A peptide.

The plurality of fused TCR polynucleotides can comprise V regions from at least 5, at least 10, at least 15, at least 20, at least 25, at least 30, at least 35, at least 40, or more different V genes. In some cases, the plurality of fused TCR polynucleotides comprise at least 20 different V genes. The at least 20 different V genes can comprise at least 10 different TRAV genes and/or at least 10 different TRBV genes. The TRAV genes or TRBV genes can be human TRAV genes or TRBV genes. The TRAV genes or TRBV genes can be mouse TRAV genes or TRBV genes. Examples of human TRAV genes include human TRAV1-1, TRAV1-2, TRAV2, TRAV3, TRAV4, TRAV5, TRAV6, TRAV7, TRAV8-1, TRAV8-2, TRAV8-3, TRAV8-4, TRAV8-6, TRAV9-1, TRAV9-2, TRAV10, TRAV12-1, TRAV12-2, TRAV12-3, TRAV13-1, TRAV13-2, TRAV14, TRAV16, TRAV17, TRAV18, TRAV19, TRAV20, TRAV21, TRAV22, TRAV23, TRAV24, TRAV25, TRAV26-1, TRAV26-2, TRAV27, TRAV29, TRAV30, TRAV34, TRAV35, TRAV36, TRAV38-1, TRAV38-2, TRAV39, TRAV40, and TRAV41. Examples of human TRBV genes include human TRBV2, TRBV3-1, TRBV4-1, TRBV4-2, TRBV4-3, TRBV5-1, TRBV5-4, TRBV5-5, TRBV5-6, TRBV5-8, TRBV6-1, TRBV6-2, TRBV6-3, TRBV6-4, TRBV6-5, TRBV6-6, TRBV6-8, TRBV6-9, TRBV7-2, TRBV7-3, TRBV7-4, TRBV7-6, TRBV7-7, TRBV7-8, TRBV7-9, TRBV9, TRBV10-1, TRBV10-2, TRBV10-3, TRBV11-1, TRBV11-2, TRBV11-3, TRBV12-3, TRBV12-4, TRBV12-5, TRBV13, TRBV14, TRBV15, TRBV16, TRBV18, TRBV19, TRBV20-1, TRBV24-1, TRBV25-1, TRBV27, TRBV28, TRBV29-1, and TRBV30.

The plurality of fused TCR polynucleotides can comprise V regions from at least 5, at least 10, at least 15, at least 20, at least 25, at least 30, at least 35, at least 40, or more different V gene subgroups. The at least 20 different V genes can comprise genes from at least 20 different V gene subgroups. The at least 20 different V gene subgroups can comprise at least 10 different TRAV gene subgroups and/or at least 10 different TRBV gene subgroups. Examples of human TRAV gene subgroups include human TRAV1, TRAV2, TRAV3, TRAV4, TRAV5, TRAV6, TRAV7, TRAV8, TRAV9, TRAV10, TRAV12, TRAV13, TRAV14, TRAV16, TRAV17, TRAV18, TRAV19, TRAV20, TRAV21, TRAV22, TRAV23, TRAV24, TRAV25, TRAV26, TRAV27, TRAV29, TRAV30, TRAV34, TRAV35, TRAV36, TRAV38, TRAV39, TRAV40, and TRAV41 subgroup. Examples of human TRBV gene subgroups include human TRBV2, TRBV3, TRBV4, TRBV5, TRBV6, TRBV7, TRBV9, TRBV10, TRBV11, TRBV12, TRBV13, TRBV14, TRBV15, TRBV16, TRBV18, TRBV19, TRBV20, TRBV24, TRBV25, TRBV27, TRBV28, TRBV29, and TRBV30 subgroup.

Examples of mouse TRAV genes include mouse TRAV1, TRAV2, TRAV3-1, TRAV3-3, TRAV3-4, TRAV3D-3, TRAV3N-3, TRAV4-2, TRAV4-3, TRAV4-4, TRAV4D-2, TRAV4D-3, TRAV4D-4, TRAV4N-3, TRAV4N-4, TRAV5-1, TRAV5-2, TRAV5-4, TRAV5D-2, TRAV5D-4, TRAV5N-2, TRAV5N-4, TRAV6-1, TRAV6-2, TRAV6-3, TRAV6-4, TRAV6-5, TRAV6-6, TRAV6-7, TRAV6D-3, TRAV6D-4, TRAV6D-5, TRAV6D-6, TRAV6D-7, TRAV6N-5, TRAV6N-6, TRAV6N-7, TRAV7-1, TRAV7-2, TRAV7-3, TRAV7-4, TRAV7-5, TRAV7-6, TRAV7D-2, TRAV7D-3, TRAV7D-4, TRAV7D-5, TRAV7D-6, TRAV7N-4, TRAV7N-5, TRAV7N-6, TRAV8-1, TRAV8-2, TRAV8D-1, TRAV8D-2, TRAV8N-2, TRAV9-1, TRAV9-2, TRAV9-3, TRAV9-4, TRAV9D-1, TRAV9D-2, TRAV9D-3, TRAV9D-4, TRAV9N-2, TRAV9N-3, TRAV9N-4, TRAV10, TRAV10D, TRAV10N, TRAV11, TRAV11D, TRAV11N, TRAV12-1, TRAV12-2, TRAV12-3, TRAV12D-1, TRAV12D-2, TRAV12D-3, TRAV12N-1, TRAV12N-2, TRAV12N-3, TRAV13-1, TRAV13-2, TRAV13-3, TRAV13-4, TRAV13-5, TRAV13D-1, TRAV13D-2, TRAV13D-3, TRAV13D-4, TRAV13N-1, TRAV13N-2, TRAV13N-3, TRAV13N-4, TRAV14-1, TRAV14-2, TRAV14-3, TRAV14D-1, TRAV14D-2, TRAV14D-3, TRAV14N-1, TRAV14N-2, TRAV14N-3, TRAV15-1, TRAV15-2, TRAV15D-1, TRAV15D-2, TRAV15N-1, TRAV15N-2, TRAV16, TRAV16D, TRAV16N, TRAV17, TRAV18, TRAV19, TRAV20, and TRAV21. Examples of mouse TRBV genes include mouse TRBV1, TRBV2, TRBV3, TRBV4, TRBV5, TRBV8, TRBV9, TRBV10, TRBV12-1, TRBV12-2, TRBV13-1, TRBV13-2, TRBV13-3, TRBV14, TRBV15, TRBV16, TRBV17, TRBV19, TRBV20, TRBV21, TRBV23, TRBV24, TRBV26, TRBV29, TRBV30, and TRBV31. Examples of mouse TRAV gene subgroups include mouse TRAV1, TRAV2, TRAV3, TRAV4, TRAV5, TRAV6, TRAV7, TRAV8, TRAV9, TRAV10, TRAV11, TRAV12, TRAV13, TRAV14, TRAV15, TRAV16, TRAV17, TRAV18, TRAV19, TRAV20, and TRAV21 subgroup. Examples of mouse TRBV gene subgroups include mouse TRBV1, TRBV2, TRBV3, TRBV4, TRBV5, TRBV8, TRBV9, TRBV10, TRBV12, TRBV13, TRBV14, TRBV15, TRBV16, TRBV17, TRBV19, TRBV20, TRBV21, TRBV23, TRBV24, TRBV26, TRBV29, TRBV30, and TRBV31 subgroup.

The fused TCR polynucleotide can be circularized. The plurality of fused TCR polynucleotides can comprise at least 100, at least 200, at least 500, at least 1,000, at least 10,000, at least 100,000, at least 1,000,000, or at least 10,000,000 different (or unique) sequences.

The fused TCR polynucleotides can be delivered into a host cell for expression. Various gene delivery methods can be used. As discussed above, in some cases, the fused TCR polynucleotides can be delivered into host cells by electroporation, and in some other cases, the fused TCR polynucleotides can be delivered into host cells by vectors. In some embodiments, provided herein is a plurality of vectors, each comprising a different fused TCR polynucleotide from the plurality of fused TCR polynucleotides described herein. The plurality of vectors can comprise at least 100, at least 200, at least 500, at least 1,000, at least 10,000, at least 100,000, at least 1,000,000, at least 10,000,000 vectors. The plurality of vectors can be self-amplifying RNA replicons, plasmids, phages, transposons, cosmids, viruses, or virions. The plurality of vectors can be viral vectors. The plurality of vectors can be derived from a retrovirus, a lentivirus, an adenovirus, an adeno-associated virus, a herpes virus, a pox virus, an alpha virus, a vaccinia virus, a hepatitis B virus, or a human papillomavirus or a pseudotype thereof. The plurality of vectors of can be non-viral vectors. The non-viral vectors can be nanoparticles, cationic lipids, cationic polymers, metallic nanopolymers, nanorods, liposomes, micelles, microbubbles, cell-penetrating peptides, or lipospheres.

In another aspect, provided herein is a composition comprising a plurality of vectors, each vector of the plurality comprises a fused TCR polynucleotide having a first nucleic acid sequence and a second nucleic acid sequence, wherein (1) the first nucleic acid sequence encodes a first variable domain of a first TCR peptide chain, wherein the first variable domain comprises a CDR1, a CDR2 and a CDR3, and (2) the second nucleic acid sequence encodes a second variable domain of a second TCR peptide chain, wherein the second variable domain comprises a CDR1, a CDR2, and a CDR3; wherein the first and the second nucleic acid sequence of each fused TCR sequence encode a cognate pair of the first and the second TCR peptide chains from an immune cell. The plurality of fused TCR polynucleotides may comprise at least 5, at least 10, at least 15, at least 20, at least 25, at least 30, at least 35, at least 40, or more different V genes. In some cases, the plurality of fused TCR polynucleotides comprises at least 20 different V genes. In some cases, the plurality of vectors comprises at least 50, at least 100, at least 200, at least 500, at least 1,000, at least 10,000, at least 100,000, at least 1,000,000, or at least 10,000,000 different cognate pairs. The at least 20 different V genes may comprise at least 10 different TRAV gene subgroups and/or at least 10 different TRBV gene subgroups.

In another aspect, provided herein is a plurality of TCRs. Each TCR of the plurality can be encoded by a different fused TCR polynucleotide from the plurality of fused TCR polynucleotides. Each TCR of the plurality can be encoded by a different fused TCR polynucleotide from the plurality of vectors as described herein. The plurality of TCRs can comprise at least 100, at least 200, at least 500, at least 1,000, at least 10,000, at least 100,000, at least 1,000,000, or at least 10,000,000 TCRs.

In another aspect, provided herein is a plurality of host cells. As described herein, such host cells are referred to as "recipient cells". Each host cell of the plurality can comprise a different fused TCR polynucleotide from the plurality of fused TCR polynucleotides as described herein. Each host cell of the plurality can comprise a different vector of the plurality of vectors as described herein. Each host cell of the plurality can express the fused TCR polynucleotide. Each host cell of the plurality may comprise a different TCR of the plurality of TCRs. The plurality of host cells can be T cells or B cells. The T cells can be an inflammatory T cell, a cytotoxic T cell, a regulatory T cell, a helper T cell, a natural killer T cell, or a combination thereof. The T cells can be CD4+ T cells or CD8+ T cells. The plurality of host cells can be autologous cells. The plurality of host cells can be allogeneic cells. The plurality of host cells can be obtained from a donor. The donor can be a human. The donor can be a healthy donor or a diseased donor. The plurality of host cells can be obtained from a sample. For example, the sample can be a blood sample, a bone marrow sample, a cord blood sample, an ascites sample, a pleural effusion sample, a cerebrospinal sample, a seminal fluid sample, a sputum sample, a urine sample, a stool sample, or a combination thereof. For another example, the sample can be a tissue sample obtained from brain, liver, lung, kidney, prostate, ovary, spleen, lymph node, tonsil, thyroid, pancreas, heart, skeletal muscle, intestine, larynx, esophagus, thymus, stomach, tumor, site of infection, or a combination thereof. The plurality of host cells can be cell line cells. Examples of cell line cells include, but are not limited to, CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; or Molt 4 cells. The plurality of host cells can be genetically modified cells. In some cases, an endogenous gene encoding a TCR alpha peptide sequence, a TCR beta peptide sequence, a TCR gamma peptide sequence, a TCR delta peptide sequence, a BCR heavy peptide sequence, or a BCR light peptide sequence can be downregulated or inactivated. In some cases, endogenous genes encoding both TCR alpha and beta peptide sequence are downregulated or inactivated. In some cases, an additional endogenous gene is downregulated or inactivated. Examples of the additional endogenous gene include, but are not limited to, PD1, CTLA-4, LAG3, Tim3, BTLA, BY55, TIGIT, B7H5, LAIR1, SIGLEC10, and 2B4. In some cases, two or more of the additional endogenous genes are downregulated or inactivated. The host cell can be engineered to express an additional agent to enhance a function of the host cell. The function may be a cytotoxic function, a pro-inflammatory function, or an anti-inflammatory function. The additional agent can be a cytokine. The cytokine can be a pro-inflammatory cytokine or an anti-inflammatory cytokine. The cytokine can be tumor necrosis factor alpha (TNFα), interleukin (IL)-1α, IL-10, IL-2, IL-5, IL-6, IL-8, IL-15, IL-18, interferon (IFN-γ), platelet-activating factor (PAF), Monocyte chemotactic proteins 1 and 2 (MCP-1, MCP-2), macrophage migration inhibitory factor (MIF), CXCL8, CXCL9, CXCL10, high mobility group box protein 1 (HMGB-1), IL-1ra, IL-4, IL-10, IL-11, IL-13, transforming growth factor beta (TGF-β), IL-16, or any combination thereof.

Also provided herein is a composition comprising a plurality of hydrogel particles or beads. In some aspects, each hydrogel particle or bead of the plurality can comprise: (a) a first nucleic acid molecule and a first amplification product thereof encoding a first variable domain of a first immunoreceptor peptide sequence, wherein the first variable domain comprises a CDR3, and (b) a second nucleic acid molecule and a second amplification product thereof encoding a second variable domain of a second immunoreceptor peptide sequence, wherein the second variable domain comprises a CDR3 (e.g., TRA and TRB in FIGS. 4A, 4B, 5A-5C, 9A, 9B, 10A, and 10B). The first amplification product and the second amplification product can be embedded or entrapped within a matrix having a polymerized or gelled plurality of polymers and/or monomers. The diffusion of the first amplification product and the second amplification product can be restricted. In some other aspects, each hydrogel particle or bead of the plurality comprising: (a) a first nucleic acid molecule and a first primer extension product thereof encoding a first variable domain of a first immunoreceptor peptide sequence, wherein the first variable domain comprises a CDR3, and (b) a second nucleic acid molecule and a second primer extension product thereof encoding a second variable domain of a second immunoreceptor peptide sequence, wherein the second variable domain comprises a CDR3. The first primer extension product and the second primer extension product can be embedded or entrapped within a matrix having a polymerized or gelled plurality of polymers and/or monomers. The diffusion of the first primer extension product and the second primer extension product can be restricted. The first and the second primer extension product can comprise an adaptor sequence having a pre-designed sequence. The adaptor sequence may not be hybridizable or complementary to the first or the second nucleic acid. The adaptor sequence can be a sequence or a reverse complement sequence of a template-switch oligonucleotide. The first and the second primer extension product can be a reverse transcription (RT) product. The first and the second primer extension product can be a second strand synthesis (SSS) product. The RT product can be linked to a diffusion-restricting agent. The SSS product can be linked to a diffusion-restricting agent. The SSS product may be indirectly linked to the diffusion restricting agent. For example, the SSS product may hybridize to a polynucleotide which is in turn linked to the diffusion restricting agent (e.g., FIGS. 5A and 5B and FIGS. 10A and 10B).

The first and the second primer extension product can be a first and a second amplification product. The first amplification product and/or the second amplification product can be linked to a diffusion restricting agent. The first amplification product and/or the second amplification product can be linked to a diffusion restricting agent through a capture agent. The capture agent can comprise an oligonucleotide having a complementary sequence to an adaptor sequence of the first amplification product and/or the second amplification product. The diffusion restricting agent can be a polymer. The polymer may be a linear polymer. The polymer may be a polyacrylamide, a polyethylene glycol, or a polysaccharide. The diffusion restricting agent may be a particle. The particle can have a diameter that is larger than a pore size of the matrix such that the particle may not diffuse out of the matrix of the hydrogel particle or bead. The diffusion restricting agent can be the matrix itself. For example, a polynucleotide can be directly linked to the matrix, thereby restricting the diffusion of the polynucleotide. The first nucleic acid molecule and the second nucleic acid molecule can be released from a cell. The cell can be a single cell. The cell can be a lymphocyte. The cell can be a T cell or B cell. The T cell can be a CD3+ T cell, a CD28+ T cell, a CD4+ T cell, a CD8+ T cell, a CD45RA+ T cell, a CD45RO+ T cell, or any combination thereof. The B cell can be a plasmablast cell, a plasma cell, a lymphoplasmacytoid cell, a memory B cell, a follicular B cell, a marginal zone B cell, a B-1 cell, a B-2 cell, or a regulatory B cell. The first immunoreceptor peptide sequence can be a TCR alpha peptide sequence and the second immunoreceptor peptide sequence can be a TCR beta peptide sequence.

The first immunoreceptor peptide chain can be a TCR gamma peptide chain and the second immunoreceptor peptide chain can be a TCR delta peptide chain. The first immunoreceptor peptide chain can be an immunoglobulin heavy peptide chain and the second immunoreceptor peptide chain can be an immunoglobulin light peptide chain. The first immunoreceptor peptide chain and the second immunoreceptor peptide chain can be a cognate pair of a bipartite immunoreceptor.

The first amplification product and the second amplification product can be linked to form a continuous polynucleotide. The first amplification product and/or the second amplification product can comprise at least about 100, at least about 500, at least about 1000, at least about 10000, or more copies of the first nucleic acid molecule and/or the second nucleic acid molecule. The first or the second nucleic acid can be diffusion restricted. For example, the first or the second nucleic acid can be linked directly or indirectly to a diffusion-restricting agent. The first nucleic acid molecule and/or the second nucleic acid molecule can be a deoxyribonucleic acid or a ribonucleic acid. The first nucleic acid molecule and/or the second nucleic acid molecule can be a single-stranded nucleic acid or a double-stranded nucleic acid. The first nucleic acid molecule further can encode a first constant domain and/or the second nucleic acid molecule further can encode a second constant domain.

The plurality of hydrogel particles or beads can comprise at least 50, at least 100, at least 200, at least 500, at least 1,000, at least 10,000, at least 100,000, at least 1,000,000, or at least 10,000,000 hydrogel particles or beads. The plurality of hydrogel particles or beads can comprise at least 50, at least 100, at least 200, at least 500, at least 1,000, at least 10,000, at least 100,000, at least 1,000,000, or at least 10,000,000 different cognate pairs of a bipartite immunoreceptor.

The polymers used to make the hydrogel particles or beads can be polysaccharides, polyacrylamides, or a combination thereof. The polysaccharides can be agarose, hyaluronic acids, carboxymethycellose, chitosan, dextran, starch, or alginate. The monomers used to make the hydrogel particle or beads can be acrylamide or methacrylamide monomers. The polymerized or gelled plurality of polymers and/or monomers can comprise a mixture of agarose and polyacrylamides. The polymerized or gelled plurality of polymers and/or monomers can be cross-linked. The first variable domain and/or the second variable domain can further comprise a CDR1, a CDR2, or a combination thereof. In some cases, each hydrogel particle or bead is an agarose gel particle.

In another aspect, provided herein is a composition comprising a plurality of at least five hydrogel particles, wherein each of the at least five hydrogel particles comprises polynucleotides comprising (a) a first polynucleotide comprising a sequence encoding a first immunoreceptor peptide chain and (b) a second polynucleotide comprising a sequence encoding a second immunoreceptor peptide chain, wherein each of the first and second immunoreceptor peptide chains comprise unique cognate immunoreceptor paired chains, wherein the first polynucleotide and the second polynucleotide of an individual hydrogel particle of the at least five hydrogel particles are (i) from a single cell, and (ii) linked to each other; and wherein diffusion of the first polynucleotide and the second polynucleotide from the hydrogel particle is restricted. The first polynucleotide or the second polynucleotide can be a DNA. The DNA can be an amplification product. The first polynucleotide and the second polynucleotide can be covalently linked. The first polynucleotide and the second polynucleotide can be linked by a phosphodiester bond. The first polynucleotide or the second polynucleotide can be linked to a diffusion-restricting agent.

In another aspect, provided herein is a composition comprising a plurality of at least five hydrogel particles, wherein each of the at least five hydrogel particles comprises (a) a first RNA comprising a sequence encoding a first immunoreceptor peptide chain and (b) a second RNA comprising a sequence encoding a second immunoreceptor peptide chain, wherein each of the first and second immunoreceptor peptide chains comprise unique cognate immunoreceptor paired chains, wherein each first RNA and second RNA of an individual hydrogel particle of the at least five hydrogel particles is from a single cell, and wherein (1) each first RNA is hybridized to a first cDNA comprising a reverse complement sequence of the first RNA and (2) each second RNA is hybridized to a second cDNA comprising a reverse complement sequence of the second RNA; and wherein diffusion of the first cDNA and the second cDNA from the hydrogel particle is restricted. The first cDNA or the second cDNA can further comprise a sequence that is not hybridizable or complementary to the first RNA or the second RNA. The first cDNA or the second cDNA can further comprise reverse complement sequence of a template-switch oligonucleotide. The first cDNA or the second cDNA can be linked to a diffusion-restricting agent.

In another aspect, provided herein is a composition comprising a plurality of at least five hydrogel particles, wherein each of the at least five hydrogel particles comprises (a) a first polynucleotide comprising a sequence encoding a first immunoreceptor peptide chain and (b) a second polynucleotide comprising a sequence encoding a second immunoreceptor peptide chain, wherein each of the first and second immunoreceptor peptide chains comprise unique cognate immunoreceptor paired chains, wherein each first polynucleotide and second polynucleotide of an individual hydrogel particle of the at least five hydrogel particles is from a single cell, and wherein (1) each first polynucleotide is hybridized to a first primer and (2) each second polynucleotide is hybridized to a second primer; and wherein diffusion of the first primer and the second primer from the hydrogel particle is restricted. The first primer or the second primer can be a reverse transcription primer. The first primer or the second primer can be an amplification primer. The first polynucleotide or the second polynucleotide can be RNA. The first polynucleotide or the second polynucleotide can be DNA. The first primer or the second primer can be linked to a diffusion-restricting agent.

In another aspect, provided herein is a composition comprising a plurality of at least five hydrogel particles, wherein each of the at least five hydrogel particles comprises (a) a first DNA comprising a sequence encoding a first immunoreceptor peptide chain and (b) a second DNA comprising a sequence encoding a second immunoreceptor peptide chain, wherein each of the first and second immunoreceptor peptide chains comprise unique cognate immunoreceptor paired chains, wherein each first DNA and second DNA of an individual hydrogel particle of the at least five hydrogel particles is from a single cell, and wherein (1) each first DNA is hybridized to a first polynucleotide comprising a reverse complement sequence of the sequence encoding the first immunoreceptor chain and (2) each second DNA is hybridized to a second polynucleotide comprising a reverse complement sequence of the sequence encoding the second immunoreceptor chain; and wherein diffusion of the first polynucleotide and the second polynucleotide from the hydrogel particle is restricted. The first DNA or the second DNA can be cDNA. The first DNA or the second DNA can be genomic DNA, and in such cases, a primer with an adaptor sequence can be used to hybridize the first DNA or the second DNA to generate an extension product of the first or the second DNA. The first polynucleotide or the second polynucleotide can be RNA. The RNA can be a messenger RNA. For example, FIG. 4A or FIG. 5A shows a cDNA hybridizes to an mRNA. The diffusion of the first DNA or the second DNA from the hydrogel particle can be restricted. In some cases, the first DNA or the second DNA is a cDNA, and in such cases, the first polynucleotide or the second polynucleotide can be a second strand synthesis (SSS) product. The first polynucleotide or the second polynucleotide can be an amplification product. The amplification product can comprise an adaptor sequence that is not hybridizable or complementary to the first or the second DNA. The adaptor sequence can further hybridize to a capture agent. The capture agent can be linked to a diffusion-restricting agent.

The diffusion-restricting agent can be a polymer or a particle. The first and the second immunoreceptor peptide chains can be TCR alpha and TCR beta peptide chains, TCR gamma and TCR delta peptide chains, or BCR heavy and light peptide chains. The single cell can be an immune cell. The immune cell can be a T cell or a B cell.

In another aspect, provided herein is a composition comprising a plurality of at least 1,000 compartments, each compartment of the at least 1,000 compartments comprising a solid support, wherein the solid support comprises: (a) a first polynucleotide, comprising a first common sequence, a second common sequence, and a protein-coding sequence encoding a TCR alpha chain between the first and the second common sequence, and (b) a second polynucleotide, comprising a third common sequence, a fourth common sequence, and a protein-coding sequence encoding a TCR beta chain between the third and the fourth common sequence, wherein, (i) the TCR alpha chain and the TCR beta chain in each compartment is a cognate pair, (ii) a plurality of first common sequences in the plurality of compartments has the same sequence and is hybridizable or complementary to a first primer, (iii) a plurality of second common sequences in the plurality of compartments has the same sequence and is hybridizable or complementary to a second primer, (iv) a plurality of third common sequences in the plurality of compartments has the same sequence and is hybridizable or complementary to a third primer, and (v) a plurality of fourth common sequences in the plurality of compartments has the same sequence and is hybridizable or complementary to a fourth primer. Each compartment can further comprise the first primer, the second primer, the third primer, and the fourth primer. The concentration of the first primer can be at least 1 nM, the concentration of the second primer can be at least 1 nM, the concentration of the third primer can be at least 1 nM, and concentration of the fourth primer can be at least 1 nM. The concentration of each of the primers can be at least about 0.5 nM, at least about 1 nM, at least about 1.5 nM, at least about 2 nM, at least about 2.5 nM, at least about 3 nM, at least about 3.5 nM, or at least about 4 nM. The second common sequence can be hybridizable or complementary to the fourth common sequence or a reverse complement sequence thereof in each compartment.

In another aspect, provided herein is a composition comprising a plurality of at least 1,000 compartments, each compartment of the at least 1,000 compartments comprising: (a) a first fully or partially single-stranded polynucleotide, comprising a first common sequence at the 5' end, a second common sequence at the 3' end, and a protein-coding sequence encoding a TCR alpha chain between the first and the second common sequence, and (b) a second fully or partially single-stranded polynucleotide, comprising a third common sequence at the 5' end, a fourth common sequence at the 3' end, and a protein-coding sequence encoding a TCR beta chain between the third and the fourth common sequence, wherein, (i) the TCR alpha chain and the TCR beta chain is a cognate pair, and (ii) the second common sequence is hybridized to the fourth common sequence. The first common sequence, the second common sequence, the third common sequence, or the fourth common sequence can be the same in the plurality of at least 1,000 compartments. Each compartment can further comprise a solid support. The solid support can be a bead or a hydrogel particle.

Methods

The present disclosure provides methods to make or use the fused bipartite immunoreceptor polynucleotide as described herein. Various methods and applications are provided.

In an aspect, provided herein is a method for preparing a fused bipartite immunoreceptor sequence library, comprising: (a) generating a plurality of vessels, each comprising (1) a cell, wherein the cell comprises a first nucleic acid encoding a first peptide sequence of a bipartite immunoreceptor and a second nucleic acid encoding a second peptide sequence of the bipartite immunoreceptor, and (2) a plurality of polymerizable or gellable polymers and/or monomers; and (b) polymerizing or gelling the plurality of polymerizable or gellable polymers and/or monomers to form a plurality of hardened particles, each hardened particle of the plurality having a matrix composed of the polymerized or gelled plurality of polymers and/or monomers, wherein each hardened particle of the plurality comprises a first primer extension product of the first nucleic acid and a second primer extension product of the second nucleic acid. In some cases, the first primer extension product and the second primer extension product are embedded or entrapped within the matrix. In some cases, the diffusion of the first primer extension product and the second primer extension product are restricted. The first and the second primer extension product can be a reverse transcription (RT) product, a second strand synthesis (SSS) product, or an amplification product. The first and/or the second primer extension product can comprise an adaptor sequence. The adaptor sequence may not be hybridizable or complementary to the first or the second nucleic acid molecule. The first and the second primer extension product can encode a variable domain. The variable domain can comprise a CDR1, a CDR2, and/or a CDR3. The first and/or the second primer extension product can further encode a constant domain.

The cell in each vessel may be lysed to release the first nucleic acid and the second nucleic acid. The first nucleic acid and the second nucleic acid can be reverse transcribed. The reverse transcription can be performed by using a RT primer. The RT primer can be linked to a diffusion-restricting agent, wherein the diffusion-restricting agent restricts diffusion of the RT primer within the matrix. In some cases, a template-switch reaction or a SSS reaction is performed. The first nucleic acid and the second nucleic acid can be amplified to generate a first and a second amplification product. In some cases, for each of the first or the second nucleic acid, the amplifying is performed by using a first amplification primer and a second amplification primer. The first amplification primer can be linked to a diffusion-restricting agent, wherein the diffusion-restricting agent restricts diffusion of the first amplification primer within the matrix.

In some cases, the hardened particles can be washed. The hardened particles can be washed to allow a reagent to diffuse out from the hardened particles. The reagent may comprise a RT primer, an amplification primer, a template-switch primer, a SSS primer, or any combination thereof. In some cases, the hardened particles can be washed to allow another reagent to diffuse into the hardened particles. In some cases, the method can further comprise repeatedly washing the hardened particles. The hardened particles can be re-emulsified in oil after a washing step. The re-emulsified hardened particles can be used again as single-cell reactions to carry out reactions. During certain reactions when temperature increases, the hardened particles may dissolve completely or partially.

The first and the second primer extension product can be linked to a diffusion-restricting agent. The diffusion-restricting agent can be a polymer. The polymer used as a diffusion-restricting agent can be a polyacrylamide, a polyethylene glycol, or a polysaccharide. The diffusion restricting agent can be a particle. The particle can have a diameter that is larger than a pore size of the matrix. The diffusion restricting agent can be the matrix itself.

There are various ways to link a polynucleotide to a matrix or diffusion-restricting agent such that the polynucleotide can be restricted. For example, the first and the second primer extension product can be linked to the diffusion-restricting agent through a capture agent. The capture agent can comprise an immobilization moiety. The immobilization moiety can link the capture agent to the diffusion-restricting agent. The immobilization moiety can comprise a reactive group. The capture agent can further comprise a targeting moiety. The targeting moiety can be a capture oligonucleotide. The first amplification primer can comprise an oligonucleotide sequence that hybridizes to the capture oligonucleotide. The first and the second amplification product can comprise the oligonucleotide sequence that hybridizes to the capture oligonucleotide, thereby linking the first and the second amplification product to the capture agent and thereby linking to the diffusion-restricting agent. The reactive group can be a succinimidyl ester, an amide, an acrylamide, an acyl azide, an acyl halide, an acyl nitrile, an aldehyde, a ketone, an alkyl halide, an alkyl sulfonate, an anhydride, an aryl halide, an aziridine, a boronate, a carbodiimide, a diazoalkane, an epoxide, a haloacetamide, a haloplatinate, a halotriazine, an imido ester, an isocyanate, an isothiocyanate, a maleimide, a phosphoramidite, a silyl halide, a sulfonate ester, a sulfonyl halide, an amine, an aniline, a thiol, an alcohol, a phenol, a hyrazine, a hydroxylamine, a carboxylic acid, a glycol, or a heterocycle.

The first amplification product and the second amplification product can further be linked to form a fused bipartite immunoreceptor polynucleotide within each vessel or hardened particle, thereby generating the fused bipartite immunoreceptor polynucleotide library having a plurality of fused bipartite immunoreceptor polynucleotides. Each of the fused polynucleotide may have a unique sequence. The first amplification product and the second amplification product can be linked by ligation or PCR. The first amplification product and the second amplification product can be linked by a phosphodiester bond to form a continuous polynucleotide. The first amplification product and the second amplification product can be linked in-frame.

The plurality of fused bipartite immunoreceptor polynucleotides can be released from the plurality of vessels or hardened particles. Each fused bipartite immunoreceptor polynucleotide of the plurality can be circularized.

Each fused bipartite immunoreceptor polynucleotide of the plurality can be converted into a vector (e.g., by ligating the fused linear polynucleotide into a polynucleotide vector backbone). In some cases, the vector is not a polynucleotide, and the fused bipartite immunoreceptor polynucleotide can be delivered into a host cell by a non-polynucleotide vector.

The vector can be a self-amplifying RNA replicon, a plasmid, a phage, a transposon, a cosmid, a virus, or a virion. The vector can be a viral vector. The viral vector can be derived from a retrovirus, a lentivirus, an adenovirus, an adeno-associated virus, a herpes virus, a pox virus, an alpha virus, a vaccina virus, a hepatitis B virus, a human papillomavirus or a pseudotype thereof. The vector can be a non-viral vector. The non-viral vector can be a nanoparticle, a cationic lipid, a cationic polymer, a metallic nanopolymer, a nanorod, a liposome, a micelle, a microbubble, a cell-penetrating peptide, or a liposphere.

The bipartite immunoreceptor can be a T-cell receptor (TCR) or a B-cell receptor (BCR). The TCR can comprise a TCR alpha peptide sequence and a TCR beta peptide sequence, or a TCR gamma peptide sequence and a TCR delta peptide sequence; the BCR can comprise a heavy peptide sequence and a light peptide sequence.

The cell used as the source cell can be an immune cell. The immune cell can be a lymphocyte. The lymphocyte can be a T cell or a B cell. The T cell can be an inflammatory T cell, a cytotoxic T cell, a regulatory T cell, a helper T cell, a natural killer T cell, or a combination thereof. The T cell can be a CD4+ T cell or a CD8+ T cell. The B cell can be a plasmablast cell, a plasma cell, a lymphoplasmacytoid cell, a memory B cell, a follicular B cell, a marginal zone B cell, a B-1 cell, a B-2 cell, or a regulatory B cell. The immune cell can be isolated from a tumor tissue or a blood sample.

The fused bipartite immunoreceptor polynucleotide can be delivered into a host cell. The fused bipartite immunoreceptor polynucleotide library can comprise at least 50, at least 100, at least 200, at least 500, at least 1,000, at least 10,000, at least 100,000, at least 1,000,000, or at least 10,000,000 different fused bipartite immunoreceptor polynucleotides, each having a different sequence. The first peptide chain and the second peptide chain encoded by the first nucleic acid and the second nucleic acid can be a cognate pair of the bipartite immunoreceptor.

The vessel used in the methods described herein can be a droplet. The droplet can be a water-in-oil droplet. A hardened particle can be formed within the droplet by polymerizing or gelling the polymers and/or monomers. The hardened particle can be a hydrogel particle. The polymers used to form the hydrogel particles can be polysaccharides, polyacrylamides, or a combination thereof. The polysaccharides can be agarose, hyaluronic acids, carboxymethycellose, chitosan, starch, dextran, or alginate. The monomers used to form the hydrogel particles can be acrylamide or methacrylamide monomers. The polymerized or gelled plurality of polymers and/or monomers can comprise a mixture of agarose and polyacrylamides. The polymerized or gelled plurality of polymers and/or monomers can be cross-linked. In some cases, the plurality of polymerizable or gellable polymers and/or monomers can be polymerized or gelled by using an imitator. The initiator can be a UV light or a chemical. In some cases, the plurality of polymerizable or gellable polymers and/or monomers can be polymerized or gelled by reducing temperature of the vessel. For example, agarose particle can be formed by reducing the temperature of the agarose.

In another aspect, provided herein are methods performed in a liquid to make fused bipartite immunoreceptor polynucleotides. An example procedure of the methods may comprise: (a) generating a plurality of vessels (e.g., droplets), each comprising a single cell (e.g., an immune cell) and a plurality of polymerizable or gellable polymers and/or monomers; (b) lysing the single cell in each vessel to release its nucleic acids having a first nucleic acid and a second nucleic acid, wherein the first nucleic acid and the second nucleic acid encode a first peptide chain and a second peptide chain of an immunoreceptor; (c) reverse transcribing the first and the second nucleic acid in cases where the first and the second nucleic acid are RNA; (d) generating a hydrogel particle by polymerizing or gelling the polymers and/or monomers such that the first and the second nucleic acid or derivatives thereof (e.g., cDNA) are entrapped within the hydrogel particle; (e) washing the hydrogel particle to perform reagent exchange; (f) re-emulsifying the hydrogel particle; (g) amplifying the first and the second nucleic acid or derivatives thereof to generate amplification products for the first and the second nucleic acid; and (h) linking or fusing the amplification products of the first and the second nucleic acid to form a plurality of fused bipartite immunoreceptor polynucleotides. In some cases, a template switch reaction is performed during the reverse transcription. In some other cases, a second strand synthesis reaction is performed after reverse transcription. In some cases, generating a hydrogel particle can be performed after amplifying the first and the second nucleic acid, and then washing the hydrogel particle can remove the inner primers used to amplify the first and the second nucleic acid. In some other cases, generating a hydrogel particle may not be performed after reverse transcription and before amplification.

In some embodiments, provided herein is a method performed in a liquid comprising: (a) extending a first oligonucleotide hybridized to a nucleic acid molecule, thereby forming a first extension product; (b) amplifying the first extension product or a reverse complement strand thereof with a primer set comprising a first primer and a second primer, thereby forming an amplification product; (c) generating a polymer matrix in the liquid to form a hydrogel particle, thereby restricting diffusion of the amplification product; and (d) washing the hydrogel particle, thereby depleting the second primer from the hydrogel particle. The first primer or the amplification product can be linked to a diffusion-restricting agent. The method can further comprise extending a second oligonucleotide hybridized to an additional nucleic acid molecule. The nucleic acid molecule and the additional nucleic acid molecule can be a cognate pair of an immunoreceptor.

In some embodiments, provided herein is a method performed in a liquid comprising: (a) extending a first oligonucleotide hybridized to a nucleic acid molecule, thereby forming a first extension product; (b) generating a polymer matrix in the liquid to form a hydrogel particle, thereby restricting diffusion of the first extension product or a reverse complement strand thereof; (c) washing the hydrogel particle; and (d) amplifying the first extension product or the reverse complement strand thereof with a primer set comprising a first primer and a second primer, thereby forming an amplification product. The first oligonucleotide or the first extension product can be linked to a diffusion-restricting agent.

The diffusion-restricting agent can be a polymer or a particle. The polymer can be a polyacrylamide, a polyethylene glycol, or a polysaccharide. The particle can have a diameter that is larger than a pore size of the polymer matrix. The diffusion-restricting agent can be the polymer matrix. The nucleic acid molecule can be DNA or RNA. The nucleic acid molecule can be a genomic DNA. The nucleic acid molecule can be a messenger RNA. The first oligonucleotide can be a reverse transcription (RT) primer. The RT primer can be further extended with a template-switch oligonucleotide, thereby generating the first extension product having a reverse complement sequence of the template-switch oligonucleotide. In some cases, a second strand synthesis (SSS) primer having an adaptor sequence can be used to synthesize the reverse complement strand of the first extension product. The adaptor sequence may not be hybridizable or complementary to the nucleic acid molecule or the first extension product. The first extension product can comprise the adaptor sequence. The nucleic acid molecule can encode a peptide sequence of an immunoreceptor. In some cases, the methods can further comprise, after or during washing the hydrogel particle, contacting a reagent with the hydrogel particle such that the reagent diffuses into the hydrogel particle. The reagent can be an oligonucleotide or an enzyme. The enzyme can be a polymerase. The polymerase can have a proof-reading activity. Examples of polymerases include a DNA polymerase, a thermostable polymerase, a wild-type polymerase, a modified polymerase, E. coli DNA polymerase I, T7 DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfu-turbo polymerase, Pyrobest polymerase, Pwo polymerase, KOD polymerase, Bst polymerase, Sac polymerase, Klenow fragment, and variants, modified products and derivatives thereof.

In various embodiments, the hydrogel particle can be re-emulsified in oil after washing.

In some embodiments, provided herein is a method performed in a liquid comprising: (a) forming a plurality of droplets, wherein at least two droplets of the plurality comprise a single cell; (b) extending a first oligonucleotide hybridized to a first nucleic acid molecule from the single cell, thereby forming a first extension product; and extending a second oligonucleotide hybridized to a second nucleic acid molecule from the single cell, thereby forming a second extension product; (c) amplifying the first extension product or a reverse complement strand thereof with a first primer set comprising a first primer and a second primer, thereby forming a first set of amplification products; and amplifying the second extension product or a reverse complement strand thereof with a second primer set comprising a third primer and a fourth primer, thereby forming a second set of amplification products; and (d) linking an amplification product of the first set of amplification products to an amplification product of the second set of amplification products, wherein linking comprises linking in the liquid in the absence of the second and the fourth primer.

In some embodiments, provided herein is a method performed in a liquid comprising: (a) forming a plurality of droplets, wherein at least two droplets of the plurality comprise a single cell; (b) extending a first oligonucleotide hybridized to a first nucleic acid molecule from the single cell, thereby forming a first extension product; and extending a second oligonucleotide hybridized to a second nucleic acid molecule from the single cell, thereby forming a second extension product; (c) amplifying the first extension product or a reverse complement strand thereof with a first primer set comprising a first primer and a second primer, thereby forming a first set of amplification products; and amplifying the second extension product or a reverse complement strand thereof with a second primer set comprising a third primer and a fourth primer, thereby forming a second set of amplification products; (d) removing the second and the fourth primer; and (e) linking an amplification product of the first set of amplification products to an amplification product of the second set of amplification products. Each droplet of the plurality can comprise a plurality of polymerizable or gellable polymers and/or monomers. A polymer matrix in the liquid can be generated to form a hydrogel particle, thereby restricting diffusion of the first set of amplification products and the second set of amplification products. The hydrogel particle can be washed in a buffer to deplete the second primer and the fourth primer from the hydrogel particle.

In various embodiments, linking comprises generating a sticky end on the amplification product of the first and the second set. A USER enzyme may be used to generate the sticky end on the amplification product. In some cases, linking comprises hybridizing the amplification product of the first and the second set. In some cases, linking comprises ligating the amplification product of the first and the second set. The first primer and the third primer can be the same primer (i.e., have the same sequence). The first primer, the third primer, the first set of amplification products, or the second set of amplification products can be linked to a diffusion-restricting agent.

In some embodiments, provided herein is a method performed in a liquid comprising: (a) forming a plurality of droplets, wherein at least two droplets of the plurality comprise a single cell; (b) extending a first oligonucleotide hybridized to a first nucleic acid molecule from the single cell, thereby forming a first extension product; and extending a second oligonucleotide hybridized to a second nucleic acid molecule from the single cell, thereby forming a second extension product; (c) generating a polymer matrix in the liquid to form a hydrogel particle, thereby restricting the diffusion of the first extension product and the second extension product are restricted; (d) amplifying the first extension product or a reverse complement strand thereof with a first primer set comprising a first primer and a second primer, thereby forming a first set of amplification products; and amplifying the second extension product or a reverse complement strand thereof with a second primer set comprising a third primer and a fourth primer, thereby forming a second set of amplification products; and (e) linking an amplification product of the first set of amplification products to an amplification product of the second set of amplification products. The method may further comprise washing the hydrogel particle after (c). The method may further comprise contacting a reagent with the hydrogel particle such that the reagent diffuses into the hydrogel particle. The reagent can comprise an enzyme or an oligonucleotide. The reagent can be the first primer set and/or the second primer set. The enzyme can be a polymerase, a ligase, a USER enzyme, or a combination thereof. The method may further comprise emulsifying the hydrogel particle in oil after washing. The first oligonucleotide or the second oligonucleotide can be linked to a diffusion-restricting agent. The first oligonucleotide or the second oligonucleotide can be a RT primer in the cases where the first and the second nucleic acid molecules are mRNA. The RT primer can be further extended with a template-switch oligonucleotide. In some cases, a second strand synthesis (SSS) primer can be used to synthesize the reverse complement strand of the first and/or the second extension product. The SSS primer can comprise an adaptor sequence. The adaptor sequence may not be hybridizable or complementary with the first and/or the second extension product. The SSS primer can be added together with RT primer or can be added separately by diffusing into the polymer matrix. The single cell can be an immune cell. The immune cell can be a T cell or a B cell. The first nucleic acid molecule and the second nucleic acid molecule are DNA (e.g., genomic DNA) or RNA (e.g., mRNA).

In various embodiments, the first nucleic acid molecule can encode a first peptide chain of an immunoreceptor and the second nucleic acid molecule can encode a second peptide sequence of the immunoreceptor. The first peptide chain and the second peptide chain are a cognate pair of the immunoreceptor. The first peptide chain or the second peptide chain can comprise a partial or full-length variable domain. The variable domain can comprise a CDR1, CDR2, CDR3, or a combination thereof. The first peptide chain or the second peptide chain can comprise a constant domain. In some cases, the first peptide chain and the second peptide chain are TCR chains, and they can further comprise hinge region, transmembrane region, and cytoplasmic tail. The first peptide chain and the second peptide chain can form a functional TCR. The immunoreceptor can be a TCR or a BCR.

In another aspect, provided herein are methods of using the fused bipartite immunoreceptor polynucleotide, immunoreceptor-expressing vector, or host cells (e.g., recipient cells) as described herein. Various applications are provided in the present disclosure. For example, the method can comprise: (a) obtaining a population of host cells, each host cell in the population expressing a TCR having a natively paired TCR alpha and beta peptide sequences or a BCR having a natively paired BCR heavy and light peptide sequence; (b) enriching (i) a subpopulation of host cells from the population, or (ii) expressed TCRs or BCRs of a subpopulation of host cells from the population, wherein the subpopulation of host cells or the expressed TCRs or BCRs of the subpopulation of host cells bind to a target antigen or a target MHC-antigen complex; and (c) administering the subpopulation of host cells or the expressed TCRs or BCRs of the subpopulation enriched from step (b) to a subject expressing the target antigen or the target MHC-antigen complex.

The population of host cells can be obtained using the methods as described herein. The subpopulation of T cells can be enriched by contacting the population of host cells or the expressed TCRs or BCRs with the target antigen or the target MHC-antigen complex. The MHC can be a MHC tetramer. The enriched subpopulation of host cells or the expressed TCRs or BCRs can be administered into a subject by injection. The injection can comprise injecting intravenously, subcutaneously, intradermally, or intramuscularly. The target antigen is a neoantigen or a tumor-associated antigen. The subject may have cancer or autoimmune disease.

In another aspect, provided herein is a method comprising: (1) providing a plurality of at least 1,000 cells, each cell of the at least 1,000 cells comprising a TCR alpha chain and a TCR beta chain; (2) providing a plurality of at least 1,000 compartments, each compartment of the at least 1,000 compartments comprising a solid support, wherein the solid support comprises: (a) a first polynucleotide, comprising a first common sequence, a second common sequence, and a protein-coding sequence encoding a TCR alpha chain between the first and the second common sequence, (b) a second polynucleotide, comprising a third common sequence, a fourth common sequence, and a protein-coding sequence encoding a TCR beta chain between the third and the fourth common sequence, wherein, the TCR alpha chain and the TCR beta chain in each compartment is a cognate pair present in at least one of the plurality of cells, thereby providing a first plurality of protein-coding sequences each encoding a TCR alpha chain and a second plurality of protein-coding sequences each encoding a TCR beta chain; and (3) physically linking the first polynucleotide and the second polynucleotide in each compartment. The first plurality of protein-coding sequences can comprise at least 10 TRAV subgroups and the second plurality of protein-coding sequences can comprise at least 10 TRBV subgroups. Each compartment of the at least 1,000 compartments can comprise a cell from the plurality of at least 1,000 cells. The compartment can be a well, a microwell, or a droplet. The solid support can be a bead, a hydrogel particle, or a surface of the well or microwell. The first common sequence, the second common sequence, the third common sequence, or the fourth common sequence can be the same sequence in the plurality of at least 1,000 compartments.

Treatment Regimes

Disclosed herein can be cells (e.g., immunoreceptor-programmed recipient cells) used in a treatment regime. For example, a subject can receive the cells as part of a treatment regime for treatment of a cancer or disease. Treatment regimes can include: surgery, chemotherapy, radiation, immunosuppressive agents, immunostimulatory agents, antifungals, antivirals, antibiotics, or antiemetics, to name a few. In some cases, cellular compositions can be administered to a subject in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In some cases, expanded cells can be administered before or following surgery. A surgery can be a tumor resection in some cases. A surgery can be performed to isolate a TIL or TIT.

A therapeutically effective amount of cells can be used for administration. In some cases, about $5 \times 10^{10}$ cells are administered to a subject. In some cases, about $5 \times 10^{10}$ cells represent the median amount of cells administered to a subject. In some embodiments, about $5 \times 10^{10}$ cells are necessary to effect a therapeutic response in a subject. In some embodiments, at least about $1 \times 10^6$ cells, at least about $2 \times 10^6$ cells, at least about $3 \times 10^6$ cells, at least about $4 \times 10^6$ cells, at least about $5 \times 10^6$ cells, at least about $6 \times 10^6$ cells, at least about $6 \times 10^6$ cells, at least about $8 \times 10^6$ cells, at least about $9 \times 10^6$ cells, $1 \times 10^7$ cells, at least about $2 \times 10^7$ cells, at least about $3 \times 10^7$ cells, at least about $4 \times 10^7$ cells, at least about $5 \times 10^7$ cells, at least about $6 \times 10^7$ cells, at least about $6 \times 10^7$ cells, at least about $8 \times 10^7$ cells, at least about $9 \times 10^7$ cells, at least about $1 \times 10^8$ cells, at least about $2 \times 10^8$ cells, at least about $3 \times 10^8$ cells, at least about $4 \times 10^8$ cells, at least about $5 \times 10^8$ cells, at least about $6 \times 10^8$ cells, at least about $6 \times 10^8$ cells, at least about $8 \times 10^8$ cells, at least about $9 \times 10^8$ cells, at least about $1 \times 10^9$ cells, at least about $2 \times 10^9$ cells, at least about $3 \times 10^9$ cells, at least about $4 \times 10^9$ cells, at least about $5 \times 10^9$ cells, at least about $6 \times 10^9$ cells, at least about $6 \times 10^9$ cells, at least about $8 \times 10^9$ cells, at least about $9 \times 10^9$ cells, at least about $1 \times 10^{10}$ cells, at least about $2 \times 10^{10}$ cells, at least about $3 \times 10^{10}$ cells, at least about $4 \times 10^{10}$ cells, at least about $5 \times 10^{10}$ cells, at least about $6 \times 10^{10}$ cells, at least about $6 \times 10^{10}$ cells, at least about $8 \times 10^{10}$ cells, at least about $9 \times 10^{10}$ cells, at least about $1 \times 10^{11}$ cells, at least about $2 \times 10^{11}$ cells, at least about $3 \times 10^{11}$ cells, at least about $4 \times 10^{11}$ cells, at least about $5 \times 10^{11}$ cells, at least about $6 \times 10^{11}$ cells, at least about $6 \times 10^{11}$ cells, at least about $8 \times 10^{11}$ cells, at least about $9 \times 10^{11}$ cells, or at least about $1 \times 10^{12}$ cells are administered to a subject. For example, about $5 \times 10^{10}$ cells may be administered to a subject. In another example, starting with $3 \times 10^6$ cells, the cells may be expanded to about $5 \times 10^{10}$ cells and administered to a subject. In some cases, cells are expanded to sufficient numbers for therapy. For example, $5 \times 10^7$ cells can undergo rapid expansion to generate sufficient numbers for therapeutic use. In some cases, sufficient numbers for therapeutic use can be $5 \times 10^{10}$. Any number of cells can be infused for therapeutic use. For example, a patient may be infused with a number of cells between $1 \times 10^6$ to $5 \times 10^{12}$, inclusive. A patient may be infused with as many cells that can be generated for them. In some cases, cells that are infused into a patient are not all engineered. For example, at least 90% of cells that are infused into a patient can be engineered. In other instances, at least 40% of cells that are infused into a patient can be engineered. The amount of cells that are necessary to be therapeutically effective in a patient may vary depending on the viability of the cells, and the efficiency with which the cells have been genetically modified. In some cases, the product (e.g., multiplication) of the viability of cells post genetic modification may correspond to the therapeutic aliquot of cells available for administration to a subject. In some cases, an increase in the viability of cells post genetic modification may correspond to a decrease in the amount of cells that are necessary for administration to be therapeutically effective in a patient.

In some cases, a method can comprise calculating and/or administering to a subject an amount of engineered cells necessary to effect a therapeutic response in the subject. In some embodiments, calculating the amount of engineered cells necessary to effect a therapeutic response comprises determining the viability of the engineered cells. In some embodiments, in order to effect a therapeutic response in a subject, the cells administered to the subject are viable cells. In some embodiments, in order to effect a therapeutic response in a subject, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, at least about 10% of the cells are viable cells. In some embodiments, in order to effect a therapeutic response in a subject, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, at least about 10% of the cells have introduced with the polynucleotides encoding cognate pairs of immunoreceptors.

In some cases, adoptively transplanted cells can be monitored by quantitative PCR (qPCR). A qPCR assay of adoptively transplanted cells can indicate a level of modified cells that exist in a subject after an introduction. In some cases, adoptively transferred cells can be monitored using flow cytometry. For example, a flow cytometry assay may determine a level of 4-1BB vs TCR. In some cases, a single-cell TCR PCR can be performed. Levels of adoptively transferred cells can be identified on day 40 post infusion. Levels of adoptively transferred cells, such as modified cells, can be identified of day 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or up to day 200 post infusion.

Immunostimulants

In some cases, an immunostimulant can be introduced to cells or a subject. An immunostimulant can be specific or non-specific. A specific immunostimulant can provide antigenic specificity such as a vaccine or an antigen. A non-specific immunostimulant can augment an immune response or stimulate an immune response. A non-specific immunostimulant can be an adjuvant. Immunostimulants can be vaccines, colony stimulating agents, interferons, interleukins, viruses, antigens, co-stimulatory agents, immunogenicity agents, immunomodulators, or immunotherapeutic agents. An immunostimulant can be a cytokine such as an interleukin. One or more cytokines can be introduced with cells of the present disclosure. Cytokines can be utilized to boost cytotoxic T lymphocytes (including adoptively transferred tumor-specific cytotoxic T lymphocytes) to expand within a tumor microenvironment. In some cases, IL-2 can be used to facilitate expansion of the cells described herein. Cytokines such as IL-15 can also be employed. Other relevant cytokines in the field of immunotherapy can also be utilized, such as IL-2, IL-7, IL-12, IL-15, IL-21, or any combination thereof. In some cases, IL-2, IL-7, and IL-15 are used to culture cells of the present disclosure. An interleukin can be IL-2, or aldeskeukin. Aldesleukin can be administered in low dose or high dose. A high dose aldesleukin regimen can involve administering aldesleukin intravenously every 8 hours, as tolerated, for up to about 14 doses at about 0.037 mg/kg (600,000 IU/kg). An immunostimulant (e.g., aldesleukin) can be administered within 24 hours after a cellular administration. An immunostimulant (e.g., aldesleukin) can be administered in as an infusion over about 15 minutes about every 8 hours for up to about 4 days after a cellular infusion. An immunostimulant (e.g., aldesleukin) can be administered at a dose from about 100,000 IU/kg, 200,000 IU/kg, 300,000 IU/kg, 400,000 IU/kg, 500,000 IU/kg, 600,000 IU/kg, 700,000 IU/kg, 800,000 IU/kg, 900,000 IU/kg, or up to about 1,000,000 IU/kg. In some cases, aldesleukin can be administered at a dose from about 100,000 IU/kg to 300,000 IU/kg, from 300,000 IU/kg to 500,000 IU/kg, from 500,000 IU/kg to 700,000 IU/kg, from 700,000 IU/kg to about 1,000,000 IU/kg. An immunostimulant (e.g., aldesleukin) can be administered from 1 dose to about 14 doses. An immunostimulant (e.g., aldesleukin) can be administered from at least about 1 dose, 2 doses, 3 doses, 4 doses, 5 doses, 6 doses, 7 doses, 8 doses, 9 doses, 10 doses, 11 doses, 12 doses, 13 doses, 14 doses, 15 doses, 16 doses, 17 doses, 18 doses, 19 doses, or up to about 20 doses. In some cases, an immunostimulant such as aldesleukin can be administered from about 1 dose to 3 doses, from 3 doses to 5 doses, from 5 doses, to 8 doses, from 8 doses to 10 doses, from 10 doses to 14 doses, from 14 doses to 20 doses. In some cases, aldeskeukin is administered over 20 doses. In some cases, an immunostimulant, such as aldesleukin, can be administered in sequence or concurrent with a cellular administration. For example, an immunostimulant can be administered from about day: −14, −13, −12, −11, −10, −9, −8, −7, −6, −5, −4, −3, −2, −1, 0, 1, 2, 3, 4, 5, 6, 7, 8, 9, 10, 11, 12, 13, or up to about day 14. In some cases, an immunostimulant, such as aldesleukin, is administered from day 0 to day 4 after administration of a population of cells. In some cases, an immunostimulant (e.g., aldesleukin) is administered over a period of about 10 min, 15 min, 20 min, 30 min, 40 min, 50 min, 1 hour, 2 hours or up to about 3 hours. In some cases, an immunostimulant (e.g., aldesleukin) can be administered from about 24 hours prior to an administration of engineered cell to about 4 days after an administration of engineered cells. An immunostimulant (e.g., aldesleukin) can be administered from day −7, −6, −5, −4, −3, −2, −1, 0, 1, 2, 3, 4, 5, 6, 7, 8, 9, 10, 11, 12, 13, 14, 15, 16, 17, 18, 19, or up to about 20 days after an administration of engineered cells.

Immunostimulants such as aldesleukin can be provided as single-use vials containing 22 million IU (−1.3 mg) IL-2 as a sterile, white to off-white lyophilized cake plus 50 mg mannitol and 0.18 mg sodium dodecyl sulfate, buffered with approximately 0.17 mg monobasic and 0.89 mg dibasic sodium phosphate to a pH of 7.5 (range 7.2 to 7.8). The vial can be reconstituted with 1.2 mL of Sterile Water for Injection, USP, and the resultant concentration is 18 million IU/ml or 1.1 mg/mL. Diluent should be directed against the side of the vial to avoid excess foaming. Since vials contain no preservative, reconstituted solution should be used with 24 hours. Reconstituted aldesleukin can be further diluted with 50 mL of 5% Human Serum Albumin (HSA). The HSA can be added to the diluent prior to the addition of RIL-2. Dilutions of the reconstituted solution over a 1000-fold range (i.e., 1 mg/mL to 1 mcg/mL) can be acceptable in either glass bottles or polyvinyl chloride bags. Aldesleukin may be chemically stable for 48 hours at refrigerated and room temperatures, 2°-30° C. Administration of aldesleukin can be calculated based on total body weight. The final dilution of aldesleukin can be infused over 15 minutes.

In some cases, an immunostimulant is a colony stimulating factor. A colony stimulating factor can be G-CSF (filgrastim). Filgrastim can be stored in 300 mcg/ml and 480 ug/1.6 ml vials. Filgrastim can be administered daily as a subcutaneous injection. A filgrastim administration can be from about 5 mcg/kg/day. A filgrastim administration can be from about 1 mcg/kg/day, a filgrastim administration can be from about 2 mcg/kg/day, a filgrastim administration can be from about 3 mcg/kg/day, a filgrastim administration can be from about 4 mcg/kg/day, a filgrastim administration can be from about 5 mcg/kg/day, a filgrastim administration can be from about 6 mcg/kg/day, a filgrastim administration can be from about 7 mcg/kg/day, a filgrastim administration can be from about 8 meg/kg/day, a filgrastim administration can be from about 9 mcg/kg/day, a filgrastim administration can be from about 10 mcg/kg/day. In some cases, Filgrastim can be administered at a dose ranging from about 0.5 meg/kg/day to about 1.0 meg/kg/day, from about 1.0 mcg/kg/day to 1.5 meg/kg/day, from about 1.5 meg/kg/day to about 2.0 mcg/kg/day, from about 2.0 mcg/kg/day to about 3.0 mcg/kg/day, from about 2.5 meg/kg/day to about 3.5 meg/kg/day, from about 3.5 meg/kg/day to about 4.0 mcg/kg/day, from about 4.0 meg/kg/day to about 4.5 meg/kg/day. Filgrastim administration can continue daily until neutrophil count is at least about $1.0 \times 10^9$/L×3 days or at least about $5.0 \times 10^9$/L. An immunostimulant such as Filgrastim can be administered from day −7, −6, −5, −4, −3, −2, −1, 0, 1, 2, 3, 4, 5, 6, 7, 8, 9, 10, 11, 12, 13, 14, 15, 16, 17, 18, 19, or up to about 20 days after an administration of engineered cells.

Chemotherapeutic Agents

A chemotherapeutic agent or compound can be a chemical compound useful in the treatment of cancer. The chemotherapeutic cancer agents that can be used in combination with the disclosed T cell include, but are not limited to, mitotic inhibitors (vinca alkaloids). These include vincristine, vinblastine, vindesine and Navelbine™ (vinorelbine, 5'-noranhydroblastine). In yet other cases, chemotherapeutic cancer agents include topoisomerase I inhibitors, such as camptothecin compounds. As used herein, "camptothecin compounds" include Camptosar™ (irinotecan HCL), Hycamtin™ (topotecan HCL) and other compounds derived from camptothecin and its analogues. Another category of chemotherapeutic cancer agents that can be used in the methods and compositions disclosed herein are podophyllotoxin derivatives, such as etoposide, teniposide and mitopodozide. The present disclosure further encompasses other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin, and dacarbazine. The disclosure encompasses antimetabolites as chemotherapeutic agents. Examples of these types of agents include cytosine arabinoside, fluorouracil, methotrexate, mercaptopurine, azathioprime, and procarbazine. An additional category of chemotherapeutic cancer agents that may be used in the methods and compositions disclosed herein includes antibiotics. Examples include without limitation doxorubicin, bleomycin, dactinomycin, daunorubicin, mithramycin, mitomycin, mytomycin C, and daunomycin. There are numerous liposomal formulations commercially available for these compounds. The present disclosure further encompasses other chemotherapeutic cancer agents including without limitation anti-tumor antibodies, dacarbazine, azacytidine, amsacrine, melphalan, ifosfamide and mitoxantrone.

The disclosed immunoreceptor-programmed recipient cells herein can be administered in combination with other anti-tumor agents, including cytotoxic/antineoplastic agents and anti-angiogenic agents. Cytotoxic/anti-neoplastic agents can be defined as agents who attack and kill cancer cells. Some cytotoxic/anti-neoplastic agents can be alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents can be antimetabolites for tumor cells, e.g., cytosine arabinoside, fluorouracil, methotrexate, mercaptopuirine, azathioprime, and procarbazine. Other cytotoxic/anti-neoplastic agents can be antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents can be mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents can also be used. Suitable anti-angiogenic agents for use in the disclosed methods and compositions include anti-VEGF antibodies, including humanized and chimeric antibodies, anti-VEGF aptamers and antisense oligonucleotides. Other inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed engineered cells can include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; avastin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; erythrocyte gene therapy; velaresol; veramine; verdins; verteporfin; vinorelbine; vinxaltine; vitaxin; vorozole; zanoterone; zeniplatin; zilascorb; and zinostatin stimalamer. Any of the aforementioned chemotherapeutics can be administered at a clinically effective dose. A chemotherapeutic can also be administered from about day: −14, −13, −12, −11, −10, −9, −8, −7, −6, −5, −4, −3, −2, −1, 0, 1, 2, 3, 4, 5, 6, 7, 8, 9, 10, 11, 12, 13, or up to about day 14 after administration of a population of cells. In some cases, a subject can have a refractory cancer that is unresponsive to a chemotherapeutic.

Antifungal Agents

In some cases, an antifungal therapy is administered to a subject receiving immunoreceptor-programmed recipient cells. Antifungals can be drugs that can kill or prevent the growth of fungi. Targets of antifungal agents can include sterol biosynthesis, DNA biosynthesis, and β-glucan biosynthesis. Antifungals can also be folate synthesis inhibitors or nucleic acid cross-linking agents. A folate synthesis inhibitor can be a sulpha based drug. For example, a folate synthesis inhibitor can be an agent that inhibits a fungal synthesis of folate or a competitive inhibitor. A sulpha based drug, or folate synthesis inhibitor, can be methotrexate or sulfamethaxazole. In some cases, an antifungal can be a nucleic acid cross-linking agent. A cross-linking agent may inhibit a DNA or RNA process in fungi. For example, a cross-linking agent can be 5-fluorocytosine, which can be a fluorinated analog of cytosine. 5-fluorocytosine can inhibit both DNA and RNA synthesis via intracytoplasmic conversion to 5-fluorouracil. Other anti-fungal agents can be griseofulvin. Griseofulvin is an antifungal antibiotic produced by *Penicilhum griseofulvum*. Griseofulvin inhibits mitosis in fungi and can be considered a cross linking agent. Additional cross linking agent can be allylamines (naftifine and terbinafine) inhibit ergosterol synthesis at the level of squalene epoxidase; one morpholene derivative (amorolfine) inhibits at a subsequent step in the ergosterol pathway.

In some cases, an antifungal agent can be from a class of polyene, azole, allylamine, or echinocandin. In some embodiments, a polyene antifungal is amphotericin B, candicidin, filipin, hamycin, natamycin, nystatin, or rimocidin. In some cases, an antifungal can be from an azole family. Azole antifungals can inhibit lanosterol 14 α-demethylase. An azole antifungal can be an imidazole such as bifonazole, butoconazole, clotrimazole, econazole, fenticonazole, isoconazole, ketoconazole, luliconazole, miconazole, omoconazole, oxiconazole, sertaconazole, sulcoazole, or tioconazole. An azole antifungal can be a triazole such as albaconazole, efinaconazole, epoxiconazole, fluconazole, isavuvonazole, itraconazole, posaconazole, propiconazole, ravuconazole, terconazole, or voriconazole. In some cases an azole can be a thiazole such as abafungin. An antifungal can be an allylamine such as amorolfin, butenafine, naftifine, or terbinafine. An antifungal can also be an echinocandin such as anidulafungin, caspofungin, or micafungin. Additional agents that can be antifungals can be aurones, benzoic acid, ciclopirox, flucytosine, griseofulvin, haloprogin, tolnaftate, undecylenic acid, cystal violet or balsam of Peru.

A person of skill in the art can appropriately determine which known antifungal medication to apply based on the fungus infecting the individual. In some cases, a subject can receive fluconazole in combination with engineered cells. An anti-fungal therapy can be administered prophalaytically.

Fluconazole can be available in 200 mg tablets. In some cases, fluconazole can be administered as a 50 mg, 100 mg, 150 mg, 200 mg, 250 mg, 300 mg, 350 mg, or up to about 400 mg tablet. For IV administration in subjects who cannot tolerate an oral preparation, fluconazole comes in 2 MG/ML solution for injection. It should be administered at a maximum IV rate of 200 mg/hr. In some cases, an infusion rate can be from about 50 mg/hr to about 500 mg/hr. An infusion rate can also be from about 20 mg/hr to about 30 mg/hr, from about 30 mg/hr to about 40 mg/hr, from about 40 mg/hr to about 50 mg/hr, from about 50 mg/hr to about 60 mg/hr, from about 60 mg/hr to about 70 mg/hr, from about 70 mg/hr to about 80 mg/hr, from about 80 mg/hr to about 90 mg/hr, from about 90 mg/hr to about 100 mg/hr, from about 100 mg/hr to about 120 mg/hr, from about 120 mg/hr to about 140 mg/hr, from about 140 mg/hr to about 160 mg/hr, from about 160 mg/hr to about 180 mg/hr, from about 180 mg/hr to about 200 mg/hr, from about 180 mg/hr to about 220 mg/hr, from about 220 mg/hr to about 240 mg/hr, or from about 240 mg/hr to about 275 mg/hr.

Antifungals can be administered at therapeutically effective doses. A therapeutically effective dose is a dose that treats or prevents a fungal infection but that is not effective for treating a cancer. For example an antifungal such as fluconazole can be administered from about 10 mg to about 1000 mg. Fluconazole can be administered from about 10 mg, 20 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or up to about 1000 mg. Fluconazole can be administered at 400 mg. In some cases, an antifungal administration can be before a cellular therapy, during a cellular therapy or after a cellular therapy has been administered. For example a fluconazole administration can be from about day 0 (day a cellular therapy is introduced into a subject) to about day 4 after administration of a cellular therapy. An antifungal can be administered from about 14 days leading up to a cellular therapy administration to about 14 days after a cellular therapy is completed. An antifungal can be administered from about day: −14, −13, −12, −11, −10, −9, −8, −7, −6, −5, −4, −3, −2, −1, 0, 1, 2, 3, 4, 5, 6, 7, 8, 9, 10, 11, 12, 13, or up to about day 14.

Immunosuppressive Agents

In some cases, a subject may receive an immunosuppressive agent as part of a therapy regime. An immunosuppressive agent can refer to a radiotherapeutic, a biologic, or a chemical agent. In some cases, an immunosuppressive agent can include a chemical agent. For example, a chemical agent can comprise at least one member from the group consisting of cyclophosphamide, mechlorethamine, chlorambucil, melphalan, ifosfamide, thiotepa, hexamethylmelamine, busulfan, fludarabine, nitrosoureas, platinum, methotrexate, azathioprine, mercaptopurine, procarbazine, dacarbazine, temozolomide, carmustine, lomustine, streptozocin, fluorouracil, dactinomycin, anthracycline, mitomycin C, bleomycin, and mithramycin. A chemical agent can be cyclophosphamide or fludarabine.

Additionally, immunosuppressive agents can include glucocorticoids, cytostatic, antibodies, anti-immunophilins, or any derivatives thereof. A glucocorticoid can suppress an allergic response, inflammation, and autoimmune conditions. Glucocorticoids can be prednisone, dexamethasone, and hydrocortisone. Immunosuppressive therapy can comprise any treatment that suppresses the immune system. Immunosuppressive therapy can help to alleviate, minimize, or eliminate transplant rejection in a recipient. For example, immunosuppressive therapy can comprise immuno-suppressive drugs. Immunosuppressive drugs that can be used before, during and/or after transplant, but are not limited to, MMF (mycophenolate mofetil (Cellcept)), ATG (anti-thymocyte globulin), anti-CD154 (CD40L), anti-CD40 (2C10, ASKP1240, CCFZ533X2201), alemtuzumab (Campath), anti-CD20 (rituximab), anti-IL-6R antibody (tocilizumab, Actemra), anti-IL-6 antibody (sarilumab, olokizumab), CTLA4-Ig (Abatacept/Orencia), belatacept (LEA29Y), sirolimus (Rapimune), everolimus, tacrolimus (Prograf), daclizumab (Ze-napax), basiliximab (Simulect), infliximab (Remicade), cyclosporin, deoxyspergualin, soluble complement receptor 1, cobra venom factor, compstatin, anti C5 antibody (eculizumab/Soliris), methylprednisolone, FTY720, everolimus, leflunomide, anti-IL-2R-Ab, rapamycin, anti-CXCR3 antibody, anti-ICOS antibody, anti-OX40 antibody, and anti- CD122 antibody. Furthermore, one or more than one immunosuppressive agents/drugs can be used together or sequentially. One or more than one immunosuppressive agents/drugs can be used for induction therapy or for maintenance therapy. The same or different drugs can be used during induction and maintenance stages. In some cases, daclizumab (Zenapax) can be used for induction therapy and tacrolimus (Prograf) and sirolimus (Rapimune) can be used for maintenance therapy. Daclizumab (Zenapax) can also be used for induction therapy and low dose tacrolimus (Prograf) and low dose sirolimus (Rapimune) can be used for maintenance therapy. Immunosuppression can also be achieved using non-drug regimens including, but not limited to, whole body irradiation, thymic irradiation, and full and/or partial splenectomy.

In some cases, a cytostatic agent can be administered for immunosuppression. Cytostatic agents can inhibit cell division. A cytostatic agent can be a purine analog. A cytostatic agent can be an alkylating agent, an antimetabolite such as methotrexate, azathioprine, or mercaptopurine. A cytostatic agent can be at least one of cyclophosphamide, mechlorethamine, chlorambucil, melphalan, ifosfamide, thiotepa, hexamethylmelamine, busulfan, fludarabine, nitrosoureas, platinum, methotrexate, azathioprine, mercaptopurine, procarbazine, dacarbazine, temozolomide, carmustine, lomustine, streptozocin, fluorouracil, dactinomycin, anthracycline, mitomycin C, bleomycin, and mithramycin.

In some cases, an immunosuppressive agent such as fludarabine can be administered as part of a treatment regime. Fludarabine phosphate can be a synthetic purine nucleoside that differs from physiologic nucleosides in that the sugar moiety can be arabinose instead of ribose or deoxyribose. Fludarabine can be a purine antagonist antimetabolite. Fludarabine can be supplied in a 50 mg vial as a fludarabine phosphate powder in the form of a white, lyophilized solid cake. Following reconstitution with 2 mL of sterile water for injection to a concentration of 25 mg/ml, the solution can have a pH of 7.7. The fludarabine powder can be stable for at least 18 months at 2-8° C.; when reconstituted, fludarabine is stable for at least 16 days at room temperature. Because no preservative is present, reconstituted fludarabine can be administered within 8 hours. Specialized references should be consulted for specific compatibility information. Fludarabine can be dephosphorylated in serum, transported intracellularly and converted to the nucleotide fludarabine triphosphate; this 2-fluoro-ara-ATP molecule is thought to be required for the drug's cytotoxic effects. Fludarabine inhibits DNA polymerase, ribonucleotide reductase, DNA primase, and may interfere with chain elongation, and RNA and protein synthesis. Fludarabine can be administered as an IV infusion in 100 ml 0.9% sodium chloride, USP over 15 to 30 minutes. The doses can be based on body surface area (BSA). If patient is obese (BMI>35) drug dosage can be calculated using practical weight. In some cases, an immunosuppressive agent such as fludarabine can be administered from about 20 mg/m$^2$ to about 30 mg/m$^2$ of body surface area of a subject. In some cases, an immunosuppressive agent such as fludarabine can be administered from about 5 mg/m$^2$ to about 10 mg/m$^2$ of body surface area of a subject, from about 10 mg/m$^2$ to about 15 mg/m$^2$ of body surface area of a subject, from about 15 mg/m$^2$ to about 20 mg/m$^2$ of body surface area of a subject, from about 20 mg/m$^2$ to about 25 mg/m$^2$ of body surface area of a subject, from about 25 mg/m$^2$ to about 30 mg/m$^2$ of body surface area of a subject, from about 30 mg/m$^2$ to about 40 mg/m$^2$ of body surface area of a subject. In some cases, an immunosuppressive agent such as fludarabine can be administered from about 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 11 mg/m$^2$, 12 mg/m$^2$, 13 mg/m$^2$, 14 mg/m$^2$, 15 mg/m$^2$, 16 mg/m$^2$, 17 mg/m$^2$, 18 mg/m$^2$, 19 mg/m$^2$, 20 mg/m$^2$, 21 mg/m$^2$, 22 mg/m$^2$, 23 mg/m$^2$, 24 mg/m$^2$, 25 mg/m$^2$, 26 mg/m$^2$, 27 mg/m$^2$, 28 mg/m$^2$, 29 mg/m$^2$, 30 mg/m$^2$, 31 mg/m$^2$, 32 mg/m$^2$, 33 mg/m$^2$, 34 mg/m$^2$, 35 mg/m$^2$, 36 mg/m$^2$, 37 mg/m$^2$, 38 mg/m$^2$, 39 mg/m$^2$, 40 mg/m$^2$, 41 mg/m$^2$, 42 mg/m$^2$, 43 mg/m$^2$, 44 mg/m$^2$, 45 mg/m$^2$, 46 mg/m$^2$, 47 mg/m$^2$, 48 mg/m$^2$, 49 mg/m$^2$, 50 mg/m$^2$, 51 mg/m$^2$, 52 mg/m$^2$, 53 mg/m$^2$, 54 mg/m$^2$, 55 mg/m$^2$, 56 mg/m$^2$, 57 mg/m$^2$, 58 mg/m$^2$, 59 mg/m$^2$, 60 mg/m$^2$, 61 mg/m$^2$, 62 mg/m$^2$, 63 mg/m$^2$, 64 mg/m$^2$, 65 mg/m$^2$, 66 mg/m$^2$, 67 mg/m$^2$, 68 mg/m$^2$, 69 mg/m$^2$, 70 mg/m$^2$, 71 mg/m$^2$, 72 mg/m$^2$, 73 mg/m$^2$, 74 mg/m$^2$, 75 mg/m$^2$, 76 mg/m$^2$, 77 mg/m$^2$, 78 mg/m$^2$, 79 mg/m$^2$, 80 mg/m$^2$, 81 mg/m$^2$, 82 mg/m$^2$, 83 mg/m$^2$, 84 mg/m$^2$, 85 mg/m$^2$, 86 mg/m$^2$, 87 mg/m$^2$, 88 mg/m$^2$, 89 mg/m$^2$, 90 mg/m$^2$, 91 mg/m$^2$, 92 mg/m$^2$, 93 mg/m$^2$, 94 mg/m$^2$, 95 mg/m$^2$, 96 mg/m$^2$, 97 mg/m$^2$, 98 mg/m$^2$, 99 mg/m$^2$, up to about 100 mg/m$^2$ of body surface area of a subject. In some cases, an immunosuppressive agent such as fludarabine is at a dose of 25 mg/m$^2$ in 100 ml 0.9% sodium chloride, USP and infused over about 15 to about 30 minutes.

In some cases, an immunosuppressive agent such as cyclophosphamide can be administered as part of a treatment regime. Cyclophosphamide can be a nitrogen mustard-derivative alkylating agent. Following conversion to active metabolites in the liver, cyclophosphamide functions as an alkyating agent; the drug also possesses potent immunosuppressive activity. The serum half-life after IV administration ranges from 3-12 hours; the drug and/or its metabolites can be detected in the serum for up to 72 hours after administration. Following reconstitution as directed with sterile water for injection, cyclophosphamide can be stable for 24 hours at room temperature or 6 days when kept at 2-8° C. Cyclophosphamide can be diluted in 250 ml D5W and infused over one hour. The dose can be based on a subject's body weight. If a subject is obese (BMI>35) drug dosage can be calculated using practical weight as described in. In some cases, an immunosuppressive agent such as cyclophosphamide can be administered from about 1 mg/kg to about 3 mg/kg, from about 3 mg/kg to about 5 mg/kg, from about 5 mg/kg to about 10 mg/kg, from about 10 mg/kg to about 20 mg/kg, 20 mg/kg to about 30 mg/kg, from about 30 mg/kg to about 40 mg/kg, from about 40 mg/kg to about 50 mg/kg, from about 50 mg/kg to about 60 mg/kg, from about 60 mg/kg to about 70 mg/kg, from about 70 mg/kg to about 80 mg/kg, from about 80 mg/kg to about 90 mg/kg, from about 90 mg/kg to about 100 mg/kg. In some cases, an immunosuppressive agent such as cyclophosphamide is administered in excess of 50 mg/kg of a subject. In some cases, an immunosuppressive agent such as cyclophosphamide can be administered from about 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, 61 mg/kg, 62 mg/kg, 63 mg/kg, 64 mg/kg, 65 mg/kg, 66 mg/kg, 67 mg/kg, 68 mg/kg, 69 mg/kg, 70 mg/kg, 71 mg/kg, 72 mg/kg, 73 mg/kg, 74 mg/kg, 75 mg/kg, 76 mg/kg, 77 mg/kg, 78 mg/kg, 79 mg/kg, 80 mg/kg, 81 mg/kg, 82 mg/kg, 83 mg/kg, 84 mg/kg, 85 mg/kg, 86 mg/kg, 87 mg/kg, 88 mg/kg, 89 mg/kg, 90 mg/kg, 91 mg/kg, 92 mg/kg, 93 mg/kg, 94 mg/kg, 95 mg/kg, 96 mg/kg, 97 mg/kg, 98 mg/kg, 99 mg/kg, up to about 100 mg/kg of a subject. In some cases, an immunosuppressive agent such as cyclophosphamide can be administered over at least about 1 day to about 3 days, from 3 days to 5 days, from 5 days to 7 days, from 7 days to about 10 days, from 10 days to 14 days, from 14 days to about 20 days. In some cases, cyclophosphamide can be at a dose of about 60 mg/kg and is diluted in 250 ml 5% dextrose in water and infused over one hour.

An immunosuppressive agent can be, for example, a regime of cyclophosphamide and fludarabine. For example, a cyclophosphamide fludarabine regimen can be administered to a subject receiving an engineered cellular therapy. A cyclophosphamide fludarabine regimen can be administered at a regime of 60 mg/kg qd for 2 days and 25 mg/m$^2$ qd for 5 days. A chemotherapeutic regime, for example, cyclophosphamide fludarabine, can be administered from 1 hour to 14 days preceding administration of engineered cells of the present disclosure. A chemotherapy regime can be administered at different doses. For example, a subject may receive a higher initial dose followed by a lower dose. A subject may receive a lower initial dose followed by a higher dose.

In some cases, an immunosuppressive agent can be an antibody. An antibody can be administered at a therapeutically effective dose. An antibody can be a polyclonal antibody or a monoclonal antibody. A polyclonal antibody that can be administered can be an antilymphocyte or antithymocyte antigen. A monoclonal antibody can be an anti-IL-2 receptor antibody, an anti-CD25 antibody, or an anti-CD3 antibody. An anti-CD20 antibody can also be used. B-cell ablative therapy such as agents that react with CD20, e.g., Rituxan can also be used as immunosuppressive agents.

An immunosuppressive can also be an anti-immunophilin. Anti-immunophilins can be ciclosporin, tacrolimus, everolimus, or sirolimus. Additional immunosuppressive agents can be interferons such as IFN-beta, opiods, anti-TNF binding agents, mycophenolate, or fingolimod.

Immunosuppressive agents can also refer to radiotherapeutics. Radiotherapy can include radiation. Whole body radiation may be administered at 12 Gy. A radiation dose may comprise a cumulative dose of 12 Gy to the whole body, including healthy tissues. A radiation dose may comprise from 5 Gy to 20 Gy. A radiation dose may be 5 Gy, 6 Gy, 7 Gy, 8 Gy, 9 Gy, 10 Gy, 11 Gy, 12, Gy, 13 Gy, 14 Gy, 15 Gy, 16 Gy, 17 Gy, 18 Gy, 19 Gy, or up to 20 Gy. Radiation may be whole body radiation or partial body radiation. In the case that radiation is whole body radiation it may be uniform or not uniform. For example, when radiation may not be uniform, narrower regions of a body such as the neck may receive a higher dose than broader regions such as the hips. For example, in one embodiment, subjects may undergo standard treatment with high dose chemotherapy followed by peripheral blood stem cell transplantation. In certain embodiments, following the transplant, subjects receive an infusion of the expanded cells (e.g., immunoreceptor-programmed recipient cells) of the present disclosure. The dosage of the above treatments to be administered to a patient can vary with the precise nature of the condition being treated and the recipient of the treatment. The scaling of dosages for human administration can be performed according to art-accepted practices. The dose for CAMPATH, for example, can be in the range 1 to about 100 mg for an adult patient, usually administered daily for a period between 1 and 30 days. The daily dose can be 1 to 10 mg per day although in some instances larger doses of up to 40 mg per day may be used (described in U.S. Pat. No. 6,120,766).

Antibiotic Agents

An antibiotic can be administered to a subject as part of a therapeutic regime. An antibiotic can be administered at a therapeutically effective dose. An antibiotic can kill or inhibit growth of bacteria. An antibiotic can be a broad spectrum antibiotic that can target a wide range of bacteria. Broad spectrum antibiotics, either a 3$^{rd}$ or 4$^{th}$ generation, can be cephalosporin or a quinolone.

An antibiotic can also be a narrow spectrum antibiotic that can target specific types of bacteria. An antibiotic can target a bacterial cell wall such as penicillins and cephalosporins. An antibiotic can target a cellular membrane such as polymyxins. An antibiotic can interfere with essential bacterial enzymes such as antibiotics: rifamycins, lipiarmycins, quinolones, and sulfonamides. An antibiotic can also be a protein synthesis inhibitor such as macrolides, lincosamides, and tetracyclines. An antibiotic can also be a cyclic lipopeptide such as daptomycin, glycylcyclines such as tigecycline, oxazolidiones such as linezolid, and lipiarmycins such as fidaxomicin.

In some cases, an antibiotic can be 1$^{st}$ generation, 2$^{th}$ generation, 3$^{rd}$ generation, 4$^{th}$ generation, or 5$^{th}$ generation. A first generation antibiotic can have a narrow spectrum. Examples of 15$^{th}$ generation antibiotics can be penicillins (Penicillin G or Penicillin V), Cephalosporins (Cephazolin, Cephalothin, Cephapirin, Cephalethin, Cephradin, or Cephadroxin). In some cases, an antibiotic can be 2$^{nd}$ generation. 2$^{nd}$ generation antibiotics can be a penicillin (Amoxicillin or Ampicillin), Cephalosporin (Cefuroxime, Cephamandole, Cephoxitin, Cephaclor, Cephrozil, Loracarbef). In some cases, an antibiotic can be 3$^{rd}$ generation. A 3$^{rd}$ generation antibiotic can be penicillin (carbenicillin and ticarcillin) or cephalosporin (Cephixime, Cephtriaxone, Cephotaxime, Cephtizoxime, and Cephtazidime). An antibiotic can also be a 4$^{th}$ generation antibiotic. A 4$^{th}$ generation antibiotic can be Cephipime. An antibiotic can also be 5$^{th}$ generation. 5$^{th}$ generation antibiotics can be Cephtaroline or Cephtobiprole.

In some cases, an antibiotic can be a bacterial wall targeting agent, a cell membrane targeting agent, a bacterial enzyme interfering agent, a bactericidal agent, a protein synthesis inhibitor, or a bacteriostatic agent. A bacterial wall targeting agent can be a penicillin derivatives (penams), cephalosporins (cephems), monobactams, and carbapenems. β-Lactam antibiotics are bactericidal or bacteriostatic and act by inhibiting the synthesis of the peptidoglycan layer of bacterial cell walls. In some cases, an antibiotic may be a protein synthesis inhibitor. A protein synthesis inhibitor can be ampicillin which acts as an irreversible inhibitor of the enzyme transpeptidase, which is needed by bacteria to make the cell wall. It inhibits the third and final stage of bacterial cell wall synthesis in binary fission, which ultimately leads to cell lysis; therefore, ampicillin is usually bacteriolytic. In some cases, a bactericidal agent can be cephalosporin or quinolone. In other cases, a bacteriostatic agent is trimethoprim, sulfamethoxazole, or pentamidine.

In some cases, an agent for the prevention of PCP pneumonia may be administered. For example, Trimethoprim and Sulfamethoxazole can be administered to prevent pneumonia. A dose of trimethoprim and sulfamethoxazole (TMP/SMX; an example sulfa drug) can be 1 tablet PO daily three times a week, on non-consecutive days, on or after the first dose of chemotherapy and continuing for at least about 6 months and until a CD4 count is greater than 200 on at least 2 consecutive lab studies. In some cases, trimethoprim can be administered at 160 mg. Trimethoprim can be administered from about 100 to about 300 mgs. Trimethoprim can be administered from about 100 mg, 125 mg, 150 mg, 175 mg, 200 mg, 225 mg, 250 mg, 275 mg, or up to about 300 mg. In some cases, sulfamethoxazole is administered at 800 mg. Sulfamethoxazole can be administered from about 500 mg to about 1000 mg. Sulfamethoxazole can be administered from about 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or up to about 1000 mgs. In some cases, a TMP/SMX regime can be administered at a therapeutically effective amount. TMP/SMX can be administered from about 1× to about 10× daily. TMP/SMX can be administered 1×, 2×, 3×, 4×, 5×, 6×, 7×, 8×, 9×, 10×, 11×, 12×, 13×, 14×, 15×, 16×, 17×, 18×, 19×, or up to about 20× daily. In some cases, TMP/SMX can be administered on a weekly basis. For example, TMP/SMX can be administered from 1×, 2×, 3×, 4×, 5×, 6×, or up to about 7× a week. A TMP/SMX regime can be administered from about day: −14, −13, −12, −11, −10, −9, −8, −7, −6, −5, −4, −3, −2, −1, 0, 1, 2, 3, 4, 5, 6, 7, 8, 9, 10, 11, 12, 13, or up to about day 14 after administration of a cellular therapy, such as the recipient cells described herein.

In some cases, a subject that has a sulfa allergy may receive pentamidine. Pentamidine can be administered by aerosol. Pentamidine 300 mg per nebulizer within one week prior to admission and continued monthly until the CD4 count is above 200 on two consecutive follow up lab studies and for at least 6 months post chemotherapy. Pentamidine can be used to prevent the occurrence of PCP infections. It can be supplied in 300 mg vials of lyophilized powder and can be administered via nebulizer. Pentamidine can be administered from about 300 mg to about 500 mgs. In some cases, petamidine can be administered from about 100 mg, 200 mg, 300 mg, 400 mg, 500 mg, 600 mg, 700 mg, or up to about 800 mgs.

In some cases, a bacteriostatic agent, such as an antibiotic can be administered prior to the administration of immunoreceptor-programmed recipient cells, concurrent with these cells, or after these cells. In some cases, a bacteriostatic agent can be administered from about 14 days prior to an administration of the immunoreceptor-programmed recipient cells to about 6 months after the administration of these cells.

Anti-Viral Agents

In some cases, an anti-viral agent may be administered as part of a treatment regime. In some cases, a herpes virus prophylaxis can be administered to a subject as part of a treatment regime. A herpes virus prophylaxis can be valacyclovir (Valtrex). Valtrex can be used orally to prevent the occurrence of herpes virus infections in subjects with positive HSV serology. It can be supplied in 500 mg tablets. Valacyclovir can be administered at a therapeutically effective amount. For example, valacyclovir can be administered from about 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, or up to about 700 mg tablets. Valacyclovir can be started the day after the last dose of fludarabine at a dose of 500 mg orally daily if a subject is able to tolerate oral intake. An antiviral therapy can be administered from about day: −14, −13, −12, −11, −10, −9, −8, −7, −6, −5, −4, −3, −2, −1, 0, 1, 2, 3, 4, 5, 6, 7, 8, 9, 10, 11, 12, 13, or up to about day 14 after administration of a cellular therapy.

In some cases, a subject may not be able to take oral medication for the prophylaxis of herpes. In those cases, acyclovir can be administered. Acyclovir can be supplied as a powder for injection in 500 mg/vials. In some cases, acyclovir can be administered at a therapeutically effective amount. Acyclovir can be administered orally from about 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, or up to about 700 mgs. Acyclovir can be administered 1×, 2×, 3×, 4×, 5×, 6×, or up to about 7× per day. Acyclovir can be administered from about day: −14, −13, −12, −11, −10, −9, −8, −7, −6, −5, −4, −3, −2, −1, 0, 1, 2, 3, 4, 5, 6, 7, 8, 9, 10, 11, 12, 13, or up to about day 14 after administration of a cellular therapy. In some cases, acyclovir can be administered intravenously. For example, acyclovir can be administered at 1 mg/kg to about 3 mg/kg, from about 3 mg/kg to about 5 mg/kg, from about 5 mg/kg to about 10 mg/kg, from about 10 mg/kg to about 20 mg/kg, 20 mg/kg to about 30 mg/kg, from about 30 mg/kg to about 40 mg/kg, from about 40 mg/kg to about 50 mg/kg, from about 50 mg/kg to about 60 mg/kg, from about 60 mg/kg to about 70 mg/kg, from about 70 mg/kg to about 80 mg/kg, from about 80 mg/kg to about 90 mg/kg, from about 90 mg/kg to about 100 mg/kg. In some cases, acyclovir is administered in excess of 50 mg/kg. Acyclovir can be reconstituted in 10 mL of sterile water for injection to a concentration of 50 mg/mL. Reconstituted solutions should be used within 12 hours. IV solutions can be diluted to a concentration of 7 mg/mL or less and infused over 1 hour to avoid renal damage.

Administration

Provided herein can be methods for administering a therapeutic regime to a subject having a condition such as cancer. In some instances, a cellular composition (for example, comprising immunoreceptor-programmed recipient cells) can be provided in a unit dosage form. A cellular composition can be resuspended in solution and administered as an infusion. Provided herein can also be a treatment regime that includes immunostimulants, immunosuppressants, antibiotics, antifungals, antiemetics, chemotherapeutics, radiotherapy, and any combination thereof. A treatment regime that includes any of the above can be lyophilized and reconstituted in an aqueous solution (e.g., saline solution). In some instances, a treatment (for example, a cellular treatment) is administered by a route selected from subcutaneous injection, intramuscular injection, intradermal injection, percutaneous administration, intravenous ("i.v.") administration, intranasal administration, intralymphatic injection, and oral administration. In some instances, a subject is infused with a cellular composition comprising immunoreceptor-programmed recipient cells by an intralymphatic microcatheter.

Many drugs can be administered orally as liquids, capsules, tablets, or chewable tablets. Because the oral route may be the most convenient and usually the safest and least expensive, it can be the one most often used. However, it may have limitations because of the way a drug typically moves through the digestive tract. For drugs administered orally, absorption may begin in the mouth and stomach. However, most drugs can be absorbed from the small intestine. The drug passes through the intestinal wall and travels to the liver before being transported via the bloodstream to its target site. The intestinal wall and liver can chemically alter (metabolize) many drugs, decreasing the amount of drug reaching the bloodstream. Consequently, these drugs can be given in smaller doses when injected intravenously to produce the same effect.

For a subcutaneous route, a needle may be inserted into fatty tissue just beneath the skin. After a drug is injected, it then moves into small blood vessels (capillaries) and is carried away by the bloodstream. Alternatively, a drug can reach the bloodstream through the lymphatic vessels. The intramuscular route may be used when larger volumes of a drug product are needed. Because the muscles lie below the skin and fatty tissues, a longer needle may be used. Drugs are usually injected into the muscle of the upper arm, thigh, or buttock. For the intravenous route, a needle can be inserted directly into a vein. A solution containing the drug may be given in a single dose or by continuous infusion. For infusion, the solution can be moved by gravity (from a collapsible plastic bag) or, more commonly, by an infusion pump through thin flexible tubing to a tube (catheter) inserted in a vein, usually in the forearm. In some cases, cells or therapeutic regimes are administered as infusions. An infusion can take place over a period of time. For example, an infusion can be an administration of a cell or therapeutic regime over a period of about 5 minutes to about 5 hours. An infusion can take place over a period of about 5 min, 10 min, 20 min, 30 min, 40 min, 50 min, 1 hour, 1.5 hours, 2 hours, 2.5 hours, 3 hours, 3.5 hours, 4 hours, 4.5 hours, or up to about 5 hours.

In some embodiments, intravenous administration is used to deliver a precise dose quickly and in a well-controlled manner throughout the body. It can also be used for irritating solutions, which would cause pain and damage tissues if given by subcutaneous or intramuscular injection. An intravenous injection may be more difficult to administer than a subcutaneous or intramuscular injection because inserting a needle or catheter into a vein may be difficult, especially if the person is obese. When given intravenously, a drug can be delivered immediately to the bloodstream and tend to take effect more quickly than when given by any other route. Consequently, health care practitioners can closely monitor people who receive an intravenous injection for signs that the drug is working or is causing undesired side effects. Also, the effect of a drug given by this route may tend to last for a shorter time. Therefore, some drugs can be given by continuous infusion to keep their effect constant. For the intrathecal route, a needle can be inserted between two vertebrae in the lower spine and into the space around the spinal cord. The drug can then be injected into the spinal canal. A small amount of local anesthetic can be used to numb the injection site. This route can be used when a drug is needed to produce rapid or local effects on the brain, spinal cord, or the layers of tissue covering them (meninges)—for example, to treat infections of these structures.

Drugs administered by inhalation through the mouth can be atomized into smaller droplets than those administered by the nasal route, so that the drugs can pass through the windpipe (trachea) and into the lungs. How deeply into the lungs they go can depend on the size of the droplets. Smaller droplets can go deeper, which can increase the amount of drug absorbed. Inside the lungs, they can be absorbed into the bloodstream.

In some cases, a treatment regime may be dosed according to a body weight of a subject. In subjects who are determined obese (BMI>35) a practical weight may need to be utilized. BMI is calculated by: BMI=weight (kg)/[height (m)]$^2$.

An ideal body weight may be calculated for men as 50 kg+2.3×(number of inches over 60 inches) or for women 45.5 kg+2.3×(number of inches over 60 inches). An adjusted body weight may be calculated for subjects who are more than 20% of their ideal body weight. An adjusted body weight may be the sum of an ideal body weight+(0.4× (Actual body weight −ideal body weight)). In some cases a body surface area may be utilized to calculate a dosage. A body surface area (BSA) may be calculated by: BSA (m2)=√Height (cm)*Weight (kg)/3600.

In some cases, a pharmaceutical composition comprising a cellular therapy can be administered either alone or together with a pharmaceutically acceptable carrier or excipient, by any routes, and such administration can be carried out in both single and multiple dosages. More particularly, the pharmaceutical composition can be combined with various pharmaceutically acceptable inert carriers in the form of tablets, capsules, lozenges, troches, hand candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes.

In some cases, a therapeutic regime can be administered along with a carrier or excipient. Examples of carriers and excipients can include dextrose, sodium chloride, sucrose, lactose, cellulose, xylitol, sorbitol, malitol, gelatin, PEG, PVP, and any combination thereof. In some cases, an excipient such as dextrose or sodium chloride can be at a percent from about 0.5%, 1%, 1.5%, 2%, 2.5%, 3% 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, or up to about 15%. In some cases, a method of treating a disease in a subject may comprise transplanting to the subject one or more cells (including organs and/or tissues) comprising engineered cells (e.g., immucoreceptor-programmed recipient cells). Cells prepared by intracellular genomic transplant can be used to treat cancer.

EXAMPLES

Example 1: Paired TCR Cloning Using Droplet-Based Single-Cell Reactors, in a Tail-to-Tail Orientation Step 1: Preparation of the Oligonucleotide-Laden, Thermo-Reversible Hydrogel.

The oligonucleotide-laden, thermo-reversible hydrogel can be made by ultra-low gelling temperature (ULGT) agarose (which serves as the thermo-reversible hydrogel) and linear polyacrylamide polymer covalently modified with oligonucleotide. The ULGT agarose can be type IX-A, and can be obtained from Sigma Aldrich (Cat. #A2576).

The oligonucleotide-modified linear polyacrylamide can be made by co-polymerizing the oligonucleotides and the acrylamide monomers. Specifically, a solution containing ~4% acrylamide, 100 μM Acrydite-dT$_{30}$ (SEQ ID NO: 21), 100 μM Acrydite-T1d in PBS buffer will be prepared, appropriate amount of ammonium persulfate (APS) and TEMED will be added to the solution, and the solution will be incubated at room temperature for ~6 h, during which acrylamide, Acrydite-dT$_{30}$ (SEQ ID NO: 21) Acrydite-T1d (the sequence of T1d can be 5'-CGGGAAAGCA GA-3' (SEQ ID NO: 6)) will be co-polymerized in to high molecular-weight linear polymer.

This solution will be dialyzed against PBS to remove wastes such as acrylamide monomers, short polyacrylamide-chains and oligonucleotide that are not incorporated into long-chain linear polyacrylamide. This dialysis will also remove APS, TEMED, their reaction/decomposition product. Then, 2% melted ULGT agarose and the solution containing oligonucleotide-modified linear polyacrylamide can be made by mixing at 1:1 ratio to obtain oligonucleotide-laden 1% ULGT agarose.

In this example, $dT_{30}$ (SEQ ID NO: 21) serves as the diffusion-restricted TCR alpha constant domain (TRAC) RT primer and the diffusion-restricted TCR beta constant domain (TRBC) RT primer shown in FIG. 4A and FIG. 5A. Alternatively, gene specific primers targeting TRAC and TRBC can be used as RT primers. An example of TRAC-targeting gene-specific primer sequence is 5'-ttgagaatca aaatcggtga ata-3' (SEQ ID NO: 7). An example of TRBC-targeting gene-specific primer sequence is 5'-tgtgcacctc cttccc-3' (SEQ ID NO: 8).

In this example, T1d serves as the affinity capture oligo (ACO) which can hybridize with the affinity retention sequence (ARS) shown in FIG. 4A and FIG. 5B, so that molecules (e.g., primers and PCR products) carrying an ARS are diffusion-restricted. The polymerization condition can be optimized so that the final concentrations of $dT_{30}$ (SEQ ID NO: 21) and T1d in the 1% ULGT agarose gel are in the range of 100 nM to 500 nM.

Step 2: Encapsulate T Cells in Hydrogel Droplets.

About 10,000 T cells will be added to ~50 µL of melted oligonucleotide-laden, thermo-reversible hydrogel described above at 37° C., gently mixed, and emulsified with carrier oil using a flow-focusing microfluidic devise to form ~200,000 uniform-sized water-in-oil droplets with median volume of ~250 µL, or by vortexing using TissueLyser LT (Qiagen) to form heterogenous-sized water-in-oil droplets. The carrier oil can be detergent-containing fluorocarbon oil (e.g., RAN Biotechnologies, Cat #008-FluoroSurfactant-2wtH), or detergent-containing mineral oil (e.g., Tegosoft DEC, mineral oil, Abil WE09 mixed at the ratio of 73:20:7, see Abil et al., 2017). For the vortexing method, the frequency and duration of the vortexing can be tuned so that reasonable fraction of T cells (e.g., >20%) are in droplets whose volume is between 0.1 nL and 0.5 nL.

Step 3: Capture and Reverse-Transcribe mRNAs

The emulsion produced above can be incubated at 65 to 75° C. for 5 min to rupture the cells and release the mRNA. Then the emulsion will be placed on ice to allow $dT_{30}$ (SEQ ID NO: 21) to hybridize with the poly A tail (FIG. 4A, top). This on-ice incubation will also promote the agarose to gel. Next, the emulsion will be demulsified to obtain hydrogel beads in aqueous solution. The demulsification method will depend on the carrier oil used. For fluorocarbon oil, the emulsion can be demulsified by adding 20% (vol/vol) 1H,1H,2H,2H-Perfluorooctanol in HFE-7500 oil (20% PFO). For mineral oil, the emulsion can be demulsified by Phenol/chloroform/isoamyl alcohol (25:24:1; vol/vol/vol; Fisher, cat. no. BP17521).

Reagent exchange can be performed to deliver buffer and reagents to the aqueous content of the hydrogel beads so that reverse transcription (RT) and template switching (TS) can occur (FIG. 4A, arrow (1)). To do this, the hydrogel beads can be washed with RT buffer containing sufficient amount of dNTPs (e.g., SmartScribe RT buffer) at 4° C., then sufficient amount of RT enzyme (e.g., SmartScript reverse transcriptase) and template-switching oligo (TSO) will be added to the bead suspension and allowed to diffuse into the hydrogel beads. The TSO may have the sequence of 5'-AAGCAGTGGTATCAACGCAGAGTACAT/rG//rG//+G/-3' (SEQ ID NO: 9), where /rG/ means ribose G nucleotide, and /+G/ means LNA G nucleotide. The hydrogel beads will then be compacted by brief centrifugation (e.g., 500 g for 1 min) and the supernatant can be removed. Then the hydrogel beads will be re-emulsified using an agitation method. To do this, a small amount (e.g., ~500 uL) of carrier oil can be added to the tube containing the compacted hydrogel beads. The tube will be agitated (e.g., by vortexing or hand-flicking) to form water-in-oil emulsions where the hydrogel beads will be surrounded by carrier oil with little amount (e.g., 50 µL) or no fluid aqueous solution in between. This emulsion will be incubated to finish RT and template switching (e.g., at 42° C. for 1 hr), followed by incubation at 4° C. for 5 min to let the agarose gel. Then the emulsion can be demulsified again as described above.

Step 4: PCR-Amplify TRA and TRB

With the first-strand cDNA diffusion-restricted in the hydrogel, the hydrogel beads can be subject to reagent exchange again (as described above) to deliver buffer, DNA polymerase (e.g., Taq or KOD) and primers for PCR-amplification of TRA and TRB in the droplet-based single-cell reactors. A set of 3 primers can be used to amplify TRAC and TRBC: Primers 'ARS-pTSO', '1R' and '2R' (See FIG. 4A, arrow (2)). Primer ARS-pTSO may have the sequence of [T1i|3×Spacer18|pTSO}, where Tli is complimentary to T1d, 3×Spacer18 is a flexible linker consisting of three consecutive internal Spacer18 (i.e., hexaethylene glycol) modifications, and pTSO has essentially the same sequence as TSO can prime on template-switched cDNA. pTSO may have the following sequence: 5'-GCAGTGGTAT CAACGCAGAG TAC-3'(SEQ ID NO: 10). Primers 1R and 2R can be designed according to the strategy outlined in "Fusion of Paired Bipartite Immunoreceptor Sequences: tail-to-tail design" section. Domain TRAC-5A may have the sequence 5'-GACCCTGCCGTGTACCAG-3'(SEQ ID NO: 11); domain TRBC-5A may have the sequence 5'-TGTGTTTGAGCCATCAGAAGCAGAG-3' (SEQ ID NO: 12); domain OL-1 may have the sequence 5'-ACCAG-3'; domain OL-2 may have the sequence 5'-CTCTGCT-3'.

After reagent exchange, the hydrogel beads can be emulsified again using the agitation method described above. The emulsion can be subject to PCR (FIG. 4B, arrow (3)), after which amplified and diffusion-restricted TRA and TRB can be produced. The amplified TRA and TRB also have overlapping sequences to facilitate fusion. The emulsion can be cooled again for the agarose to gel, and then demulsified.

Step 5. Fusion of TRA and TRB

The fusion of amplified TRA and TRB can be carried out following the strategy outlined in "Fusion of Paired Bipartite Immunoreceptor Sequences: tail-to-tail design" section. For example, USER (New England Biolabs) and ligase can be used. To do this, the primers 1R and 2R need to be modified with deoxyuridine at selected positions. For example, primer 1R can have the sequence 5'-AGCAGAGC/dU/GG/dU/ACACGGCAGGGTC-3' (SEQ ID NO: 13), and primer 2R can have the sequence 5'-ACCAGCTC/dU/GC/dU/TCT-GATGGCTCAAACACA-3' (SEQ ID NO: 14), where /dU/ means deoxyuridine modification.

After PCR amplification in the previous step, the emulsion can be demulsified and reagent exchange can be carried out to deliver USER buffer and enzyme mix to the aqueous content in the agarose beads. The hydrogel beads can be emulsified again using the agitation method, and the emulsion can be incubated at a temperature suited for USER digestion (e.g., at 37° C. for 1 hr). The temperature can be slightly raised to ensure that the agarose is melt, which allows USER-digested PCR product to freely diffuse. Then the emulsion can be incubated at 37° C. again for the sticky ends on the USER-digested TRA and TRB can hybridize (FIG. 4B, arrow (4)). Then the emulsion can be cooled on ice to let the agarose gel, and demulsified.

Next, reagent exchange can be applied to introduce ligase buffer and enzyme (e.g., Taq DNA ligase) to the agarose beads, which can then be re-emulsified using the agitation method. The emulsion can then be incubated at the optimal temperature for the ligase, which will ligate the sticky ends (FIG. 4B, arrow (5)). The emulsion can be cooled again and demulsified to harvest agarose beads in aqueous solution.

The agarose beads can be diluted with ~100 μL 1×TE and melted again so that the agarose concentration is low enough that it will not gel at room temperature. To this mixture, primer having the sequence pTSO can be added along with PCR buffer and enzyme, and bulk PCR can be carried out to further amplify the fused product. This new PCR product will no longer be diffusion restricted, and can be purified using Agencourt AMPure beads. The purified PCR product represents a library of fused bipartite immunoreceptor polynucleotides.

Example 2: Paired TCR Cloning Using Droplet-Based Single-Cell Reactors, in a Head-to-Tail Orientation The first 3 steps can be essentially the same as Example 1, except that TSO may be dispensable (FIG. 5A, top and arrow (1)).

Step 4: Second Strand Synthesis on Diffusion-Restricted cDNA

After RT, the hydrogel beads can be subject to reagent exchange to deliver a group of second-strand synthesis (SSS) primers (FIG. 5A, arrow (2)). The group may comprise two panels: the TRA panel and the TRB panel. Each panel may contain 10 to 100 primers depending on the species. For human, a 45-primer TRA panel and a 48-primer TRB panel can be used to cover all functional V gene variants as annotated in IMGT database. Each primer in the TRA panel can have a general structure of [AdptA|$CDS_{TRA}$}, and each primer in the TRB panel can have a general structure [AdptB|$CDS_{TRB}$}. AdptA and AdptB are described in the present disclosure. AdptA may have the sequence of P2A-3A. P2A-3A can be the last ~20 bases of the coding sequence for P2A 'self-cleaving' peptide. The coding sequence of P2A can be 'gcgacgaatt ttagtttgct taagcaagcc ggagatgtgg aggaaaatcc tggaccg' (SEQ ID NO: 15). AdptB can have the sequence of attB1-K, whose nucleotide sequence can be 'ACAAGTTTGTA-CAAAAAAGCAGGCT tacc' (SEQ ID NO: 16). The $CDS_TRA$ can be the first 20 to 45 bases of the coding sequence of each TRA-L1 gene (encoding the leader sequence of TRAV genes). The $CDS_{TRB}$ can be the first 20 to 45 bases of the coding sequence of each TRB-L1 gene (encoding the leader sequence of TRBV genes). In this case, $CDS_{TRA}$ and $CDS_{TRB}$ can also be called TRAV-L1UE and TRBV-L1UE, respectively (where U stands for upstream, and E stands for exact, meaning that the sequence starts exactly from the start codon). All $CDS_{TRA}$ and $CDS_{TRB}$ sequences should be designed to have similar Tm so that they can all bind their target site on the cDNA with reasonably good efficiency and specificity.

After reagent exchange, the concentration of the primers in the hydrogel bead can be ~10 nM for each primer (~1 uM total). Since the presence of AdptA and AdptB may cause non-specific binding for the SSS primers, blocker oligonucleotides with sequence complementary to AdptA and AdptB (here called BlockerA and BlockerB, respectively) may be added to hybridize to AdptA and AdptB. The 3' end of BlockerA and BlockerB may be modified with an extension blocker (e.g., amine, C3 spacer, dideoxy modification, or inverted dT). One may ensure that the concentration of Blocker A is equal or higher than the total concentration of TRA panel SSS primers, and that the concentration of BlockerB is equal or higher than the total concentration of TRB panel SSS primers.

After reagent exchange, the hydrogel beads can be re-emulsified using the agitation method. The emulsion can be first heated to ~95° C. for 3 to 10 min to denature the mRNA:cDNA duplex, and then cooled to the annealing temperature, which can be 3 to 10° C. lower than the Tm of the typical $CDS_{TRA}$ and $CDS_{TRB}$ sequences. The annealing can last 3 to 6 hr. Then the emulsion can be cooled to let the agarose gel, demulsified, and the hydrogel beads can be washed at room temperature to remove unbound SSS primers. Optionally, ssDNA 3'-to-5' exonuclease (e.g., Exo I) can be added to the agarose beads (via reagent exchange) to degrade the remaining and unhybridized SSS primers. If the exonuclease requires incubation temperature higher than the melting temperature of the agarose, this exonuclease treatment step may require another emulsification→reaction→demulsification→reagent exchange.

Next, DNA polymerase (e.g., DNA polymerase I, Phi 29, Klenow fragment, Taq, etc.) and proper buffer can be added to the agarose via reagent exchange. The agarose beads can be emulsified again by the agitation method, and the emulsion can be incubated at the optimal temperature of the DNA polymerase for 10 to 60 min to carry out the SSS (FIG. 5B, arrow (3)).

Step 5: PCR Amplification of TRA and TRB, Fusion

After SSS, the emulsion can be cooled to let the agarose gel, demulsified, and washed with PCR buffer. Primers ht1F, ht1R, ht2F, ht2R, as well as thermostable DNA polymerase (e.g., Hotstart Taq) can be added to the hydrogel via reagent exchange (FIG. 5B, arrow (4)). The primer ht1F may have the sequence [T1i|3×Spacer18|AdptA}, where Tli serves as the affinity retention sequence (ARS). The primer ht2R may have the sequence [T1i|3×Spacer18|TRBC-3A*}, where TRBC-3A* is a reverse primer for TRBC, and may have the sequence 5'-CTCTGCTTCTGATGGCTCAAACACA-3' (SEQ ID NO: 17). The primers ht1R and ht2F are described herein. Domain [htTRAC-5A} may have the sequence 5'-gaccctgccgtgtaccagc-3' (SEQ ID NO: 18).

The hydrogel beads can be emulsified using the agitation method, and subject to PCR (FIGS. 5B and 5C, arrow (5)). The TRA and TRB PCR products have overlapping sequence and can be fused using the method described in Example 1 (FIG. 5C). The fusion product represents a library of fused bipartite immunoreceptor polynucleotides.

Figure 6A:
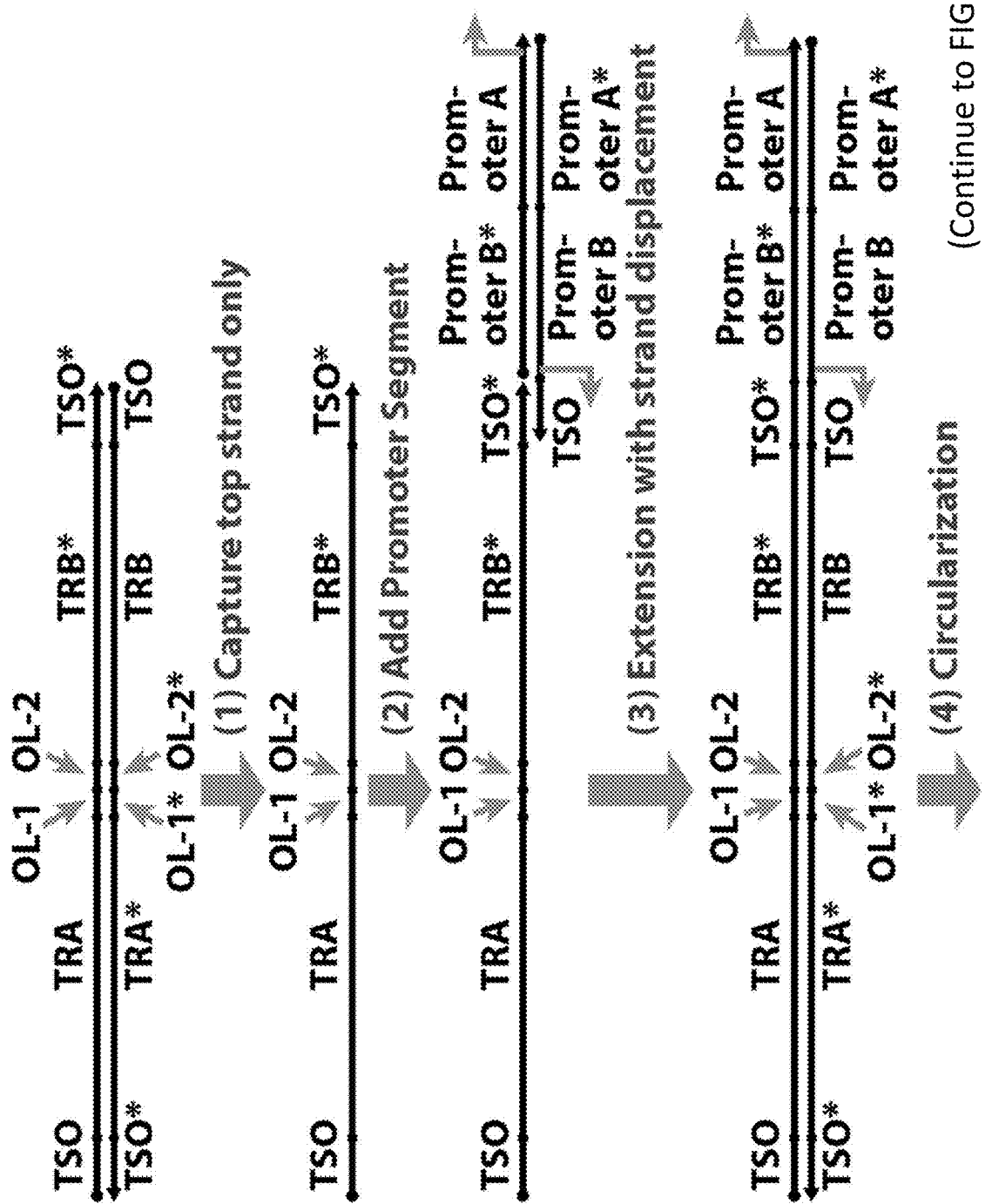
FIG. 6A depicts an example method to convert tail-to-tail fused bipartite immunoreceptor polynucleotides to immunoreceptor-expressing vectors with bidirectional promoters.
Figure 6B:
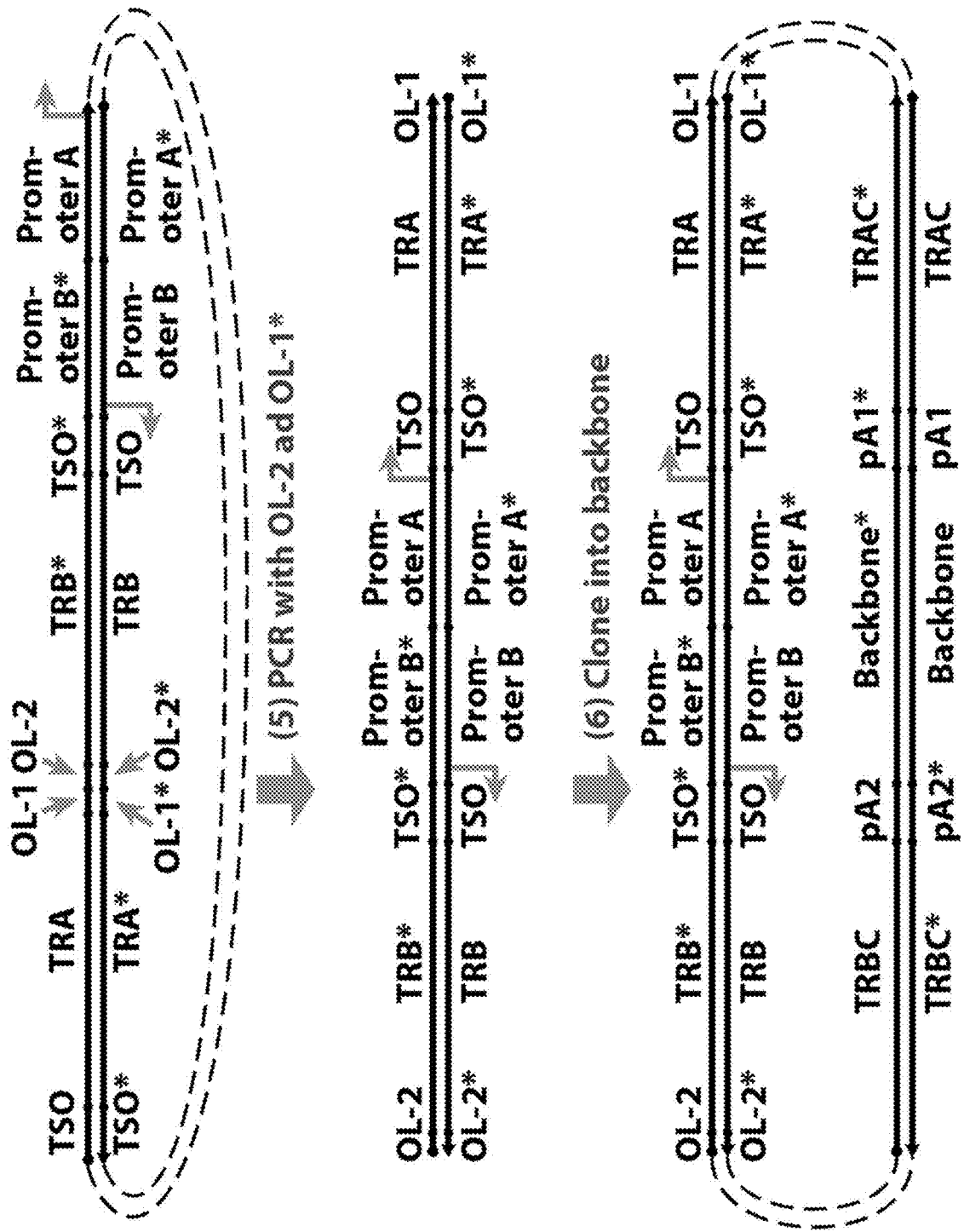
FIG. 6B depicts an example method to convert tail-to-tail fused bipartite immunoreceptor polynucleotides to immunoreceptor-expressing vectors with bidirectional promoters.

Example 3: Converting Tail-to-Tail Fused Bipartite Immunoreceptor Polynucleotides to Immunoreceptor-Expressing Vectors with Bidirectional Promoters Tail-to-tail fused bipartite immunoreceptor polynucleotides obtained from Example 1 may only contain partial C region sequences. The rest of C region sequences, along with promoters may be added to form full expression cassettes in expression vectors. FIGS. 6A and 6B outline an example strategy to achieve this. First, the top strand can be selectively captured and released (FIG. 6A, arrow (1)). This can be done using a capture oligonucleotide that specifically recognizes a conserved sequence the top strand (e.g., [OL-1|OL-2}). Next, a linear DNA construct (here named Promoter Segment) comprising two human promoters facing the opposite direction can be fused with the captured top strand (FIG. 6A, arrows (2) and (3)). To facilitate the fusion, the bottom strand of the Promoter Segment (as shown in FIG. 6A) may comprise a single-stranded region with the sequence [TSO} to hybridize to the captured top strand. The single-stranded region can be created by USER digestion. To do this, the forward primer used to amplify the Promoter Segment can have a few (e.g., 1 to 5) deoxyuridine modifications, and the PCR product can be treated with the USER enzyme mix. To obtain dsDNA (FIG. 6A, arrow (3)), DNA polymerase with strong strand-displacement activity (e.g., phi 29, Bst) can be used. Alternatively, a ligase can be used to seal the top strand.

This fused product may be further amplified by PCR. To ensure the forward primer (essentially having the sequence of [TSO} does not hybridize to the [TSO*} in the middle of the top strand (which we call an interfering primer-binding site), a blocker oligonucleotide can be used. This blocker oligonucleotide can have the sequence [PB3|TSO}, where the [PB3} has the sequence of the last 10 to 20 bases of [Promoter B}. As a result the blocker oligonucleotide may have a substantially higher Tm than the forward primer. In the PCR reaction, the blocker oligonucleotide can be used at a concentration lower than the concentration of the forward primer. A two-step annealing may be applied in the thermocycling program. In each PCR cycle, after the denaturation step, a first annealing step at a relatively high temperature (e.g., 68° C.) can be used to ensure the blocker hybridizes to the top strand, but the forward primer does not hydridize to either the top or the bottom strand. Next, a second annealing step at a relatively low temperature (e.g, 58° C.) can be used to ensure the forward primer binds the bottom strand. Since the [TSO*} sequence on the top strand is already occupied by the blocker during the first annealing step, the forward primer may not bind this sequence effectively. Although at the second annealing step the blocker may also bind the [TSO*} (the forward primer-binding site) on the bottom strand, since the forward primer has a higher concentration, it may bind the [TSO*} site on the bottom strand more efficiently than the blocker.

Next, the amplification product may be circularized using known methods (FIG. 6A, arrow (4)). The circularized product can be linearized by essentially cutting between [OL-1} and [OL-2}. This can be simply achieved by PCR amplification using a forward primer essentially having the sequence [OL-2} and a reverse primer essentially having the sequence [OL-1*}. Both primers may be extended at the 3' end to reach proper Tm for PCR. In the linearized product, the a first promoter of the Promoter Segment (e.g., Promoter A) is positioned and oriented to transcribe TRA, and the second promoter of the Promoter Segment (e.g., Promoter B) is positioned and oriented to transcribe TRB.

The linearized product may be cloned into a plasmid backbone using existing methods (FIG. 6B, arrow (6)). The linearized product may not contain full sequence of the C region of either TRA or TRB. These constant sequences (complete or partial sequences of TRAC and TRBC) may be included in the plasmid backbone, so that the translated products of TRA and TRB are functional. The plasmid backbone may have terminator sequences for TRA (e.g., pA1) and TRB (e.g., pA2). The plasmid backbone may also have other elements for the propagation and function of the vector such as replication origin, selection marker (e.g., antibiotic resistance gene), LTRs for retro-viral vector function, or sequence elements for transposase-dependent insertion.

Example 4: Converting Tail-to-Tail Fused Bipartite Immunoreceptor Polynucleotides to Bicistronic Immunoreceptor-Expressing Vectors In the TCR-expressing vector, the coding sequence of TRA and TRB may be fused in head-to-tail orientation in an in-frame fashion, so that one promoter can be used to transcribe an mRNA encoding both TRA and TRB, and that the ribosome may transcribe TRA and TRB as either a continuous polypeptide, or, if a 'self-cleaving peptide' such as P2A is used, two polypeptides. A linker sequence between TRA and TRB can be inserted.

In this example we show how to convert tail-to-tail fused TCR genes generated using the method described in FIGS. 4A and 4B and Example 1 into a TCR-expressing vectors where the TRA and TRB is fused in the head-to-tail orientation, in-frame, and with a linker between TRA and TRB. The strategy is illustrated in FIGS. 7A-7D.

Figure 7A:
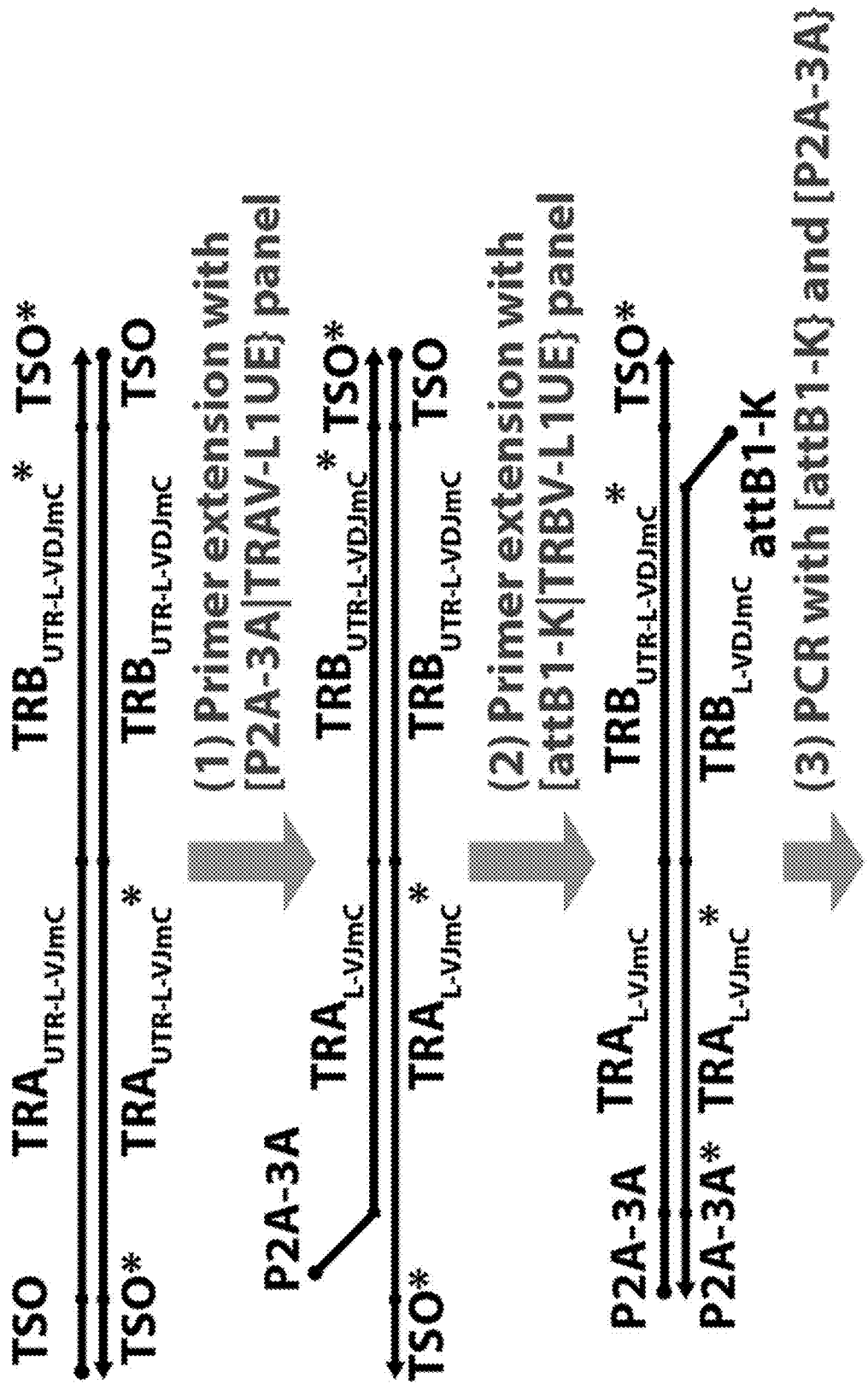
FIG. 7A depicts an example method to convert tail-to-tail fused bipartite immunoreceptor polynucleotides to bicistronic immunoreceptor-expressing vectors.

In this example, the start site of TRA and TRB can be controlled. In this example, a more precise naming system to describe sequences is used. The top of FIG. 7A shows the fused product generated using the method described in FIGS. 4A and 4B and Example 1. The TRA sequence may contain 5' UTR, L domain of the TRA, rearranged VDJ sequences of TRA, and a short sequence at 5' end of the C region (which we call mini-C or mC) of TRA. Thus, the TRA sequence is called $TRA_{UTR-L-VDJmC}$. Similarly, the TRB sequence is called $TRB_{UTR-L-VDJmC}$.

The [P2A-3A|TRAV-L1UE} panel described in Example 2 can be used to 'trim' the top strand so that (1) the TRA sequence may precisely start from the start codon of the L1 region of TRA, and (2) a common sequence [P2A-3A} is introduced facilitating further manipulation such as amplification (FIG. 7A, arrow (1)). The reaction can be similar to the SSS reaction described in Example 2, except that the tail-to-tail fused TCR genes are used as templates. In a similar fashion, the [attB1-K|TRBV-L1UE} panel can be used to trim the bottom strand (FIG. 7A, arrow (2)). Further PCR amplification using primers having sequences [P2A-3A} and [attB1-K} can yield blunt-ended dsDNA (FIG. 7A, arrow (3)). Note that in this example, after trimming, [$TRA_{UTR-L-VDJmC}$} becomes [$TRA_{L-VDJmC}$} because the UTR sequence has been trimmed away; same for TRB.

Then the PCR product can be fused with another dsDNA called ds[Lox66|P2A-5} (see description later) downstream of [$TRB_L$—$V_{DJ}$mC*} (FIG. 7B, arrow (4)). This can be achieved using a process similar to that described for arrows (2)-(3) of FIG. 6A.

Figure 7B:
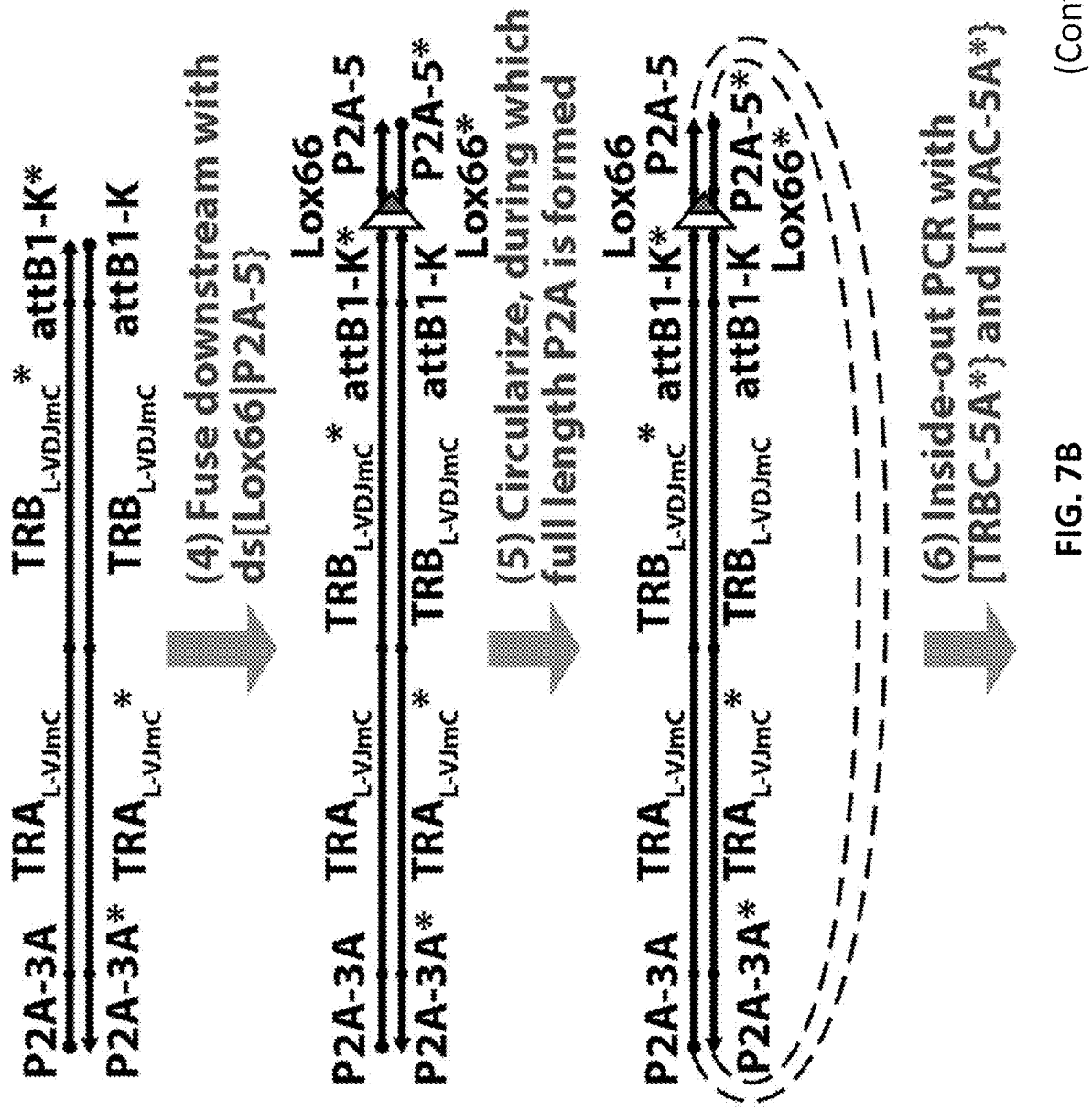
FIG. 7B depicts an example method to convert tail-to-tail fused bipartite immunoreceptor polynucleotides to bicistronic immunoreceptor-expressing vectors.

Next, fused dsDNA can be circularized (FIG. 7B, arrow (5)) using a process similar to that described for arrow (4) of FIG. 6A. After circularization, [P2A-5} can be ligated to [P2A-3A} to form [P2A-5|P2A-3A}, which may have the exact sequence of [P2A}. The circularized DNA can be linearized at a break point between TRA and TRB (FIG. 7B, arrow (6)). This can be achieved, for example, by PCR-amplifying the circularized DNA using primers [TRAC-5A*} and [TRBC-5A*}, as described herein. This linearized product can be fused ds[Lox71*|FF*|TRBC-3*} upstream of [$TRB_L$—$V_{DJ}$mC} (FIG. 7C, arrow (7)). Here, TRBC-3 is the sequence of TRBC (note: for human this can be either TRBC1 or TRBC2) downstream of [TRBC-5A}, and FF encodes a polypeptide sequence that is a furin-cleavage site followed by a flexible linker. Lox66 and Lox71 are a pair of Cre-recombination sites that undergo irreversible recombination. Since [$TRB_{L-VDJmC}$|TRBC-3} is the full length sequence of TRB, we can rewrite [$TRB_{L-VDJmC}$|TRBC-3} as [$TRB_{L-VDJ}$| $TRB_C$}, where [$TRB_{L-VDJ}$} is the sequence of TRB from the start codon on the L region till the end of the rearranged VDJ segment, and $TRB_C$ is the sequence of TRBC. (See the vertical "=" sign in FIG. 7C).

Figure 7C:
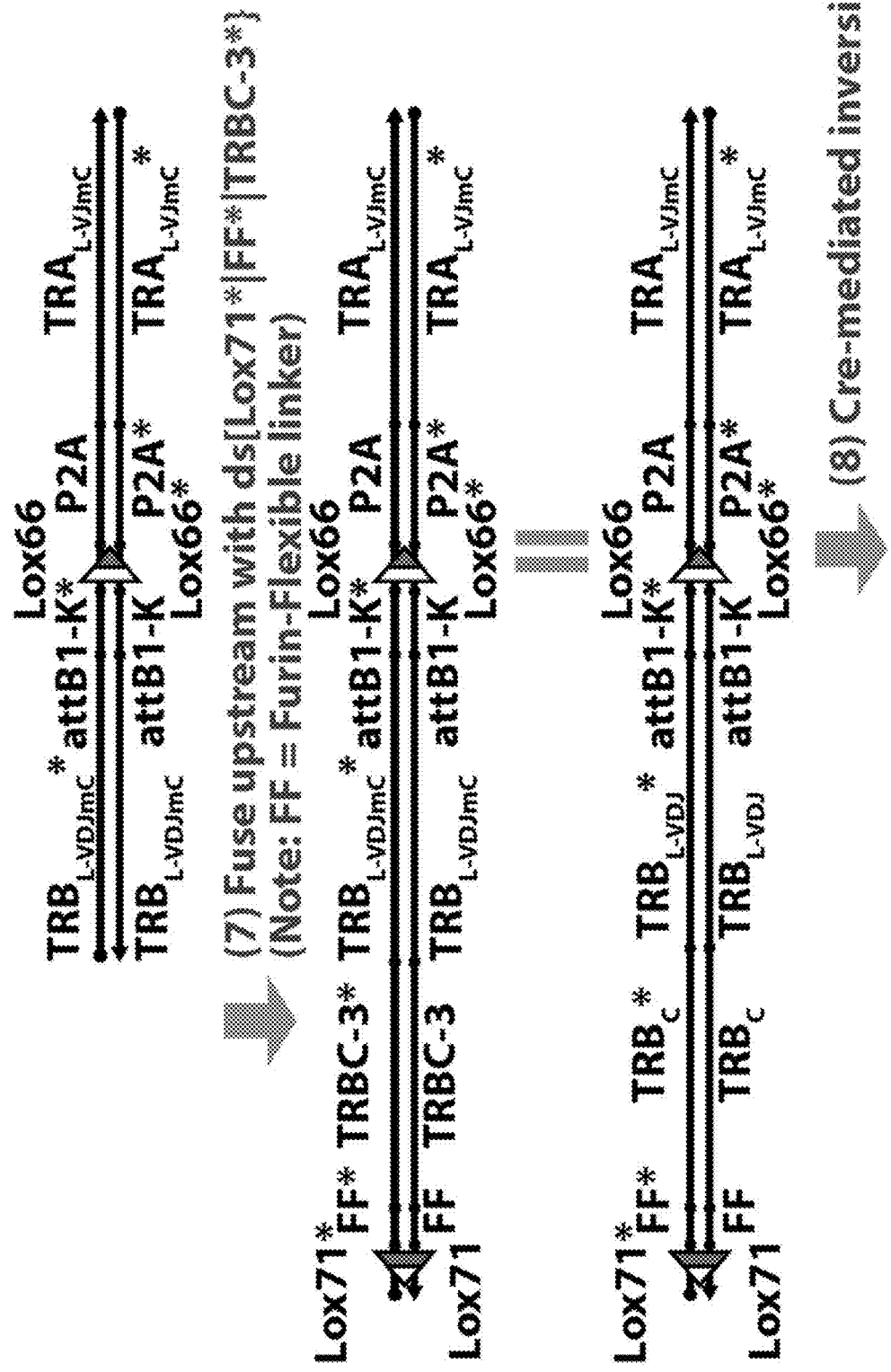
FIG. 7C depicts an example method to convert tail-to-tail fused bipartite immunoreceptor polynucleotides to bicistronic immunoreceptor-expressing vectors.

Treating the fused product above with Cre recombinase may cause the inversion the DNA sequence between Lox66 and Lox71, and result in the formation of double-mutant Lox site [dmLox] and a [LoxP] site (FIG. 7C, arrow (8)). The sequences of [Lox66} and [Lox71} are designed such that after conversion, FF, dmLox, and P2A are connected in-frame without stop codon (see nucleotide and amino acid sequence after arrow (8) in FIG. 7D).

Figure 7D:
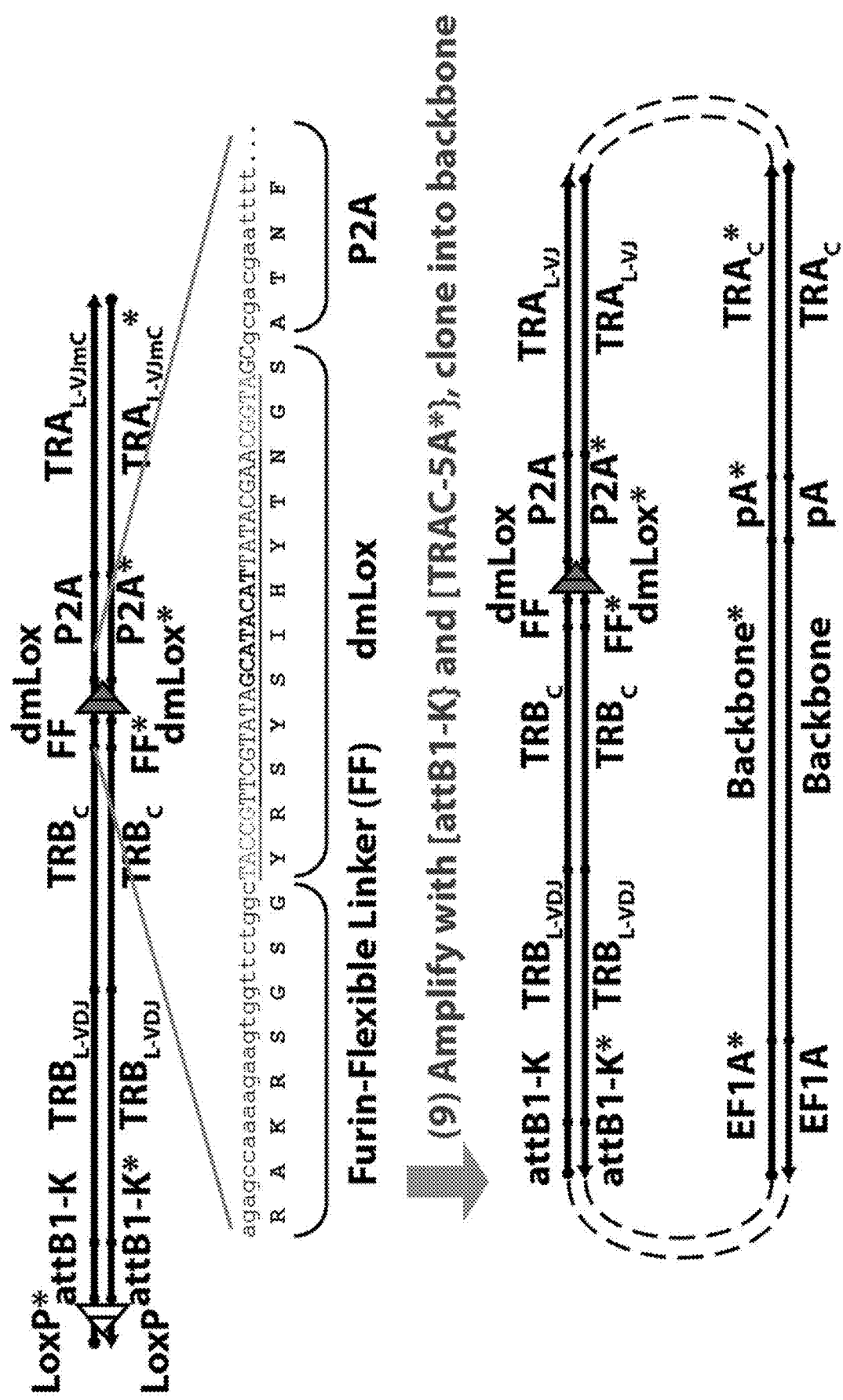
FIG. 7D depicts an example method to convert tail-to-tail fused bipartite immunoreceptor polynucleotides to bicistronic immunoreceptor-expressing vectors (SEQ ID NO: 19 and 20, respectively, in order of appearance).

This inverted product may be PCR-amplified with [attB1-K} and [TRAC-5A*}, and the PCR product may be cloned into a vector backbone (FIG. 7D, arrow (9)). The backbone may have enough sequence to complete TRAC, and may also have a promoter, a terminator, and other necessary elements for the function of the vector as described above.

Figure 8A:
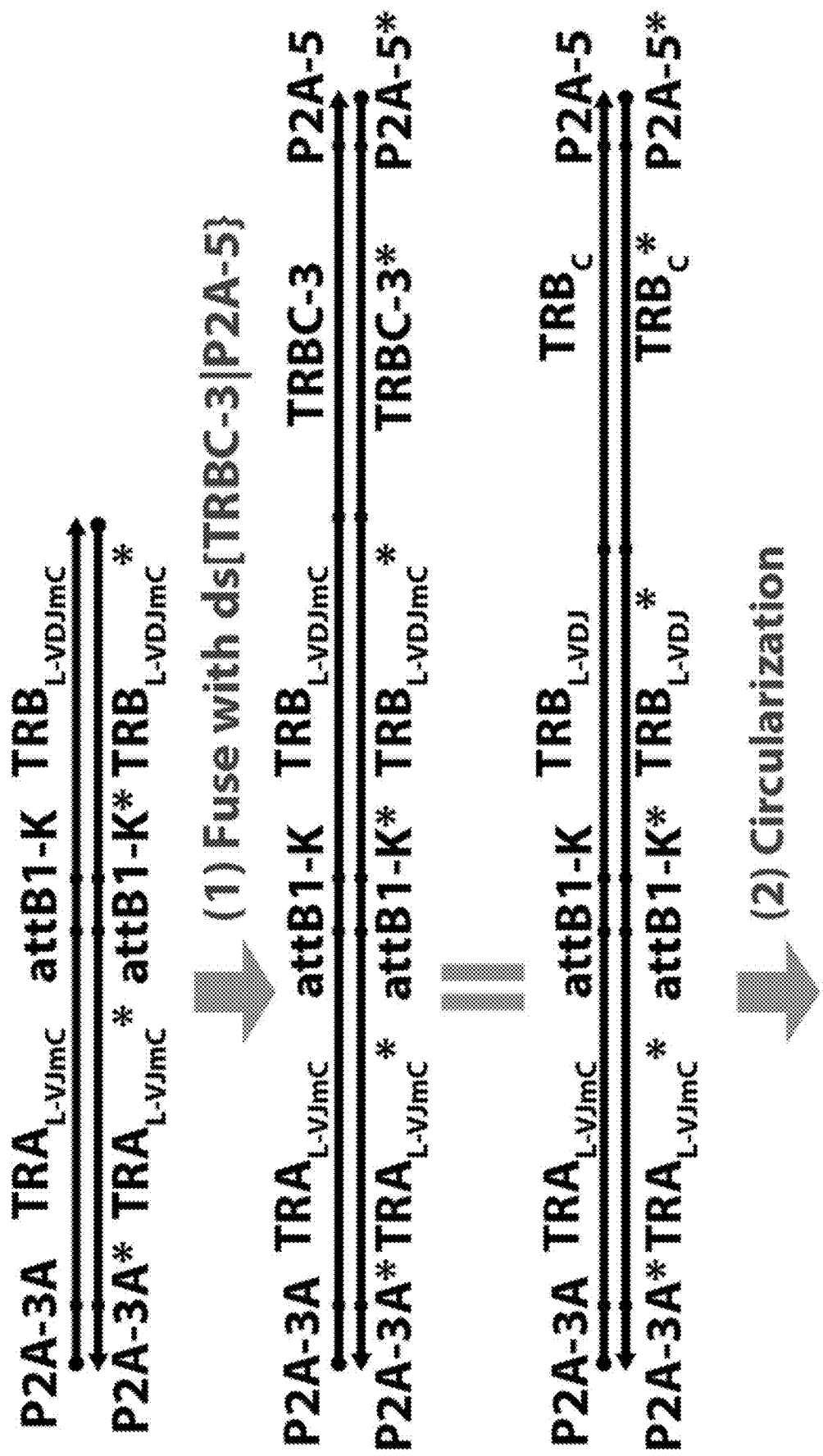
FIG. 8A depicts an example method to convert head-to-tail fused bipartite immunoreceptor polynucleotides to bicistronic immunoreceptor-expressing vectors.
Figure 8B:
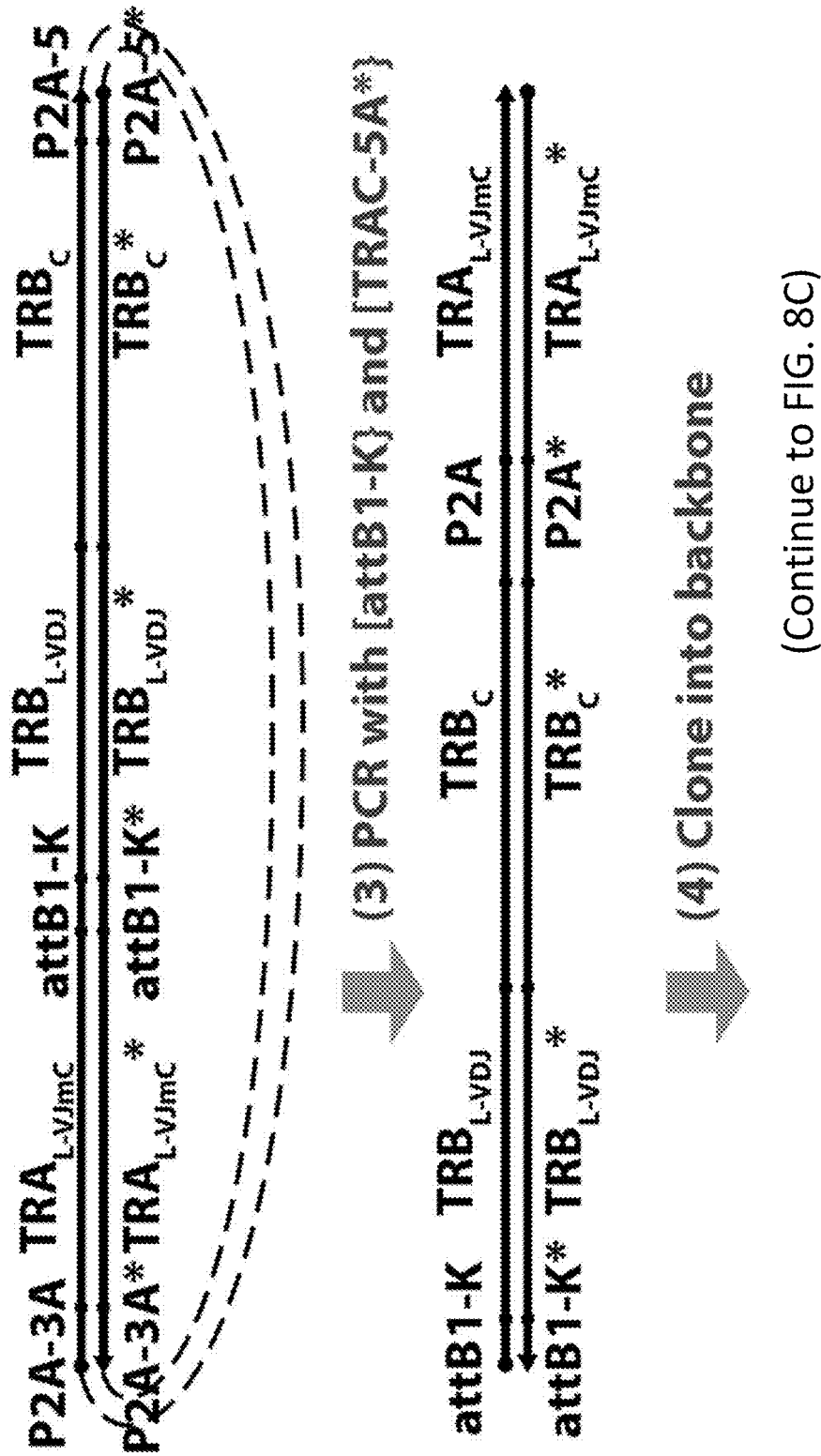
FIG. 8B depicts an example method to convert head-to-tail fused bipartite immunoreceptor polynucleotides to bicistronic immunoreceptor-expressing vectors.
Figure 8C:
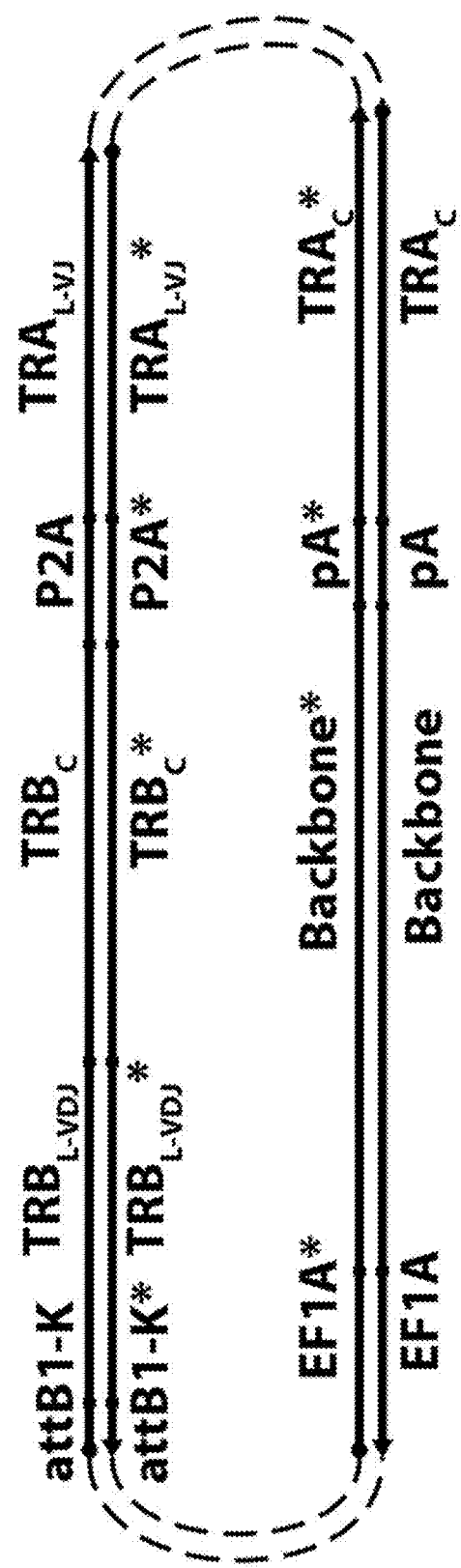
FIG. 8C depicts an example method to convert head-to-tail fused bipartite immunoreceptor polynucleotides to bicistronic immunoreceptor-expressing vectors.

Example 5: Converting Head-to-Tail Fused Bipartite Immunoreceptor Polynucleotides to Bicistronic Immunoreceptor-Expressing Vectors The head-to-tail fused TCR genes generated by the method described in Example 2, whose sequence construct is described in FIG. 8A, can be converted to TCR-expressing vectors using a similar strategy as the previous examples. The naming convention is the same as Example 4. First, the fused TCR gene can be fused with ds[TRBC-3|P2A-5} (FIG. 8A, arrow (1)) using conventional overlapping PCR or other methods described for arrow (2)-(3) of FIG. 6A. This fusion creates the complete $TRB_C$ sequence downstream of $[TRB_{L-VDJ}]$ (the vertical "=" sign in FIG. 8A). This fused product can be circularized (FIG. 8A, arrow (2)) as described before, and linearized by PCR amplification using primers [attB1-K} and [TRAC-5A*} (FIG. 8B, arrow (3)). The linearization product can be cloned into a vector backbone as described before, to complete $TRA_C$ sequence and bring in other necessary elements (FIG. 8C).

Example 6: Paired TCR Cloning Using OE-PCR

Examples 1 and 2 describe methods to fuse pre-amplified TRA and TRB using USER-mediated sticky-end generation and ligation. Alternatively, pre-amplified TRA and TRB may be fused using overlap extension PCR (OE-PCR). In some cases, removing inner primers (e.g., primers 1R and 2R in Example 1, or primers ht1R and ht2F in Example 2) may facilitate the fusion. Removal of inner primers can be achieved as previously described. In other cases, OE-PCR can be performed without removing the inner primers. In these cases, the pre-amplification products do not need to be diffusion-restricted. Accordingly, the outer primers (e.g., pTSO in Example 1, or [Adpt1} and [TRBC-5A*} in Example 2 do not need to be linked to the ARS.

Figure 9A:
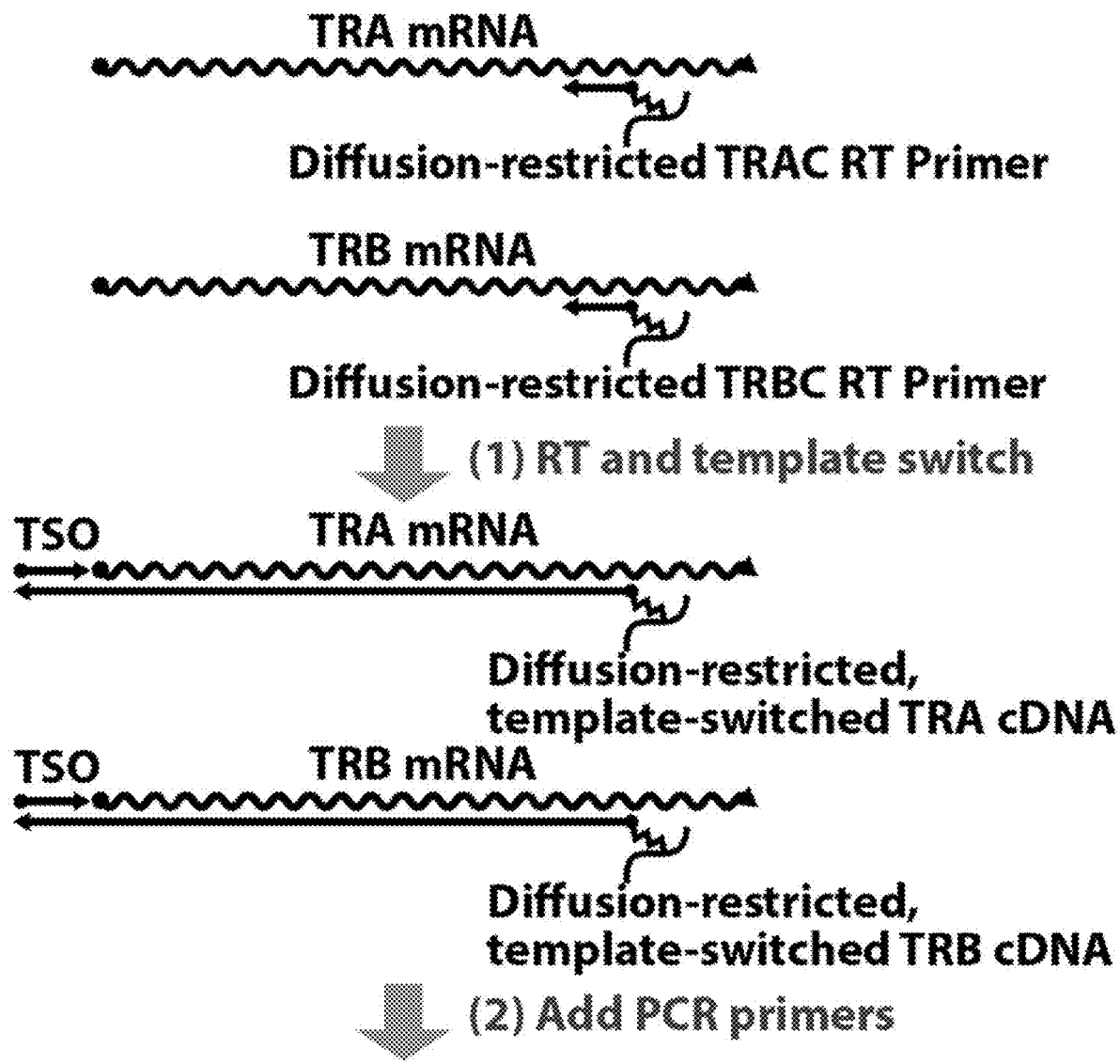
FIG. 9A depicts an example strategy to fuse TRA and TRB in a tail-to-tail orientation.
Figure 9B:
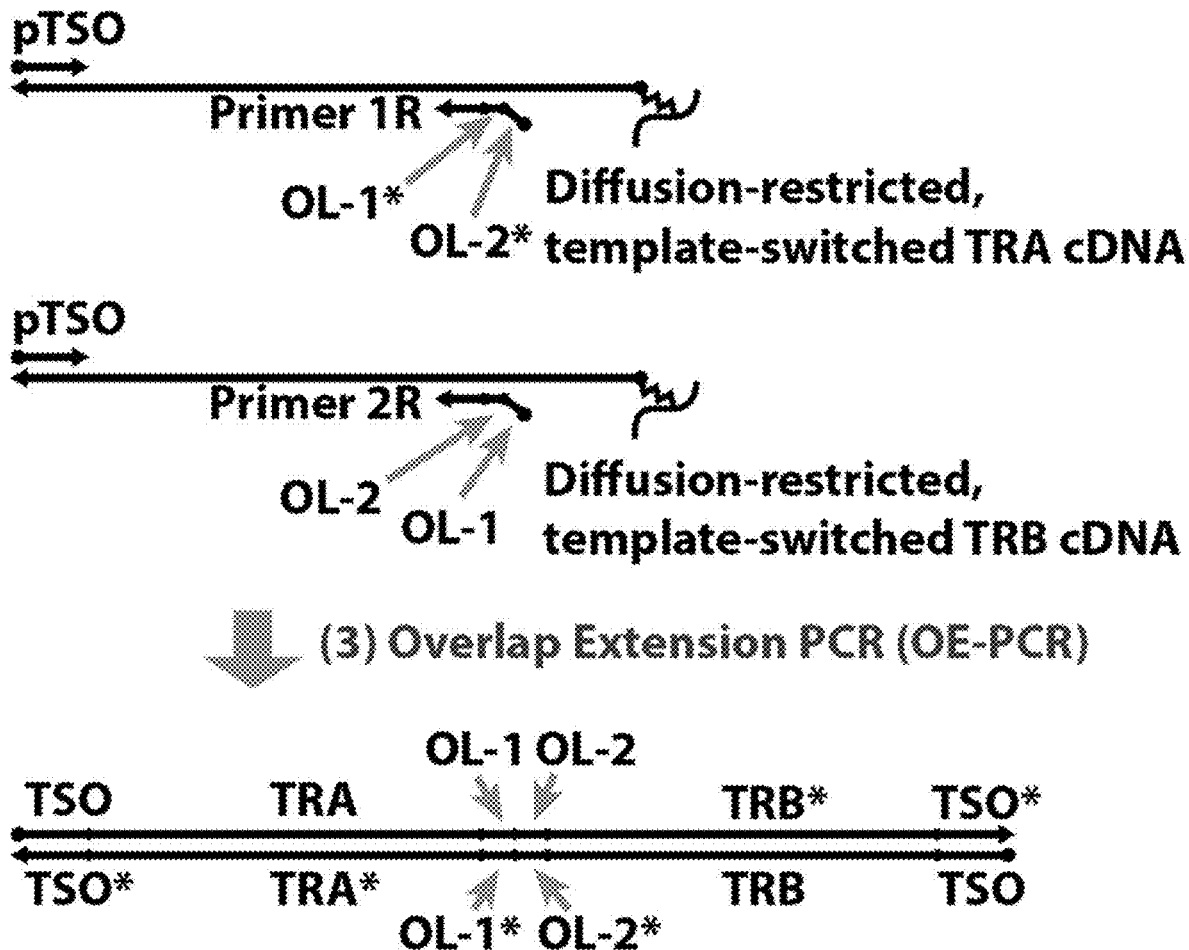
FIG. 9B depicts an example strategy to fuse TRA and TRB in a tail-to-tail orientation.

FIGS. 9A and 9B describe a method to fuse TRA and TRB in tail-to-tail orientation using OE-PCR. The Steps 1 to 3 are identical to Example 1 (FIG. 9A, arrow (1)). In Step 4, reagent exchange can be applied to deliver high concentration of pTSO (e.g., 400 nM), low concentration of primers 1R and 2R (e.g., 80 nM each), thermostable DNA polymerase, and PCR buffer to the agarose beads (FIG. 9A, arrow (2)). The agarose beads can be re-emulsified with detergent-containing fluorocarbon oil using the agitation method (FIG. 9B, arrow (3)). Then emulsion PCR can be carried out using an OE-PCR thermocycling program. The thermocycling program can have 3 stages. The goal of the first stage is to amplify TRA and TRB. The goal of the second stage is to generate ssDNA products having the sense sequences of TRA and TRB as well as the 3' end overlap region using pTSO as the primer. The goal of the third stage is to fuse the ssDNS products.

Figure 10A:
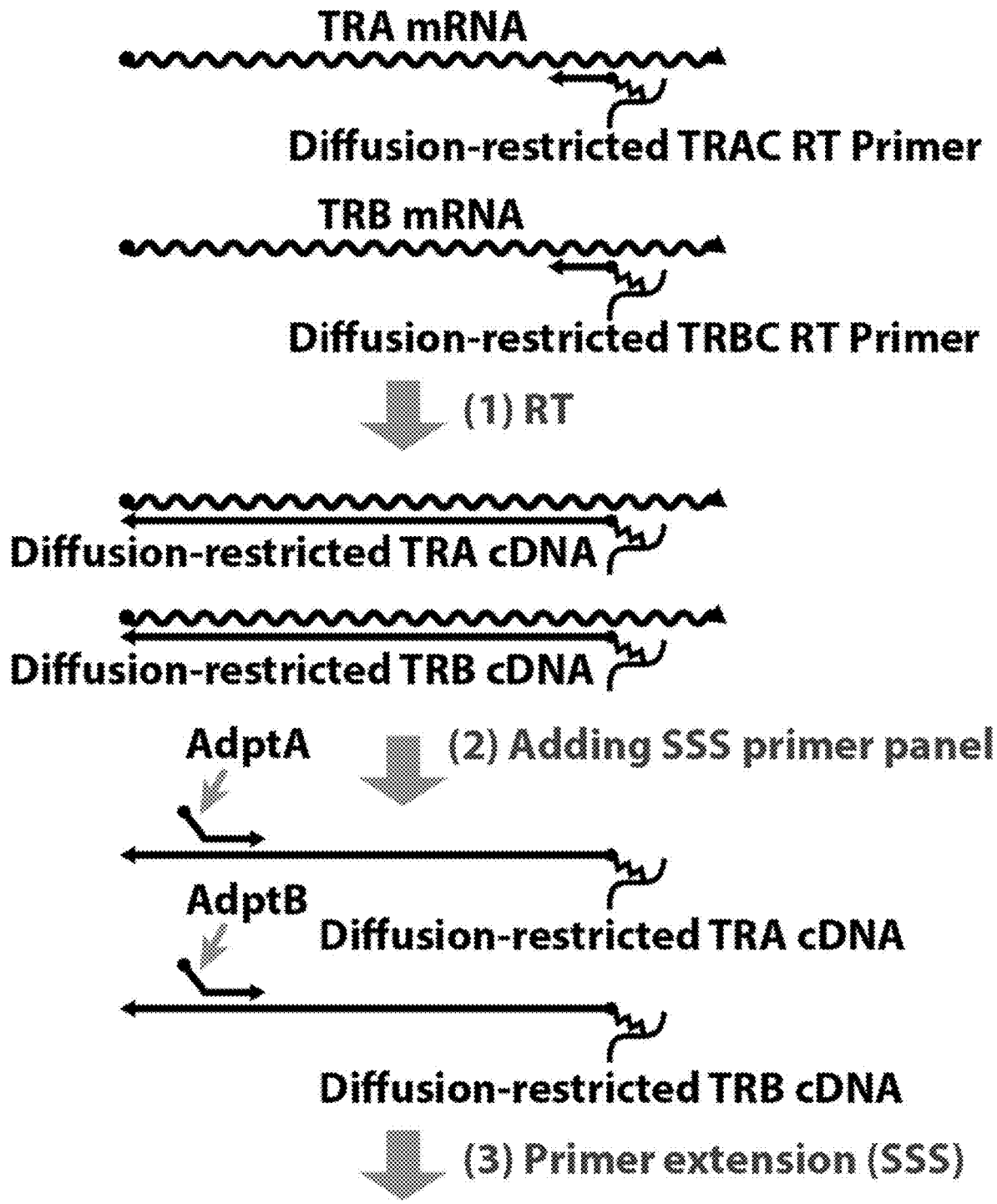
FIG. 10A depicts an example strategy to fuse TRA and TRB in head-to-tail orientation.
Figure 10B:
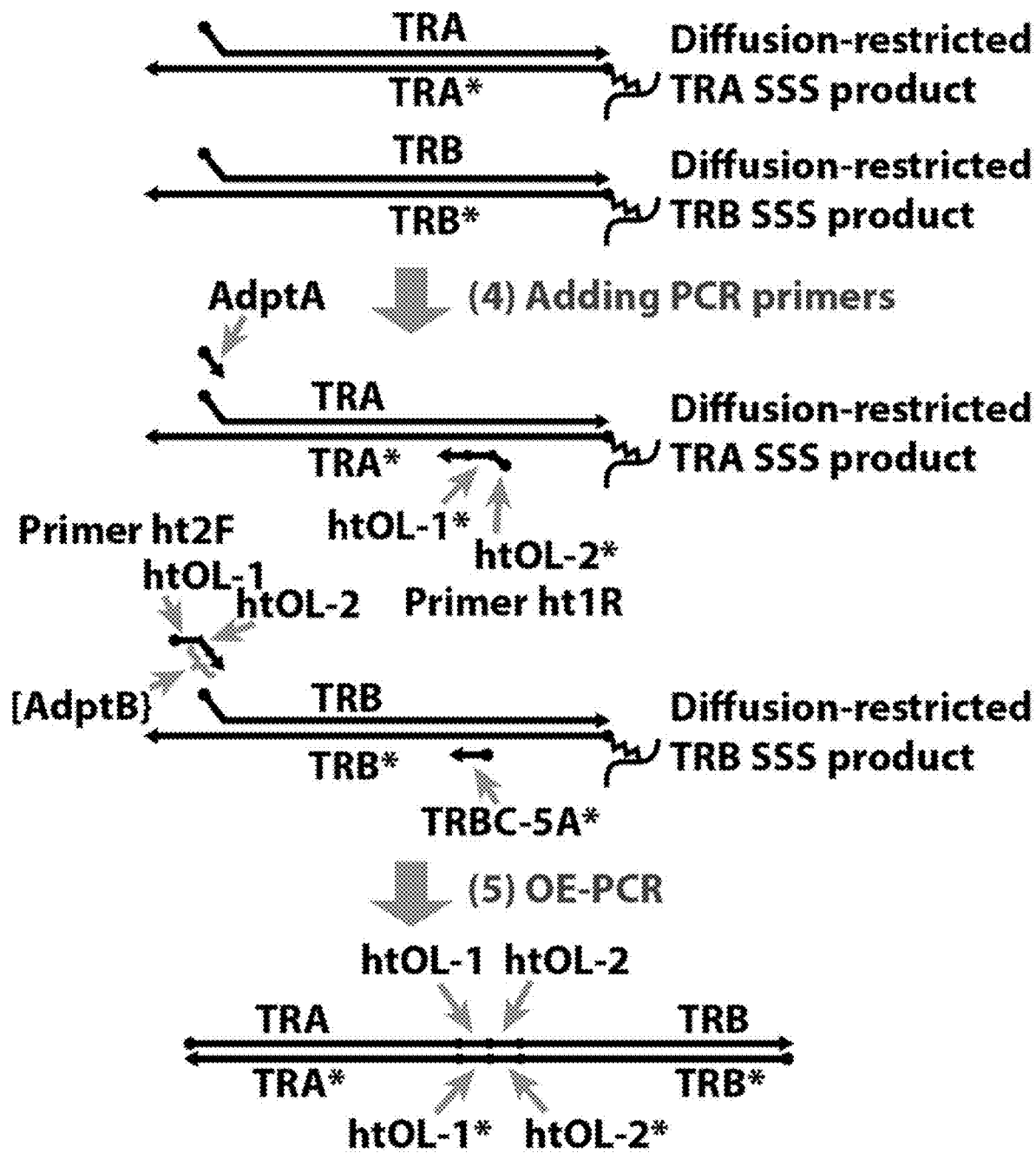
FIG. 10B depicts an example strategy to fuse TRA and TRB in head-to-tail orientation.

FIGS. 10A and 10B describes a method to fuse TRA and TRB in head-to-tail orientation using OE-PCR. The Steps 1 to 4 are identical to Example 2 (FIG. 10A, arrows (1) to (3)). In Step 5, reagent exchange can be applied to deliver high concentration of outer primers [AdptA} and [TRBC-5A*} (e.g., 400 nM each), low concentration of primers 1R and 2R (e.g., 80 nM each), thermostable DNA polymerase, and PCR buffer to the agarose beads (FIG. 10B, arrow (4)). Then OE-PCR can be performed as described above (FIG. 10B, arrow (5)).

Example 7: Primer-Modified Agarose

Two example methods to prepare primer-modified agarose are provided herein. In the first method, solutions containing about 4% agarose and 100 to 500 mM of sodium periodate ($NaIO^4$) was prepared at 70° C. After a brief incubation at 70° C., the solutions were emulsified with a surfactant-containing oil using by vortexing. Virtually any surfactant-containing oil used in the art to make stable water-in-oil emulsion can be used here. The emulsions were incubated on ice for about 20 min and then demulsified using 20% to 100% PFO. The resultant agarose beads suspensions were washed in water, packed by centrifugation and removal of supernatant, melted again and mixed with equal volume of solution containing amine-labeled RT primers in the presence of 0.1 to 1 mM sodium cyanoborohydride ($NaCNBH_3$). After overnight incubation at 37° C., the solutions were emulsified, incubated on ice, demulsified and washed, as described above, resulting in suspensions of 2% agarose beads with covalently attached RT primers. The concentration of immobilized RT primers can be measured by staining with a DNA-binding dye or fluorescent-labeled oligonucleotide complementary to the RT primer. Agarose beads with immobilized RT primers at 100 nM to 10 µM were obtained.

In the second method, RT primers were covalently linked to linear polyacrylamide. To do this, amine-modified linear polyacrylamide was first prepared by copolymerizing acrylamide and N-(3-Aminopropyl)methacrylamide hydrochloride, and then reacted with NHS-azide and DBCO-modified primer. The primer-modified linear polyacrylamide was mixed with 2% agarose, emulsified, incubated on ice, and demulsified, and washed as described above.

There are many sources of agarose under many brand names. The gelling temperatures may vary and modification may affect the gelling temperature. As a quality control step, the resulting primer-modified agarose can be controlled to stay molten at about 37° C., and stay gelled at room temperature.

Example 8: Physically Linking TCR Alpha and Beta Chains in Head-to-Tail Fashion from Peripheral T Cells and NGS-Based Characterization Peripheral T cells from a healthy donor were used to prepare DNA libraries of physically linked (in head-to-tail orientation), natively paired TCRs (i.e., fused TCR polynucleotides). In a typical run, a cell suspension (CS) was created by mixing the following components: peripheral T cells (typical final concentration 1000 to 5000 cells per µL), 1% primer-modified agarose comprising two RT primers, one targeting human TRAC mRNA and the other targeting human TRBC mRNA (in this example: the TRBC-targeting RT primer does not distinguish TRBC1 and TRBC2), and PBS.

A solution called Reagent Complete Mix (RCM) comprising the following components was prepared: 1% agarose, SSIV reaction buffer (prepared according to the manufacture's unit-definition test), Maxima H Minus reverse transcriptase (final concentration: 5 to 50 U/μL), Q5 DNA polymerase (final concentration: 0.02 to 0.2 U/μL), SYBR Gold (final concentration: 1× as defined by manufacture), dNTPs (0.1 to 1 mM each), RNaseOUT (final concentration: 10×-diluted from stock), [AdptA|CDS$_{TRA}$] panel (final concentration: 1 to 5 nM each), and [AdptB|CDS$_{TRB}$] panel (final concentration: 1 to 5 nM each).

When preparing the [AdptA|CDS$_{TRA}$] and [AdptB|CDS$_{TRB}$] panels, each primer may first be annealed with the BlockerA/B and an additional blocker called V-specific blocker (VSB). VSB may be complementary to the 3' portion of the corresponding CDS$_{TR}$A or CDS$_{TRB}$ region but 10- to 15-nt shorter than the corresponding CDS$_{TRA}$ or CDS$_{TRB}$ region. In other words, the 3' end of each [AdptA|CDS$_{TRA}$] and [AdptB|CDS$_{TRB}$] may form a blunt end with VSB. The 3' VSB may also be modified to make the VSB non-extendable.

Figure 11B:
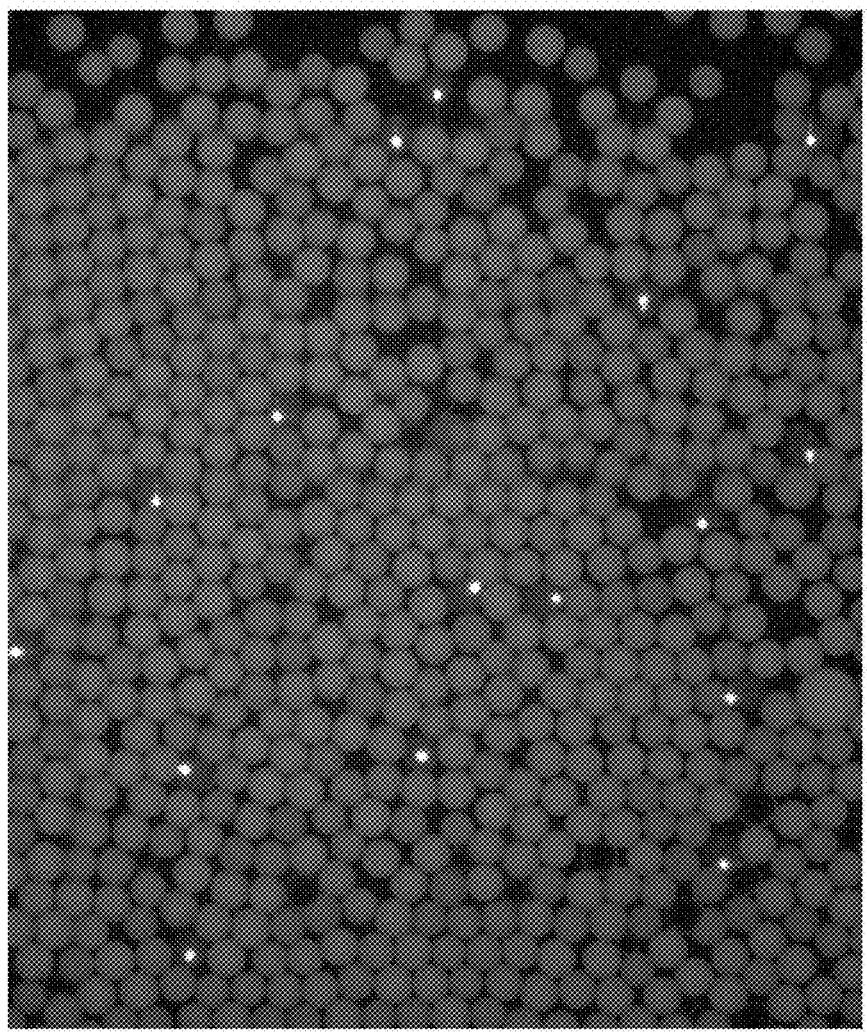
FIG. 11B depicts an example of formed droplets. The bright spots indicate cell nuclei stained by a dye and the larger spheres indicate agarose beads.
Figure 11A:
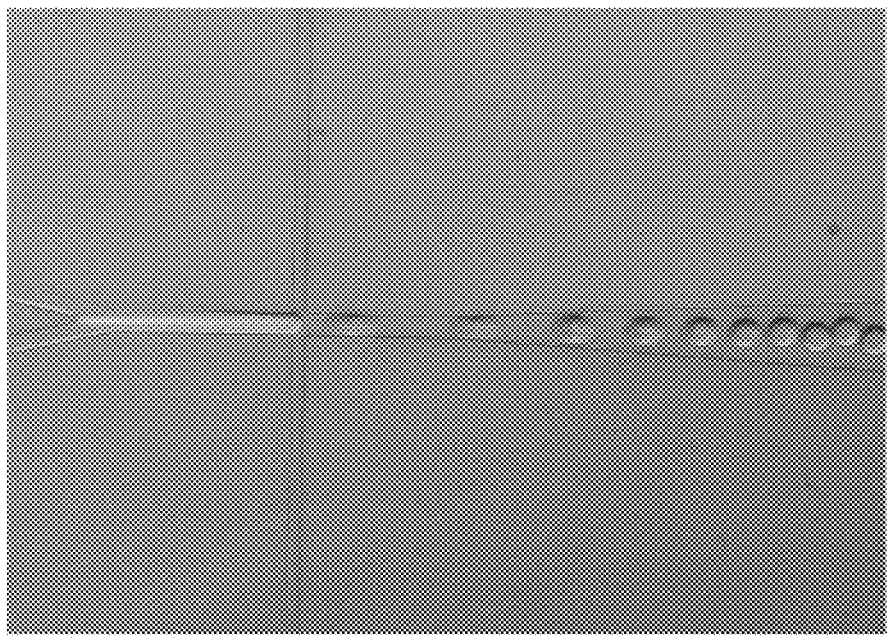
FIG. 11A depicts an example of droplet formation where the aqueous phase comprises cells and primer-modified agarose.

In a typical run, the RCM and CS were injected into the two imports of a standard 2-inlet droplet-generation microfluidics chip (e.g., the hydrogel bead generation device of Zilionis et al., 2017 Nature Protocol doi:10.1038/nprot.2016.154) at equal flow rate to produce droplets with diameter around 30 to 70 μm. A thermostable surfactant-containing fluorocarbon oil (e.g., RAN 008-FluoroSurfactant-2wtF, RAN 008-FluoroSurfactant-5wtH, or Bio-Rad droplet oil) can be used as the oil phase. FIG. 11A shows a snapshot of the droplet generation process. The resulting emulsion was incubated at 50° C. for 1 to 2 hr. During the incubation a small fraction of the emulsion can be examined by fluorescence microscopy since SYBR Gold can stain the primers and cell nuclei. An example image is provided in FIG. 11B. The emulsion was then incubated at 93° C. for 2 min, 65° C. for 20 min, and 72° C. for 1 min. Five to eight cycles of 93° C. for 30 s, 60° C. for 1 min, 72° C. for 1 min, 80° C. for 1 min may be added.

Figure 12:
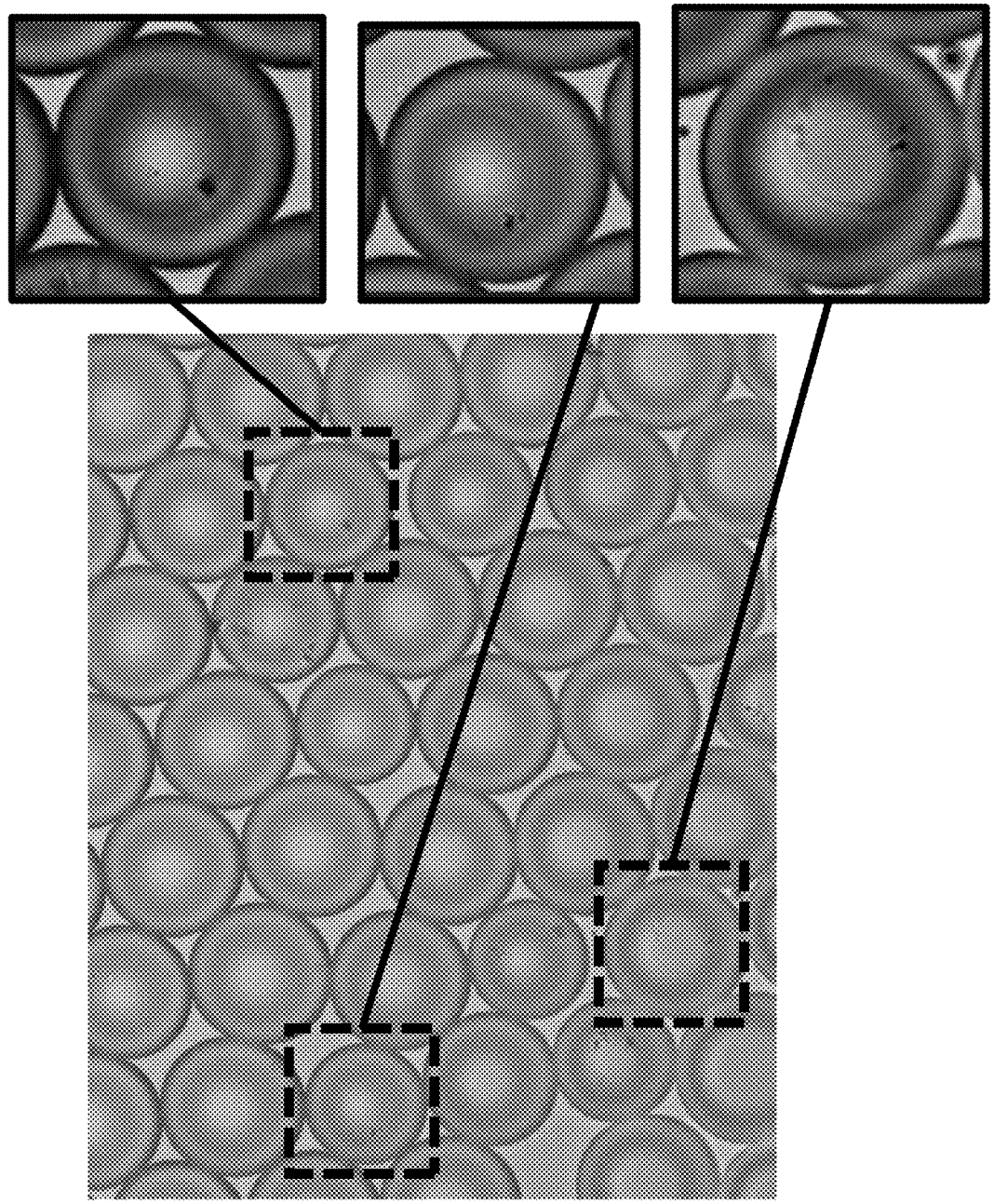
FIG. 12 depicts an example image of the emulsion for OE-PCR as described in Example 8. Zoom-in views depict some droplets containing an agarose bead entrapping adaptor-containing TCR alpha chain and beta chain polynucleotides.

The emulsion was then cooled to form agarose gel beads and demulsified by incubating with sufficient amount of 20% PFO. The agarose gel beads were washed in Low-EDTA TE, and then mixed with primers AdptA, ht1R, ht2F and TRBC-5A* (as described in FIGS. 10A and 10B) as well as hot-start KOD, commercial KOD reaction buffer, and sufficient dNTPs to form Bead Suspension. The Bead Suspension was injected into an aqueous phase inlet of a DropSeq or inDrop chip (e.g., the cell encapsulation device of Zilionis et al., 2017 Nature Protocol doi:10.1038/nprot.2016.154). A carrier solution containing all the components of the Bead Suspension except beads was injected to other aqueous phase inlet(s). The flow rate of the Bead Suspension and the carrier solution was adjusted so that there is only 0 or 1 agarose bead in the majority of the droplets. The same surfactant-containing fluorocarbon oil as before was used here as the oil phase. FIG. 12 shows a microscopic image of a typical emulsion, with droplets containing the agarose beads highlighted.

Figure 13:
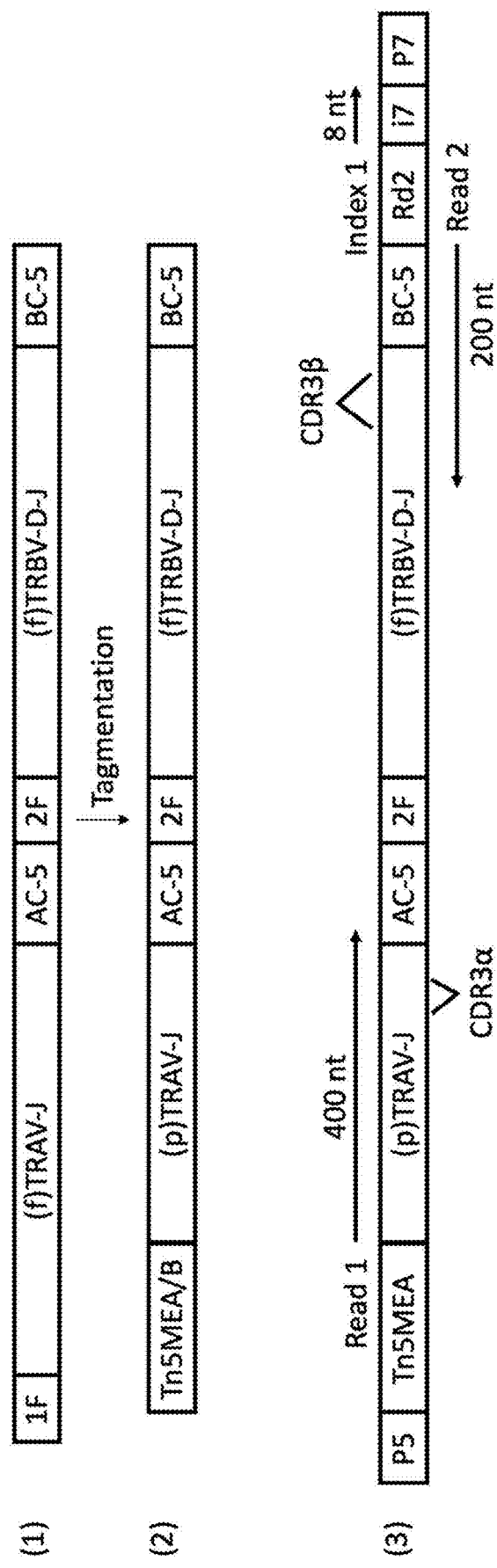
FIG. 13 depicts an example scheme for sequencing library construction and sequencing. As used in this figure, (p) means partial, (f) means full-length.

The emulsion was subject to the OE-PCR thermocycle program. An example OE-PCR thermocycle program is as follows: 93° C. for 2 min, 35 cycles of [93° C. for 15 s, 63° C. for 30 s, 70° C. for 1 min], and 70° C. for 3 min. The emulsion was then demulsified using 20% PFO, SPRI-purified, and further amplified using AdptA and a nested version of TRBC-5A*. The amplification product can be considered DNA libraries of physically linked (in head-to-tail orientation), natively paired TCRs. Each member of this library has the structure shown in FIG. 13-(1), where 1F and 2F are adaptor sequences AdptA and AdptB, respectively, and AC-5 and BC-5 are 5' segments of TRAC and TRBC, respectively. The amplification product was treated with Nextera XT kit lightly to remove part of the TRAV sequences (but not overly cut the PCR product, see FIG. 13-(2)) and then PCR amplified using the nested TRBC-5A* and another primers targeting the Nextera adaptor (Tn5MEA or Tn5MEB). The PCR product was resolved on agarose gel and DNA fragments with length between 650 bp and 800 bp were recovered analyzed using MiSeq (600-cycle kit) using the strategy shown in FIG. 13-(3).

With this fragmentation and size-selection strategy, a substantial fraction of the paired-end reads contain sufficient information to identify the TRAV, TRAJ, TRBV, TRBJ genes as well as the CDR3α and CDR3β sequences of the same physically linked molecule using the MiXCR software package. In a typical NGS run, the TCR alpha chain (TRA) sequences can be clustered into 1000 to 100,000 clones (depending on the input cell number and read depth). Similarly, the TCR beta chain (TRB) sequences can be clustered into 1000 to 100,000 clones. Note that only reads that are mapped to a TRA and a TRB clone were kept. The rest were disregarded.

Figure 14:
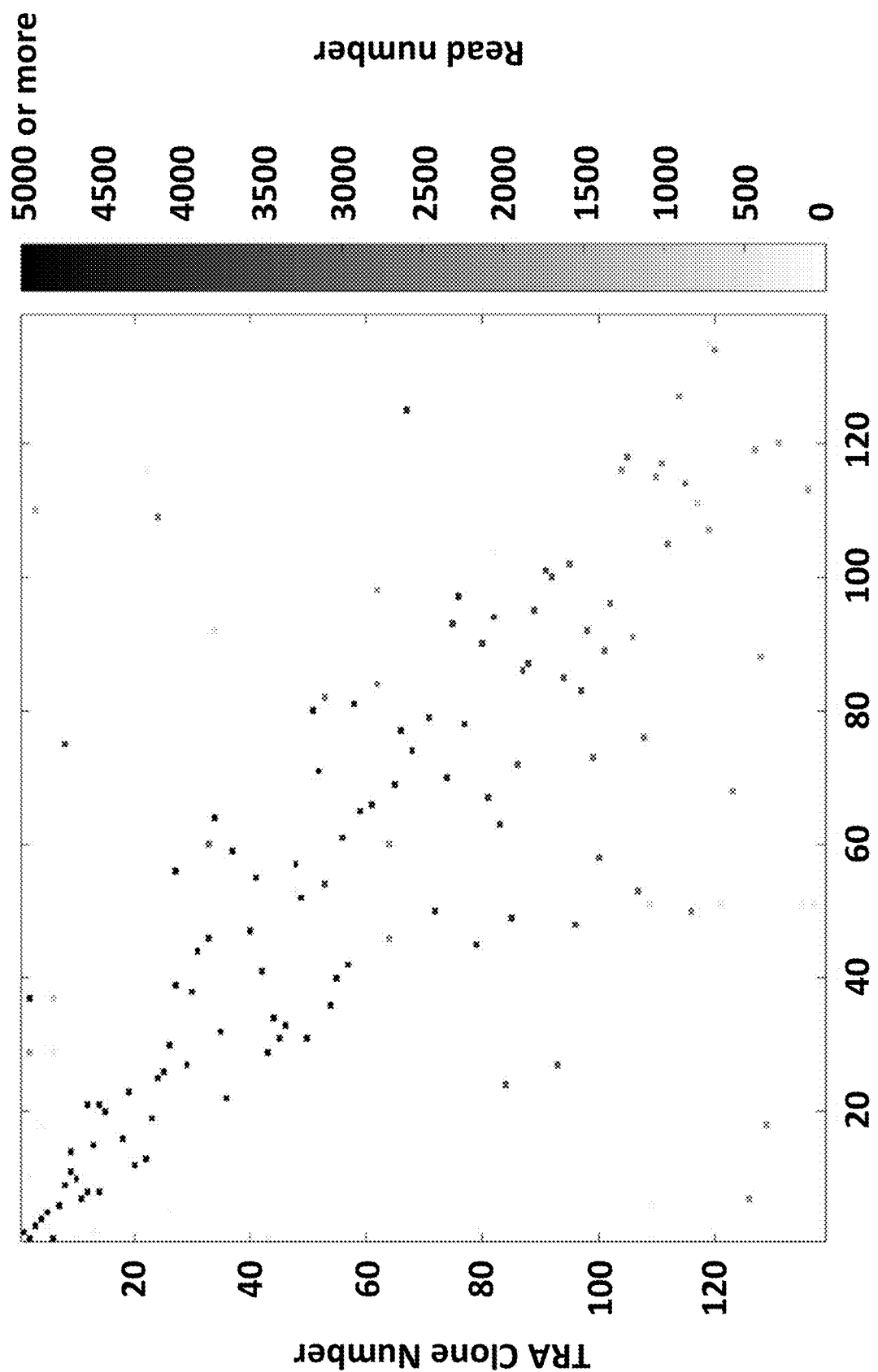
FIG. 14 depicts an example sequencing data showing paired read count matrix (M0).

A numerical matrix called M0 can be created where each row is a TRA clone and each column is a TRB clone, the value of element (i,j) of the matrix shows the total number of reads whose Read1 sequence mapped to the i-th TRA clone and Read2 sequence mapped to the j-th TRB clone. The heat map visualization of a portion of a M0 matrix is shown in FIG. 14.

Figure 15A:
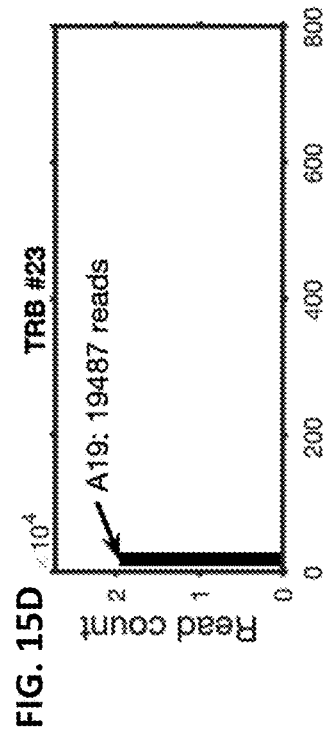
FIG. 15A depicts an example sequencing data showing dominant pairing of TRA and TRB clones.
Figure 15B:
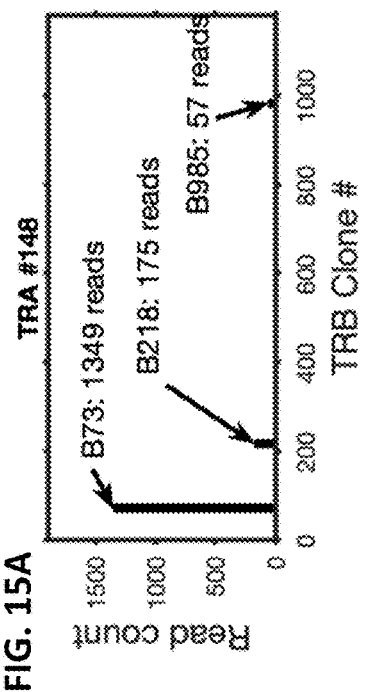
FIG. 15B depicts an example sequencing data showing dominant pairing of TRA and TRB clones.
Figure 15C:
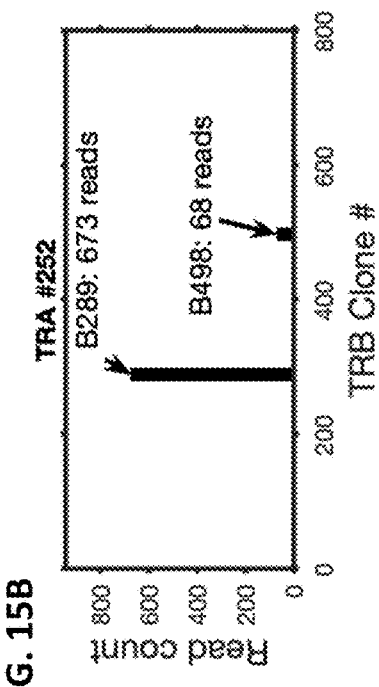
FIG. 15C depicts an example sequencing data showing dominant pairing of TRA and TRB clones.
Figure 15D:
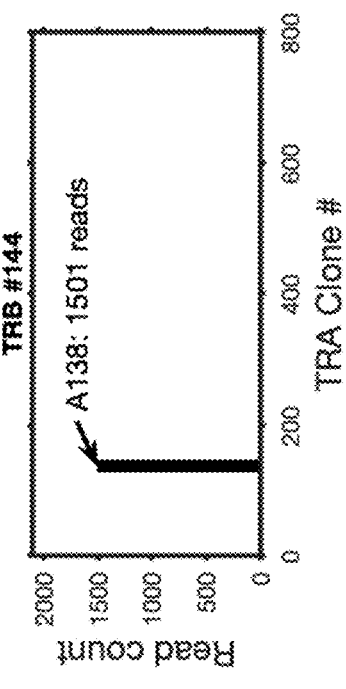
FIG. 15D depicts an example sequencing data showing dominant pairing of TRA and TRB clones.
Figure 15E:
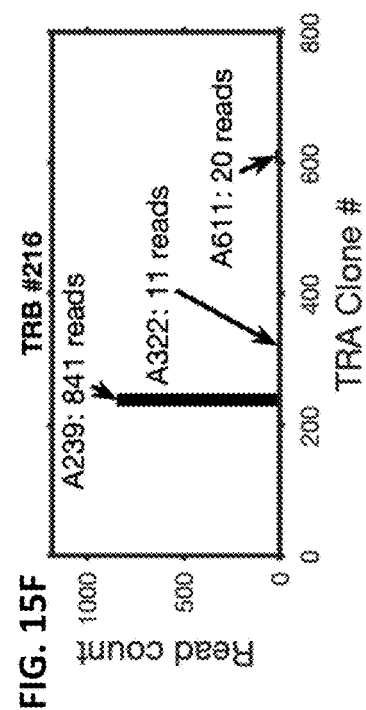
FIG. 15E depicts an example sequencing data showing dominant pairing of TRA and TRB clones.
Figure 15F:
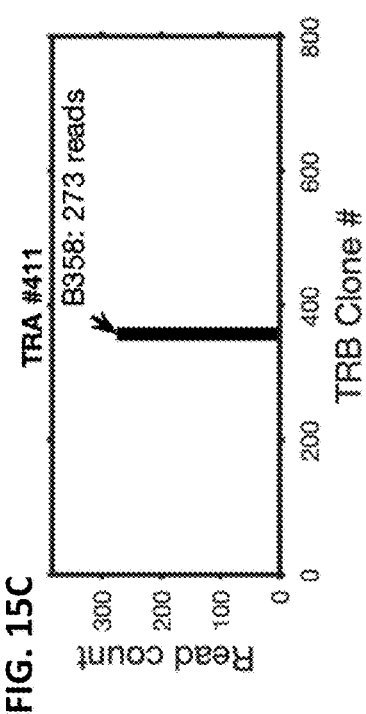
FIG. 15F depicts an example sequencing data showing dominant pairing of TRA and TRB clones.

To access whether one TRA clone is primarily paired with one TRB clone, and whether one TRB clone is primarily paired with one TRA clone, 3 TRA clones were randomly picked (FIGS. 15A-C) from a sequencing dataset, and read counts of pairings with all TRB clones were plotted. It can be seen that each of these TRA clones is primarily paired with one TRB clone. The same is true for the 3 randomly picked TRB clones (FIGS. 15D-F).

Figure 16A:
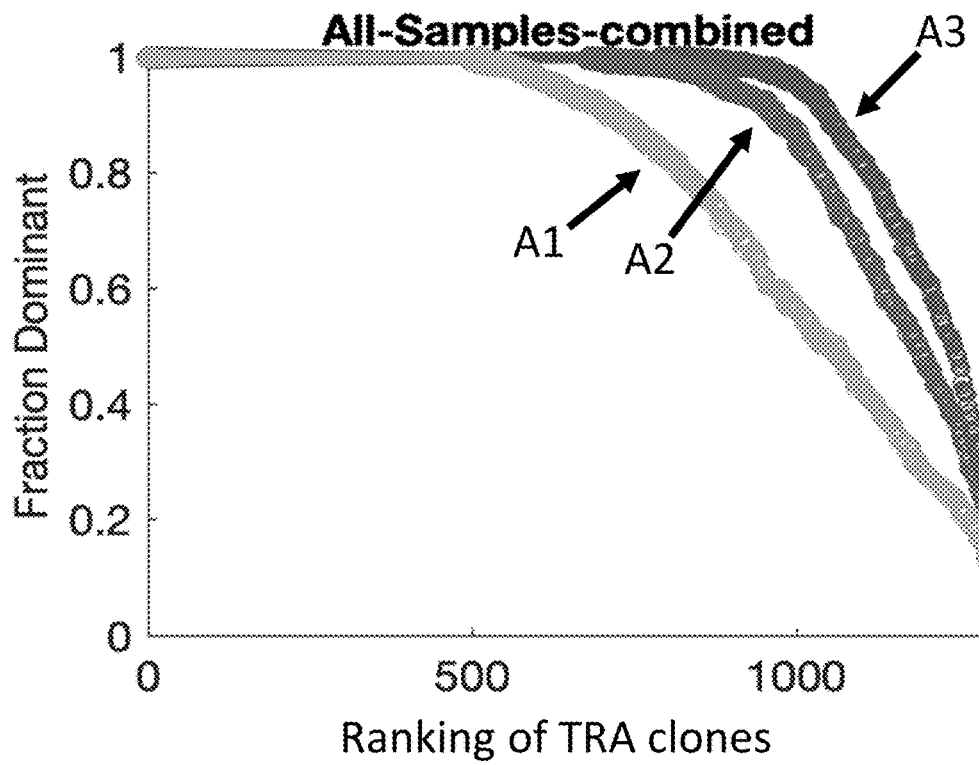
FIG. 16A depicts an example sequencing data showing clone-wise fraction of reads of a TRA clone mapped to the top 1, 2, or 3 TRB pairing partner(s) as indicated by A1, A2, or A3.
Figure 16B:
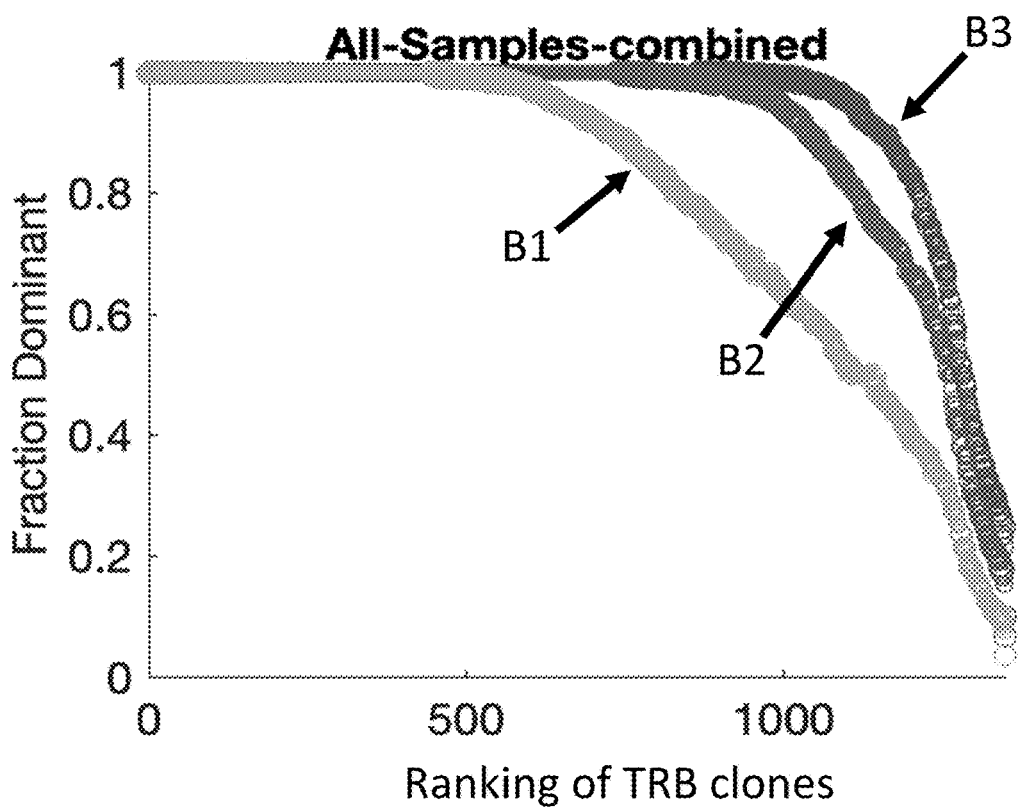
FIG. 16B depicts an example sequencing data showing clone-wise fraction of reads of a TRB clone mapped to the top 1, 2, or 3 TRA pairing partner(s) as indicated by B1, B2, or B3.
Figure 17A:
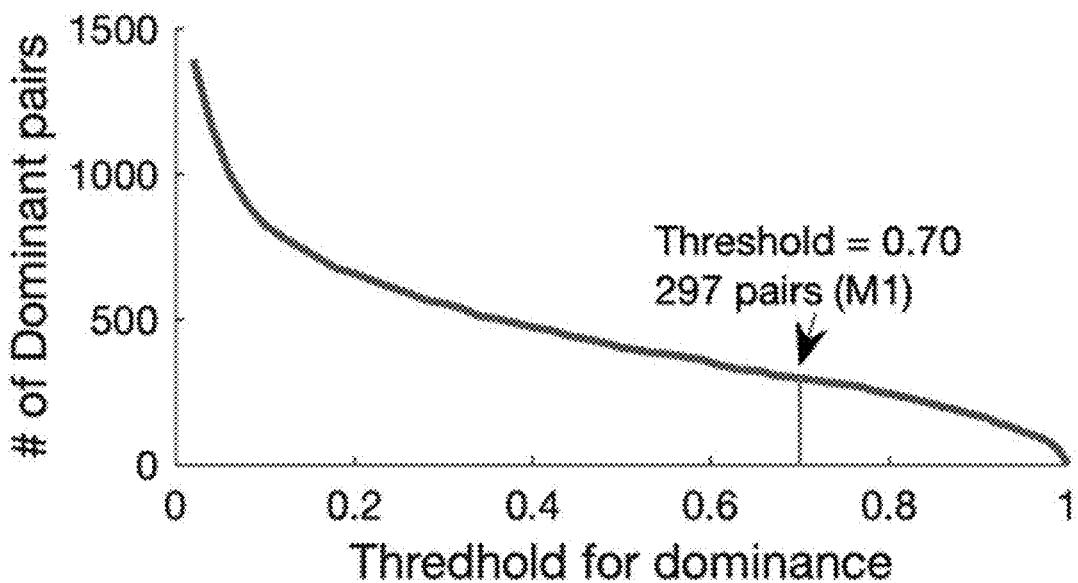
FIG. 17A depicts an example sequencing data showing number of dominant pairs detected.

To provide an overall view beyond randomly picked clones, we calculated, for each TRA clone (i.e., for each row of the M0 matrix), the fraction reads that is contributed by the top 1, 2, or 3 pairs. These fractions are called FTop1, FTop2, and FTop3, respectively. Using TRA clone #148 as an example (FIG. 15A), a total of 1581 reads were mapped to this TRA clone, of which 1349 reads were mapped to TRB clone #73, 175 reads were mapped to TRB clone #218, and 57 reads were mapped to TRB clone #985, and none were mapped to other TRB clones. Thus FTop1(TRA #148)= 1349/1581=0.85, FTop2(TRA #148)=(1349+175)/1581=0.96, FTop3(TRA #148)=(1349+175+57)/1581=1. Using this method, all TRA clones can be ranked by the FTop1 value. The descending rank orders and the corresponding FTop1 values of each TRA clone can be plotted (FIG. 16A, data series A1). Similarly, the TRA clones can be ranked by the FTop2 value. The descending rank orders and the corresponding FTop2 values of each TRA clone can be plotted (FIG. 16A, data series A2). Similarly, the TRA clones can be ranked by the FTop3 value. The descending rank orders and the corresponding FTop3 values of each TRA clone can be plotted (FIG. 17A, data A3). In these plots the size of the circle reflects the total read counts mapped to this TRA clone. Similar plots can be made for TRB clones (FIG. 16B), where the data series B1, B2, B3 show rank orders and values of FTop1, FTop2, and FTop3, respectively. It can be seen that for more than half of the TRA clones, more than 70% of the reads are contributed by one single pairs. The same conclusion can be drawn for TRB clones.

A metric that reflects the pairing accuracy across the entire library can be created. Since dominant pairs are more likely to be native pairs, one can calculate the fraction of reads that are contributed by the dominant pairs. To define dominant pairs while considering that some clones are better represented than others, matrix M0 was normalized to create matrix M1. M1 has the same dimension as M0. The value of each elements of M1 is calculated as follows:

$$M1_{i,j} = \frac{M0_{i,j}}{\sum_i M0_{i,j}} \cdot \frac{M0_{i,j}}{\sum_j M0_{i,j}}$$

Figure 17B:
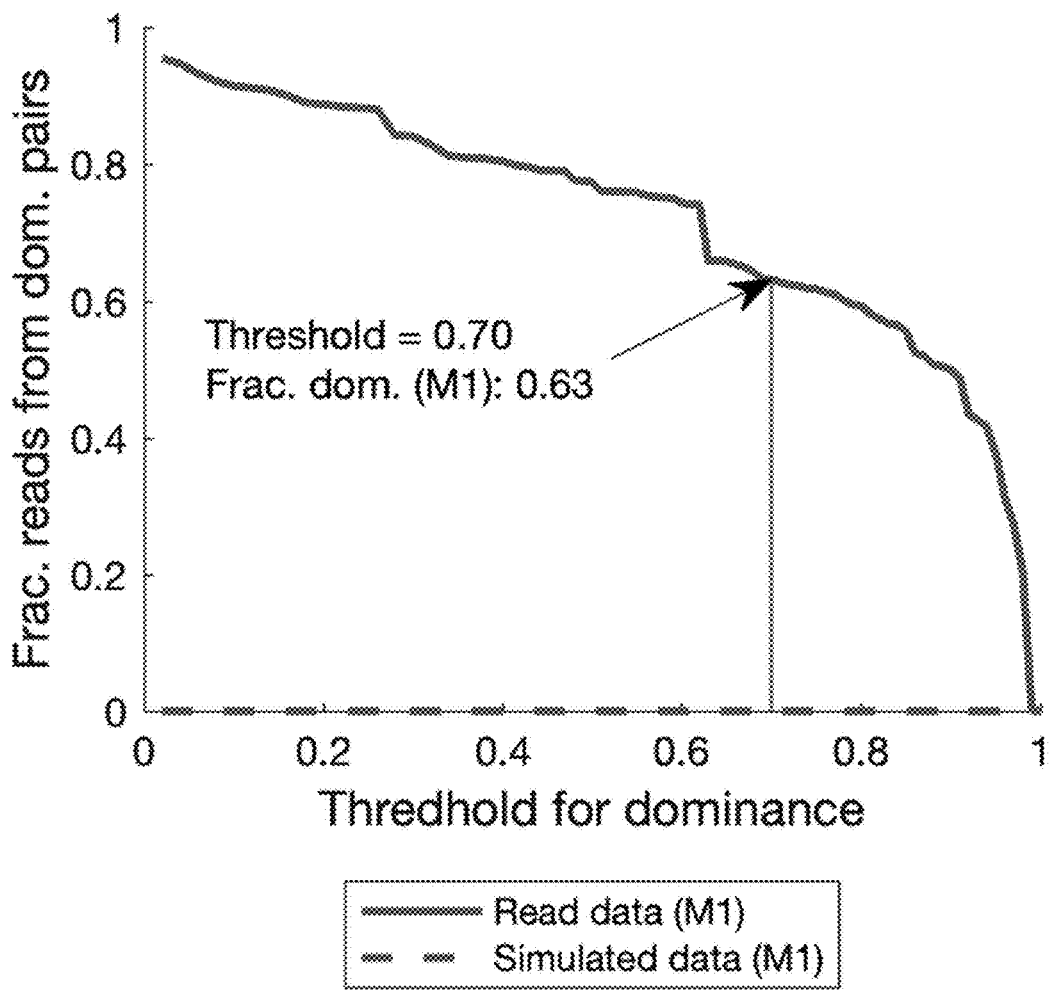
FIG. 17B depicts an example sequencing data showing the fraction of reads contributed by the dominant pairs.

Therefore all values of M1 is between 0 and 1. A pair can be defined as dominant if $M1_{i,j}$ is greater than a predetermined threshold (termed Dominance Threshold). As expected, the number of dominant pairs decreases as the Dominance Threshold increases (FIG. 17A). Similarly, the fraction of reads contributed by dominant pairs decreases as the Dominance Threshold increases (FIG. 17B, solid line). For this example library, when the Dominance Threshold is 0.7, 297 dominant pairs were identified and 63% of all reads were contributed by these dominant pairs. As a control, if the TRA-TRB pairing from the sequencing data is randomly reshuffled, the fractions of reads contributed by the dominant pairs are almost 0% (FIG. 17B, dashed line).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of identifying a plurality of target-reactive T-cell receptors (TCRs), comprising:
   (a) providing a mixture comprising a plurality of cells expressing a plurality of TCRs, each cell of the plurality of cells expressing a TCR of the plurality of TCRs, wherein the plurality of TCRs comprises at least 50 different cognate pairs from a sample from a subject and comprises V regions from a plurality of V genes, wherein each cognate pair of the at least 50 different cognate pairs comprises a TCR alpha (TCRα) chain paired with a TCR beta (TCRβ) chain, and wherein the plurality of TCRs are exogenous to the plurality of cells;
   (b) contacting the mixture comprising the plurality of cells from (a) with one or more target peptide antigens in complex with a major histocompatibility complex (MHC) molecule, wherein a subset of the plurality of cells expressing the plurality of target-reactive TCRs bind to the one or more target peptide antigens in complex with the MHC molecule; and
   (c) identifying at least two cells of the subset of the plurality of cells from (b) that express at least two target-reactive TCRs of the plurality of target-reactive TCRs, thereby identifying the at least two target-reactive TCRs of the plurality of target-reactive TCRs.

2. The method of claim 1, wherein the plurality of V genes comprises at least 10 different V genes.

3. The method of claim 1, wherein the plurality of cells is isolated from a sample from a subject, and wherein the sample is a tissue sample, a blood sample, a peripheral blood mononuclear cell (PBMC) sample, or a combination thereof.

4. The method of claim 1, wherein the plurality of TCRs comprises at least 100 different cognate pairs, wherein each cognate pair of the at least 100 different cognate pairs comprises a TCRα chain paired with a TCRβ chain.

5. The method of claim 1, wherein (b) comprises contacting the plurality of cells with one or more cells presenting the one or more target peptide antigens in complex with the MHC molecule.

6. The method of claim 5, wherein the one or more cells are one or more tumor cells, tumorspheres, tumor lysate-pulsed antigen-presenting cells (APCs), or APCs engineered to present the one or more target peptide antigens.

7. The method of claim 6, wherein the one or more APCs engineered to present the one or more target peptide antigens comprise a DNA or RNA encoding the target peptide antigen.

8. The method of claim 6, wherein the one or more APCs engineered to present the one or more target peptide antigens exogenously expresses an MHC molecule from a subject.

9. The method of claim 1, wherein the plurality of TCRs comprises a TCR from an exhausted T cell.

10. The method of claim 1, wherein the MHC molecule is an MHC tetramer.

11. The method of claim 1, wherein the sequence or identity of the one or more target peptide antigens is unknown.

12. The method of claim 1, further comprising administering at least one of the at least two cells of the subset of the plurality of cells from (b) identified to express a target-reactive TCR into a subject, or administering a cell expressing a target-reactive TCR of at least one of the at least two cells of the subset of the plurality of cells from (b) into a subject.

13. The method of claim 1, wherein each cell of the plurality of cells comprises a reporter gene, which reporter gene is regulated to send a signal when a TCR of the cell binds to a target peptide antigen of the one or more target peptide antigens.

14. The method of claim 13, wherein identifying in (c) comprises selecting the at least two cells based on the reporter gene.

15. The method of claim 1, wherein identifying in (c) comprises selecting the at least two cells based on expression of a cell surface marker.

16. The method of claim 1, wherein identifying in (c) comprises selecting the at least two cells based on calcium influx.

17. The method of claim 1, wherein the plurality of cells is cell line cells.

18. The method of claim 1, wherein the plurality of TCRs comprises at least 100 different VJ combinations.

19. The method of claim 1, wherein the plurality of TCRs comprises TCRs from a sample from a subject with a disease or a condition.

20. The method of claim 1, wherein the plurality of TCRs comprises TCRs from a sample comprising tumor-infiltrating lymphocytes from a subject.

21. The method of claim 1, further comprising, prior to (a), physically linking a first polynucleotide encoding a TCRα chain and a second polynucleotide encoding a TCRβ chain of each TCR of the plurality of TCRs, thereby generating a plurality of fused polynucleotides; and delivering the plurality of fused polynucleotides or a derivative thereof into the plurality of cells.

22. The method of claim 1, further comprising, prior to (a), sequencing the plurality of TCRs to identify cognate pairs of the plurality of TCRs; and delivering sequences encoding the cognate pairs of the plurality of TCRs into the plurality of cells.

23. The method of claim 1, wherein identifying in (c) comprises selecting at least two cells of the subset of the plurality of cells, which at least two cells express at least two target-reactive TCRs of the plurality of target-reactive TCRs, thereby selecting the at least two target-reactive TCRs of the plurality of target-reactive TCRs.

24. The method of claim 23, wherein selecting comprises selecting a cell expressing a target-reactive TCR based on a marker associated with the cell expressing a target-reactive TCR.

25. The method of claim 23, wherein selecting comprises separating a cell expressing a target-reactive TCR from cells expressing target-nonreactive TCR in the plurality of cells of (b).

26. The method of claim 25, wherein selecting comprises separating a cell expressing a target-reactive TCR from cells expressing target-nonreactive TCR in the plurality of cells of (b) based on a marker associated with the cell expressing a target-reactive TCR.

* * * * *